(12) United States Patent
Rosson et al.

(10) Patent No.: US 6,706,501 B1
(45) Date of Patent: Mar. 16, 2004

(54) **POLYNUCLEOTIDE ENCODING A *PROPIONIBACTERIUM* LINOLEATE ISOMERASE AND USES THEREOF**

(75) Inventors: Reinhardt A. Rosson, Manitowoc, WI (US); Ming-De Deng, Manitowoc, WI (US); Alan D. Grund, Manitowoc, WI (US)

(73) Assignee: Arkion Life Sciences LLC, Wilmington, DE (US)

( * ) Notice: Subject to any disclaimer, the term of this patent is extended or adjusted under 35 U.S.C. 154(b) by 0 days.

(21) Appl. No.: 09/561,077

(22) Filed: Apr. 28, 2000

Related U.S. Application Data

(60) Provisional application No. 60/141,798, filed on Jun. 30, 1999.

(51) Int. Cl.⁷ .............. C12P 7/64; C07H 21/04; C12N 1/20

(52) U.S. Cl. .............. 435/134; 435/233; 435/235.1; 435/325; 435/348; 435/419; 435/252.3; 435/254.11; 435/254.2; 435/252.31; 435/252.33; 435/257.2; 435/174; 435/320.1; 536/232; 536/23.7; 536/24.3

(58) Field of Search .............. 435/174, 233, 435/252.3, 254.11, 257.2, 348, 325, 419, 252.31, 252.33, 254.2, 320.1, 235.1, 134; 536/23.2, 23.7, 24.3

(56) References Cited

U.S. PATENT DOCUMENTS

| | | | |
|---|---|---|---|
| 5,856,149 A | 1/1999 | Pariza et al. | 435/134 |
| 6,015,833 A | 1/2000 | Sæbø et al. | 514/558 |

FOREIGN PATENT DOCUMENTS

| | | |
|---|---|---|
| WO | WO 96/38137 | 12/1996 |
| WO | WO 99/29886 | 6/1999 |

OTHER PUBLICATIONS

Burgess et al., *Lipids*, 26(2):162–165 (1991).
Chibata, 1978, Immobilized Enzymes, pp. 73–81, Halsted Press, Japan.
Eyssen et al., *Amer. J. Clin. Nutrition*, 27:1329–1340 (1974).
Eyssen et al., *Applied and Environmental Microbiol.*, 47(1):39–43 (1984).
Faber, Ch 3. Special Techniques, pp. 270–340. In (ed.), Biotransformations in organic chemistry (1995).
Fujimoto et al., *Bioscience and Biotechnology Biochemistry*, 57(6):1026–1027 (1993).
Fukui et al., *Endeavour, New Series*, 9(1):10–17 (1985).
Garcia et al., *Biochimica et Biophysica Acta*, 424:296–302 (1976).
Giesel–Bühler et al., 1986, The aneaerobic transformation of linoleic acid by *Acetobacterium woodii*. International Symposium—Biocatalysis in organic media. Wageningen, The Netherlands. Elsevier Science Publishers B.V.
Hamberg, *Biochem. and Biophys. Res. Comm.*, 188(3): 1220–1227 (1992).
Hart et al., *J. Virol.*, 70:3606–3616 (1996) Sequence Search.
Hughes et al., *J. Biological Chemistry*, 257(7):3643–3649 (1982).
Hunter et al., *J. Biological Chemistry*, 251(8):2241–2247 (1976).
Jack et al., *Clinica Chimica Acta*, 224:139–146 (1994).
Jiang et al., *J. Applied Microbiology*, 85:95–102 (1998).
Kemp et al., *J. General Microbiology*, 130:527–533 (1984).
Kemp et al., *British J. Nutrition*, 52:165–170 (1984).
Kemp et al., *British J. Nutrition*, 52:171–177 (1984).
Kemp et al., *J. General Microbiology*, 90:100–114 (1975).
Kepler et al., *J. Biological Chemistry*, 242(24):5686–5692 (1967).
Kepler et al., *Methods in Enzymology*, 14:105–110 (1969).
Kepler et al., *J. Biological Chemistry*, 241(6):1350–1354 (1966).
Kepler et al., *J. Biological Chemistry*, 245(14):3612–3620 (1970).
Kepler et al., *J. Biological Chemistry*, 246(9):2765–2771 (1971).
Kil et al., *Infect. Immun.*, 62:2440–2449 (sequence search) (1994).
Klein et al., 1983, Immobilized Microbial Cells, vol. 4, pp. 11–51, "Methods for the Immobilization of Microbial Cells", In Wingard & Katchalski–Katzir (eds.) Academic Press.
Koritala et al., *Applied Microbiology and Biotechnology*, 32:299–304 (1989).
Lanser, *J. American Oil Chemists Society*, 75(12):1809–1813 (1998).
Lilly, *Chemical Engineering Science*, 49(2):151–159 (1994).
Mills et al., *Australian J. of Biological Sciences*, 23:1109–1113 (1970).
Mortimer et al., *J. Biological Chemistry*, 249(9):2833–2842 (1974).
Niehaus, Mechanisms of cis–trans isomerization of unsaturated fatty acids, pp. 229–245, In E.E. van Tamelen (ed.) Bioorganic Chemistry, Academic Press, New York, 1977.
Niehaus et al., *J. Bacteriology*, 134(1):177–183 (1978).
Niehaus et al., *J. Biological Chemistry*, 245(15):3790–3797 (1970).

(List continued on next page.)

*Primary Examiner*—Rebecca E. Prouty
*Assistant Examiner*—David J Steadman
(74) *Attorney, Agent, or Firm*—Sheridan Ross P.C.

(57) ABSTRACT

The present invention provides an isolated (trans,cis)-10,12-linoleate isomerase and its nucleic acid and amino acid sequences. The present invention also provides a method for producing conjugated linoleic acid or conjugated linolenic acid (CLA), or derivatives thereof, from an oil using an immobilized cell and/or an isolated linoleate isomerase. The present invention also provides an isolated lipase-like protein and its nucleic acid and amino acid sequences. The present invention also provides an isolated acetyltransferase-like enzyme and its nucleic acid and amino acid sequences.

51 Claims, 59 Drawing Sheets

OTHER PUBLICATIONS

Niehaus et al., *J. Biological Chemistry*, 245(15):3802–3809 (1970).

Park et al., *J. Food Sci. and Nutr.*, 1(2):244–251 (1996).

Polan et al., *J. Bacteriology*, 88(4):1056–1064 (1964).

Powell, 1996, Chapter 2.14—Immobilized Enzymes, pp. 267–272, In T. Godfrey and S. West (ed.), Industrial Enzymology. The Nature Press, New York.

Sako et al., *Nucleic Acids Res.*, 11:7679–7693 (sequence search) (1983).

Schwab et al., *Chemical Reviews*, 90:1203–1245 (1990).

Seltzer, 1972, *Cis–Trans* Isomerization, pp. 381–406, In P.D. Boyer (ed.), The Enzymes, Academic Press, New York.

Seo et al., *Agricultural Biological Chemistry*, 45(9):2025–2030 (1981).

Swaisgood, (1985), Chapter 1—Enzymes and Immobilized cells in Biotechnology, pp. 1–24, In Allen I. Laskin (ed.), New Jersey Center for Advanced Biotechnology and Medicine, New Jersey.

Tulloch, *Lipids*, 17:544–550 (1982).

Uchida, *Biochimica et Biophysica Acta*, 348:86–93 (1974).

Uchida, *Agricultural and Biological Chemistry*, 39(2):561–563 (1975).

Uchida et al., *General and Applied Microbiology*, 18:109–129 (1972).

Uchida et al., *J. General and Applied Microbiology*, 19:233–249 (1973).

Van Sonsbeek et al., *Enzyme and Microbial Technology*, 15:722–729 (1993).

Verhulst et al., *Systematic and Applied Microbiology*, 9:12–15 (1987).

Verhulst et al., *Appl. Environ Microbiol.*, 51(3):532–538 (1986).

Verhulst et al., *FEMS Microbiology Ecology*, 31:255–259 (1985).

Wise et al., *Biochemistry*, 36(10):2985–2992 (1998).

Wise et al., *Experientia*, 52:88–92 (1996).

Yamazaki et al., *J. Biological Chemistry*, 254(10):3812–3817 (1979).

Miskin et al., *Microbiology*, 143:1745–1755 (1997).

Steiner et al., *Can. J. Microbiol.*, 43:315–321 (1997).

Yang, "Isolation, identification and characterization of linoleate isomerase from *Lactobacillus reuteri*" (1997) 180 pp., UMI Order No. DA9823268.

```
                      A — T
                      A — T
                      A — T
                      G — C
                   T         G
                      C — G
                      G — C
                      A — T
                      A — T
                      G — C
                      A — T
                      A — T
5'-TTA CTA TAA AGA TGA — TTTTTATA-3'
    L   L   STOP
```

FIG. 10

Tested Two Constructs
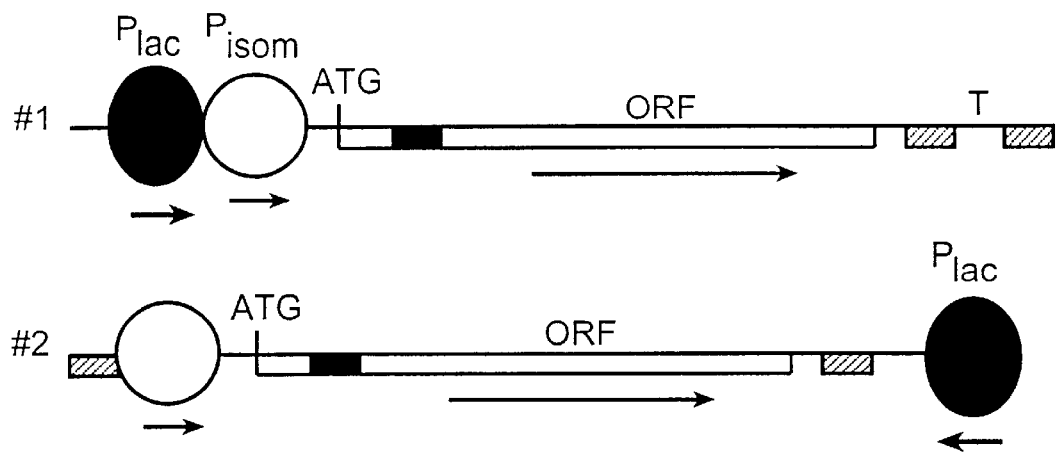
New Construct #3:
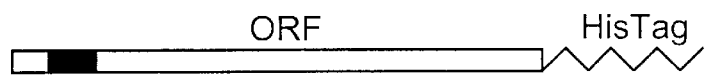
New Construct #4:
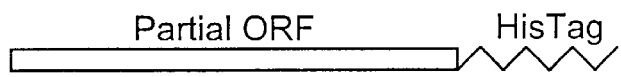
FIG. 11

Expression System:
  HapII promoter
  LAT promoter
  — with the secretion signal peptide
  — without the secretion signal peptide

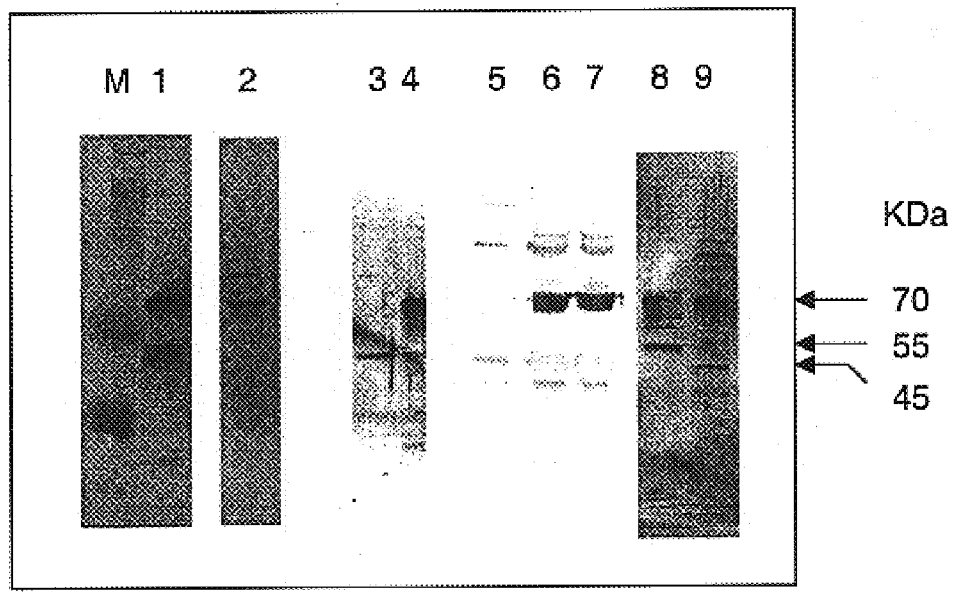

Western Blot analysis of linoleate isomerase using rabbit antibodies specific for the cloned L. reuteri PYR8 isomerase. Total protein of cell lysates prepared from different strains was used in the analysis.

M. Protein size marker
1. E. coli expressing the isomerase-histag fusion protein
2. L. reuteri PYR8
3. B. subtilis wild type
4. B. subtilis transformed with the vector pBH1 containing the isomerase gene under HpaII promoter control
5. L. reuteri 23272 wild type
6. L. reuteri 23272 transformed with the vector pTRKH2 containing the isomerase gene under the control of both its native promoter and the lac promoter
7. L. reuteri 23272 transformed with the vector pTRKH2 containing the isomerase gene under the control of its native promoter
8. P. acnes 6919
9. C. sporogenes 23272

FIG. 42

Time course of isomerization of linoleic acid. The isomerization reaction was initiated by adding 20 µM linoleic acid at 50 seconds.

Effect of pH on isomerization of linoleic acid to CLA by
C. sporogenes linoleate isomerase. Activity as nmol CLA/min/mg protein.

Effect of linoleic acid concentration on the rate of isomerization.
Vo as nmols CLA/min/mg protein. [LA] as µM.

Lineweaver-Burk plot of reaction kinetics of *C. sporogenes* linoleate isomerase. Vo as nmols CLA/min/mg protein. [LA] as µM.

Effect of oleic acid on isomerase activity with linoleic acid as substrate. The concentration of linoleic acid was fixed at 36 µM. Oleic acid was added at the indicated concentrations.

Secondary plot of oleic acid inhibition. Vo as nmols CLA/min/mg protein. [Oleic Acid] as µM Secondary plot of palmitoleic acid inhibition. Vo as nmols CLA/min/mg protein. [Palmitoleic Acid] as µM Linweaver-Burk plot of linoleic acid isomerization kinetics in the presence or absence of oleic acid. Vo as nmols CLA/min/mg protein. [LA] as µM.

Hanes-Woolf plot of oleic acid inhibition of linoleic acid isomerization kinetics. Vo as nmols CLA/min/mg protein. [LA] as µM.

A putative NAD-binding domain shared by
linoleate isomerases and some other enzymes

```
          NAD-binding domain
          ─────────────────
CONSENSUS       G-G--G---A--L------G-------E-----GG-------G-----G

#1   183 SEAYSAKIALF*A*PASISC*SF*----ARL*YSDITIF*KQEYV**                    (SEQ ID NO:73)
#2     8 KVAIV*A*LS*LVV*SE*----LHA*IDDVTLY*ASDRI**KLWS                      (SEQ ID NO:74)
#3   140 VKTGKKVAVV*S*PA*LAA*QQ*----ARA*-HDVTVF*KNDRV**RIEQ                 (SEQ ID NO:75)
#4     6 VV*G*FS*LKA*RD*------TNA*-KKVLLL*GGERL**RAYS                       (SEQ ID NO:76)
#5     8 RIAII*A*LA*MAT*VE*----VDA*-HEVELY*ARSFI**KVGSWVDGD*NHI-EM*          (SEQ ID NO:77)
#6     3 STSKRPTAIVI*S*VG*VST*AR*----ARA*FH-VTVL*KNNFT**RCSL-IHHE*YRF-DQ*    (SEQ ID NO:78)
#7     8 RVIVV*A*MS*ISA*KR*----SEA*ITDLLIL*ATDHI**RMHK-TNFA*INV-EL*          (SEQ ID NO:79)
#8     2 SISKDSRIAII*A*PA*LAAGMY*----EQA*FHDYTIL*RTDHV**KCHS-PNYH*RRY-EM*    (SEQ ID NO:80)
#9    19 GVDKK-HAYIV*G*LA*LSA*VF*IRDAQMP*-ENIHIL*ELPVA**SLDG-EDRP*IGFVTR*    (POS. 2-59 OF SEQ ID NO:61)
                                                                            (POS. 19-79 OF SEQ ID NO:18)
```

SEQUENCE ORIGIN:

1: Dihydropyrimidine dehydrogenase (Human), Q12882
2: Tryptophane monoxygenase (Agrobacterium vitis), AAC77909.1
3: Glutamate synthase (Deinococcus radiodurans), AAF09769.1
4: 6-hydroxy-L-nicotine oxidase (Arthrobacter nicotinovorans), AJ223391
5: ζ-Caroten desaturase (Synechocystis sp.), D90914
6: Phytoene dehydrogenase (Cercospora nicotianae), P48537
7: Polyamine oxidase (Zea mays), O64411
8: (t, c)-10,12-Linoleate isomerase (Propionibacterium acnes)
9: (c, t)-9,11-Linoleate isomerase (Lactobacillus reuteri)

POLYNUCLEOTIDE ENCODING A *PROPIONIBACTERIUM* LINOLEATE ISOMERASE AND USES THEREOF

CROSS-REFERENCE TO RELATED APPLICATIONS

This application claims priority under 35 U.S.C. § 119(e) to U.S. Provisional Application Ser. No. 60/141,798, filed Jun. 30, 1999. The entire disclosure of U.S. Provisional Application Ser. No. 60/141,798 is incorporated herein by reference.

FIELD OF THE INVENTION

The present invention relates to an isolated (trans,cis)-10,12-linoleate isomerase enzyme, to a nucleic acid molecule encoding a (trans,cis)-10,12-linoleate isomerase enzyme, to immobilized cells containing a linoleate isomerase enzyme, to an immobilized (trans,cis)-10,12-linoleate isomerase enzyme, and to a method for converting linoleic acid or linolenic acid to CLA or derivatives thereof using the isolated linoleate isomerase enzyme, nucleic acid molecule and/or immobilized cells.

BACKGROUND OF THE INVENTION

The term "CLA" is used herein as a generic term to describe both conjugated linoleic acid and conjugated linolenic acid. The CLA compounds (cis,trans)-9,11-linoleic acid and (trans,cis)-10,12-linoleic acid are recognized nutritional supplements and effective inhibitors of epidermal carcinogenesis and forestomach neoplasia in mice, and of carcinogen-induced rat mammary tumors. CLA has also been shown to prevent adverse effects caused by immune stimulation in chicks, mice and rats, and has been shown to decrease the ratio of low density lipoprotein cholesterol to high density lipoprotein cholesterol in rabbits fed an atherogenic diet. CLA also reduces body fat in mouse, rat, chick and pig models. CLA has also been shown to be effective in treating skin lesions when included in the diet.

CLA occurs naturally in various amounts in virtually all foods. The principle natural sources of CLA are dairy products, beef and foods derived from ruminant animals. In the U.S., beef, beef tallow, veal, lamb (3–4 mg CLA/g fat; 84% cis-9,trans-11) and dairy products (3–7 mg CLA/g fat; 80–90% cis-9,trans-11) have the highest concentration of CLA. CLA concentrations 2–3 times higher are found in Australian dairy products and pasture-fed beef and lamb. Very low concentrations of CLA (0.1–0.7 mg CLA/g fat; ca. 40% each cis-9,trans-11 and trans-10,cis-12) are found in commercial vegetable oils.

CLA is a normal intermediate of linoleic acid metabolism. In cows, (cis,trans)-9,11-CLA produced by natural bacterial flora that is not further metabolized is incorporated into lipids and then into host tissues and milk. Animals take up and incorporate CLA into normal tissue and milk from dietary sources such as milk, milk products or meat containing CLA, or from CLA dietary supplements.

CLA can be synthetically obtained from alkaline isomerization of linoleic or linolenic acid, or of vegetable oils which contain linoleic acid, linolenic acid or their derivatives. Heating vegetable oil at about 180° C. under alkaline conditions catalyzes two reactions: (1) fatty acid ester bonds from the triglyceride lipid backbone are hydrolyzed, producing free fatty acids; and (2) unconjugated unsaturated fatty acids with two or more appropriate double bonds are conjugated. Commercial CLA oils available at the present time, typically made from sunflower oil, are sold without further purification. They contain a mixture of CLA isomers as well as other saturated and unsaturated fatty acids. Generally, chemical synthesis produces about 20–35% (cis,trans)-9,11-CLA and about 20–35% (trans,cis)-10,12-CLA, and the balance as a variety of other isomers. The presence of the non-active, non-natural isomers introduces the need to purify (cis,trans)-9,11-CLA and/or (trans,cis)-10,12-CLA, or to demonstrate the safety and seek regulatory approval of these non-beneficial, non-natural isomers for human use. It is not feasible economically, however, to isolate single isomers of CLA from the CLA made by alkaline isomerization. Using a fractional crystallization procedure, it is possible to enrich 9,11-CLA relative to 10,12-CLA and vice versa. U.S. Pat. No. 6,015,833, issued Jan. 18, 2000, to Saebø et al. describes the chemical production of CLA compositions from seed oils with a total CLA content of at least 50%, and with less than 1% contaminating octadecadienoic acid isomers. Another approach, described in WO 97/18320 to Loders Croklaan B. V. uses lipases to selectively esterify 10,12-CLA and thus enrich the 9,11-CLA fraction. The above-described methods, however, do not typically allow for the production of high purity, single isomer CLA, and if single isomer production is achieved on a large scale level, such a process is expected to be expensive.

One method of overcoming the shortcomings of chemical transformation is a whole cell transformation or an enzymatic transformation of linoleic acid, linolenic acid or their derivatives to CLA. It is well known that a biological system can be an effective alternative to chemical synthesis in producing a desired chemical compound where such a biological system is available. The existence of linoleate isomerase enzyme to convert linoleic acid to CLA has been known for over thirty years, however, no one has yet successfully isolated the enzyme. And because it has not yet been isolated, the linoleate isomerase enzyme has not been sequenced.

In many microorganisms, the linoleate isomerase enzyme converts linoleic acid to CLA as an intermediate in the biohydrogenation step. Kepler and Tove have identified this enzyme in *Butyrivibrio fibrisolvens* (Kepler and Tove, *J. Biol. Chem.*, 1966, 241, 1350). However, they could not solubilize the enzyme; i.e., they were unable to isolate the enzyme in any significantly pure form (Kepler and Tove, *J. Biol. Chem.*, 1967, 242, 5686). In addition, earlier studies have indicated that only compounds which possess a free carboxyl group and a cis-9,cis-12 double bond moieties are isomerized by linoleate isomerase. See Kepler and Tove, *Methods in Enzymology*, 1969, 14, 105–109, and Kepler et al., *J. Biol. Chem.*, 1970, 245, 3612.

Another research group, Park and colleagues, published an article in *J. Food Science Nutrition* (Vol. 1: 244–251, 1996), describing the purification of a protein which Park et al. believed to be the *Butyrivibrio fibrisolvens* linoleate isomerase. However, based on the initial characterization of the enzyme's activity by Kepler and Tove (see above) and the present inventors' purification, sequencing and characterization of three demonstrated linoleate isomerases, the present inventors believe that it is very unlikely that the protein that was purified and described by Park et al. is actually a linoleate isomerase. More particularly, it is well established in the art that for successful purification of particulate enzymes, such enzymes must first be converted into a soluble form. Although Park et al. demonstrate that the *Butyrivibrio fibrisolvens* linoleic acid isomerase is membrane bound, Park et al. describe no such solubilization of the enzyme. Instead, an isolated protein pellet was simply resuspended in phosphate buffer, a procedure that will generally not solubilize any membrane protein, and therefore raises significant doubts about the described purification, particularly in view of previously described purification attempts by Kepler and Tove (*J. Biol. Chem.* 242:5686–5692, 1967). Indeed, as discussed above, Kepler and Tove had described their extensive but unsuccessful efforts using well accepted solubilization methods (e.g., chelators, organic solvents, high salt, detergents) to attempt to solubilize the isomerase. Furthermore, in contrast to the 19 kD molecular weight of the putative isomerase that was eventually reported by Park et al., the main isomerase activity eluted quite early from the column during purification, indicating an apparent molecular weight of several hundred kD, and not 19 kD. When this initial material was applied to a phenyl sepharose 4B column, multiple broad peaks of activity were observed. This is not typical, and again indicates that the isomerase preparation was heterogeneous, had not been solubilized properly, and was undoubtedly associated with other membrane proteins. One of these activity peaks was then applied to a Superose 6 gel filtration column, yielding a single 19 kD band on gel electrophoresis. Finally, this sample was assayed by Park et al. for isomerase activity using HPLC, which is not appropriate for detection of CLA, since it does not resolve the various positional isomers. The retention time shown for the standard CLA was significantly different than the retention time for the putative CLA formed from linoleic acid using the 19 kD putative linoleate isomerase, and should have lead Park et al. to the firm conclusion that the peak was not CLA, but something else. Therefore, the present inventors believe that the data presented by Park et al. does not support the conclusion that a linoleate isomerase had been purified.

Therefore, there remains a need for purifying and identifying a linoleate isomerase enzyme and/or producing one by recombinant techniques. There also remains a need for finding and identifying an linoleate isomerase enzyme which does not require presence of a free carboxylic acid group in the fatty acid for isomerization. In addition, there remains a need for a method for producing CLA utilizing whole cells or isolated linoleate isomerase enzyme.

SUMMARY OF THE INVENTION

The present invention generally relates to isolated linoleate isomerase nucleic acid molecules, isolated linoleate isomerase proteins, immobilized bacterial cells having a genetic modification that increases the action of linoleate isomerase, and methods of using such nucleic acid molecules, proteins and cells to produce CLA.

One embodiment of the invention relates to an isolated 10,12-linoleate isomerase. Included in the invention are linoleate isomerases from Propionibacterium, and particularly, from *Propionibacterium acnes, Propionibacterium acidipropionici*, and *Propionibacterium freudenreichii*. Particularly preferred linoleate isomerases include linoleate isomerases from *Propionibacterium acnes*. In one embodiment, an isolated linoleate isomerase of the present invention converts linoleic acid and linolenic acid to CLA, including (trans,cis)-10,12-linoleic acid. In one embodiment, the protein has a specific linoleic acid isomerization activity of at least about 10 moles CLA mg$^{-1}$ min$^{-1}$.

One embodiment of the present invention relates to an isolated protein, comprising an amino acid sequence selected from the group of: (a) an amino acid sequence selected from the group of SEQ ID NO:42 and SEQ ID NO:61; and, (b) a homologue of the amino acid sequence of (a), wherein the homologue is at least about 35% identical to SEQ ID NO:61 over at least about 170 contiguous amino acids of SEQ ID NO:61. In this embodiment, the protein 10,12-linoleate isomerase enzymatic activity. In one embodiment, the protein is encoded by a nucleic acid molecule comprising a nucleic acid sequence that hybridizes under low, moderate, or high stringency hybridization conditions to the complement of SEQ ID NO:60. In another embodiment, the protein comprises an amino acid sequence comprising at least 15 contiguous amino acids of SEQ ID NO:61, and more preferably, at least 30 contiguous amino acids of SEQ ID NO:61, and even more preferably, at least 45 contiguous amino acids of SEQ ID NO:61. In one embodiment, the protein is encoded by a nucleic acid molecule comprising a nucleic acid sequence comprising at least 24 contiguous nucleotides of SEQ ID NO:60. In a preferred embodiment, the protein is encoded by a nucleic acid molecule comprising a nucleic acid sequence selected from the group consisting of SEQ ID NO:59 and SEQ ID NO:60, with SEQ ID NO:60 being most preferred. In another preferred embodiment, the protein comprises an amino acid sequence selected from the group consisting of SEQ ID NO:42 and SEQ ID NO:61, with SEQ ID NO:61 being most preferred. In another embodiment, the protein comprises an amino acid sequence that aligns with SEQ ID NO:73 using Martinez/Needleman-Wunsch DNA alignment method with a minimum match of 9, a gap penalty of 1.10 and a gap length penalty of 0.33, wherein amino acid residues in the amino acid sequence align with at least about 70%, and in another embodiment, with at least about 90%, of non-Xaa residues in SEQ ID NO:73.

In one embodiment, the protein is a soluble enzyme. In another embodiment, the protein comprises a leader sequence which causes insertion of the protein into the membrane of a cell which expresses the protein. In one embodiment, the linoleate isomerase is bound to a solid support, which includes, but is not limited to artificial membranes, organic supports, biopolymer supports and inorganic supports.

Another embodiment of the present invention relates to an isolated antibody that selectively binds to the isolated linoleate isomerase of the present invention.

Yet another embodiment of the present invention relates to a method for producing CLA or derivatives thereof, including contacting an oil, which comprises a compound selected from the group of linoleic acid, linolenic acid, and/or derivatives thereof, with an isolated linoleate isomerase enzyme of the present invention to convert at least a portion of the compound to CLA or derivatives thereof (e.g., when the substrate is a derivative). In one embodiment, the compound is in the form of a triglyceride and the method further includes contacting the oil with a hydrolysis enzyme to convert at least a portion of the triglyceride to free fatty acids. Such a hydrolysis enzyme can include lipases, phospholipases and esterases. The method of the present invention can also include a step of recovering the CLA. The CLA is preferably (trans,cis)-10,12-linoleic acid. The oil can include, but is not limited to, sunflower oil, safflower oil, corn oil, linseed oil, palm oil, rapeseed oil, sardine oil, herring oil, mustard seed oil, peanut oil, sesame oil, perilla oil, cottonseed oil, soybean oil, dehydrated castor oil and walnut oil. In one embodiment of the method, the linoleate isomerase enzyme is bound to a solid support, which can include organic supports, biopolymer supports and inorganic supports.

Another embodiment of the present invention relates to an isolated nucleic acid molecule comprising a nucleic acid sequence selected from the group of: (a) a nucleic acid sequence encoding a protein having 10,12-linoleate isomerase enzymatic activity, wherein the protein comprises an amino acid sequence selected from the group consisting of SEQ ID NO:42 and SEQ ID NO:61; (b) a nucleic acid sequence encoding a homologue of a protein of (a), wherein the homologue has 10,12-linoleate isomerase enzymatic activity, and wherein the homologue is at least about 35% identical to SEQ ID NO:61 over at least about 170 contiguous amino acids of SEQ ID NO:61; and/or, (c) a nucleic acid sequence that is fully complementary to any of the nucleic acid sequences of (a) or (b). In one embodiment, the nucleic acid sequence of (b) hybridizes under low, moderate, or high stringency hybridization conditions to the complement of SEQ ID NO:60.

In another embodiment, the homologue comprises at least 15 contiguous amino acids of SEQ ID NO:61, and more preferably, at least 30 contiguous amino acids of SEQ ID NO:61, and even more preferably, at least 45 contiguous amino acids of SEQ ID NO:61. In another embodiment, the nucleic acid sequence of (b) comprises at least 24 contiguous nucleotides of SEQ ID NO:60. The nucleic acid molecule preferably comprises a nucleic acid sequence selected from the group of SEQ ID NO:59 and SEQ ID NO:60, with SEQ ID NO:60 being most preferred. Preferably, the nucleic acid molecule comprises a nucleic acid sequence encoding an amino acid sequence selected from the group of SEQ ID NO:42 and SEQ ID NO:61, with SEQ ID NO:61 being most preferred.

The isolate nucleic acid molecule of the present invention includes linoleate isomerase nucleic acid molecules from microorganisms including, but not limited to, Propionibacterium, with *Propionibacterium acnes, Propionibacterium acidipropionici*, and *Propionibacterium freudenreichii* being particularly preferred. Most preferred linoleate isomerase nucleic acid molecules are from *Propionibacterium acnes*.

Also included in the present invention are recombinant molecules, recombinant viruses and recombinant cells which include an isolated nucleic acid molecule of the present invention. In one embodiment, as recombinant cell of the present invention is from a microorganism which includes, but is not limited to, *Propionibacterium acnes, Propionibacterium freudenreichii, Propionibacterium acidipropionici, Escherichia coli, Bacillus subtilis*, or *Bacillus licheniformis*, with *Escherichia coli, Bacillus subtilis* and *Bacillus licheniformis* being most preferred.

Yet another embodiment of the present invention relates to a method to produce linoleate isomerase, comprising culturing a recombinant cell transfected with an isolated nucleic acid molecule encoding linoleate isomerase.

Another embodiment of the present invention relates to a method for producing CLA or derivatives thereof, including contacting an oil which comprises a compound selected from the group of linoleic acid, linolenic acid, and/or derivatives thereof, with an isolated linoleate isomerase enzyme encoded by the isolated nucleic acid molecule of the present invention to convert at least a portion of the compound to CLA and/or a derivative thereof.

Yet another embodiment of the present invention relates to an immobilized cell having a genetic modification that increases the action of linoleate isomerase. The cell can be any cell, including immobilized bacterial, fungal (e.g., yeast), microalgal, insect, plant or mammalian cells. In one embodiment, the cell is a microorganism which includes, but is not limited to Propionibacterium, Escherichia, Bacillus or yeast cells. In one embodiment, the genetic modification results in overexpression of linoleate isomerase by the cell. The genetic modification can result in at least one amino acid modification selected from the group consisting of deletion, insertion, inversion, substitution and derivatization of at least one amino acid residue of the linoleate isomerase, wherein such modification results in increased linoleate isomerase action, reduced substrate inhibition, and/or reduced product inhibition. In another embodiment, the genetic modification includes transfection of the cell with a recombinant nucleic acid molecule encoding a linoleate isomerase of the present invention, wherein the recombinant nucleic acid molecule is operatively linked to a transcription control sequence. The recombinant nucleic acid molecule can include any of the isolated nucleic acid molecules described above, including a nucleic acid sequence encoding a homologue of linoleate isomerase.

In one embodiment, the recombinant nucleic acid molecule is integrated into the genome of the cell. In another embodiment, the recombinant nucleic acid molecule is a plasmid transformed/transfected into a cell. In another embodiment, the recombinant nucleic acid molecule encoding linoleate isomerase comprises a genetic modification which increases the action of the linoleate isomerase and in another embodiment, the genetic modification reduces substrate and/or product inhibition of the linoleate isomerase.

In another embodiment, an immobilized cell of the present invention can be lysed. The cell can be immobilized by crosslinking with a bifunctional or multifunctional crosslinking agent, including, but not limited to glutaraldehyde.

Yet another embodiment of the present invention relates to a method for producing CLA or a derivative thereof, including contacting an oil which includes a fatty acid selected from the group of linoleic acid, linolenic acid, and derivatives thereof with an immobilized cell having a linoleate isomerase, to convert at least a portion of the compound to CLA or a derivative thereof. Such cells are described above. The cell can be a naturally occurring bacterial cell having a linoleate isomerase, or a genetically modified cell, such as a genetically modified microorganism, as described above. Preferably, a genetically modified cell has increased linoleate isomerase action. The fatty acid can include fatty acids in the form of a triglyceride such that at least a portion of the triglycerides are converted to free fatty acids. Other features of the method are as described above in the method to produce CLA.

Another embodiment of the present invention relates to an isolated lipase-like protein. Such a protein comprises an amino acid sequence selected from the group of: (a) SEQ ID NO:64; and, (b) a homologue of SEQ ID NO:64, wherein the homologue is at least about 35% identical to SEQ ID NO:64. In one embodiment, the protein is encoded by a nucleic acid molecule comprising a nucleic acid sequence that hybridizes under moderate or high stringency conditions to the complement of SEQ ID NO:63. In another embodiment, the protein is encoded by a nucleic sequence comprising at least 24 contiguous nucleotides of SEQ ID NO:63, and more preferably, the protein is encoded by a nucleic acid molecule comprising a nucleic acid sequence represented by SEQ ID NO:63. In one embodiment, the protein comprises amino acid sequence SEQ ID NO:64. In another embodiment, the protein comprises an amino acid sequence having an esterase/lipase/thioresterase active site denoted by ProfileScan Profile No. PS50187. In yet another embodiment, the protein comprises an amino acid sequence having a carboxylesterase type-B active site denoted by ProfileScan Profile No. GC0265. Preferably, the protein has lipase enzymatic activity. Also included in the present invention is an isolated nucleic acid molecule comprising a nucleic acid sequence encoding any of the above-described lipase-like proteins.

Yet another embodiment of the present invention relates to an isolated acetyltransferase-like protein. Such a protein comprises an amino acid sequence selected from the group of: (a) SEQ ID NO:69; and, (b) a homologue of SEQ ID NO:69, wherein the homologue is at least about 40% identical to SEQ ID NO:69 over at least about 60 contiguous amino acid residues of SEQ ID NO:69. In one embodiment, such a protein is encoded by a nucleic acid molecule comprising a nucleic acid sequence that hybridizes under moderate or high stringency conditions to the complement of SEQ ID NO:68. In another embodiment, the protein is encoded by a nucleic acid molecule comprising a nucleic acid sequence represented by SEQ ID NO:68. In one embodiment, the protein comprises amino acid sequence SEQ ID NO:69. In another embodiment, the protein comprises an amino acid sequence having an acetyltransferase (GNAT) family profile denoted by ProScan Profile No. PF00583. Preferably, the protein has acetyltransferase enzymatic activity. Also included in the present invention is an isolated nucleic acid molecule comprising a nucleic acid sequence encoding any of the above-identified acetyltransferase proteins.

BRIEF DESCRIPTION OF THE FIGURES

FIG. 10 is a schematic illustration of the putative transcription terminator in the linoleate isomerase gene.

FIG. 11 is an illustration of several constructs for linoleate isomerase expression in *E. coli*.

FIG. 42 is a digitized image of a Western blot analysis in cell lysates prepared from different strains of linoleate isomerase using rabbit antibodies specific for the cloned *L. reuteri* PYR8 isomerase.

FIG. 58 is a sequence alignment showing a putative NAD-binding domain shared by linoleate isomerases of the present invention and other enzymes.

DETAILED DESCRIPTION OF THE INVENTION

Figure 1B:
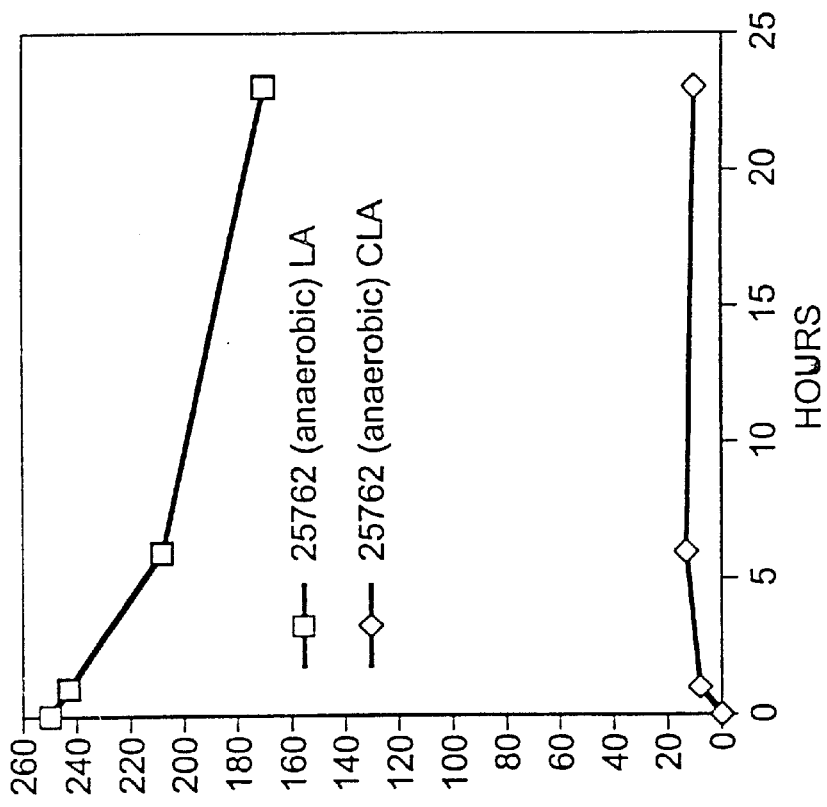
FIG. 1B is a line graph showing whole cell biotransformation of CLA from linoleic acid by *Clostridium sporogenes* ATCC 25762 under anaerobic conditions.

One embodiment of the present invention is an isolated linoleate isomerase enzyme. According to the present invention, the isolated linoleate isomerase can be used to produce conjugated double bonds in fatty acids, in derivatives of fatty acids, and/or in related molecules. More particularly, the isolated linoleate isomerase can be used to produce CLA from linoleic acid, linolenic acid or their derivatives (e.g., (cis,cis,cis)-6,9,12-octadecatrienoic acid (18:3) (γ-linolenic acid); (cis,cis,cis,cis)-6,9,12,15 octadecatetraenoic acid (18:4) (stearidonic acid); (cis,cis)-11,14 eicosadienoic acid (20:2); and methyl esters and branched forms of CLA). More specifically, isolated linoleate isomerase can convert linoleic acid to conjugated linoleic acid and/or linolenic acid to conjugated linolenic acid. The term "conjugated" refers to a molecule which has two or more double bonds which alternate with single bonds in an unsaturated compound. Linoleate isomerase is a part of a biohydrogenation pathway in microorganisms which convert linoleic acid and other unsaturated fatty acids containing a 9,12-diene moiety into a 9,11-conjugated diene moiety which is then further metabolized to other fatty acids containing a 9–11 monoene moiety. For example, most linoleate isomerases convert (cis,cis)-9,12-linoleic acid to (cis,trans)-9,11-linoleic acid as an intermediate in the biohydrogenation pathway. In many cases, the formation of CLA is followed by metabolism to other CLA isomers as well as metabolism to non-CLA compounds, such as a monoene fatty acid. *Lactobacillus reuteri*, however, produces and accumulates CLA as an end product. Other microorganisms such as *Propionibacterium acnes*, produce a linoleate isomerase which converts (cis,cis)-9,12-linoleic acid to (trans,cis)-10,12-linoleic acid. According to the present invention, the term "CLA" is used herein as a generic term to describe both conjugated linoleic acid and conjugated linolenic acid, and the term "CLA-derivative" is used to describe derivatives of CLA which are formed from derivatives of linoleic acid or linolenic acid. Such derivatives of CLA include, but are not limited to CLA-lipids, CLA-methyl-esters, and branched forms of CLA. For example, using derivatives of linoleic acid or linolenic acid as a substrate (e.g., (cis,cis,cis)-6,9, 12-octadecatrienoic acid (18:3) (γ-linolenic acid); (cis,cis, cis,cis)-6,9,12,15 octadecatetraenoic acid (18:4) (stearidonic acid); (cis,cis)-11,14 eicosadienoic acid (20:2)), CLA-lipid derivatives can be formed.

The term "isolated linoleate isomerase" refers to a linoleate isomerase outside of its natural environment in a pure enough form to achieve a significant increase in activity over crude extracts having linoleate isomerase activity. Such a linoleate isomerase can include, but is not limited to, purified linoleate isomerase, recombinantly produced linoleate isomerase, membrane bound linoleate isomerase, linoleate isomerase complexed with lipids, linoleate isomerase having an artificial membrane, soluble linoleate isomerase and isolated linoleate isomerase containing other proteins. An "artificial membrane" refers to any membrane-like structure that is not part of the natural membrane which contain linoleate isomerase. Isolated linoleate isomerases are described in related U.S. patent application Ser. No.

09/221,014, filed Dec. 23, 1998, incorporated herein by reference in its entirety.

An isolated linoleate isomerase of the present invention can be characterized by its specific activity. A "specific activity" refers to the rate of conversion of linoleic acid to CLA by the enzyme. More specifically, it refers to the number of molecules of linoleic acid converted to CLA per mg of the enzyme per time unit. Preferably, the isolated linoleate isomerase of the present invention has a specific activity of at least about 10 nmoles CLA mg$^{-1}$ min$^{-1}$, and more preferably at least about 25 nmoles CLA mg$^{-1}$ min$^{-1}$, and more preferably at least about 100 nmoles CLA mg$^{-1}$ min$^{-1}$, and more preferably at least about 250 nmoles CLA mg$^{-1}$ min$^{-1}$, and more preferably at least about 500 nmoles CLA mg$^{-1}$ min$^{-1}$, and more preferably at least about 1000 nmoles CLA mg$^{-1}$ min$^{-1}$, and even more preferably at least about 10,000 nmoles CLA mg$^{-1}$ min$^{-1}$.

Another way to characterize the isolated linoleate isomerase is by its Michaelis-Menten constant ($K_m$). $K_m$ is a kinetic (i.e., rate) constant of the enzyme-linoleic acid complex under conditions of the steady state. For example, an isolated linoleate isomerase from *Lactobacillus reuteri* has a $K_m$ for linoleic acid of at least about 8.1 $\mu$M at a pH of about 7.5 and at a temperature of about 20° C. An isolated linoleate isomerase from *Clostridium sporogenes* has a $K_m$ for linoleic acid of at least about 11.3 $\mu$M at a pH of about 7.5 and at a temperature of about 20° C. An isolated linoleate isomerase from *Propionibacterium acnes* has a $K_m$ for linoleic acid of at least about 17.2 $\mu$M at a pH of about 7.5 and at a temperature of about 20° C.

Yet another way to characterize the linoleate isomerase is by oleic acid inhibition rate constant ($K_i$). Specifically, $K_i$ is a dissociation rate of the oleic acid-enzyme complex. For example, an isolated (cis,trans)-9,11-linoleate isomerase of the present invention has a $K_i$ of from about 20 $\mu$M to about 100 $\mu$M at a pH of about 7.5 and at a temperature of about 20° C., and more preferably, from about 50 $\mu$M to about 100 $\mu$M, and even more preferably, greater than 100 $\mu$M, with no inhibition being most preferred.

Still another way to characterize the isolated linoleate isomerase is by its initial velocity ($v_0$), i.e., initial rate of product formation. The initial velocity ($v_0$) refers to the initial conversion rate of linoleic acid to CLA by the enzyme. Specifically, it refers to the number of molecules of linoleic acid converted to CLA per mg of the enzyme per time unit. For example, the maximum initial velocity rate of an isolated 9,11-linoleate isomerase, such as an isolated linoleate isomerase from *Lactobacillus reuteri* or *Clostridium sporogenes*, at a pH of about 7.5 is at least about 100 nmoles/min/mg of protein, more preferably at least about 1,000 nmoles/min/mg of protein, and most preferably at least about 10,000 nmoles/min/mg of protein. The maximum initial velocity rate of an isolated 10,12-linoleate isomerase, such as an isolated linoleate isomerase from *Propionibacterium acnes*, at a pH of about 7.3 is at least about 100 nmoles/min/mg of protein, more preferably at least about 1,000 nmoles/min/mg of protein, and most preferably at least about 10,000 nmoles/min/mg of protein.

The isolated linoleate isomerase can be further characterized by its optimum pH. The optimum pH refers to the pH at which the linoleate isomerase has a maximum initial velocity. Preferably the optimum pH is between about 5 and about 10, more preferably between about 6 and about 8, and most preferably from about 6.8 to about 7.5. The pH optimum for a linoleate isomerase from *P. acnes* is about 6.8 to about 7.3 and most preferably, about 7.3.

Further embodiments of the isolated linoleate isomerase of the present invention include proteins which are encoded by any of the nucleic acid molecules which are described below. As used herein, reference to an isolated linoleate isomerase includes full-length linoleate isomerase proteins, fusion proteins, or any homologue of such a protein. According to the present invention, a homologue of a linoleate isomerase protein includes linoleate isomerase proteins in which at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). A linoleate isomerase protein homologue includes proteins having an amino acid sequence comprising at least 15 contiguous amino acid residues (i.e., 15 contiguous amino acid residues having 100% identity with), and preferably 30 contiguous amino acid residues of SEQ ID NO:42 or SEQ ID NO:61. In a preferred embodiment, a homologue of a linoleate isomerase amino acid sequence includes amino acid sequences comprising at least 45, and more preferably, at least 60, and more preferably at least 120, and even more preferably, at least 240, contiguous amino acid residues of SEQ ID NO:61. A linoleate isomerase protein homologue includes proteins encoded by a nucleic acid sequence comprising at least 24, and preferably at least 45, and more preferably at least 90, and more preferably at least 180, and more preferably at least 360, and even more preferably at least 720, contiguous nucleotides of SEQ ID NO:60. In a preferred embodiment, a linoleate isomerase protein homologue has measurable linoleate isomerase enzymatic activity (i.e., has biological activity). Methods of detecting and measuring linoleate isomerase biological activity are described in detail in the Examples section. In another embodiment, a linoleate isomerase homologue may or may not have measurable linoleate isomerase enzymatic activity, but is used for the preparation of antibodies or the development of oligonucleotides useful for identifying other linoleate isomerases.

According to the present invention, the term "contiguous" or "consecutive", with regard to nucleic acid or amino acid sequences described herein, means to be connected in an unbroken sequence. For example, for a first sequence to comprise 15 contiguous (or consecutive) amino acids of a second sequence, means that the first sequence includes an unbroken sequence of 15 amino acid residues that is 100% identical to an unbroken sequence of 15 amino acid residues in the second sequence. Similarly, for a first sequence to have "100% identity" with a second sequence means that the first sequence exactly matches the second sequence with no gaps between nucleotides or amino acids.

In one embodiment, a linoleate isomerase protein homologue comprises an amino acid sequence that is at least about 35% identical to SEQ ID NO:61 over at least about 170 contiguous amino acids of SEQ ID NO:61. Preferably, a linoleate isomerase protein homologue comprises an amino acid sequence that is at least about 45%, and more preferably, at least about 55%, and more preferably, at least about 65%, and more preferably at least about 75%, and more preferably at least about 85%, and even more preferably at least about 95% identical to SEQ ID NO:61 over at least about 170 amino acids of SEQ ID NO:61, and more preferably over at least about 200 amino acids, and more preferably over at least about 250 amino acids, and more preferably over at least about 300 amino acids, and more preferably over at least about 350 amino acids, and even more preferably over at least about 400 amino acids of SEQ ID NO:61. As discussed above, such a linoleate isomerase protein homologue preferably has linoleate isomerase enzymatic activity (i.e., (trans,cis)-10,12-linoleate isomerase enzymatic activity). According to the present invention, the terms "(trans,cis)-10,12-linoleate isomerase activity" and "10,12-linoleate isomerase activity" can be used interchangeably.

As used herein, unless otherwise specified, reference to a percent (%) identity refers to an evaluation of homology which is performed using: (1) a BLAST 2.0 Basic BLAST homology search (ncbi.nlm.nih.gov/BLAST) using blastp for amino acid searches and blastn for nucleic acid searches with standard default parameters, wherein the query sequence is filtered for low complexity regions by default (described in Altschul, S. F., Madden, T. L., Schäaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389–3402, incorporated herein by reference in its entirety); (2) a BLAST 2 alignment (using the parameters described below) www.ncbi.nlm.nih.gov/BLAST); or (3) both BLAST 2.0 and BLAST 2. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. Therefore, it is to be understood that percent identity can be determined by using either one or both of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174:247–250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
  Reward for match=1
  Penalty for mismatch=−2
  Open gap (5) and extension gap (2) penalties
  gap x_dropoff (50) expect (10) word size (11) filter (on)
For blastp, using 0 BLOSUM62 matrix:
  Open gap (11) and extension gap (1) penalties
  gap x_dropoff (50) expect (10) word size (3) filter (on)

In some embodiments, as indicated, to align and calculate the percent identity between two amino acid sequences, the Martinez/Needleman-Wunsch DNA alignment method is used. This method is provided by the Lasergene MegAlign, a module within the DNASTAR program (DNASTAR, Inc., Madison, Wis.), and the standard default parameters are used as follows:

(1) Minimum match=9;
  (2) Gap penalty=1.10;
  (3) Gap length penalty=0.33.

In another embodiment, a linoleate isomerase, including a linoleate isomerase homologue, includes a protein having an amino acid sequence that is sufficiently similar to a natural linoleate isomerase amino acid sequence that a nucleic acid sequence encoding the homologue is capable of hybridizing under low, moderate or high stringency conditions (described below) to (i.e., with) a nucleic acid molecule encoding the natural linoleate isomerase (i.e., to the complement of the nucleic acid strand encoding the natural linoleate isomerase amino acid sequence). Preferably, a homologue of a linoleate isomerase protein is encoded by a nucleic acid molecule comprising a nucleic acid sequence that hybridizes under low, moderate, or high stringency conditions to the complement of a nucleic acid sequence that encodes a protein comprising an amino acid sequence represented by SEQ ID NO:42 or SEQ ID NO:61. Even more preferably, a homologue of a linoleate isomerase protein is encoded by a nucleic acid molecule comprising a nucleic acid sequence that hybridizes under low, moderate, or high stringency conditions to the complement of SEQ ID NO:60. Such hybridization conditions are described in detail below. A nucleic acid sequence complement of nucleic acid sequence encoding a linoleate isomerase of the present invention refers to the nucleic acid sequence of the nucleic acid strand that is complementary to (i.e., can form a complete double helix with) the strand for which the nucleic acid sequence encodes linoleate isomerase. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes the amino acid sequence selected from the group consisting of SEQ ID NO:42 or SEQ ID NO:61, and/or with the complement of the nucleic acid that encodes amino acid sequence selected from the group of SEQ ID NO:42 or SEQ ID NO:61. Methods to deduce a complementary sequence are known to those skilled in the art. It should be noted that since amino acid sequencing and nucleic acid sequencing technologies are not entirely error-free, the sequences presented herein, at best, represent apparent sequences of linoleate isomerase of the present invention.

Linoleate isomerase homologues can be the result of natural allelic variation or natural mutation. Linoleate isomerase homologues of the present invention can also be produced using techniques known in the art including, but not limited to, direct modifications to the protein or modifications to the gene encoding the protein using, for example, classic or recombinant DNA techniques to effect random or targeted mutagenesis. A naturally occurring allelic variant of a nucleic acid encoding linoleate isomerase is a gene that occurs at essentially the same locus (or loci) in the genome as the gene which encodes an amino acid sequence selected from the group consisting of SEQ ID NO:42 or SEQ ID NO:61, but which, due to natural variations caused by, for example, mutation or recombination, has a similar but not identical sequence. Natural allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art and would be expected to be found within a given bacterial species since the genome is haploid and/or among a group of two or more bacterial species.

Linoleate isomerase proteins also include expression products of gene fusions (for example, used to overexpress soluble, active forms of the recombinant enzyme), of mutagenized genes (such as genes having codon modifications to enhance gene transcription and translation), and of truncated genes (such as genes having membrane binding domains removed to generate soluble forms of a membrane enzyme, or genes having signal sequences removed which are poorly tolerated in a particular recombinant host). It is noted that linoleate isomerase proteins and protein homologues of the present invention include proteins which do not have linoleate isomerase enzymatic activity. Such proteins are useful, for example, for the production of antibodies and for diagnostic assays.

An isolated linoleate isomerase of the present invention, including full-length proteins, truncated proteins, fusion proteins and homologues, can be identified in a straightforward manner by: the proteins' ability to convert linoleic acid and/or linolenic acid to CLA, such as is illustrated in the Examples; the biochemical properties of the protein as described in the Examples; by selective binding to an antibody against a linoleate isomerase; and/or by homology with other linoleate isomerase amino acid and nucleic acid sequences as disclosed in the Examples. In particular, an isolated linoleate isomerase of the present invention is capable of converting linoleic acid and/or linolenic acid to (trans,cis)-10,12-linoleic acid.

The minimum size of a protein and/or homologue of the present invention is a size sufficient to have linoleate isomerase biological activity or, when the protein is not required to have such enzyme activity, sufficient to be useful for another purpose associated with a linoleate isomerase of the present invention, such as for the production of antibodies that bind to a naturally occurring linoleate isomerase. As such, the minimum size of linoleate isomerase protein or homologue of the present invention is a size suitable to form at least one epitope that can be recognized by an antibody, and is typically at least 8 amino acids in length, and preferably 10, and more preferably 15, and more preferably 20, and more preferably 25, and even more preferably 30 amino acids in length, with preferred sizes depending on whether full-length, multivalent (i.e., fusion protein having more than one domain each of which has a function), or functional portions of such proteins are desired. There is no limit, other than a practical limit, on the maximum size of such a protein in that the protein can include a portion of a linoleate isomerase (including linoleate isomerase homologues) or a full-length linoleate isomerase.

Similarly, the minimum size of a nucleic acid molecule of the present invention is a size sufficient to encode a protein having linoleate isomerase activity, sufficient to encode a protein comprising at least one epitope which binds to an antibody, or sufficient to form a probe or oligonucleotide primer that is capable of forming a stable hybrid with the complementary sequence of a nucleic acid molecule encoding a natural linoleate isomerase (e.g., under low, moderate or high stringency conditions). As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich.

There is no limit, other than a practical limit, on the maximal size of a nucleic acid molecule of the present invention, in that the nucleic acid molecule can include a portion of a linoleate isomerase encoding sequence, a nucleic acid sequence encoding a full-length linoleate isomerase (including a linoleate isomerase gene), or multiple genes, or portions thereof.

Preferred linoleate isomerases of the present invention include proteins which comprise an amino acid sequence having at least about 35%, and preferably at least about 40%, and more preferably at least about 50%, and more preferably at least about 60%, and more preferably at least about 70%, more preferably, at least about 80% and most preferably, at least about 90% identity with an amino acid sequence selected from SEQ ID NO:42 and/or SEQ ID NO:61. Preferred linoleate isomerases of the present invention also include proteins which comprise an amino acid sequence selected from SEQ ID NO:42 and/or SEQ ID NO:61. Preferred linoleate isomerases of the present invention also include proteins which comprise a protein selected from PPAISOM$_{35}$ (also known as PCLA$_{35}$) and/or PPAISOM$_{424}$. It is noted that a protein of the present invention can be identified as a protein by use of the letter "P" at the beginning, by its apparent size (e.g., subscript "35" is a 35 amino acid protein), by association with its function, substrate or product (e.g., CLA or ISOM designates a linoleate isomerase of the present invention), and in some instances, by its source (e.g., PPAISOM$_{424}$ is a linoleate isomerase protein from *Propionibacterium acnes* which is about 424 amino acids in length). As discussed above, as used herein, percent identity between two or more amino acid sequences is determined using a BLAST 2.0 Basic BLAST search or alignment, using the standard default parameters.

In one embodiment of the present invention, an isolated linoleate isomerase comprises a putative NAD/FAD binding domain. Preferably, the NAD/FAD binding domain corresponds to ProfileScan PROSITE Profile No. PS50205, from ProfileScan at expasy.ch. Such an NAD/FAD binding domain has the signature sequence Gly-Xaa-Gly-(Xaa)$_2$-Gly-(Xaa)$_3$-Ala-(Xaa)$_6$-Gly (positions 1 through 21 of SEQ ID NO:73, minus four additional Xaa residues from positions 14–17 of SEQ ID NO:73). Such a sequence is present in many different enzymes, as set forth in Example 13. To align two or more sequences such as SEQ ID NO:73 and another sequence, and to compare the homology/percent identity between such sequences, for example, a module contained within DNASTAR (DNASTAR, Inc. Madison, Wis.) is preferably used. In particular, to align and calculate the percent identity between two amino acid sequences, the Martinez/Needleman-Wunsch DNA alignment method is used. This method is provided by the Lasergene MegAlign module within the DNASTAR program, with the following parameters, also referred to herein as the standard default parameters:

(1) Minimum match 9;
(2) Gap penalty=1.10;
(3) Gap length penalty=0.33.

Using the Martinez/Needleman-Wunsch method with these parameters, for example, the alignment and calculation of percent identity between the amino acid sequences shown in FIG. 58 were performed. In a preferred embodiment, an isolated linoleate isomerase of the present invention comprises an amino acid sequence that aligns with SEQ ID NO:73 using the Martinez/Needleman-Wunsch alignment program as defined above, wherein amino acid residues in the amino acid sequence align with and are identical to at least about 50% of the non-Xaa residues in SEQ ID NO:73.

More preferably, an isolated linoleate isomerase of the present invention comprises an amino acid sequence that aligns with SEQ ID NO:73 using this alignment program, wherein amino acid residues in the amino acid sequence align with and are identical to at least about 60%, and more preferably at least about 70%, and more preferably at least about 80%, and even more preferably at least about 90% of the non-Xaa residues in SEQ ID NO:73. Even more preferably, an isolated linoleate isomerase of the present invention comprises an amino acid sequence that is identified as having a match with a ProfileScan PROSITE Profile No. PS50205, using the standard default parameters for normalized match score (NScores) with sensitivity set to include weak matches. The ProfileScan program can be accessed publicly through expasy.ch, ExPASy (Expert Protein Analysis System) protcomics server of the Swiss Institute of Bioinformatics (SIB); Pattern and Profile Searches.

The present invention also includes a fusion protein that includes a linoleate isomerase-containing domain (including a homologue of a linoleate isomerase) attached to one or more fusion segments. Suitable fusion segments for use with the present invention include, but are not limited to, segments that can: enhance a protein's stability; provide other enzymatic activity (e.g., lipase, phospholipase, or esterase to hydrolyze esters of 9,12-diene fatty acids to 9,12-fatty acids); and/or assist purification of a linoleate isomerase (e.g., by affinity chromatography). A suitable fusion segment can be a domain of any size that has the desired function (e.g., imparts increased stability, solubility, action or activity; provides other enzymatic activity such as hydrolysis of esters; and/or simplifies purification of a protein). Fusion segments can be joined to amino and/or carboxyl termini of the linoleate isomerase-containing domain of the protein and can be susceptible to cleavage in order to enable straightforward recovery of a linoleate isomerase. Fusion proteins are preferably produced by culturing a recombinant cell transfected with a fusion nucleic acid molecule that encodes a protein including the fusion segment attached to either the carboxyl and/or amino terminal end of a linoleate isomerase-containing domain.

Linoleate isomerases can be isolated from a various microorganisms including bacteria and fungi. For example, bacterial genera such as Lactobacillus, Clostridium, Propionibacterium, Butyrivibrio, and Eubacterium have linoleate isomerase activity. In particular, bacterial species such as *Lactobacillus reuteri, Clostridium sporogenes, Propionibacterium acnes, Butyrivibrio fibrisolvens, Propionibacterium acidipropionici, Propionibacterium freudenreichii* and *Eubacterium lentum* contain linoleate isomerase. Microorganisms which have (trans,cis)-10,12-linoleate isomerase activity according to the present invention include bacteria of the genus Propionibacterium. A particularly preferred linoleate isomerase of the present invention is a *Propionibacterium acnes* linoleate isomerase.

Further embodiments of the present invention include nucleic acid molecules that encode linoleate isomerases. A nucleic acid molecule of the present invention includes a nucleic acid molecule comprising a nucleic acid sequence encoding any of the isolated linoleate isomerase proteins, including a linoleate isomerase homologue, described above. In one embodiment, such nucleic acid molecules include isolated nucleic acid molecules that hybridize under low stringency conditions, and more preferably under moderate stringency conditions, and even more preferably under high stringency conditions with the complement of a nucleic acid sequence encoding a naturally occurring *P. acnes* linoleate isomerase (i.e., including naturally occurring allelic variants encoding a *P. acnes* linoleate isomerase). Preferably, an isolated nucleic acid molecule comprises a nucleic acid sequence that hybridizes under low, moderate, or high stringency conditions to the complement of a nucleic acid sequence that encodes a protein comprising an amino acid sequence represented by SEQ ID NO:42 or SEQ ID NO:61. In one embodiment, an isolated nucleic acid molecule comprises a nucleic acid sequence that hybridizes under low, moderate, or high stringency conditions to the complement of a nucleic acid sequence represented by SEQ ID NO:60. In other embodiments, the present invention includes an isolated nucleic acid molecule that encodes a protein comprising amino acid sequence selected from the group consisting of SEQ ID NO:42 or SEQ ID NO:61, and an isolated nucleic acid molecule having a nucleic acid sequence of SEQ ID NO:60.

As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31–9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267–284; Meinkoth et al., ibid., is incorporated by reference herein in its entirety.

More particularly, low stringency hybridization and washing conditions, as referred to herein, refer to conditions which permit isolation of nucleic acid molecules having at least about 35% nucleic acid sequence identity with the nucleic acid molecule being used to probe in the hybridization reaction (i.e., conditions permitting about 65% or less mismatch of nucleotides). Moderate stringency hybridization and washing conditions, as referred to herein, refer to conditions which permit isolation of nucleic acid molecules having at least about 55% nucleic acid sequence identity with the nucleic acid molecule being used to probe in the hybridization reaction (i.e., conditions permitting about 45% or less mismatch of nucleotides). High stringency hybridization and washing conditions, as referred to herein, refer to conditions which permit isolation of nucleic acid molecules having at least about 75% nucleic acid sequence identity with the nucleic acid molecule being used to probe in the hybridization reaction (i.e., conditions permitting about 25% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C., more preferably, between about 28° C. and about 40° C., and even more preferably, between about 35° C. and about 45° C. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C. These values are based on calculations' of a melting temperature for molecules larger than about 100 nucleotides, 0% formamide and a G+C content of about 60%. Alternatively, $T_m$ can be calculated empirically as set forth in Sambrook et al., supra, pages 9.31 TO 9.62.

In one embodiment of the present invention, a nucleic acid molecule encoding a linoleate isomerase of the present invention comprises a nucleic acid sequence that encodes an amino acid sequence that is at least about 35% identical to SEQ ID NO:61 over at least about 170 contiguous amino acids of SEQ ID NO:61. Preferably, a nucleic acid molecule encoding a linoleate isomerase of the present invention comprises a nucleic acid sequence that encodes an amino acid sequence that is at least about 45%, and more preferably, at least about 55%, and more preferably, at least about 65%, and more preferably at least about 75%, and more preferably at least about 85%, and even more preferably at least about 95% identical to SEQ ID NO:61 over at least about 170 amino acids of SEQ ID NO:61, and more preferably over at least about 200 amino acids, and more preferably over at least about 250 amino acids, and more preferably over at least about 300 amino acids, and more preferably over at least about 350 amino acids, and even more preferably over at least about 400 amino acids of SEQ ID NO:61. Such a nucleic acid sequence can include a nucleic acid sequence encoding a linoleate isomerase protein homologue, and can therefore be referred to as a homologue of a nucleic acid sequence encoding a naturally occurring linoleate isomerase (i.e., a nucleic acid sequence homologue).

Preferred linoleate isomerase nucleic acid molecules of the present invention include nucleic acid molecules which comprise a nucleic acid sequence having at least about 35%, and more preferably at least about 45%, and more preferably at least about 55%, and more preferably, at least about 65%, and more preferably, at least about 75%, and even more preferably, at least about 85%, and most preferably, at least about 95% identity with a nucleic acid sequence that encodes a protein having an amino acid sequence selected from SEQ ID NO:42 and SEQ ID NO:61. In another embodiment, preferred linoleate isomerase nucleic acid molecules of the present invention include nucleic acid molecules which comprise a nucleic acid sequence having at least about 35%, and more preferably at least about 45%, and more preferably at least about 55%, and more preferably, at least about 65%, and more preferably, at least about 75%, and even more preferably, at least about 85%, and most preferably, at least about 95% identity with a nucleic acid sequence represented by SEQ ID NO:60. Preferred linoleate isomerase nucleic acid molecules of the present invention also include nucleic acid molecules which comprise a nucleic acid sequence encoding a protein comprising an amino acid sequence represented by SEQ ID NO:42 and/or SEQ ID NO:61, or a nucleic acid molecule comprising a nucleic acid sequence represented by SEQ ID NO:60. Preferred linoleate isomerase nucleic acid molecules of the present invention also include nucleic acid molecules which comprise a nucleic acid molecule selected from nPAISOM$_{5275}$ and nPAISOM$_{1275}$. Percent identity is determined using BLAST 2.0 Basic BLAST default parameters, as described above.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated linoleate isomerase nucleic acid molecule of the present invention can be isolated from its natural source or produced using recombinant DNA technology (e.g., polymerase chain reaction (PCR) amplification, cloning) or chemical synthesis. Isolated linoleate isomerase nucleic acid molecules can include, for example, linoleate isomerase genes, natural allelic variants of linoleate isomerase genes, linoleate isomerase coding regions or portions thereof, and linoleate isomerase coding and/or regulatory regions modified by nucleotide insertions, deletions, substitutions, and/or inversions in a manner such that the modifications do not substantially interfere with the nucleic acid molecule's ability to encode a linoleate isomerase of the present invention or to form stable hybrids under stringent conditions with natural gene isolates. An isolated linoleate isomerase nucleic acid molecule can include degeneracies. As used herein, nucleotide degeneracies refers to the phenomenon that one amino acid can be encoded by different nucleotide codons. Thus, the nucleic acid sequence of a nucleic acid molecule that encodes a linoleate isomerase of the present invention can vary due to degeneracies. It is noted that an isolated linoleate isomerase nucleic acid molecule of the present invention is not required to encode a protein having linoleate isomerase activity. A linoleate isomerase nucleic acid molecule can encode a truncated, mutated or inactive protein, for example. Such nucleic acid molecules and the proteins encoded by such nucleic acid molecules are useful in diagnostic assays, for example, or for other purposes such as antibody production, as is described in the Examples below.

According to the present invention, reference to a linoleate isomerase gene includes all nucleic acid sequences related to a natural (i.e. wild-type) linoleate isomerase gene, such as regulatory regions that control production of the linoleate isomerase protein encoded by that gene (such as, but not limited to, transcription, translation or post-translation control regions) as well as the coding region itself.

In another embodiment, an linoleate isomerase gene can be a naturally occurring allelic variant that includes a similar but not identical sequence to the nucleic acid sequence encoding a given linoleate isomerase. Allelic variants have been previously described above. The phrases "nucleic acid molecule" and "gene" can be used interchangeably when the nucleic acid molecule comprises a gene as described above.

A linoleate isomerase nucleic acid molecule homologue (i.e., encoding a linoleate isomerase protein homologue) can be produced using a number of methods known to those skilled in the art (see, for example, Sambrook et al.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Nucleic acid molecule homologues can be selected by hybridization with a linoleate isomerase gene or by screening the function of a protein encoded by a nucleic acid molecule (e.g., ability to convert linoleic acid to CLA). Additionally, a nucleic acid molecule homologue of the present invention includes a nucleic acid sequence comprising at least 24 contiguous nucleotides of SEQ ID NO:60, and more preferably, at least about 45, and more preferably, at least about 90, and even more preferably, at least about 135, and even more preferably at least about 180, and even more preferably at least about 360, and even more preferably at least about 720 contiguous nucleotides of SEQ ID NO:60. Similarly, a nucleic acid molecule homologue of the present invention encodes a protein comprising an amino acid sequence including at least 15, and preferably 30 contiguous amino acid residues of SEQ ID NO:42 and/or SEQ ID NO:61. In another embodiment, a preferred nucleic acid sequence homologue encodes a protein comprising an amino acid sequence including at least 45, and more preferably at least 60, and more preferably at least 120, and even more preferably, at least 240, contiguous amino acid residues of SEQ ID NO:61.

One embodiment of the present invention includes a recombinant nucleic acid molecule, which includes at least one isolated nucleic acid molecule of the present invention inserted into any nucleic acid vector (e.g., a recombinant vector) which is suitable for cloning, sequencing, and/or otherwise manipulating the nucleic acid molecule, such as expressing and/or delivering the nucleic acid molecule into a host cell to form a recombinant cell. Such a vector contains heterologous nucleic acid sequences, that is nucleic acid sequences that are not naturally found adjacent to nucleic acid molecules of the present invention, although the vector can also contain regulatory nucleic acid sequences (e.g., promoters, untranslated regions) which are naturally found adjacent to nucleic acid molecules of the present invention (discussed in detail below). The vector can be either RNA or DNA, either prokaryotic or eukaryotic, and typically is a virus or a plasmid. The vector can be maintained as an extrachromosomal element (e.g., a plasmid) or it can be integrated into the chromosome. The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome.

Typically, a recombinant molecule includes a nucleic acid molecule of the present invention operatively linked to one or more transcription control sequences. As used herein, the phrase "recombinant molecule" or "recombinant nucleic acid molecule" primarily refers to a nucleic acid molecule or!nucleic acid sequence operatively linked to a transcription control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to a transcription control sequence in a manner such that the molecule is able to be expressed when transfected (i.e., transformed, transduced, transfected, conjugated or conduced) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in at least one of the recombinant cells useful for expressing a linoleate isomerase of the present invention. A variety of such transcription control sequences are known to those skilled in the art. Preferred transcription control sequences include those which function in bacterial, fungal (e.g., yeast), insect, plant or animal cells.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed linoleate isomerase to be secreted from the cell that produces the protein. Suitable signal segments include a signal segment that is naturally associated with a linoleate isomerase of the present invention or any heterologous signal segment capable of directing the secretion of a linoleate isomerase according to the present invention. In another embodiment, a recombinant molecule of the present invention comprises a leader sequence to enable an expressed linoleate isomerase to be delivered to and inserted into the membrane of a host cell. Suitable leader sequences include a leader sequence that is naturally associated with a linoleate isomerase of the present invention, or any heterologous leader sequence capable of directing the delivery and insertion of a linoleate isomerase to the membrane of a cell.

One type of recombinant molecule, referred to herein as a recombinant virus, includes a recombinant nucleic acid molecule of the present invention that is packaged in a viral coat and that can be expressed in a cell after delivery of the virus to the cell. A number of recombinant virus particles can be used, including, but not limited to, those based on alphaviruses, baculoviruses, poxviruses, adenoviruses, herpesviruses, and retroviruses.

One or more recombinant molecules of the present invention can be used to produce an encoded product (i.e., a linoleate isomerase protein) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include any bacterial, fungal (e.g., yeast), insect, plant or animal cell that can be transfected. Host cells can be either untransfected cells or cells that are already transfected with at least one nucleic acid molecule. Preferred host cells' for use in the present invention include any microorganism cell which is suitable for expression of a (trans,cis)-10,12-linoleate isomerase of the present invention, including, but not limited to, bacterial cells of the genera Propionibacterium, Escherichia and Bacillus. Particularly preferred host cells include bacterial cells suitable as industrial expression hosts including, but not limited to *Escherichia coli* and Bacillus species, and particularly including, but not limited to *Escherichia coli, Bacillus subtilis* and *Bacillus licheniformis*. Other particularly preferred host cells include fungal cells suitable as industrial expression hosts including, but not limited to, Saccharomyces sp., Hansenula sp., Pichia sp., Kluveromyces sp., and Phaffia sp., as well as other fungal expression systems.

According to the present invention, the term "transfection" is used to refer to any method by which an exogenous nucleic acid molecule (i.e., a recombinant nucleic acid molecule) can be inserted into the cell. The term "transformation" can be used interchangeably with the term "transfection" when such term is used to refer to the introduction of nucleic acid molecules into microbial cells, such as bacteria and yeast. In microbial systems, the term "transformation" is used to describe an inherited change due to the acquisition of exogenous nucleic acids by the microorganism and is essentially synonymous with the term "transfection". However, in animal cells, transformation has acquired a second meaning which can refer to changes in the growth properties of cells in culture after they become cancerous, for example. Therefore, to avoid confusion, with regard to the introduction of exogenous nucleic acids into animal cells, the term "transfection" is preferably used, and the term "transfection" will be used herein to generally encompass both transfection of animal cells and transformation of microbial cells, to the extent that the terms pertain to the introduction of exogenous nucleic acids into a cell. Transfection techniques include, but are not limited to, transformation, electroporation, microinjection, lipofection, adsorption, infection and protoplast fusion.

In one embodiment, an isolated linoleate isomerase protein of the present invention is produced by culturing a cell that expresses the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a linoleate isomerase protein of the present invention. Such medium typically comprises an aqueous medium having assimilable carbon, nitrogen and phosphate sources, and appropriate salts, minerals, metals and other nutrients, such as vitamins. Examples of suitable media and culture conditions are discussed in detail in the Examples section. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a biocatalyst or other reagent.

To produce significantly high yields of CLA by the methods of the present invention, a microorganism can be genetically modified to increase the action of linoleate isomerase, and preferably, to enhance production of linoleate isomerase, and thereby, CLA. As used herein, a genetically modified microorganism, such as a bacterium, fungus, microalga, and particularly, any of the preferred genera of bacteria described herein, has a genome which is modified (i.e., mutated or changed) from its normal (i.e., wild-type or naturally occurring) form such that the desired result is achieved (i.e., increase the action of linoleate isomerase). Genetic modification of a microorganism can be accomplished using classical strain development and/or molecular genetic techniques. Such techniques are generally disclosed, for example, in Sambrook et al., 1989, *Molecular Cloning: A Laboratory Manual*, Cold Spring Harbor Labs Press. The reference Sambrook et al., ibid., is incorporated by reference herein in its entirety. Additionally, techniques for genetic modification of a microorganism through recombinant technology are described in detail in the Examples section.

A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

According to the present invention, a genetically modified microorganism includes a microorganism that has been modified using recombinant technology. As used herein, genetic modifications which result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). Genetic modifications which result in an increase in gene expression or function can be referred to as amplification, overproduction, overexpression, activation, enhancement, addition, or up-regulation of a gene.

In one embodiment of the present invention, a genetic modification of a microorganism increases or decreases the action of a linoleate isomerase. Such a genetic modification includes any type of modification and specifically includes modifications made by recombinant technology and by classical mutagenesis. It should be noted that reference to increasing the action (or activity) of linoleate isomerase refers to any genetic modification in the microorganism in question which results in increased functionality of the enzyme and includes higher activity of the enzyme (e.g., specific activity or in vivo enzymatic activity), reduced inhibition or degradation of the enzyme, and overexpression of the enzyme. For example, gene copy number can be increased, expression levels can be increased by use of a promoter that gives higher levels of expression than that of the native promoter, or a gene can be altered by genetic engineering or classical mutagenesis to increase the action of an enzyme. Similarly, reference to decreasing the action of an enzyme refers to any genetic modification in the microorganism in question which results in decreased functionality of the enzymes and includes decreased activity of the enzymes (e.g., specific activity), increased inhibition or degradation of the enzymes and a reduction or elimination of expression of the enzymes. For example, the action of an enzyme of the present invention can be decreased by blocking or reducing the production of the enzyme, "knocking out" the gene encoding the enzyme, reducing enzyme activity, or inhibiting the activity of the enzyme. Blocking or reducing the production of an enzyme can include placing the gene encoding the enzyme under the control of a promoter that requires the presence of an inducing compound in the growth medium. By establishing conditions such that the inducer becomes depleted from the medium, the expression of the gene encoding the enzyme (and therefore, of enzyme synthesis) could be turned off. Blocking or reducing the activity of an enzyme could also include using an excision technology approach similar to that described in U.S. Pat. No. 4,743,546, incorporated herein by reference. To use this approach, the gene encoding the enzyme of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

In one embodiment of the present invention, a genetically modified microorganism includes a microorganism which has an enhanced ability to synthesize CLA. According to the present invention, "an enhanced ability to synthesize" a product refers to any enhancement, or up-regulation, in a pathway related to the synthesis of the product such that the microorganism produces an increased amount of the product compared to the wild-type microorganism cultured under the same conditions. In one embodiment of the present invention, enhancement of the ability of a microorganism to synthesize CLA is accomplished by amplification of the expression of the linoleate isomerase gene. Amplification of the expression of linoleate isomerase can be accomplished in a bacterial cell, for example, by introduction of a recombinant nucleic acid molecule encoding the linoleate isomerase gene, or by modifying regulatory control over a native linoleate isomerase gene.

Therefore, it is an embodiment of the present invention to provide a bacterium which is transformed with a recombinant nucleic acid molecule comprising a nucleic acid sequence encoding a linoleate isomerase. Preferred recombinant nucleic acid molecules comprising such a nucleic acid sequence include recombinant nucleic acid molecules comprising a nucleic acid sequence which encodes a linoleate isomerase comprising an amino acid sequence selected from SEQ ID NO:42 or SEQ ID NO:61. Other preferred recombinant nucleic acid molecules of the present invention include nucleic acid molecules which comprise a nucleic acid sequence represented by SEQ ID NO:60. The above identified nucleic acid molecules represent nucleic acid molecules comprising wild-type (i.e., naturally occurring or natural) nucleic acid sequences encoding linoleate isomerases. Genetically modified nucleic acid molecules which include nucleic acid sequences encoding homologues of (i.e., modified and/or mutated) linoleate isomerases are also encompassed by the present invention and are described in detail above.

It is yet another embodiment of the present invention to provide a microorganism having a linoleate isomerase with reduced substrate inhibition and/or reduced product inhibition. A linoleate isomerase with reduced substrate and/or product inhibition can be a mutated (i.e., genetically modified) linoleate isomerase gene, for example, and can be produced by any suitable method of genetic modification. For example, a recombinant nucleic acid molecule encoding linoleate isomerase can be modified by any method for inserting, deleting, and/or substituting nucleotides, such as by error-prone PCR. In this method, the nucleic acid sequence encoding the linoleate isomerase is amplified under conditions that lead to a high frequency of misincorporation errors by the DNA polymerase used for the amplification. As a result, a high frequency of mutations are obtained in the PCR products. The resulting linoleate isomerase gene mutants can then be screened for reduced substrate and/or product inhibition by testing the mutant molecules for the ability to confer increased CLA production onto a test microorganism, as compared to a microorganism carrying the non-mutated recombinant linoleate isomerase nucleic acid molecule. Another method for modifying a recombinant nucleic acid molecule encoding a linoleate isomerase is gene shuffling (i.e., molecular breeding) (See, for example, U.S. Pat. No. 5,605,793 to Stemmer; Minshull and Stemmer; 1999, *Curr. Opin. Chem. Biol.* 3:284–290; Stemmer, 1994, *P.N.A.S. USA* 91:10747–10751, all of which are incorporated herein by reference in their entirety). This technique can be used to efficiently introduce multiple simultaneous positive changes in the linoleate isomerase enzyme action. It should be noted that decreased substrate and/or product inhibition of linoleate isomerase will typically result in a linoleate isomerase with increased action, even when the specific activity of the enzyme remains the same, or actually is decreased, relative to a naturally occurring linoleate isomerase enzyme. Therefore, it is an embodiment of the present invention to produce a genetically modified linoleate isomerase with increased action and increased in vivo enzymatic activity, which has unmodified or even decreased specific activity as compared to a naturally occurring linoleate isomerase. Also encompassed by the present invention are genetically modified linoleate isomerases with increased specific activity.

Therefore, it is an embodiment of the present invention to provide a microorganism which is transformed with a genetically modified recombinant nucleic acid molecule comprising a nucleic acid sequence encoding a mutant, or homologue, linoleate isomerase. Such linoleate isomerases can be referred to herein as linoleate isomerase homologues. Protein homologues have been described in detail herein.

Another embodiment of the present invention is a method for producing CLA or derivatives thereof from an oil using an isolated linoleate isomerase enzyme. The method can be operated in batch or continuous mode using a stirred tank, a plug-flow column reactor or other apparatus known to those skilled in the art. The oil comprises a fatty acid selected from the group consisting of free fatty acids, salts of free fatty acids (e.g., soaps), and mixtures containing linoleic acid, linolenic acid, derivatives of linoleic or linolenic acid, and mixtures thereof. As discussed previously herein, derivatives of linoleic acid or linolenic acid include any derivatives, including, but not limited to lipid derivatives, methyl-ester derivatives and branched forms. Some lipid derivatives of linoleic acid and linolenic acid which can be used as a substrate for a linoleate isomerase of the present invention include, but are not limited to: (cis,cis,cis)-6,9,12-octadecatrienoic acid (18:3) (γ-linolenic acid); (cis,cis,cis, cis)-6,9,12,15 octadecatetraenoic acid (18:4) (stearidonic acid); (cis,cis)-11,14 eicosadienoic acid (20:2)). Such derivatives are described in Example 19, Table 6.

Preferably, the oil comprises at least about 50% by weight of the fatty acid, more preferably at least about 60% by weight, and most preferably at least about 80% by weight. The method of the present invention converts at least a portion of the fatty acid to CLA. Preferably at least about 30% the oil is converted to CLA, and more preferably, at least about 50% of the oil is converted to CLA, and more preferably at least about 70%, and most preferably at least about 95%.

A variety of animal and plant sources are available which contain oil that is useful for the foregoing method of the present invention. Preferably, the oil is selected from the group consisting of sunflower oil, safflower oil, corn oil, linseed oil, palm oil, rapeseed oil, sardine oil, herring oil, mustard seed oil, peanut oil, sesame oil, perilla oil, cottonseed oil, soybean oil, dehydrated castor oil and walnut oil.

When the fatty acid is in the form of a triglyceride, the method includes contacting the oil with a hydrolysis enzyme to convert at least a portion of the triglyceride to free fatty acids. Hydrolysis enzymes include any enzyme which can cleave an ester bond of a triglyceride to provide a free fatty acid. Preferably, hydrolysis enzyme is selected from the group consisting of lipases, phospholipases, and esterases. The use of enzymes to hydrolyze a triglyceride is well known to one skilled in the art.

Alternatively, the oil comprising a triglyceride of a fatty acid can be chemically hydrolyzed to convert at least a portion of the triglyceride to free fatty acids. Chemical conversion of triglyceride to free fatty acids is well known to one skilled in the art. For example, a triglyceride can be hydrolyzed to provide a free fatty acid under a basic condition using a base such as hydroxides, carbonates and bicarbonates. Exemplary bases include sodium hydroxide, calcium hydroxide, potassium hydroxide, sodium carbonate, lithium hydroxide, magnesium hydroxide, calcium carbonate, sodium bicarbonate, lithium carbonate, and lithium bicarbonate. Alternatively, triglycerides can be hydrolyzed to provide a free fatty acid under an acidic condition using an acid. Exemplary acids include, hydrochloric acid, sulfuric acid, phosphoric acid, and carboxylic acids such as acetic acid and formic acid.

In a preferred method of the present invention, the linoleate isomerase is bound to a solid support, i.e., an immobilized enzyme. As used herein, a linoleate isomerase bound to a solid support (i.e., an immobilized linoleate isomerase) includes immobilized isolated linoleate isomerases, immobilized cells which contain a linoleate isomerase enzyme (including immobilized bacterial, fungal (e.g., yeast), microalgal, insect, plant or mammalian cells), stabilized intact cells and stabilized cell/membrane homogenates. Stabilized intact cells and stabilized cell/membrane homogenates include cells and homogenates from naturally occurring microorganisms expressing linoleate isomerase or from genetically modified microorganisms, insect cells or mammalian cells as disclosed elsewhere herein. Thus, although methods for immobilizing linoleate isomerase are discussed below, it will be appreciated that such methods are equally applicable to immobilizing bacterial and other cells and in such an embodiment, the cells can be lysed.

A variety of methods for immobilizing an enzyme are disclosed in Industrial Enzymology 2nd Ed., Godfrey, T. and West, S. Eds., Stockton Press, New York, N.Y., 1996, pp. 267–272; Immobilized Enzymes, Chibata, I. Ed., Halsted Press, New York, N.Y., 1978; Enzymes and Immobilized Cells in Biotechnology, Laskin, A. Ed., Benjamin/Cummings Publishing Co., Inc., Menlo Park, Calif., 1985; and Applied Biochemistry and Bioengineering, Vol. 4, Chibata, I. and Wingard, Jr., L. Eds, Academic Press, New York, N.Y., 1983, which are incorporated herein in their entirety.

Briefly, a solid support refers to any solid organic supports, artificial membranes, biopolymer supports, or inorganic supports that can form a bond with linoleate isomerase without significantly effecting the activity of isolated linoleate isomerase enzyme. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and NiO) and sand. Preferably, the solid support is selected from the group consisting of stabilized intact cells and/or crude cell homogenates. Preparation of such supports requires a minimum of handling and cost. Additionally, such supports provide excellent stability of the enzyme.

Stabilized intact cells and/or cell/membrane homogenates can be produced, for example, by using bifunctional crosslinkers (e.g., glutaraldehyde) to stabilize cells and cell homogenates. In both the intact cells and the cell membranes, the cell wall and membranes act as immobilizing supports. In such a system, integral membrane proteins are in the "best" lipid membrane environment. Whether starting with intact cells or homogenates, in this system the cells are either no longer "alive" or "metabolizing", or alternatively, are "resting" (i.e., the cells maintain metabolic potential and active linoleate isomerase, but under the culture conditions are not growing); in either case, the immobilized cells or membranes serve as biocatalysts.

Linoleate isomerase can be bound to a solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion exchange resins. Solid supports in a bead form are particularly well-suited. The particle size of an adsorption solid support can be selected such that the immobilized enzyme is retained in the reactor by a mesh filter while the substrate (e.g., the oil) is allowed to flow through the reactor at a desired rate. With porous particulate supports it is possible to control the adsorption process to allow linoleate isomerases or bacterial cells to be embedded within the cavity of the particle, thus providing protection without an unacceptable loss of activity.

Cross-linking of a linoleate isomerase to a solid support involves forming a chemical bond between a solid support and a linoleate isomerase. It will be appreciated that although cross-linking generally involves linking a linoleate isomerase to a solid support using an intermediary compound, it is also possible to achieve a covalent bonding between the enzyme and the solid support directly without the use of an intermediary compound. Cross-linking commonly uses a bifunctional or multifunctional reagent to activate and attach a carboxyl group, amino group, sulfur group, hydroxy group or other functional group of the enzyme to the solid support. The term "activate" refers to a chemical transformation of a functional group which allows a formation of a bond at the functional group. Exemplary amino group activating reagents include water-soluble carbodiimides, glutaraldehyde, cyanogen bromide, N-hydroxysuccinimide esters, triazines, cyanuric chloride, and carbonyl diimidazole. Exemplary carboxyl group activating reagents include water-soluble carbodiimides, and N-ethyl-5-phenylisoxazolium-3-sulfonate. Exemplary tyrosyl group activating reagents include diazonium compounds. And exemplary sulfhydryl group activating reagents include dithiobis-5,5'-(2-nitrobenzoic acid), and glutathione-2-pyridyl disulfide. Systems for covalently linking an enzyme directly to a solid support include Eupergit®, a polymethacrylate bead support available from Rohm Pharma (Darmstadt, Germany), kieselguhl (Macrosorbs), available from Sterling Organics, kaolinite available from English China Clay as "Biofix" supports, silica gels which can be activated by silanization, available from W.R. Grace, and high-density alumina, available from UOP (Des Plains, Ill.).

Entrapment can also be used to immobilize linoleate isomerase. Entrapment of linoleate isomerase involves formation of, inter alia, gels (using organic or biological polymers), vesicles (including microencapsulation), semipermeable membranes or other matrices. Exemplary materials used for entrapment of an enzyme include collagen, gelatin, agar, cellulose triacetate, alginate, polyacrylamide, polystyrene, polyurethane, epoxy resins, carrageenan, and egg albumin. Some of the polymers, in particular cellulose triacetate, can be used to entrap the enzyme as they are spun into a fiber. Other materials such as polyacrylamide gels can be polymerized in solution to entrap the enzyme. Still other materials such as polyglycol oligomers that are functionalized with polymerizable vinyl end groups can entrap enzymes by forming a cross-linked polymer with UV light illumination in the presence of a photosensitizer.

CLA produced by a method of the present invention can be recovered by conventional methods.

CLA can be produced in a two-phase aqueous-oil system with emulsified oil (e.g., emulsified with lecithin), in a co-solvent system, or most preferably, in a two-phase aqueous oil system comprising an oil stream containing very little water (i.e., only the minimum water required for enzyme activity). A further characteristic of linoleate isomerases of the present invention is that they are not inhibited by higher log P solvents. In fact, it has been surprisingly found that in some cases linoleate isomerases of the present invention provide higher conversion of linoleic acid to CLA when immiscible solvents are used. CLA can be produced using a variety of solvent systems. For example, CLA can be produced using an aqueous system or a combination of an aqueous and an organic system. Preferably, a solvent system for CLA production using a linoleate isomerase comprises a solvent selected from the group consisting of water, hexane decane, hexadecane, and propylene glycol.

Yet another embodiment of the present invention relates to a method for producing CLA which utilizes industrial expression systems formed from the microorganisms (or insect or mammalian cells), nucleic acid molecules, and proteins of the present invention which have been disclosed herein. In this method, immobilized intact whole cells or cell/membrane homogenates formed from naturally occurring microorganisms expressing linoleate isomerase or from a genetically modified microorganism, insect cell or mammalian cell as described herein (including recombinant microorganisms, insect cells or mammalian cells), wherein the microorganism or other cell stably expresses a linoleate isomerase of the present invention, will be grown in a suitable culture system (e.g., fermentors). The stabilized cells or homogenates will serve as a biocatalyst in a biotransformation process to convert linoleic acid and/or linolenic acid to CLA, according to the parameters specified elsewhere herein. In one embodiment, the biocatalyst will be reused (i.e., recycled) several times. In a preferred embodiment, the linoleic and/or linolenic acid-containing oil stream is added to the biocatalyst in the presence of a minimum amount of water.

Yet another embodiment of the present invention relates to a nucleic acid molecule that encodes a lipase-like protein, and to the lipase like protein encoded thereby. In one embodiment, a nucleic acid molecule encoding a lipase-like protein of the present invention is denoted nPALPL$_{1073}$. The nucleic acid sequence of nPALPL$_{1073}$ spans from nucleotide positions 1 to 1073 on the complement of SEQ ID NO:59 (with the positions recited with regard to the sense strand), and is represented herein by SEQ ID NO:63. SEQ ID NO:63 encodes a protein having an amino acid sequence of 358 amino acid residues with an incomplete C-terminus. This sequence is referred to herein as PPALPL$_{358}$ (SEQ ID NO:64). PPALPL$_{358}$ shows some homology to lipases (see below) and is therefore designated LPL (lipase-like).

A sequence of 22 contiguous nucleotides (positions 815–836 of SEQ ID NO:63) was determined to be identical to a segment of the *Bordetella pertussis* RNA polymerase sigma 80 subunit gene (Sanger 520, *B. pertussis* Contig54). The BLAST 2.0 search with the sequence PPALPL$_{358}$ showed that the protein sequence shares a low but significant homology to some lipases. For example, the region spanning the positions 146–356 of SEQ ID NO:63 shares 26% identical and 42% similar amino acid residues with lipC from *Mycobacterium tuberculosis*. It is noted that PPALPL$_{358}$ does not share significant homology with a different lipase gene previously cloned from *P. acnes* (GenBank X99255). However, the sequence GDSAG, located at positions 244–249 of SEQ ID NO:63, is conserved in many lipases and conforms to the active-site serine motif (GXSXG) which is shared by various lipases, esterases and other hydrolytic enzymes. To provide additional evidence that PPALPL$_{358}$ is a lipase, a ProfileScan (protein pattern and profile search) was carried out with the protein sequence SEQ ID NO:64. An esterase/lipase/thioresterase active site (PROSITE Profile No. PS50187) was found in the region 167–261 of SEQ ID NO:64. In addition, the region from the positions 213 to 268 of SEQ ID NO:64 contained a carboxylesterase type-B active site (GC0265). However, the sequence PPALPL$_{358}$ does not contain the exact lipase prosites (PROSITE Profile Nos. PS01173 and PS01174) that are present in the *P. acnes* lipase (GenBank X99255). Therefore, the present inventors have concluded that the protein encoded by SEQ ID NO:63 and represented by amino acid sequence SEQ ID NO:64 is a novel lipase or lipase-like enzyme.

Therefore, one embodiment of the present invention relates to an isolated lipase-like protein. Such a protein comprises an amino acid sequence selected from the group of: (a) SEQ ID NO:64; and, (b) a homologue of SEQ ID NO:64, wherein the homologue is at least about 35% identical to SEQ ID NO:64. As discussed above, identity of one amino acid sequence to another is determined using BLAST 2.0. The general definition of a homologue of a protein has been described in detail above with respect to a linoleate isomerase of the present invention and applies to a lipase-like protein of the present invention as well. Preferably, a lipase-like protein of the present invention comprises an amino acid sequence that is at least about 45%, and more preferably, at least about 55%, and more preferably, at least about 65%, and more preferably at least about 75%, and more preferably at least about 85%, and even more preferably at least about 95% identical to SEQ ID NO:64. In a more preferred embodiment, a lipase-like protein of the present invention is encoded by a nucleic acid molecule comprising a nucleic acid sequence represented by SEQ ID NO:63. Most preferably, a lipase-like protein of the present invention comprises an amino acid sequence SEQ ID NO:64. It should be noted that since amino acid sequencing and nucleic acid sequencing technologies are not entirely error-free, the sequences presented herein, at best, represent apparent sequences of lipase-like protein of the present invention.

In one embodiment, a protein homologue having an amino acid sequence that is sufficiently similar to a natural lipase-like protein of the present invention that a nucleic acid sequence encoding the homologue is capable of hybridizing under low, moderate or high stringency conditions (described above) to (i.e., with) a nucleic acid molecule encoding the natural lipase-like protein (i.e., to the complement of the nucleic acid strand encoding the natural lipase-like protein amino acid sequence). Preferably, a homologue of a lipase-like protein is encoded by a nucleic acid molecule comprising a nucleic acid sequence that hybridizes under low, moderate, or high stringency conditions to the complement of a nucleic acid sequence that encodes a protein comprising an amino acid sequence represented by SEQ ID NO:64. Even more preferably, a homologue of a lipase-like protein is encoded by a nucleic acid molecule comprising a nucleic acid sequence that hybridizes under low, moderate, or high stringency conditions to the complement of SEQ ID NO:63. Such hybridization conditions are described in detail above.

In another embodiment, a lipase-like protein homologue includes proteins having an amino acid sequence comprising at least 15 contiguous amino acid residues (i.e., 15 contiguous amino acid residues having 100% identity with), and preferably at least 30, and more preferably at least 45, and more preferably, at least 60, and more preferably at least 120, and even more preferably, at least 240, and even more preferably at least 300, contiguous amino acid residues of SEQ ID NO:64. A lipase-like protein homologue includes proteins encoded by a nucleic acid sequence comprising at least 24, and preferably at least 45, and more preferably at least 90, and more preferably at least 180, and more preferably at least 360, and even more preferably at least 720, and even more preferably at least 900, contiguous nucleotides of SEQ ID NO:63. In a preferred embodiment, a lipase-like protein homologue has measurable lipase enzymatic activity (i.e., has biological activity). Methods of detecting and measuring lipase enzymatic activity are described in Kurooka et al., 1977, "A novel and simple colorimetric assay for human serum lipase", *J. Biochem.* (Tokyo) 81:361–369, incorporated herein by reference in its entirety. In another embodiment, a lipase-like protein homologue may or may not have measurable lipase enzymatic activity, but is used for the preparation of antibodies (e.g., can be used to generate antibodies that bind to a natural lipase-like protein of the present invention such as a protein having an amino acid sequence comprising SEQ ID NO:64), or for the development of oligonucleotides useful for identifying other lipases.

In one embodiment, a lipase-like protein of the present invention comprises an amino acid sequence having an esterase/lipase/thioresterase active site denoted by ProfileScan Profile No. PS50187. In another embodiment, a lipase-like protein of the present invention comprises an amino acid sequence having a carboxylesterase type-B active site denoted by ProfileScan Profile No. GC0265.

One embodiment of the present invention relates to an isolated nucleic acid molecule comprising a nucleic acid sequence encoding any of the lipase-like proteins of the present invention described above. Also included in the present invention are recombinant nucleic acid molecules and cells comprising such an isolated nucleic acid molecule, and methods of using such molecules to produce a lipase-like protein of the present invention. In one embodiment, isolated nucleic acid molecules comprising nucleic acid sequence encoding a lipase-like protein can be used with isolated nucleic acid molecules encoding linoleate isomerase proteins of the present invention in any of the methods described above.

As described in Example 14 below, one embodiment of the present invention is a nucleic acid molecule, denoted nPAUNK$_{783}$, which spans 1604 to 2386 of the sequence nPAISOM$_{5275}$ (SEQ ID NO:59) and is represented by SEQ ID NO:65, located upstream of SEQ ID NO:60. SEQ ID NO:65 is an open reading frame encoding a protein of 260 amino acids residues which is designated PPAUNK$_{260}$ (SEQ ID NO:66). A putative ribosome binding site GAAGGAG (SEQ ID NO:67) is located up-stream from the first ATG codon, with a 4-base spacing. Therefore, this ATG codon is very likely the actual translation initiation codon of this open reading frame. This open reading frame does not show a significant homology with any sequences in GenBank or unfinished microbial genomes Therefore, the function of PPAUNK$_{260}$ is presently unknown.

Another embodiment of the present invention relates to an isolated nucleic acid molecule encoding an acetyltransferase-like protein, and the acetyltransferase protein encoded thereby. A nucleic acid molecule encoding an acetyltransferase-like enzyme is referred to herein as nPAATL$_{582}$ and has a nucleic acid sequence represented by SEQ ID NO:68. SEQ ID NO:68 spans positions 4129 to 4710 of SEQ ID NO:59 (nPAISOM$_{5275}$) and is located on nPAISOM$_{5275}$ downstream from SEQ ID NO:60 on the same nucleic acid strand. This open reading frame encodes an acetyltransferase-like enzyme (ATL) of 193 amino acid residues, the amino acid sequence of which is represented by SEQ ID NO:69. A protein having the amino acid sequence of SEQ ID NO:69 is referred herein as PPAATL$_{193}$.

Although a BLAST 2.0 search with the nucleotide sequence nPAATL$_{582}$ did not reveal any significant homology with other sequences, a ProfileScan using the protein sequence PPAATL$_{193}$ (SEQ ID NO:69) showed that PPAATL$_{193}$ contains an acetyltransferase (GNAT) family profile (ProfileScan PROSITE Profile document PF00583). A BLAST 2.0 search also showed that PPAATL$_{193}$ has a low homology to three putative acetyltransferase genes in the database (See Example 14). Therefore, the present inventors believe that the protein encoded by nucleic acid sequence SEQ ID NO:68 and represented by amino acid sequence SEQ ID NO:69 is an acetyltransferase enzyme or an acetyltransferase-like protein.

Therefore, one embodiment of the present invention relates to an isolated acetyltransferase-like protein. Such a protein comprises an amino acid sequence selected from the group of: (a) SEQ ID NO:69; and, (b) a homologue of SEQ ID NO:69, wherein the homologue is at least about 40% identical to SEQ ID NO:69 over at least 60 contiguous amino acids of SEQ ID NO:69. As discussed above, identity of one amino acid sequence to another is determined using BLAST 2.0. The general definition of a homologue of a protein has been described in detail above with respect to a linoleate isomerase of the present invention and applies to an acetyltransferase-like protein of the present invention as well. Preferably, an acetyltransferase-like protein of the present invention comprises an amino acid sequence that is at least about 50%, and more preferably, at least about 60%, and more preferably, at least about 70%, and more preferably at least about 80%, and more preferably at least about 90%, identical to SEQ ID NO:69 over at least about 60 contiguous amino acids, and more preferably over at least 100 contiguous amino acids, and more preferably over at least 150 contiguous amino acids of SEQ ID NO:69. In a more preferred embodiment, an acetyltransferase-like protein of the present invention is encoded by a nucleic acid molecule comprising a nucleic acid sequence represented by SEQ ID NO:68. Most preferably, an acetyltransferase-like protein of the present invention comprises an amino acid sequence SEQ ID NO:69. It should be noted that since amino acid sequencing and nucleic acid sequencing technologies are not entirely error-free, the sequences presented herein, at best, represent apparent sequences of an acetyltransferase-like protein of the present invention.

In one embodiment, a protein homologue having an amino acid sequence that is sufficiently similar to a natural acetyltransferase-like protein of the present invention that a nucleic acid sequence encoding the homologue is capable of hybridizing under low, moderate or high stringency conditions (described above) to (i.e., with) a nucleic acid molecule encoding the natural acetyltransferase-like protein (i.e., to the complement of the nucleic acid strand encoding the natural acetyltransferase-like protein amino acid sequence). Preferably, a homologue of an acetyltransferase-like protein is encoded by a nucleic acid molecule comprising a nucleic acid sequence that hybridizes under low, moderate, or high stringency conditions to the complement of a nucleic acid sequence that encodes a protein comprising an amino acid sequence represented by SEQ ID NO:69. Even more preferably, a homologue of an acetyltransferase-like protein is encoded by a nucleic acid molecule comprising a nucleic acid sequence that hybridizes under low, moderate, or high stringency conditions to the complement of SEQ ID NO:68. Such hybridization conditions are described in detail above.

In another embodiment, an acetyltransferase-like protein homologue includes proteins having an amino acid sequence comprising at least 15 contiguous amino acid residues (i.e., 15 contiguous amino acid residues having 100% identity with), and preferably at least 30, and more preferably at least 45, and more preferably, at least 60, and more preferably at least 120, and even more preferably, at least 150, contiguous amino acid residues of SEQ ID NO:69. An acetyltransferase-like protein homologue includes proteins encoded by a nucleic acid sequence comprising at least 24, and preferably at least 45, and more preferably at least 90, and more preferably at least 180, and more preferably at least 360, and even more preferably at least 450, contiguous nucleotides of SEQ ID NO:68. In a preferred embodiment, an acetyltransferase-like protein homologue has measurable acetyltransferase enzymatic activity (i.e., has biological activity). Methods of detecting and measuring acetyltransferase enzymatic activity are described in Freeman et al., 1983, "Acetyl CoA: alpha-glucosamidnide N-acetyl transferase: partial purification from human liver", *Biochem. Int.* 6:663–671, incorporated herein by reference in its entirety. In another embodiment, an acetyltransferase-like protein homologue may or may not have measurable acetyltransferase enzymatic activity, but is used for the preparation of antibodies (e.g., can be used to generate antibodies that bind to a natural acetyltransferase-like protein of the present invention such as a protein having an amino acid sequence comprising SEQ ID NO:69), or for the development of oligonucleotides useful for identifying other acetyltransferases.

In one embodiment, an acetyltransferase-like protein of the present invention comprises an amino acid sequence having an acetyltransferase (GNAT) family profile denoted by profile document PF00583.

One embodiment of the present invention relates to an isolated nucleic acid molecule comprising a nucleic acid sequence encoding any of the acetyltransferase-like proteins of the present invention described above. Also included in the present invention are recombinant nucleic acid molecules and cells comprising such an isolated nucleic acid molecule, and methods of using such molecules to produce a acetyltransferase-like protein of the present invention. In one embodiment, isolated nucleic acid molecules comprising nucleic acid sequence encoding an acetyltransferase-like protein can be used with isolated nucleic acid molecules encoding linoleate isomerase proteins of the present invention in any of the methods described above.

EXAMPLES

It is to be noted that the Examples include a number of molecular biology, microbiology, immunology and biochemistry techniques considered to be known to those skilled in the art. Disclosure of such techniques can be found, for example, in Sambrook et al., id. and related references. Unless otherwise noted, all column chromatography was performed at 4° C.

Example 1

This example illustrates CLA production from linoleic acid using whole cell biotransformations with a variety of microorganisms. The term "whole cell biotransformation" refers to a conversion of a suitable substrate to CLA by a microorganism.

A variety of other microorganisms were purchased from ATCC (American Type Culture Collection) and grown on Brain Heart Infusion Broth (Difco) supplemented with 0.5% yeast extract, 0.0005% hemin, 0.001% vitamin $K_1$, 0.05% cysteine, and 0.001% resazurin. Cultures were grown in closed containers with limited head space for about 12 to about 16 hours at 37° C., harvested and washed with fresh medium. Culture stocks were maintained in 10% glycerol at about −80° C.

*Lactobacillus reuteri* PYR8 (ATCC Accession No.55739, deposited on Feb. 15, 1996 with the American Type Culture Collection (ATCC), 10801 University Boulevard, Manassas, Va. 20110, USA, in connection with U.S. Pat. No. 5,674,901 to Cook et al., issued Oct. 7, 1997, incorporated herein by reference in its entirety) was obtained from Dr. Michael Pariza of the Food Research Institute at University of Wisconsin at Madison. The organism was grown on MRS Lactobacillus Broth (BBL) in closed containers with limited head space. Large scale cultures were grown (1–2% inoculum) in 2-L bottles without agitation at 37° C. for about 36 to about 40 hours, harvested by centrifugation, washed once with 0.1 M Bis-Tris, 0.9% NaCl pH 6.0 buffer, and was used immediately or stored at about −80° C.

Cultures were grown, and harvested as described above. Washed cells were resuspended in either fresh growth medium or 0.1 M Tris pH 8.0 buffer containing linoleic acid at various concentrations.

Aerobic biotransformations were carried out in baffled 250 mL shake flasks agitated at 200 rpm on a shaker at room temperature.

Anaerobic biotransformations were carried out in sealed 150 mL serum bottles under a 95% nitrogen/5% carbon dioxide head space at 37° C. Media were prepared anaerobically by boiling under a $N_2/CO_2$ atmosphere for 15 minutes, sealed with a crimped septum and autoclaved. MRS broth (BBL) was used with *L. reuteri*. Supplemented Brain Heart Infusion broth was used in anaerobic biotransformations with other microorganisms.

Samples were taken at appropriate intervals and analyzed for CLA as described in Example 2. In some experiments, various detergents were added to 0.1–0.5% final concentration. In experiments using organic solvents, linoleic acid was provided as a 5% (v/v) stock dissolved in hexane (log P=3.6), decane (log P=5.6) or hexadecane (log P=8.6). About 5 mL solvent was added to about 20 mL aqueous cell suspension in a 125 mL baffled shake flask incubated at room temperature.

Figure 1A:
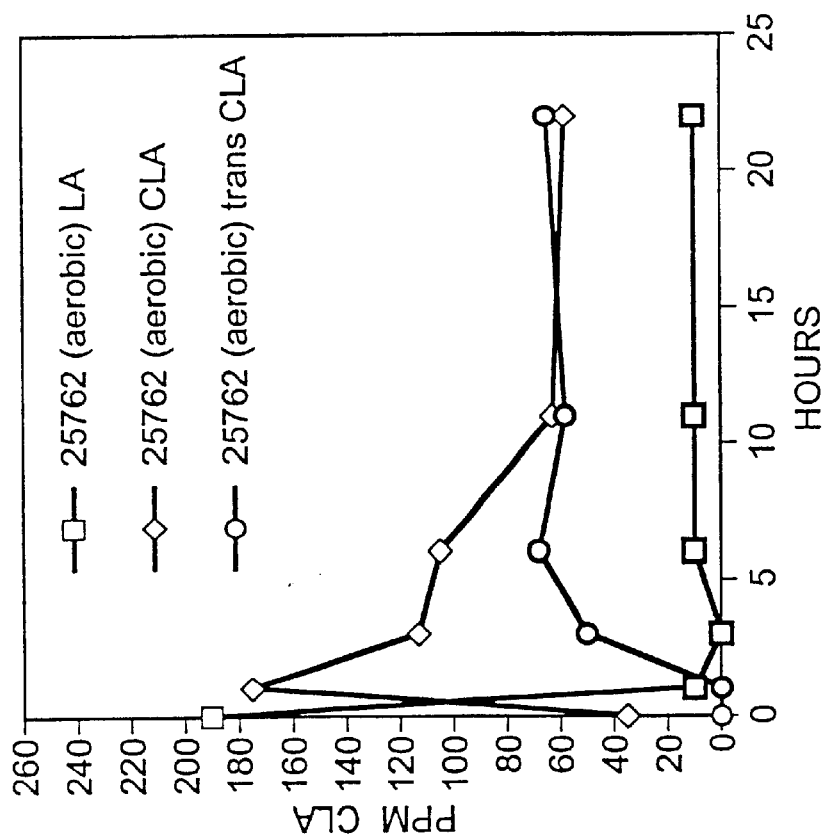
FIG. 1A is a line graph showing whole cell biotransformation of CLA from linoleic acid by *Clostridium sporogenes* ATCC 25762 under aerobic conditions.

FIGS. 1A and 1B show the results of whole cell biotransformation by *Clostridium sporogenes* ATCC 25762 under aerobic (FIG. 1A) and anaerobic (FIG. 1B) conditions. As FIG. 1A shows, under aerobic conditions, *C. sporogenes* ATCC 25762 rapidly converts linoleic acid to (cis,trans)-9, 11-CLA. However, prolonged whole cell biotransformation results in a decrease in (cis,trans)-9,11-CLA and an increase in (trans,trans)-9,11-CLA and (trans,trans)-10,12-CLA. *C. sporogenes* ATCC 25762 also produces (cis,trans)-9,11-CLA from linoleic acid under anaerobic conditions (FIG. 1B); however, no (trans,trans)-CLA is observed under anaerobic conditions.

Figure 2B:
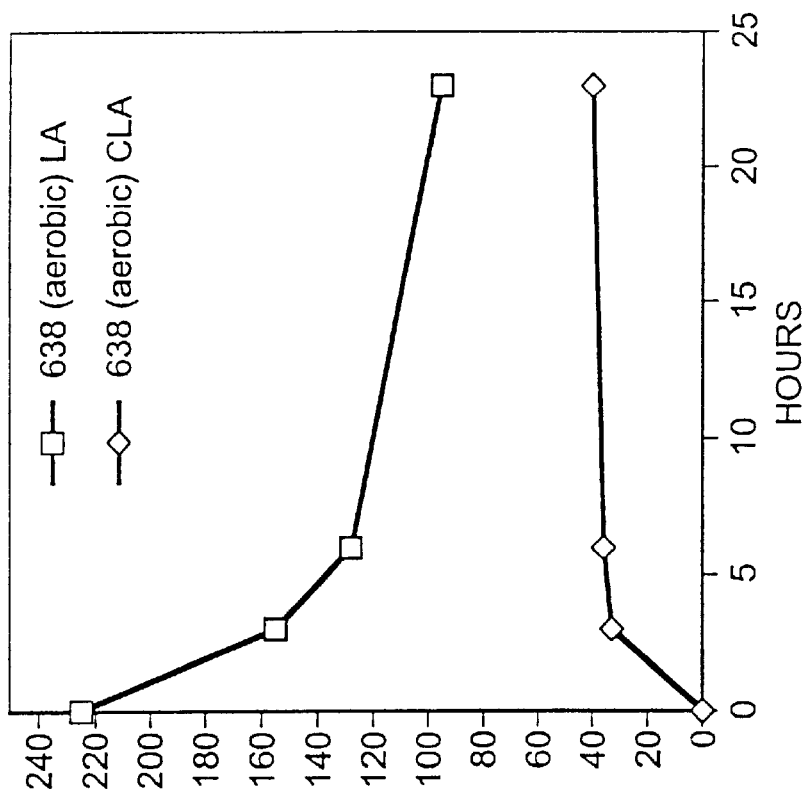
FIG. 2B is a line graph illustrating whole cell biotransformation of CLA from linoleic acid by *C. bifermentans* ATCC 638 under anaerobic conditions.
Figure 2A:
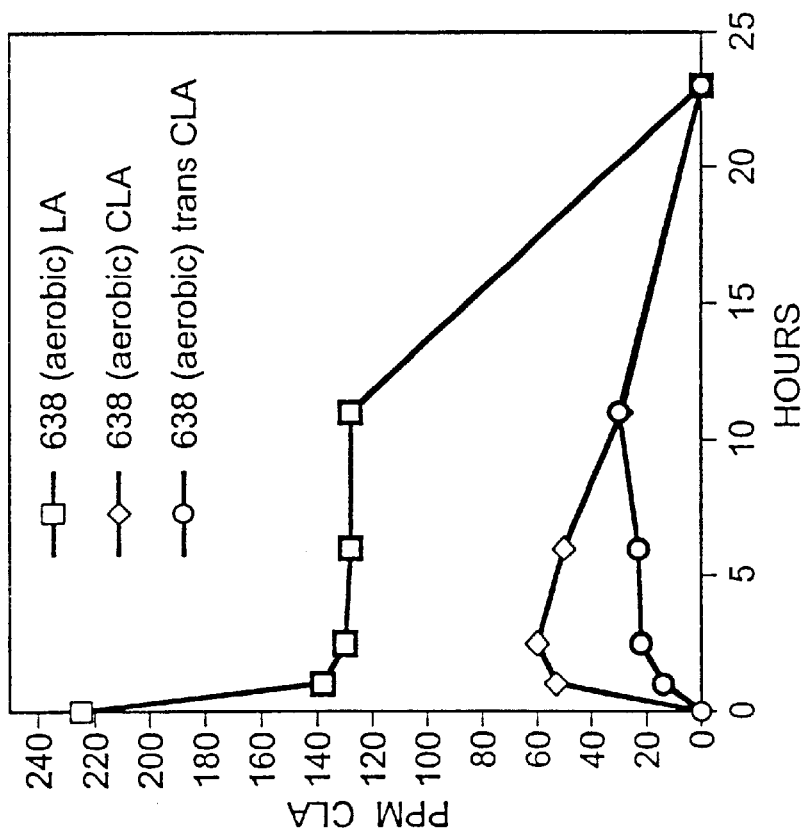
FIG. 2A is a line graph illustrating whole cell biotransformation of CLA from linoleic acid by *C. bifermentans* ATCC 638 under aerobic conditions.

FIGS. 2A and 2B show the results of whole cell biotransformation by *C. bifermentans* ATCC 638 under aerobic (FIG. 2A) and anaerobic (FIG. 2B) conditions. Linoleic acid is more rapidly converted to (cis,trans)-9,11-CLA by *C. bifermentans* ATCC 638 under aerobic conditions (FIG. 2A) than under anaerobic conditions (FIG. 2B). The highest (cis,trans)-9,11-CLA concentration is observed at about 1 to about 5 hours under aerobic conditions. *C. sordellii* ATCC 9714 also converts linoleic acid to (cis,trans)-9,11-CLA under both aerobic and anaerobic conditions (data not shown).

Figures 3A, 3B:
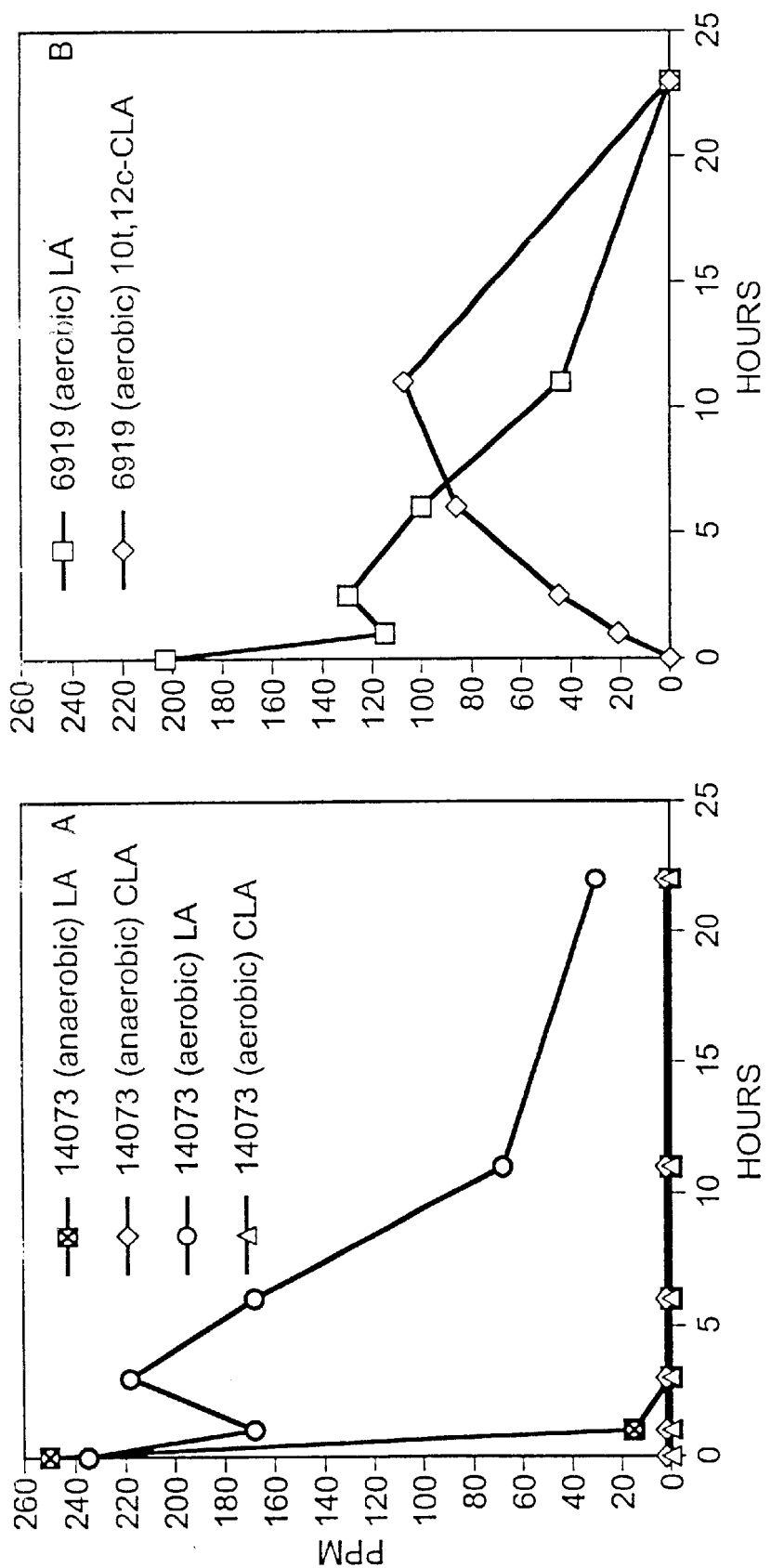
FIG. 3A is a line graph showing whole cell biotransformation of CLA from linoleic acid by *Propionibacterium jensenii* ATCC 14073.
FIG. 3B is a line graph showing whole cell biotransformation of CLA from linoleic acid by *P. acnes* ATCC 6919.
Figure 4:
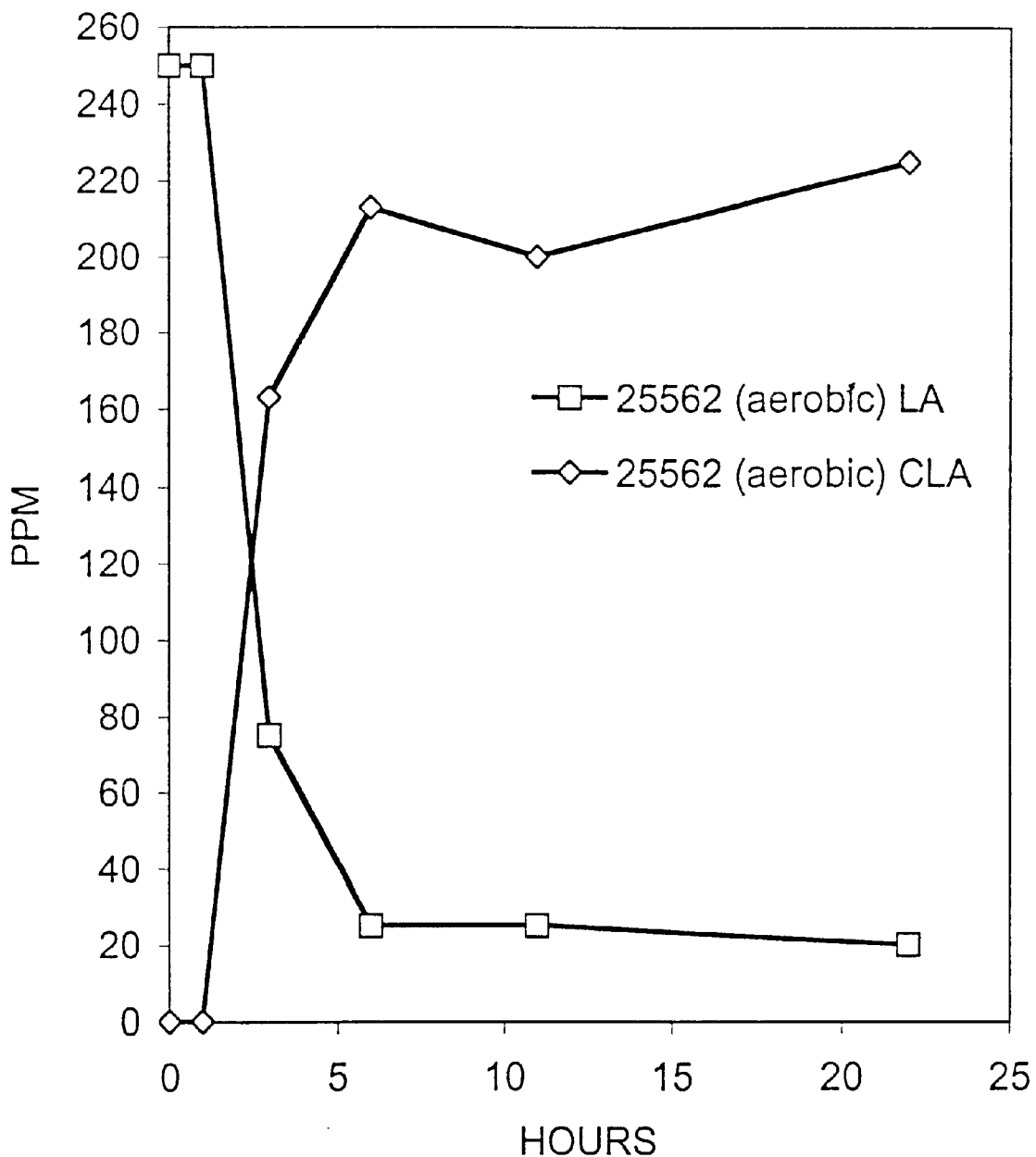
FIG. 4 is a line graph demonstrating whole cell biotransformation of CLA from linoleic acid by *P. acidipropionici* ATCC 25562.

FIGS. 3A, 3B and 4 show the results of whole cell biotransformation by *Propionibacterium jensenii* ATCC 14073 (FIG. 3A), *P. acnes* ATCC 6919 (FIG. 3B), and *P. acidipropionici* ATCC 25562 (FIG. 4), respectively. Interestingly, it has been found that while *P. acidipropionici* converts linoleic acid to (cis,trans)-9,11-CLA, *P. acnes* converts linoleic acid to (trans,cis)-10,12-CLA under aerobic conditions.

Figure 5:
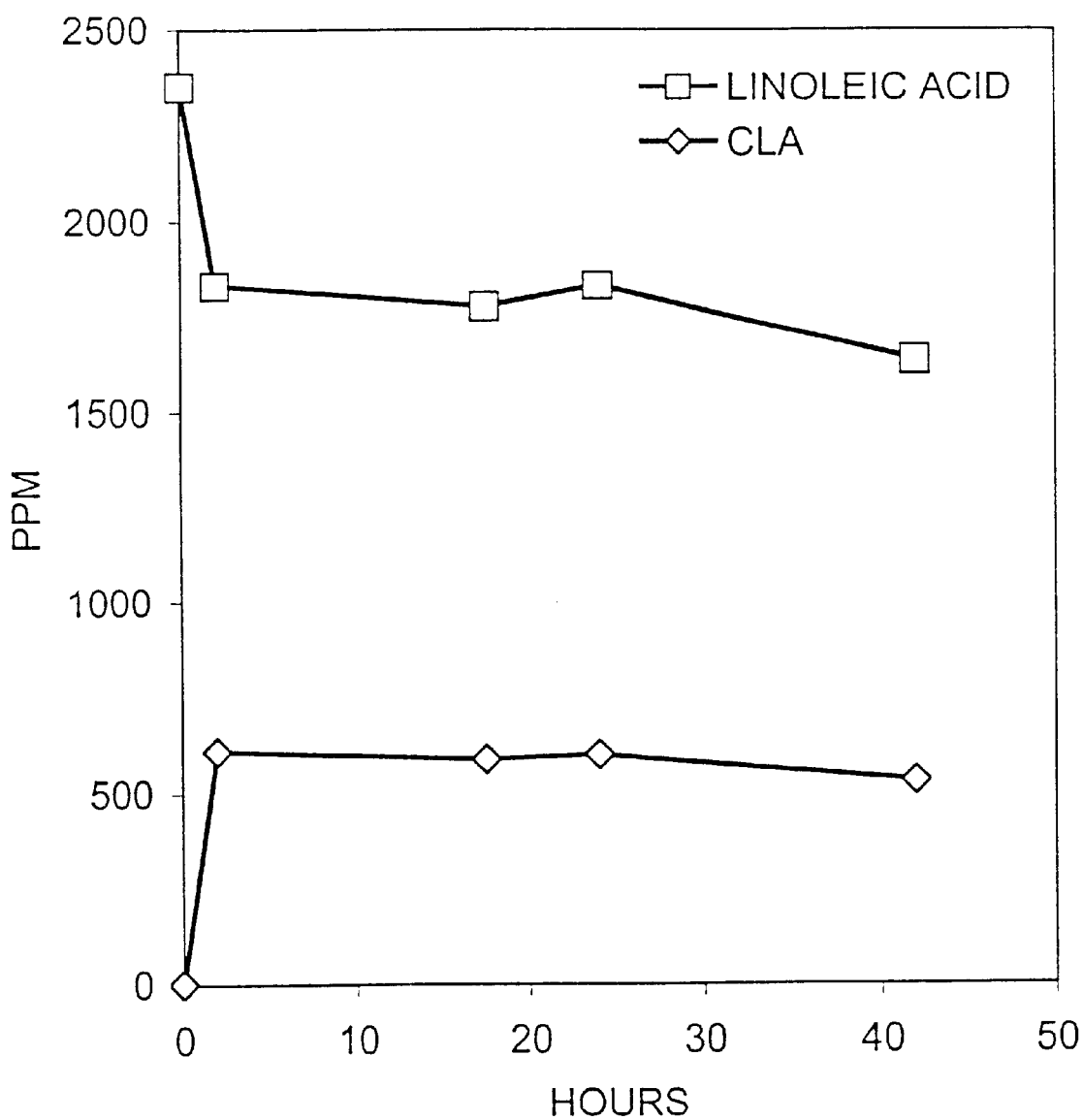
FIG. 5 is a line graph illustrating whole cell biotransformation of CLA from linoleic acid by *L. reuteri* PYR8.

FIG. 5 shows the results of whole cell biotransformation by *Lactobacillus reuteri*. Unlike other microorganisms, the concentration of(cis,trans)-9,11-CLA formed by *L. reuteri* from linoleic acid does not decrease significantly with time. Addition of various nonionic detergents, such as Tween-80 or Triton X-100, does not significantly increase (cis,trans)-9,11-CLA formation.

Example 2

This example describes a procedure for fatty acid analysis to determine the amount of conversion of linoleic acid to CLA.

Fatty acids were extracted from about 1 mL to about 2.5 mL aqueous samples with 0.5 mL of 5 M NaCl added. The samples were shaken with 5 mL of 2:1 mixture of chloroform/methanol in a glass screw cap tube with Teflon lined cap. The two phases were separated and about 1 to 2 mL of the chloroform layer was removed. The organic layer was dried with $Na_2SO_4$ and concentrated. The concentrated fatty acids were converted to methyl esters by a modification of the procedure of Chin et al., *J. Food Composition*, 1992, 5:185–192. About 6 mL of 4% HCl in methanol preheated to 60° C. was added to the glass tube containing the fatty acid sample. The tubes were sealed with a Teflon lined cap and incubated in a tube heater at 60° C. for 20 minutes, then cooled to room temperature, and 2 mL of water and 3 mL of hexane are added. After shaking, the organic layer was separated, dried with $Na_2SO_4$, and analyzed by gas chromatography. The order of four CLA peaks was (1) (cis, trans)-9,11-CLA, (2) (trans,cis)-10,12-CLA, (3) (cis,cis)-9-11-CLA and (cis,cis)-10,12-CLA, and (4) (trans,trans)-9,11-CLA and (trans,trans)-10,12-CLA.

Example 3

This Example describes the purification of linoleate isomerase from *L. reuteri*.

Detergent soluble protein fractions were prepared as follows. Frozen cells were thawed and suspended in breakage buffer on ice. The standard breakage buffer for *L. reuteri* comprised 0.1 M Bis-Tris (Calbiochem Ultrol grade) pH 5.8 (4° C.), 10 mM NaCl, 10% glycerol, 2 mM dithiothreitol. For other organisms, Tris buffer at pH 7.5 was used in place of Bis-Tris buffer. The cell suspensions were broken at 18,000 psi using a SLM Aminco French press. The extract was centrifuged at 12,000×g for 30 minutes. The supernatant was further fractionated by centrifugation at 100,000×g for 90 minutes to yield a soluble fraction and a membrane pellet. The membrane pellets were resuspended (approximately 5 mg/mL) and extracted with detergent buffer (0.1 M Bis-Tris pH 5.8, 0.25 M NaCl, 10% glycerol, 2 mM dithiothreitol, 0.3% octylthioglucopyranoside (OTGP, Calbiochem Ultrol grade)) at 4° C. for 4–18 hours with gentle stirring using a magnetic flea. After centrifugation at 100,000×g for 90 minutes, the supernatants (i.e., the detergent soluble protein fraction) were further purified by Method A, B or C, infra.

Method A

Figure 6:
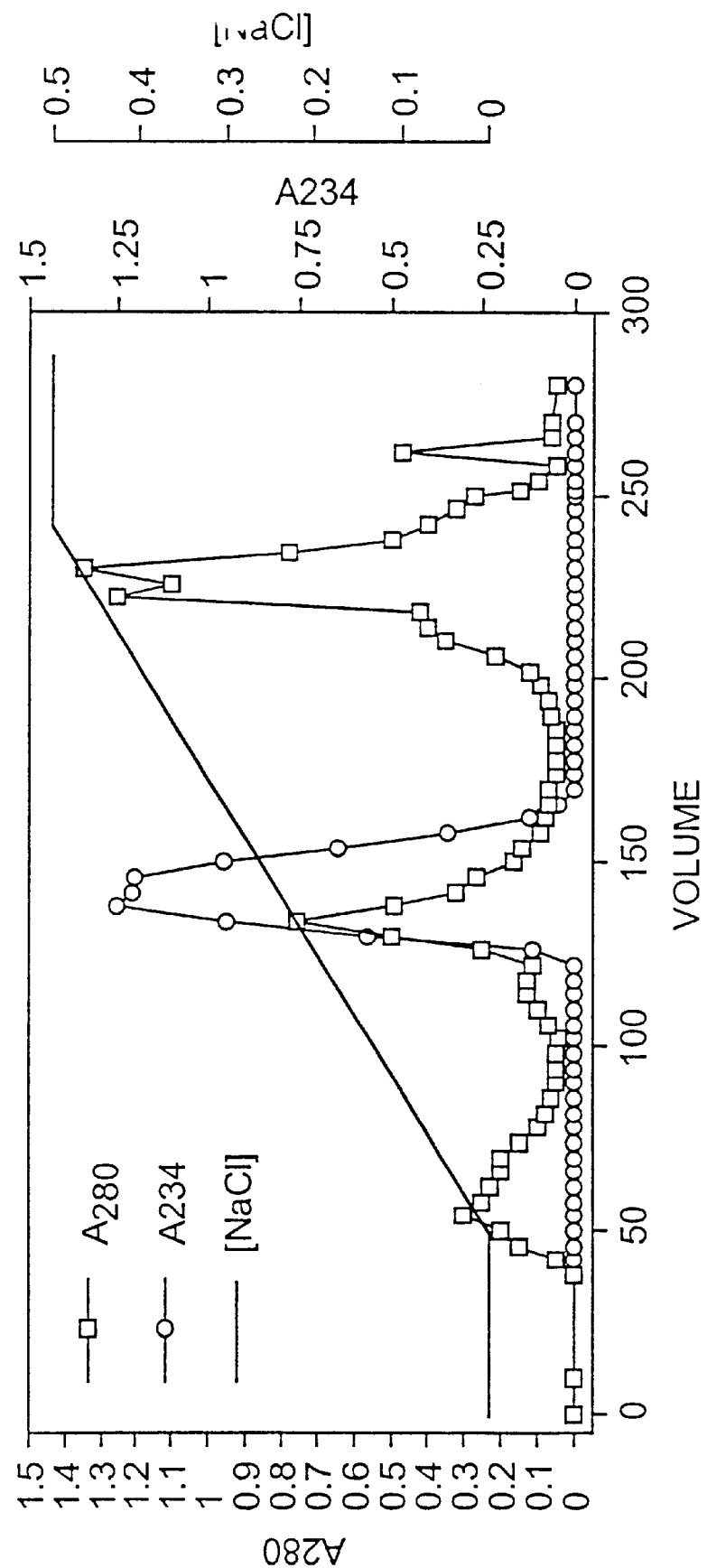
FIG. 6 is a line graph showing DEAE chromatography of detergent solubilized isomerase by *L. reuteri* PYR8.
Figure 7:
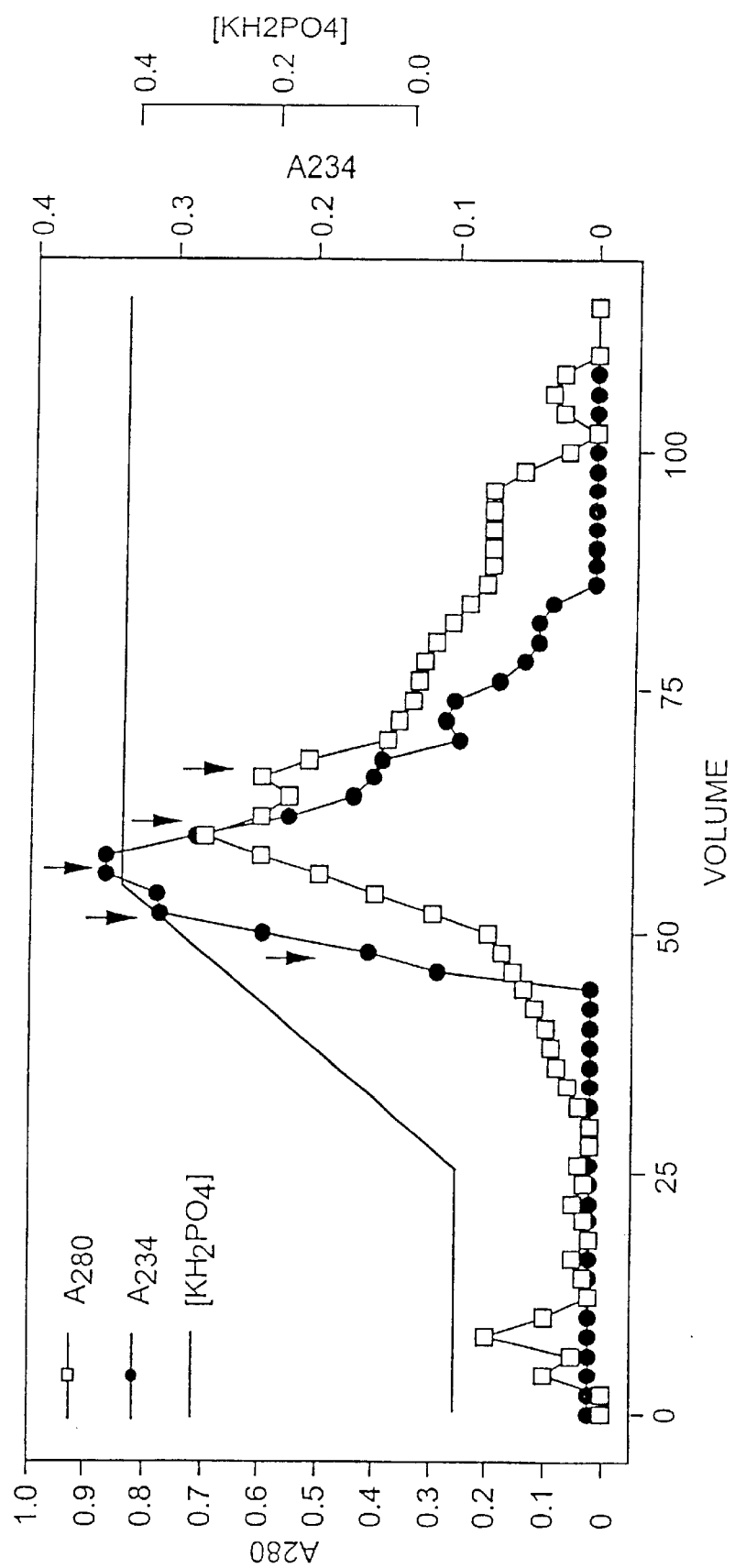
FIG. 7 is a line graph demonstrating hydroxyapatite chromatography of isomerase activity by *L. reuteri* PYR8.

Detergent soluble protein fractions were dialyzed overnight against low salt buffer (0.1 M Bis-Tris pH 5.8, 10 mM NaCl, 2 mM dithiothreitol, 10% glycerol, 0.3% OTGP), and applied to a 2.1×15 cm DEAE-5PW column (TosoHaas) previously equilibrated with low salt buffer. The column was washed (4 mL/min) with the same buffer containing 1 M NaCl (high salt buffer). The results of this step are shown in FIG. 6. Protein concentration was monitored continuously at 280 nm. About 4 mL fractions were collected and assayed for isomerase activity. Isomerase activity in the extracts was measured at 20 ppm linoleic acid. Fractions with significant isomerase activity were combined and concentrated using an Amicon ultrafiltration cell. Concentrated fractions were then applied to a 1.6×55 cm Superdex-200 (Pharmacia) gel filtration column. The column was developed with a buffer comprising 0.1 M Bis-Tris pH 5.8, 0.2 M NaCl, 10% glycerol, 2 mM dithiothreitol, 0.3% OTGP at 0.5 mL/min. Fractions of 2.0 mL were collected and assayed for isomerase activity. Active fractions were collected, concentrated and applied to a hydroxylapatite column (Bio-Rad 5 mL CHT-II cartridge) equilibrated with 0.1 M Bis-Tris pH 5.8, 10 mM $KH_2PO_4$, 10% glycerol, 2 mM dithiothreitol, 0.3% OTGP, 0.2 M NaCl. The column was washed (1 mL/min) with increasing phosphate using the same buffer containing 400 mM $KH_2PO_4$ with the results shown in FIG. 7. Active fractions were subjected to SDS PAGE using the Pharmacia Phast System on 12.5% acrylamide gels. The isomerase activity correlated with four bands on the gel, ranging from 45 to 70 kilodaltons (kD).

Method B

Detergent soluble protein fractions were applied to an affinity column. The affinity column was then sequentially washed (1 mL/min) with low salt buffer (75 mL), high salt buffer (50 mL) and linoleic acid buffer (100 mL) comprising 0.1 M Bis-Tris pH 5.8, 1 M NaCl, 0.3% OTGP, 2 mM dithiothreitol, 10% glycerol, 20% 1,2-propane diol.

The affinity column was prepared as follows. Pharmacia EAH Sepharose 4B was washed and suspended as a slurry in deionized water. A five-fold excess of ligand (linoleic acid or oleic acid) was added in an equal volume of 1,2-propane diol. Solid N-ethyl-N'-(3-dimethylaninopropyl) carbodiimide hydrochloride (EDC) was added to 0.1 M, pH adjusted to around 5.0, and the slurry was mixed by slow inversion overnight at room temperature. The gel was collected on a glass fritted funnel and extensively washed successively with 50% 1,2-propane diol, 0.1 M potassium acetate pH 4.0, 0.5 M NaCl, and 0.1 M tris pH 8.2. The resin was then washed, suspended in low salt buffer and used to prepare a 1.6×20 cm affinity column.

Method C

Figure 8:
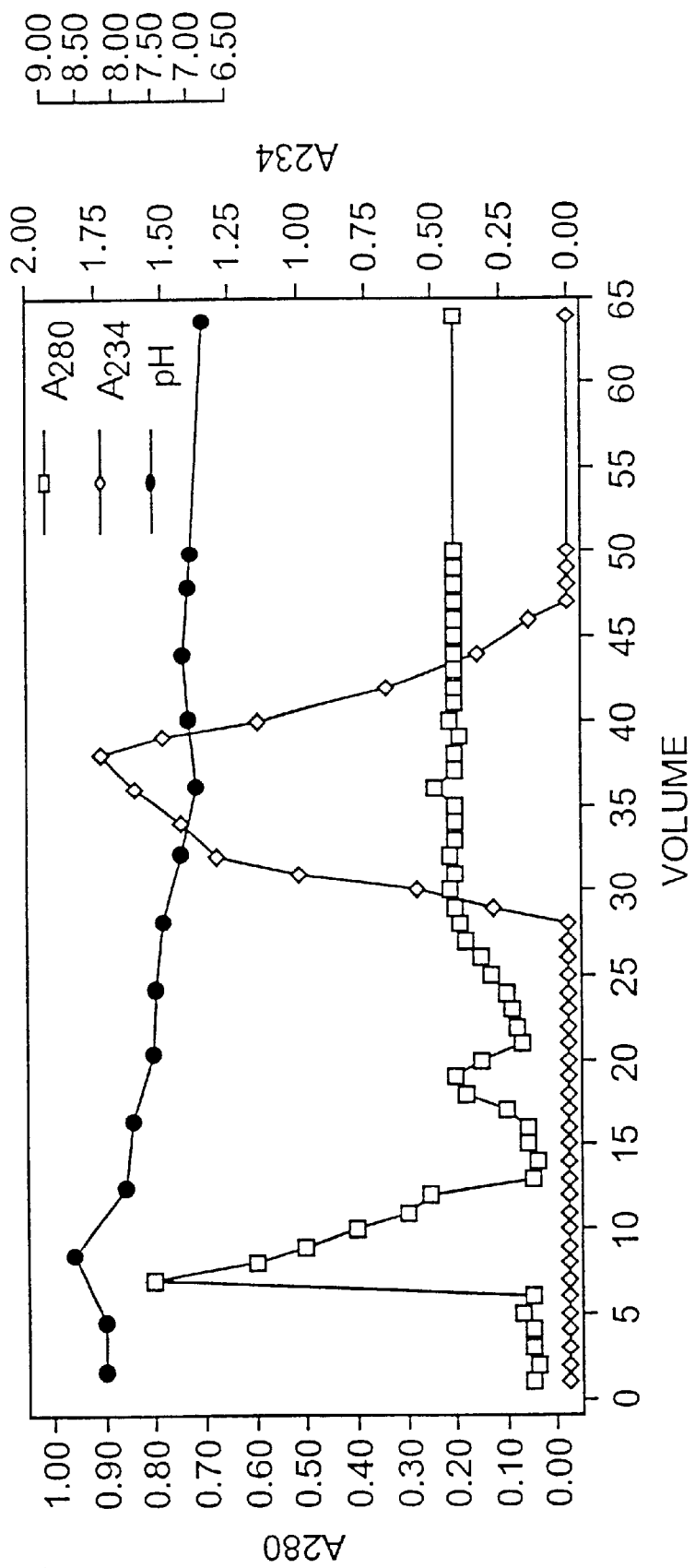
FIG. 8 is a line graph illustrating chromatofocusing of linoleic acid isomerase activity by *L. reuteri* PYR8.

Detergent soluble protein fractions were purified by a chromatography using DEAE-5PW column as described in Method A. The fractions containing isomerase activity were combined, concentrated, and desalted by ultrafiltration. The resulting sample was applied to a Mono PHR 5/20 column (Pharmacia, 0.5×20 cm) which has been previously equilibrated with a buffer comprising 25 mM triethanolamine, 1 mM dithiothreitol, 0.3% OTGP at pH 8.3. The column was then eluted with a buffer comprising 10% Polybuffer 96 (Pharmacia), 0.3% OTGP, 1 mM dithiothreitol at pH 6.5 and 1 mL fractions were collected. As shown in FIG. 8, some of the proteins were present in early fractions (fractions 5–15) and fractions containing isomerase activity were eluted typically between fractions 27 and 47. The fractions containing isomerase activity were combined and further purified by a chromatography using Superdex-200 gel filtration column as described in Method A. The fraction containing isomerase activity was eluted as a single band with a mass of about 160 kD. This same band was run on a denaturing SDS-PAGE gel and resulted in a single band of about 70 kD. This 70 kD band was excised and subjected to N-terminal amino acid sequencing using techniques known to those skilled in the art. A partial N-terminal amino acid sequence of about 35 amino acids was deduced and is represented herein as SEQ ID NO:1. A protein having the sequence of SEQ ID NO:1 is referred to herein as $PCLA_{35}$. It should be noted that since amino acid sequencing technology is not entirely error-free, SEQ ID NO:1 represents, at best, an apparent partial N-terminal amino acid sequence.

The purification of the *L. reuteri* 9,11-linoleate isomerase is summarized in Table 1A.

TABLE 1A

*Lactobacillus reuteri*

| Step | Protein | Total Activity | Specific Activity | Yield |
|---|---|---|---|---|
| Crude extract | 1125 | 2170 | 1.93 | 100 |
| Detergent soluble | 147 | 836 | 5.68 | 38.5 |
| DEAE | 21.5 | 529 | 24.6 | 24.4 |
| Chromatofocusing | 1.60 | 148 | 92.5 | 6.8 |
| Gel filtration | 0.21 | 86 | 407 | 3.9 |

Protein in milligrams. Enzyme activity units are nanomoles CLA formed per minute. Specific activity is units per milligram protein.

Example 4

This example describes the procedure for determining presence of isomerase activity of a fraction or a protein. This example also describes a method for conducting a kinetic assay.

Linoleic isomerase activity was assayed either via CLA quantification by gas chromatography as described in Example 2 or by spectrophotometry. The enzyme assay was carried out in 0.1 M Tris buffer pH 7.5, 10 mM NaCl, 1 mM dithiothreitol, with linoleic acid at 20 parts per million (ppm), unless otherwise noted.

About 50 to about 250 µL of enzyme sample was added to 1.5 mL of enzyme assay buffer for reaction. About 1 to about 2 mL of aqueous phase was separated from the enzyme reaction and was extracted with about 3 mL of hexane. In some experiments, and with chromatography fractions containing detergent, 0.5 mL of methanol and 0.5 mL of 5 M NaCl solution were first added to enhance phase separation. The organic layer was separated and the absorbence at 234 nm was measured using a HP 8452A diode array spectrophotometer. Depending on the level of activity, assay mixtures of chromatography fractions were incubated at room temperature from about 1 to about 24 hours before extraction with hexane.

Kinetic assays were performed directly in a 0.5 mL quartz cuvette at room temperature and were continuously monitored at 234 nm. Reactions were initiated by addition of linoleic acid from a concentrated stock prepared in 1,2-propane diol. Reaction buffer was the same as above except it contained 10% 1,2-propane diol.

Example 5

This Example shows the nucleic acid cloning and sequencing of a *Lactobacillus reuteri* linoleate isomerase nucleic acid molecule of the present invention.

It should be noted that since amino acid sequencing and nucleic acid sequencing technologies are not entirely error-free, the sequences presented in this example and those below, at best, represent apparent sequences of a linoleate isomerase of the present invention.

Two sets of fully degenerated oligonucleotide primers were synthesized, corresponding the sequences of the amino acid residues 1–7 and 23–29 of SEQ ID NO:1.

The first oligonucleotide primer, designated CLA01, had the following sequence:

5'-cgt gaa ttc ATG TA(T/C) TA(T/C) (T/A)(C/G)N AA(T/C) GGN AA-3'

(including an EcoRI site and 3 extra bases (shown as lower case letters) at the 5' end) (SEQ ID NO:2).

The second oligonucleotide primer, designated CLA02, had the following sequence:

5'-act gga tCC NAC (T/A/G)AT (A/G)AT NGC (A/G)TG (C/T)TT-3'

(including an Bam HI site and 3 extra bases (shown as lower case letters) at the 5' end) (SEQ ID NO:3).

PCR products were amplified from *L. reuteri* genomic DNA under optimized PCR conditions and gel purified. A single band of PCR product with the expected size (about 100 bp) was detected on 3% agarose gel. The PCR product was purified and cloned at the SrfI site into the vector pPCR-Script(Amp)SK(+) (Stratagen). Potential recombinant plasmids were analyzed by restriction digestion and sequenced.

Four clones which were sequenced contain inserts of about 87 nucleotides with the same sequence (SEQ ID NO:4) denoted herein as $nCLA_{87}$. The deduced amino acid sequence (SEQ ID NO:5) matches the N-terminal sequence of the linoleate isomerase identified in Example 3. A protein having the sequence of SEQ ID NO:5 is referred to herein as $PCLA_{28}$.

An approach of inverse PCR amplification was used to clone the DNA fragments flanking the N-terminus coding sequence, $nCLA_{87}$. Two oligonucleotide primers, designated CLA03 and CLA04 (SEQ ID NO:6 and SEQ ID NO:7, respectively) were designed for inverse PCR. CLA03 corresponded to nucleotides 25–41 of $nCLA_{87}$ (SEQ ID NO:4), and CLA04 nucleotides 46–67 of $nCLA_{87}$ (SEQ ID NO:4).

Genomic DNA from *Lactobacillus reuteri* PYR8 was digested with the restriction enzyme BamHI, treated with T4 DNA ligase to circularize the molecules, and the resulting molecules were used as a template in PCR reactions. A PCR product of 592 nucleotides was purified and cloned at the SrfI site into the vector pPCR-Script(Amp)SK(+) (Stratagen) and sequenced. A 596 bp edited version of this molecule is denoted herein as $nCLA_{596}$ (SEQ ID NO:8). $nCLA_{596}$ contains both the 5' upstream and 3' downstream sequences of a linoleate isomerase gene. The site of BamHI in the sequence would indicate the junction point. However, no BamHI site was detected in the sequence. Therefore, the sequence in $nCLA_{596}$ was tentatively edited with reference to its ORF and the sequence $nCLA_{87}$. This tentatively edited sequence contains an ORF of 475 nucleotides. The deduced amino acid sequence of this ORF is denoted $PCLA_{158}$ (SEQ ID NO:9). A protein having the sequence of SEQ ID NO:9 is referred to herein as $PCLA_{158}$.

The sequences immediately flanking CLA03 and CLA04 are identical to the sequence in $nCLA_{87}$, confirming the identity of the cloned PCR product.

$nCLA_{596}$ was labeled with $^{32}P$ and hybridized to a Southern blot of *Lactobacillus reuteri* PYR8 genomic DNA digested with different restriction enzymes. The partial linoleate isomerase sequence of $nCLA_{596}$ contains one AgeI site and one Eco 58 I site. As expected, two hybridization bands were observed on the Southern blot when the genomic DNA were digested with these two enzymes individually. Only one hybridization band was detected in the digests prepared with enzymes which do not cut the partial isomerase sequence such as BamHI, HindIII, PvuI, SalI, and XhoI while a more diffused hybridization signal in the high molecular mass region (>10 kb) was observed with EcoRI, SacI and SphI digests. These data indicate that the linoleate isomerase gene is present as a single copy in the genome of *Lactobacillus reuteri* PYR8.

In order to clone the entire linoleate isomerase gene, an approach of inverse PCR was followed. As set forth above, a restriction enzyme AgeI site is present in the middle of SEQ ID NO:8 ($nCLA_{596}$) at nucleotide position 295. Southern hybridization showed two bands in AgeI digests of *L. reuteri* PYR8 genomic DNA: about 1.1 and about 2.3 kb, respectively. Genomic DNA from *L. reuteri* PYR8 was digested with AgeI, religated with T4 DNA ligase and used as template in a PCR reaction. Under optimized conditions, a PCR product of about 1.1 kb was generated using the primer set of CLA03 and CLA04 as well as a product of 2.3 kb using the primer set CLA05 and CLA06 (SEQ ID NO:12 and SEQ ID NO:13, respectively). CLA05 corresponds to nucleotides 326–342 of $nCLA_{596}$ and CLA06 corresponds to nucleotides 396–414 of $nCLA_{596}$. These results are consistent with the Southern blot data.

Both of the PCR products were cloned into pPCR-Script (Amp)SK(+) (Stratagen). The clone containing the 1.1 kb fragment is denoted $nCLA_{1.1}$, and the clone with the 2.3 kb fragment is denoted $nCLA_{2.3}$. Initially, about 700 nucleotides of sequencing data upstream from CLA03 in $nCLA_{1.1}$ and about 700 nucleotides of sequencing data down-stream of CLA06 in $nCLA_{2.3}$ were obtained. The sequences of $nCLA_{596}$, partial $nCLA_{1.1}$, and partial $nCLA_{2.3}$ were edited to generate a composite sequence denoted herein as $nCLA_{1709}$ (SEQ ID NO:10). The deduced amino acid sequence of SEQ ID NO:10 is represented herein as SEQ ID NO:11. A protein having the sequence of SEQ ID NO:11 is referred to herein as $PCLA_{324}$.

$nCLA_{1709}$ contains part of the isomerase coding sequence as well as 5' upstream sequence. The 737 nucleotide sequence upstream from the ATG codon corresponding to the first amino acid of the purified polypeptide was compared against known sequences by using Blastx (open reading frames) and Blastn (nucleotides) searches of the BLAST network. No significant homology has been found with any entry, with the score being below 176 for Blastn and 153 for Blastx. The coding sequence downstream from the ATG start codon showed a homology with 67 kD myosin-crossreactive streptococcal antigen from *Streptococcus pyogenes* (U09352): 69% identity at the amino acid level and 66% at the nucleotide level. The longest stretch of identical nucleotides is of 23 nucleotides. The isomerase coding sequence shows also a homology to an ORF from *Staphylococcus aureus* (L19300): 62% identity at both the amino acid level and the nucleotide level.

Subsequent to the initial sequencing of $nCLA_{1.1}$ and $nCLA_{2.3}$, both clones were completely sequenced (SEQ ID NO:14 and SEQ ID NO:15, respectively) and these sequences, along with the sequence of $nCLA_{596}$ (SEQ ID NO:8), were assembled to generate a nucleic acid sequence of 3551 nucleotides, which is denoted $nCLA_{3551}$, and which is represented herein by SEQ ID NO:16. SEQ ID NO:14 spans from nucleotide 1 to 1173 of SEQ ID NO:16, and SEQ ID NO:15 spans from nucleotide 1174 to 3551 of SEQ ID NO:16.

Figure 9:
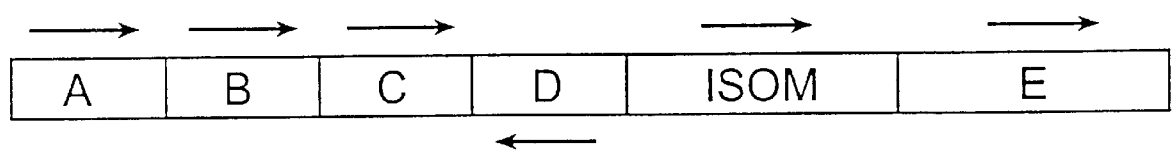
FIG. 9 is a schematic illustration of the linoleate isomerase genes and flanking open reading frames in *L. reuteri* PYR8.

$nCLA_{3551}$ contains three open reading frames (FIG. 9; ISOM, D and E), with the first ORF (FIG. 9, ISOM) being an about 1.8 kb nucleic acid molecule spanning from nucleotide positions 1000 to 2775 of SEQ ID NO:16, and represented herein as SEQ ID NO:17. SEQ ID NO:17 encodes a linoleate isomerase of the present invention. A nucleic acid molecule having a nucleic acid sequence represented by SEQ ID NO:17 is referred to herein as $nCLA_{1776}$, and encodes an approximately 67 kD (deduced) protein of 591 amino acid residues having an amino acid sequence represented by SEQ ID NO:18. A protein having amino acid sequence SEQ ID NO:18 is referred to herein as $PCLA_{591}$. The deduced size of $PCLA_{59}$ is consistent with the size of the purified isomerase protein determined on an SDS gel. Seven nucleotides upstream from the initiation codon of this first ORF (SEQ ID NO:17) is a sequence similar to the consensus ribosome-binding-site which has been reported in Lactobacillus. Also, upstream from this first ORF are sequences similar to −10 and −35 promoter sequences. These sequence characteristics are consistent with a conclusion that the start codon at position 1000 of $nCLA_{3551}$ is the translation start codon. Alternatively, the sequence of $nCLA_{3551}$ has, upstream from the first ORF, at 36 nucleotides upstream from the start codon at position 1000, in frame, two ATG start codons in tandem. If one of these codons is a translation start codon, then a leader peptide of about 12 amino acids may be produced which is subsequently cleaved to form a mature isomerase.

The complete coding sequence for the linoleate isomerase gene determined as described above (SEQ ID NO:17) was compared against known sequences by using Blastx (open reading frames) and Blastn (nucleotides) searches of the BLAST network. The linoleate isomerase encoded by SEQ ID NO:17 showed 67% identity at the nucleic acid level and 70% identity at the amino acid level with the previously-mentioned *Staphylococcus pyogenes* (U09352) 67 kD myosin-crossreactive streptococcal antigen. The *Staphylococcus pyogenes* (U09352) protein has 590 amino acid residues. The homology between the linoleate isomerase encoded by SEQ ID NO:17 and the above-described *Streptococcus aureus* (L19300) gene is slightly lower: about 60% at the nucleic acid level and about 62% at the amino acid level. The BLAST 2.0 search parameters were the standard default values as described above. No defined functions have been previously described for either the *Streptococcus pyogenes* (U09352) or the *Staphylococcus aureus* (L19300) sequences.

The second open reading frame of $nCLA_{3551}$ (FIG. 9, E) is from nucleotide positions 2896 to 3551 of SEQ ID NO:16, and is represented by SEQ ID NO:19. A nucleic acid molecule having SEQ ID NO:19 is referred to herein as $nUNK1_{656}$ which encodes a protein of about 218 amino acid residues having an amino acid sequence of SEQ ID NO:20. A protein having SEQ ID NO:20 is referred to herein as $PUNK1_{218}$. The function of $PUNK1_{218}$ is unknown. The sequence of $nUNK1_{656}$ was compared with known sequences for homology and no significant homology was identified. This second reading frame is located 122 nucleotides downstream from the first open reading frame (SEQ ID NO:17) encoding the linoleate isomerase.

The third open reading frame of $nCLA_{3551}$ (FIG. 9, D) is located on the strand of $nCLA_{3551}$ that is complementary to SEQ ID NO:16, and is represented herein as SEQ ID NO:21. SEQ ID NO:21 is positioned on the strand that is complementary to nucleotide positions 1 through 726 of SEQ ID NO:16, with start codon 275 nucleotides up-stream from position 1000 of the putative start codon of SEQ ID NO:17. A nucleic acid molecule having SEQ ID NO:21 is referred to herein as $nCSN_{726}$ which encodes at least a portion of a protein having an amino acid sequence of SEQ ID NO:22. The C-terminal portion of the protein comprising SEQ ID NO:22 was not present in the isolated clones. A 242 amino acid residue protein having SEQ ID NO:22 is referred to herein as $PCSN_{242}$. A database search (BLAST 2.0) showed that the nucleic acid sequence of this third ORF (SEQ ID NO:21) is about 66% identical to a competence-specific nuclease (DNA entry nuclease) from *Streptococcus pneumoniae* (Q03158), with the amino acid sequence SEQ ID NO:22 being about 51–72% identical to the amino acid sequence for this competence-specific nuclease. Therefore, it is believed to be possible that the third ORF identified on the complementary strand of SEQ ID NO:16 encodes a competence-specific nuclease.

Example 6

The following example demonstrates the cloning of sequences flanking the isomerase gene in the *L. reuteri* PYR8 genome.

A third round of inverse PCR was carried out on the circularized genomic DNA from *Lactobacillus reuteri* PYR8 as described in Example 5. This third round was designed to clone more sequences flanking the isomerase gene. Two oligonucleotide primers, designated CLAo9 and CLAo10 (SEQ ID NO:23 and SEQ ID NO:24, respectively) were designed for this round of PCR. CLAo9 (SEQ ID NO:23) was designed close to the 5' end of the sequence of $nCLA_{3551}$ (nucleotides 63–40 of SEQ ID NO:16). CLAo10 was designed to correspond to the 3' end of the $nCLA_{3551}$ sequence (nucleotides 3505–3522 of SEQ ID NO:16).

More particularly, *L. reuteri* PYR8 genomic DNA was digested with SalI, religated and amplified with oligonucleotide primers CLAo9 and CLAo10. A PCR product of about 3.5–4.0 kb was cloned into pPCR-Script Amp SK(+) and sequenced. This nucleic acid molecule was denoted $nSAL_{3684}$ and is represented herein by SEQ ID NO:25.

The identity of $nSAL_{3684}$ was confirmed by the sequences flanking the primers CLAo9 and CLAo10. The sequence $nSAL_{3684}$ contains a unique SalI site, which indicates the junction point of the inverse PCR product. Therefore, the sequence $nSAL_{3648}$ was spliced at the SalI site and added to the 3' and 5' ends of the sequence of $nCLA_{3551}$ (SEQ ID NO:16). This approximately 7 kb nucleic acid molecule is denoted $nCLA_{7113}$ and is represented herein by SEQ ID NO:26.

The approximately 7 kb *L. reuteri* PYR8 genomic DNA (SEQ ID NO:26) contains 6 open reading frames, schematically illustrated in FIG. 9. There are four ORF's (A, B, C and D) located 5' upstream of the isomerase gene (ISOM) and one ORF located 3' downstream of the isomerase gene.

The first open reading frame of $nCLA_{7113}$ (FIG. 9, A) spans from nucleotide positions 1 to 941 of SEQ ID NO:26, and is represented by SEQ ID NO:27. A nucleic acid molecule having SEQ ID NO:27 is referred to herein as $nBSP_{941}$ which encodes a protein of about 312 amino acid residues having an amino acid sequence of SEQ ID NO:28. A protein having SEQ ID NO:28 is referred to herein as $PBSP_{312}$. A database search (BLAST 2.0) showed that the amino acid sequence (SEQ ID NO:28) of the protein encoded by this first ORF A (SEQ ID NO:27) is about 56% identical and 74% similar (using standard BLAST 2.0 parameters) to a permease from *Bacillus subtilis* (p54425). Therefore, it is believed to be possible that the first ORF A of SEQ ID NO:26 encodes a permease.

The second open reading frame of $nCLA_{7113}$ (FIG. 9, B) spans from nucleotide positions 1146 to 1745 of SEQ ID NO:26, and is represented by SEQ ID NO:29. A nucleic acid molecule having SEQ ID NO:29 is referred to herein as $nUNK2_{600}$ which encodes a protein of about 199 amino acid residues having an amino acid sequence of SEQ ID NO:30. A protein having SEQ ID NO:30 is referred to herein as $PUNK2_{199}$. The function of $PUNK2_{199}$ is unknown. The sequence of $nUNK2_{600}$ was compared with known sequences for homology and no significant homology was identified. The highest Blastp score using standard defaults was 51.

The third open reading frame of $nCLA_{7113}$ (FIG. 9, C) spans from nucleotide positions 1742 to 2590 of SEQ ID NO:26, and is represented by SEQ ID NO:31. A nucleic acid molecule having SEQ ID NO:31 is referred to herein as $nUNK3_{849}$ which encodes a protein of about 282 amino acid residues having an amino acid sequence of SEQ ID NO:32. A protein having SEQ ID NO:32 is referred to herein as $PUNK3_{282}$. The function of $PUNK3_{282}$ is unknown. The sequence of $nUNK3_{849}$ was compared with known sequences for homology and no significant homology was identified. The highest Blastp score using standard defaults was 68.

The fourth open reading frame of $nCLA_{7113}$ (FIG. 9, D) spans from nucleotide positions 2662 to 3405 of SEQ ID NO:26, and is represented by SEQ ID NO:33. A nucleic acid molecule having SEQ ID NO:33 is referred to herein as $nCSN_{744}$ which encodes a protein having an amino acid sequence of SEQ ID NO:34. A 247 amino acid residue protein having SEQ ID NO:34 is referred to herein as $PCSN_{247}$. $PCSN_{242}$ (SEQ ID NO:22), described above in Example 5 (the third ORF identified in $nCLA_{3551}$) is included in $PCSN_{247}$, spanning from amino acid position 1 to 242 of SEQ ID NO:34. Similarly, the nucleic acid sequence of $nCSN_{726}$ (SEQ ID NO:21) spans from nucleotides 1 to 726 of SEQ ID NO:33. A database search (BLAST 2.0) showed that the amino acid sequence SEQ ID NO:34 is about 57% identical and about 71% similar (using standard parameters) to the amino acid sequence for the above-mentioned *Streptococcus pneumoniae* competence-specific nuclease.

The fifth open reading frame of nCLA$_{7113}$ (FIG. 9, ISOM) is a nucleic acid molecule (nCLA$_{1776}$, SEQ ID NO:17) encoding the linoleate isomerase (PCLA$_{591}$, SEQ ID NO:18) of the present invention, as described above in Example 5.

The sixth open reading frame of nCLA$_{7113}$ (FIG. 9, E) spans from nucleotide positions 5574–7113 of SEQ ID NO:26, and is represented by SEQ ID NO:35. A nucleic acid molecule having SEQ ID NO:35 is referred to herein as nUNK1$_{1540}$ which encodes a protein having an amino acid sequence of SEQ ID NO:36. A 513 amino acid residue protein having SEQ ID NO:36 is referred to herein as PUNK1$_{513}$. PUNK1$_{218}$ (SEQ ID NO:20), described above in Example 5 (the second ORF identified in nCLA$_{3551}$) is included in PUNK1$_{513}$, spanning from amino acid position 1 to 218 of SEQ ID NO:36. Similarly, the nucleic acid sequence of nUNK1$_{656}$ (SEQ ID NO:19) spans from nucleotides 1 to 656 of SEQ ID NO:35. The sequence of nUNK1$_{1540}$ was compared with known sequences for homology and no significant homology was identified. The highest Blastp score for PUNK1$_{513}$ using standard defaults was 51. The C-terminal sequence of PUNK1$_{513}$ is incomplete.

The isomerase gene is very likely transcribed as a monocistron. This conclusion is based on two observations. First, the ORF that is located immediately upstream from the isomerase gene (FIG. 9, D) is coded on the opposite strand. Secondly, a reverse-repeat DNA sequence was observed in the region downstream from the stop codon of the isomerase gene (FIG. 10). This 28 nucleotide structure (SEQ ID NO:37), starting at the base 6 after the stop codon, has only one unmatched base. This structure could function as a rho-dependent stem-loop transcription terminator of the isomerase gene. Therefore, it is concluded that the isomerase gene is most likely transcribed as a monocistron and that the open reading frame downstream from the isomerase gene seems to be in a separate transcription unit.

Linoleate isomerase from *L. reuteri* is a membrane protein since its activity is detected mostly in membrane fraction of cellular protein extracts and detergent is needed to solubilize the enzyme. Consistent with this data, the hydrophilicity plot of the isomerase ORF shows a major hydrophobic domain close to the N-terminal sequence, from amino acid residue 27 through 42. This hydrophobic domain may function as a transmembrane segment as well as part of an uncleaved signal peptide, which plays an important role in directing the protein into the membrane. Also, it is interesting to notice that the peptide contains 4 cysteine residues at amino acid positions 89, 124, 336 and 430, suggesting the native protein may have one or two internal disulfide bonds.

Example 7

The following example demonstrates the expression of *L. reuteri* linoleate isomerase in *E. coli*.

Two oligonucleotides were synthesized to amplify the isomerase gene (Promoter-ORF-Terminator) from *L. reuteri* PYR8 genomic DNA (described in Example 5). Nucleotide CLAo7 (SEQ ID NO:38), the forward primer, corresponds to the positions 3296 through 3314 of the sequence nCLA$_{7113}$ (SEQ ID NO:26) and it includes a SalI site and 3 extra bases at the 5' end (lower case):

5'-gcagtcgacGGAGTTAAGACTGAATTAG-3'

The nucleotide CLAo8B (SEQ ID NO:39), the reverse primer, corresponds to the positions 5577 through 5593 of the sequence nCLA$_{7113}$ (SEQ ID NO:26) and it includes a SalI site and 3 extra bases at the 5' end (lower case):

5'-ctagtcgacGCAGTTTCTGTCATGAC-3'

The PCR product of 2.3 kb was ligated with blunt ends into pPCR-Script(Amp)SK at the SrfI site. Ligated DNA was transformed into *E. coli* cells. Clones with inserts in both orientations were selected and tested for expression of the isomerase gene. In the construct #1 (FIG. 11), the isomerase gene was placed downstream from the lac promoter. In the construct #2 (FIG. 11), the isomerase gene was placed reverse to the lac promoter.

To detect isomerase activity, *E. coli* cells transformed with the different isomerase constructs were grown to mid log phase, induced with or without IPTG for 1 to 3 hours and harvested for testing in an isomerase activity assay. Linoleic acid was incubated with *E. coli* cells (biotransformation) or with a crude cell lysate. Fatty acids were extracted by hexane and analyzed on gas chromatography. With both plasmid construct #1 and plasmid construct #2 in *E. coli*, no isomerase activity was detected by biotransformation or by crude cell lysate. SDS-gel analysis, however, showed that IPTG induced expression of a 67 kD protein in cells transformed with construct #1. The size of the expressed isomerase protein is that predicted from the isomerase gene sequence analysis and is in good agreement with the size of the native isomerase purified from *L. reuteri* PYR8. The lack of catalytic activity may be a result of incorrect folding and/or membrane insertion of the isomerase in the heterologous system.

pET vectors were used to develop isomerase gene constructs where the isomerase coding sequence is fused to a His tag at the C-terminus. Using a commercial antibody specific to His tag, it would be possible to monitor the levels of isomerase-His tag fusion protein synthesized in *E. coli*, Lactobacillus, Bacillus, or any other appropriate expression host by Western blot analysis, even if the enzyme was inactive. Since the constructs would be made with *E. coli* plasmids, *E. coli* systems could be used to test the method. The isomerase-His tag protein was, expressed in *E. coli* to produce large amounts of isomerase protein. This protein can be further purified under denaturing conditions with nickel columns and used in the production of antibodies specific to the *L. reuteri* PYR8 linoleate isomerase (See Example 10). Isomerase expression in the native host and recombinant systems can be monitored with these antibodies. Additionally, the antibodies can be used in immunoscreening to identify new microorganism strains that produce linoleate isomerases, and eventually to aid in the cloning of additional linoleate isomerase genes.

In additional experiments, *E. coli* transformed with and expressing the PYR8 isomerase gene with a His tag (construct #3, FIG. 11) were grown under standard conditions to study expression of the isomerase protein. On Coomassie Blue stained SDS gel, a band between 60 and 70 kD was predominant in the cell lysate. This band was present at a high level even before induction. The addition of IPTG, however, induced a very strong overproduction of the protein (data not shown). The highest expression level was achieved two hours after IPTG induction. This protein band was strongly recognized by anti-His tag antibody on Western blot, confirming that this protein corresponds to the correct linoleate isomerase fusion protein (data not shown).

Figure 13:
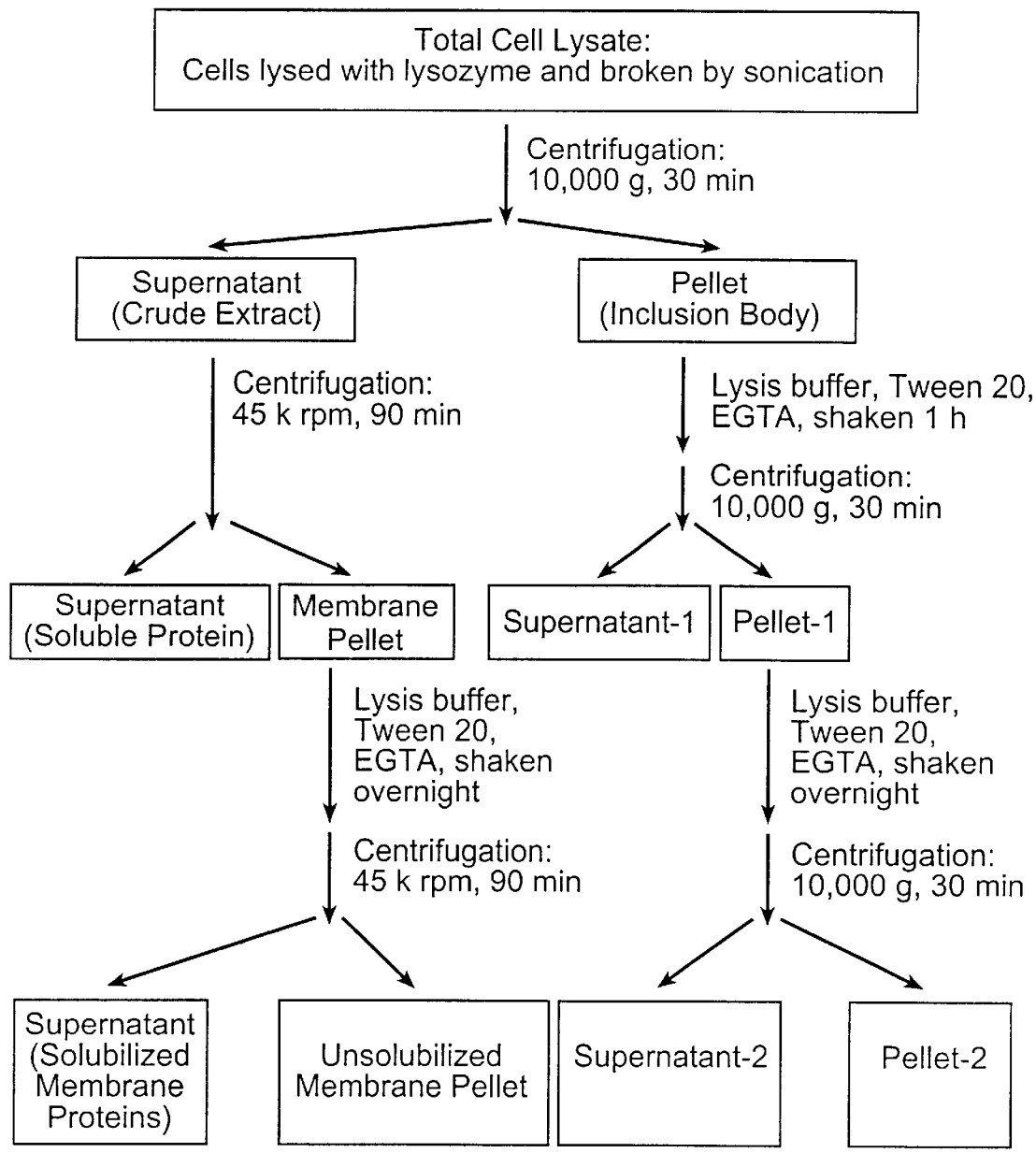
FIG. 13 is a flow diagram of the experimental protocol for the preparation of different protein fractions of *E. coli* which have expressed recombinant linoleate isomerase.

The cells expressing the linoleate isomerase gene were harvested four hours after IPTG induction and analyzed to determine the location of the isomerase-His fusion protein. FIG. 13 outlines the experimental protocol for the preparation of different protein fractions. Briefly, *E. coli* cells expressing the isomerase-His tag fusion protein were lysed in a non-denaturing buffer with lysozyme and broken by sonication. The total cell lysate was centrifuged at low speed to pellet the inclusion bodies. The crude inclusion bodies were washed twice with 0.25% Tween 20 and 0.1 mM EGTA. The proteins retained in the washed pellets were highly insoluble aggregates of improperly folded peptides (inclusion bodies). The supernatant generated by low speed centrifugation of the total cell lysate was subjected to an ultra centrifugation step to separate membrane (pellet) from soluble proteins. Detergent was used to solubilize membrane proteins, which were then separated from other insoluble membrane components by ultra-centrifugation. The total cell lysate and different protein fractions were analyzed on SDS gel and by Western blot. In the total cell lysate of $E.$ $coli$ cells expressing the isomerase gene, only the protein band between 60 and 70 kD can be seen after Coomassie staining. This protein band was recovered in the inclusion body fraction and was confirmed to be the isomerase-His tag fusion protein by Western blot. Under the conditions used in these experiments, the antibody did not cross-react with other proteins in the cell lysate of $E.$ $coli$ that did not contain the isomerase gene construct. The amount of fusion protein in the soluble and membrane fractions was under the detectable limit. The fusion protein in the inclusion body fraction was extensively washed with EGTA and Tween 20 to remove other contaminant proteins. The purified peptide will be used to produce antibodies specific for the PYR8 linoleate isomerase (See Example 10).

Additional strategies for expressing a linoleate isomerase of the present invention include, but are not limited to: (1) deleting the single hydrophobic domain of the sequence to try to convert the isomerase into a functional soluble protein for use in determination of fusion protein synthesis, solubility and isomerase activity; (2) developing constructs for production of the isomerase in $L.$ $reuteri$ using both the native promoter and non-native inducible or constitutive promoters, including an isomerase-His tag fusion gene under the control of the isomerase native promoter; (3) cloning the promoter from the erythromycin resistance gene for control of isomerase gene expression in $L.$ $reuteri$ ATCC 23272; and (4) knocking out the wild-type linoleate isomerase gene in the native $L.$ $reuteri$ PYR8 strain and recovering the activity by transforming the strain with the cloned isomerase gene. In this fourth strategy, a plasmid has been generated to knock out the wild-type gene which contains a non-functional isomerase gene interrupted by an erythromycin resistance gene as a selectable marker.

Example 8

The following example describes expression of a linoleate isomerase of the present invention in Bacillus.

To express the $L.$ $reuteri$ PYR8 linoleate isomerase gene described in Example 5 in $Bacillus$ $subtilis$ and $Bacillus$ $licheniformis$, two oligonucleotides were synthesized to amplify isomerase coding sequence from $L.$ $reuteri$ genomic DNA. The forward primer (SEQ ID NO:40) corresponds to nucleotide positions 3678 through 3706 of nCLA$_{7113}$ (SEQ ID NO:26), with a NdeI site containing the ATG start codon at the 5' end (lower case):

5'catATGTATTATTCAAACGGGAATTATGAAGC-3'.

The reverse primer(SEQ ID NO:41) corresponds to nucleotide position 5579 through 5602 of the sequence nCLA$_{7113}$ (SEQ ID NO:26) with a BclI site at the 5' end (lower case):

5'tgatcaTCTATACCAGCAGTTTCTGTCATG-3'.

The PCR product of 1.9 kb was cloned as blunt ends at the SrfI site into pPCR-Script Amp SK and transformed into cells of $E.$ $coli$ strain NovaBlue. Since dam methylation in this host prevents BclI digestion, the recombinant plasmid was transformed into cells of $E.$ $coli$ strain GM2163, which is a dam minus strain. Recombinant plasmid DNA was digested with the restriction enzymes NdeI and BclI and ligated to the vector pBHAI which had been digested with NdeI and BamHI. Recombinant plasmid DNA was digested with SacI to remove the $E.$ $coli$ portion of the vector, recircularized, and transformed into $B.$ $subtilis$ 23856.

Figure 12:
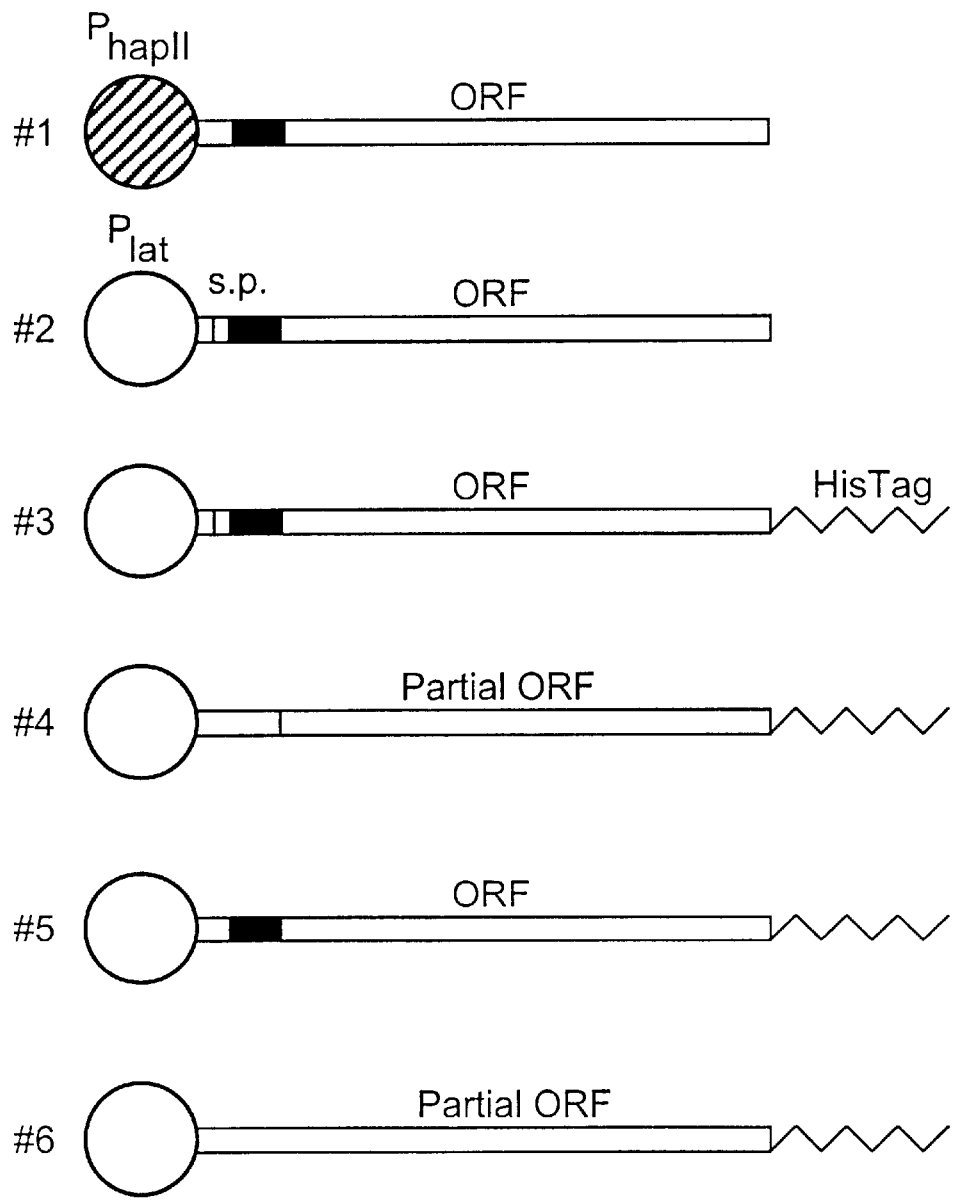
FIG. 12 is an illustration of several constructs for linoleate isomerase expression in Bacillus.

In this construct, the isomerase coding sequence was placed under the control of the HpaII promoter (FIG. 12, #1 construct) and its native ribosome-binding site was replaced by the counterpart in the vector. Clones of transformants were grown to mid-log phase and then harvested for biotransformation of linoleic acid. No CLA was detected by GC analysis in the hexane extract of fatty acids. However, after incubation for 1 hour, 2 hours, and 3 hours, the level of linoleic acid decreased drastically, being about 40% after a 3 hour incubation. The same results were observed with all sixteen $B.$ $subtilis$ clones tested. The use of linoleic acid was dependent on the presence of the cloned isomerase gene since the level of linoleic acid was constant during the incubation of $B.$ $subtilis$ wild type cell without the plasmid and the cells transformed with the empty vector. The same results were observed when the isomerase construct was transformed into $B.$ $licheniformis$ T399.

Experiments were carried out to investigate why CLA did not accumulate while linoleic acid was used up. One possibility was that linoleic acid might be converted to CLA, which was rapidly metabolized or degraded. That implied that $B.$ $subtilis$ and $B.$ $licheniformis$ cells have the ability to metabolize CLA. To test this hypothesis, Bacillus wild type cells and cell transformed with the isomerase gene construct were incubated with single 9,11 isomer produced in a biotransformation using $L.$ $reuteri$ PYR8 cells and with chemically synthesized CLA, which contains 9,11 and other CLA isomers. Bacillus cells could not metabolize the CLA. The same conclusion was also drawn with crude cell extracts.

Furthermore, a peak of unknown product (retention time= 20 minutes) on GC spectra of the biotransformation with cells containing the isomerase gene was observed. Also, the conversion of linoleic acid and formation of the unknown product seemed to be at a 1:1 ratio. Preliminary GC-MS analysis indicated that this unknown product has a molecular weight consistent with that of a hydroxylated linoleic acid derivative. Further structural analysis by different methods may help to determine the identity of the product.

Without being bound by theory, the present inventors believe that this unknown product may be an intermediate of linoleic acid conjugation. When this product was incubated with $L.$ $reuteri$ PYR8 cells or crude enzyme extracts, however, it could not be converted to CLA. It is possible that the intermediate has to be bound with the enzyme or membrane during the conjugation, and once it is released the conjugation could not be completed.

Further experiments include developing a series of constructs based on the vector pLAT10 to explore the advantage of including the His tag (FIG. 12). pLAT10 is a plasmid that can be used to directly transform $B.$ $subtilis$ and $B.$ $licheniformis$. It has the promoter, coding sequence and the terminator of the LAT gene encoding α-amylase. Also present is a signal peptide sequence for mobilizing proteins into or across the Bacillus membrane. In construct #2, the isomerase coding sequence was placed under amylase promoter control as a fusion to its signal peptide. Normally, the LAT signal sequence directs the protein into or across the membrane. Soluble proteins typically are secreted into the culture broth and in the process, the signal peptide is removed by specific proteases. Membrane proteins migrate to and integrate into the membrane. Since the hydrophobic domain of the isomerase peptide may function both as an uncleaved signal sequence and transmembrane segment in L. reuteri, it is not known if such a domain of the protein would interfere with the proper function of the secretion machinery in Bacillus and the LAT signal-isomerase may not fold into proper conformation. In construct #3 (FIG. 12), the entire coding sequence of the isomerase gene is fused to His tag at the C-terminus while in construct #4, the isomerase sequence without the hydrophobic domain is fused to His tag. In constructs #5 and #6, the secretion signal peptide is removed. With these new constructs, it can be determined whether the isomerase protein is synthesized in Bacillus cells and in which cellular fractions the protein is located.

Example 9

The following example demonstrates the expression of the L. reuteri PYR8 (cis,trans)-9,11-linoleate isomerase gene off of the native PYR8 promoter in L. reuteri (type strain) ATCC 23272.

L. reuteri PYR8 isomerase gene (promoter-ORF-terminator) was amplified from PYR8 genomic DNA using the primer pair CLAo7 (SEQ ID NO:38, see Example 7) and CLAo8B (SEQ ID NO:39, see Example 7). The PCR amplified isomerase gene product (2.3 kb) contained the complete coding sequence plus 381 bp of immediately upstream sequence containing the native promoter, as well as downstream sequence containing the putative transcription terminator (up to 124 bp downstream from the stop codon). The PCR product was cloned with blunted ends into pPCR-Script Amp SK (+). The isomerase gene was isolated from the recombinant plasmid by SalI digestion and ligated with the Lactobacillus/E. coli shuttle vector pTRKH2, which had been predigested with SalI. The ligated DNA was transformed into E. coli cells. Transformants were selected and checked by restriction analysis. The recombinant plasmids with the isomerase gene positioned either under control (downstream), or reverse to, the lac promoter were transformed into cells of L. reuteri ATCC 23272 (type strain) by electroporation.

Cells of L. reuteri 23272 transformed with the isomerase gene under control of or reverse to the lac promoter were grown at 37° C. for 28 hours before harvesting. Total cellular protein was analyzed by SDS-PAGE and Western Blot. A new protein band of about 70 kD was detected with rabbit antibodies specific for L. reuteri PYR8 isomerase in the cells of both types of transformants. This indicates that the promoter sequence of L. reuteri PYR8 linoleate isomerase gene functions in L. reuteri 23272.

Although a substantial amount of protein was produced, the transformed L. reuteri 23272 cells did not show measurable enzyme activity. Neither CLA nor the hydroxylated linoleic acid derivative (formed in B. subtilis) was detected in the linoleic acid biotransformation assay. It is, still not clear if the protein was produced as a membrane protein integrated into the membrane, or as an inclusion body (similar to expression of the gene from the T7 promoter in E. coli). It is unlikely that the protein is produced in soluble form. The present inventors are currently investigating methods to improve the quality of the PYR8 isomerase gene constructs, including confirmation of nucleic acid sequence, and methods to induce the measurable enzyme activity in the transformed cells.

Example 10

The following example describes the production and characterization of a rabbit antibody made from the cloned L. reuteri PYR8 (cis,trans)-9,11-linoleate isomerase gene in Escherichia coli.

An L. reuteri (cis,trans)-9,11-linoleate isomerase-histag fusion protein was synthesized in E. coli as inclusion bodies as described in Example 7 and was further purified under denaturing conditions using His-Bind Resin and Buffer kit (NOVAGEN, Catalogue # 70239-3), following the vendors protocols. The purified isomerase protein was used to immunize two rabbits. Serum collected from the fourth bleeding was tested in Western Blot analysis (FIG. 42). FIG. 42 shows that the rabbit antibodies showed a strong specificity for the isomerase produced in its native host L. reuteri PRY8 and for isomerase expressed in heterologous hosts, although a low background level of cross-reaction was observed when protein samples were overloaded.

The antibodies showed a very strong signal with L. reuteri isomerase-histag fusion protein expressed in E. coli (FIG. 42, lane 1). B. subtilis transformed with construct #1 (See FIG. 12: isomerase coding sequence under the HpaII promoter control in the plasmid vector pBH1) produced a protein of about 70 kD which could be seen on Coomassie-Blue stained SDS-gel (data not shown). This protein band was readily detected by the rabbit antiserum (FIG. 42, lane 4). This signal was not detected in wild type cells of Bacillus subtilis (FIG. 42, lane 3). The antibodies recognized a peptide of about 70 kD in L. reuteri 23272 cells transformed with constructs containing the L. reuteri PYR8 isomerase gene (FIG. 42; lane 5: L. reuteri 23272 wild type; lane 6: L. reuteri 23272 transformed with the vector pTRKH2 containing the isomerase gene under the control of both its native promoter and the lac promoter; and lane 7: L. reuteri 23272 transformed with the vector pTRKH2 containing the isomerase gene under the control of its native promoter; See Example 9).

The rabbit antibodies reacted specifically with the 70 kD linoleate isomerase synthesized in the native L. reuteri PYR8 (FIG. 42, lane 2). The present inventors attempted to detect cross-reaction of the antibodies with (cis,trans)-9,11-linoleate isomerase of C. sporogenes and (trans,cis)-10,12-linoleate isomerase of P. acnes. A highly purified P. acnes isomerase showed a single protein band of about 55 kD on SDS gel (data not shown). The rabbit L. reuteri PYR8 antibody recognized the 55 kD P. acnes (trans,cis)-10,12-linoleate isomerase in a total cell lysate (FIG. 42, lane 8). Similarly, the L. reuteri PYR8 antibody reacted with the 45 kD (cis,trans)-9,11-linoleate isomerase of C. sporogenes (FIG. 42, lane 9). Significant nonspecific antibody cross-reaction was observed with C. sporogenes lysates and to a lesser extent with the P. acnes lysates.

Example 11

The following example describes the purification of linoleate isomerase from Propionibacterium acnes.

Figure 14:
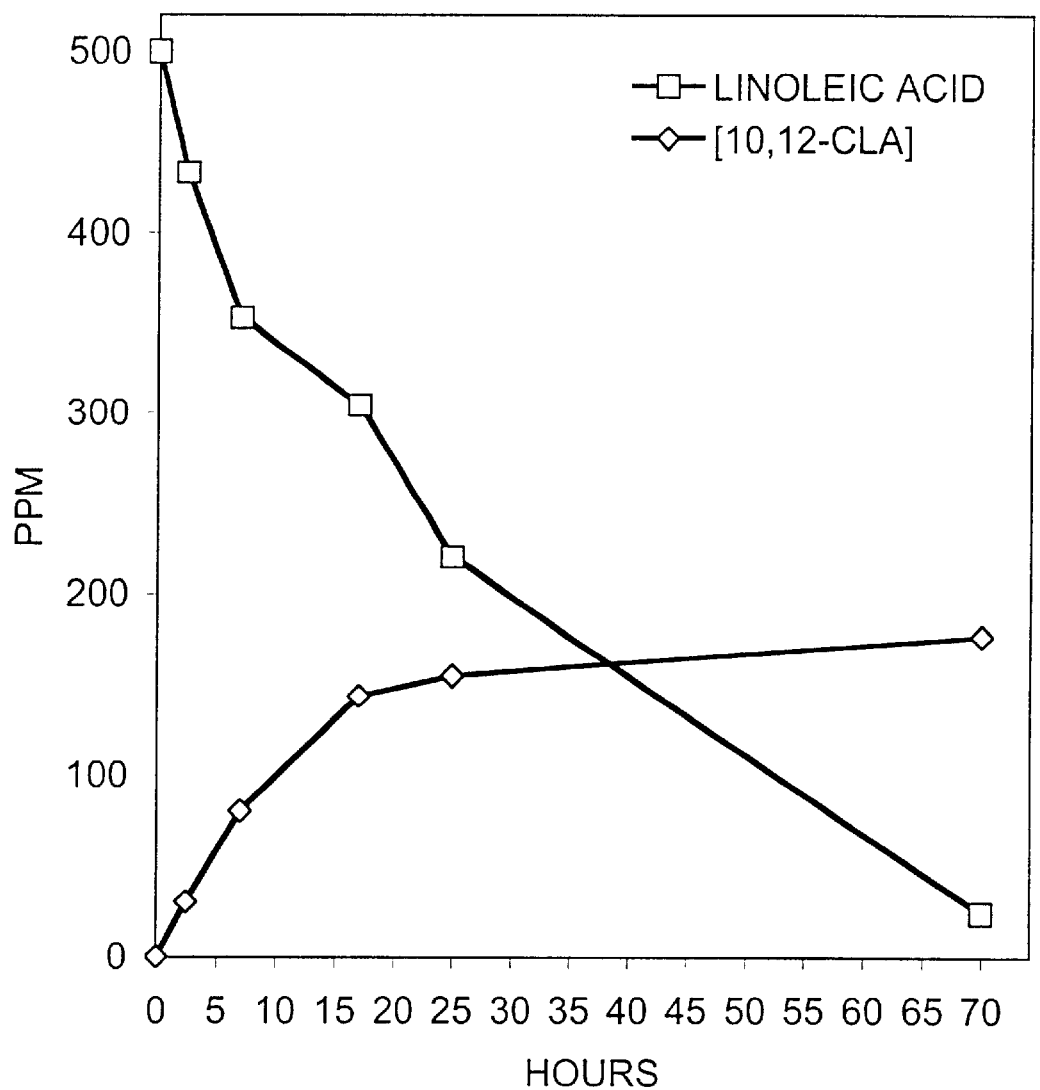
FIG. 14 is a line graph showing the formation of trans10, cis12-CLA from linoleic acid using whole cells of *P. acnes*.

P. acnes ATCC 6919 is the only microorganism known to produce trans10,cis12-CLA directly from linoleic acid. Experiments described in Example 1 using whole cells confirmed the presence of a 10,12-linoleate isomerase in this organism. Enzyme extracts were prepared by French Press. FIG. 14 shows the formation of trans10,cis12-CLA from linoleic acid using whole cells of P. acnes. Cultures were grown anaerobically to stationary phase in a complex brain heart infusion medium, harvested and resuspended in the same medium containing 500 ppm linoleic acid. Cells were incubated aerobically with shaking at ambient temperature. The level of linoleic acid decreased about 50% in 24 hours. About half of this missing linoleic acid could be detected as trans10,cis12-CLA. No cis9,trans11-CLA was observed. With prolonged incubation, the level of trans10,cis12-CLA changed only slightly, while nearly all remaining linoleic acid disappeared. At present it is unclear how linoleic acid is metabolized in this organism. In other experiments, trans10,cis12-CLA rose in concentration, but later disappeared completely, as did all of the linoleic acid (results not shown). This suggests that trans10,cis12-CLA may be subject to further metabolism, possibly by a reductase. Linoleic acid may also be a substrate for enzymes other than the isomerase.

Figure 15:
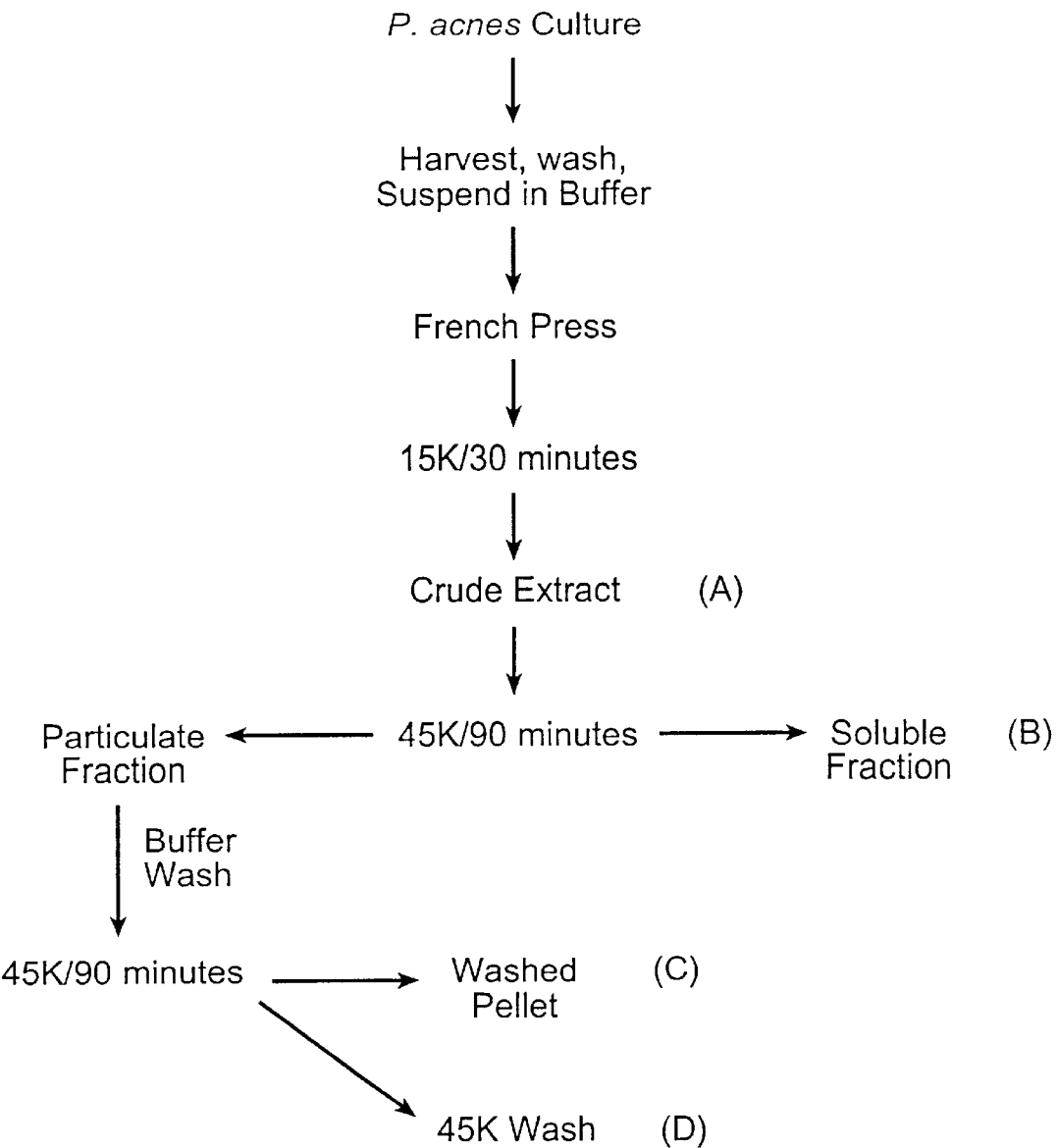
FIG. 15 is a flow diagram showing the cell fractionation protocol for *P. acnes* ATCC 6919.

Enzyme extracts were prepared by French Press and the extract fractionated as outlined in FIG. 15. Taking the total isomerase activity in fraction A as 100%, over 93% of the activity was detected in the soluble protein fraction (B). Less than 1% of the isomerase activity was found in the washed pellet, or membrane fraction (C). Approximately 2% of the activity was located in the buffer fraction (D), after the pellet washing and centrifugation steps. Thus, the *P. acnes* isomerase clearly is not a membrane protein, unlike the isomerase activities in *L. reuteri* PYR8 and other strains examined to date.

Isomerase activity, using a crude soluble enzyme preparation, was not significantly affected by overnight dialysis. A number of possible cofactors were tested for their effect on isomerase activity, including NAD, NADH, NADP, NADPH, FAD, FMN, ADP, ATP and glutathione. No significant effect was observed in 60 minute assays with any of these compounds. Calcium and magnesium also had no effect. Isomerase activity was not inhibited by the chelators EDTA (5 mM) or 1,10-phenanthroline (1 mM), or the sulfhydryl reagents p-chloromercuribenzoate (5 $\mu$M) or N-ethylmaleimide (100 $\mu$M).

Figure 16:
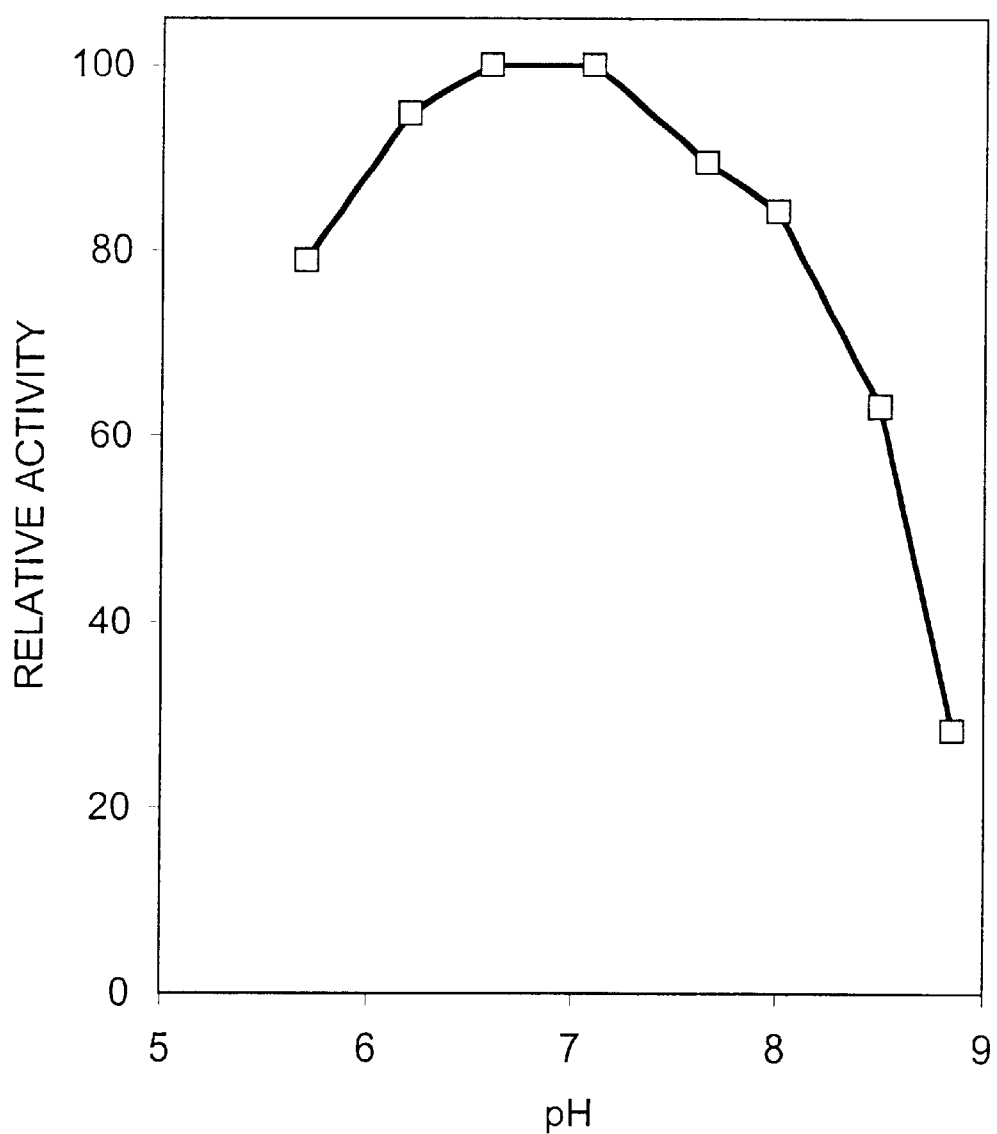
FIG. 16 is a line graph showing the effect of pH on linoleate isomerase activity in crude extracts of *P. acnes* ATCC 6919.

The effect of pH on enzyme activity in crude extracts was examined. The isomerase activity exhibits a pH optimum centered around 6.8 (FIG. 16).

Figure 17:
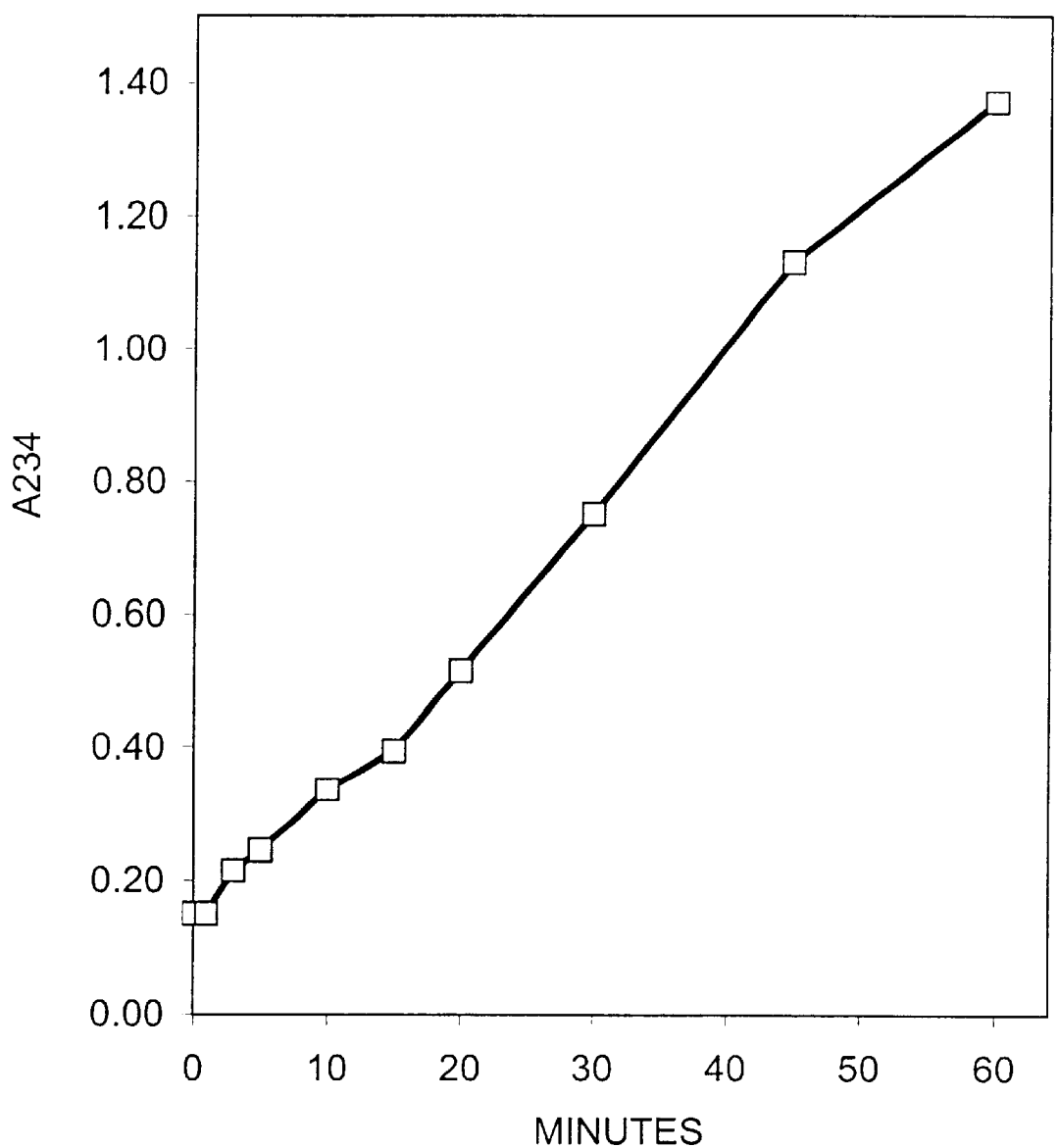
FIG. 17 is a line graph showing the time course of CLA formation in crude extracts of *P. acnes* ATCC 6919.
Figure 18:
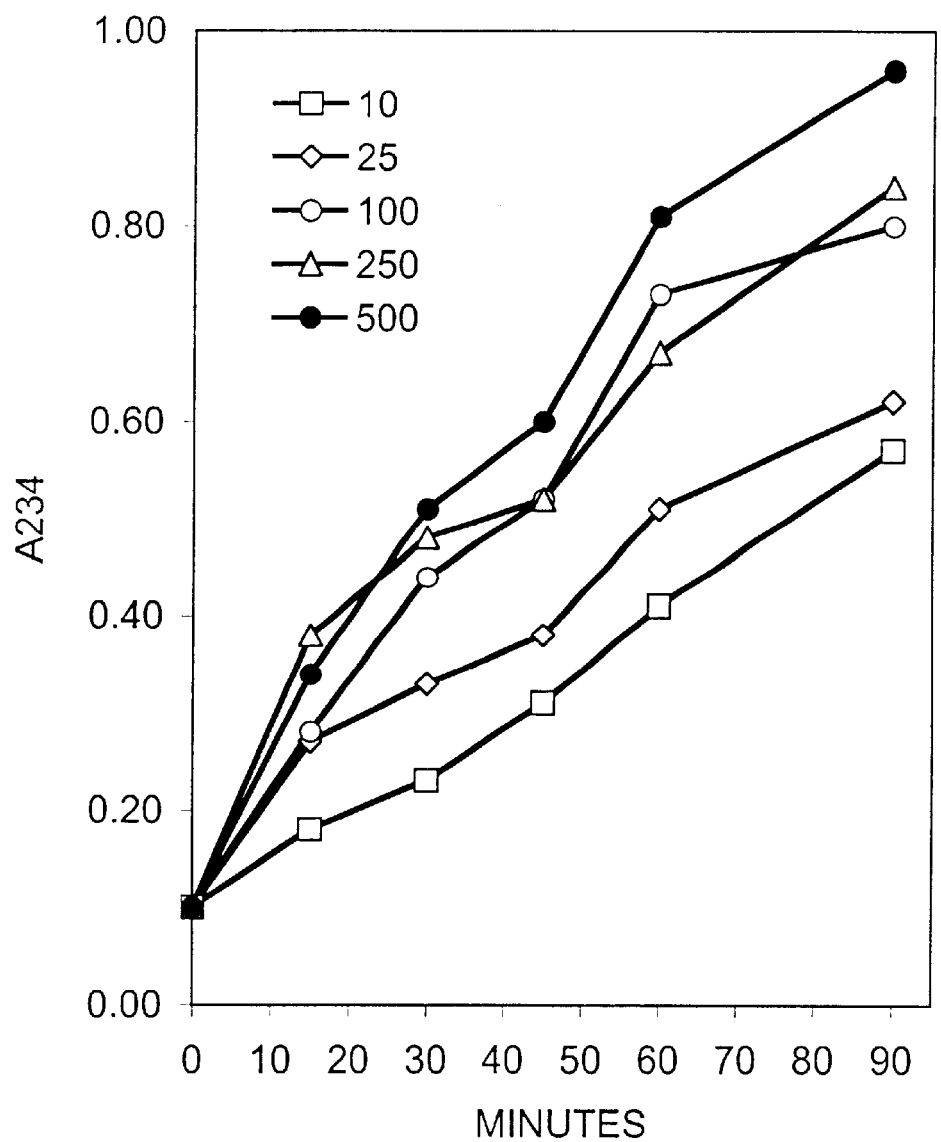
FIG. 18 is a line graph showing the time course for the formation of CLA in crude extracts of *P. acnes* ATCC 6919 at different levels of linoleic acid.
Figure 19:
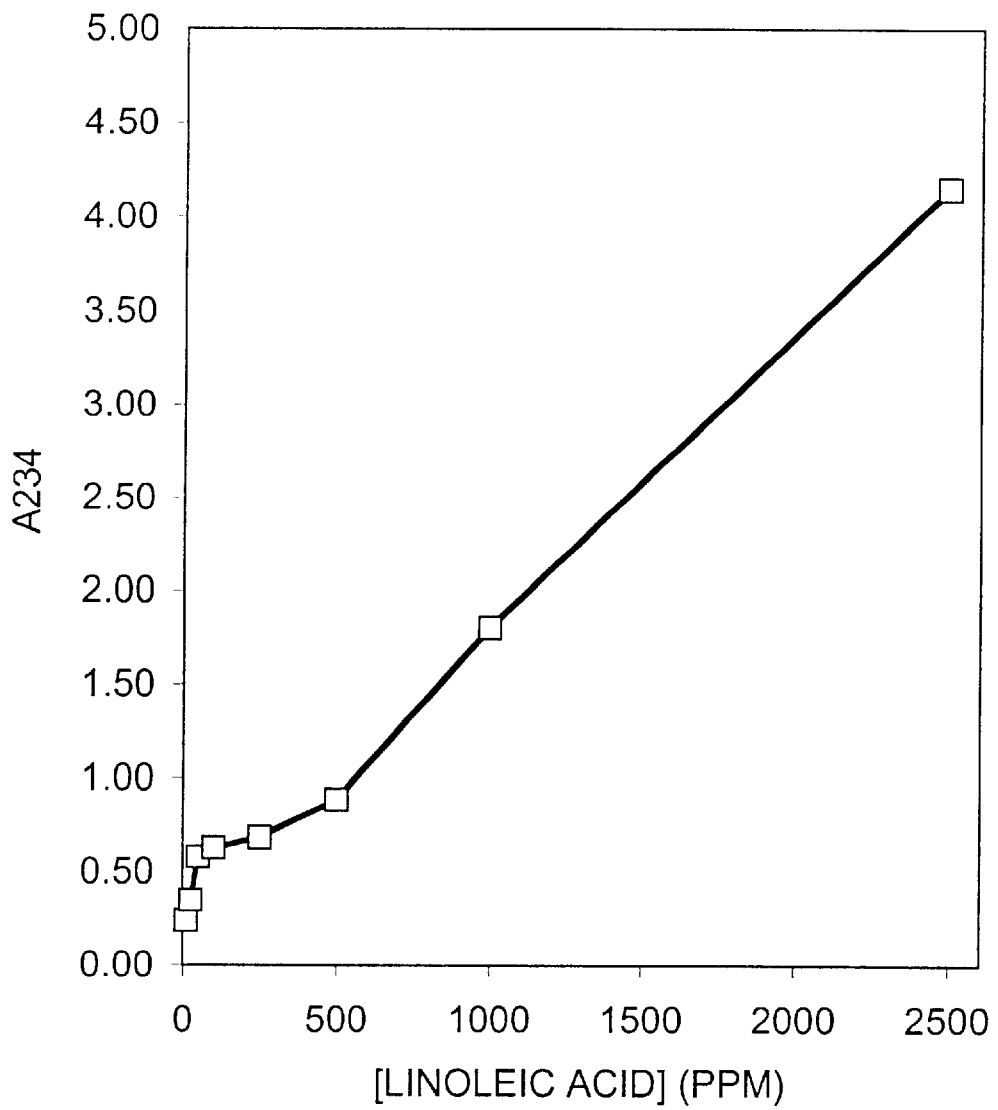
FIG. 19 is a line graph showing end point for formation of CLA in crude extracts of *P. acnes* ATCC 6919 at different levels of linoleic acid.

Formation of CLA was determined by measuring the absorbence at 234 nm. FIG. 17 shows a typical time course experiment using the crude isomerase extract as enzyme source. Generally, the isomerase was assayed using an endpoint assay after 30 to 60 minutes incubation at room temperature. FIG. 18 (time course assay at different linoleic acid levels) and FIG. 19 (end point assay at different linoleic acid levels) show the effect of increasing substrate concentration on formation of linoleic acid. These data suggest that the enzyme in *P. acnes* is not subject to the same type of substrate inhibition observed in the linoleic acid isomerases of *C. sporogenes, L. reuteri* and *B. fibrisolvens*.

The effect of temperature on isomerase activity has been examined to a limited extent. The enzyme works very slowly at 4° C., demonstrating much better activity at room temperature. CLA formation was virtually the same at 37° C. as at room temperature (data not shown). These results again differ significantly from those observed with the particulate *L. reuteri* isomerase.

Figure 20:
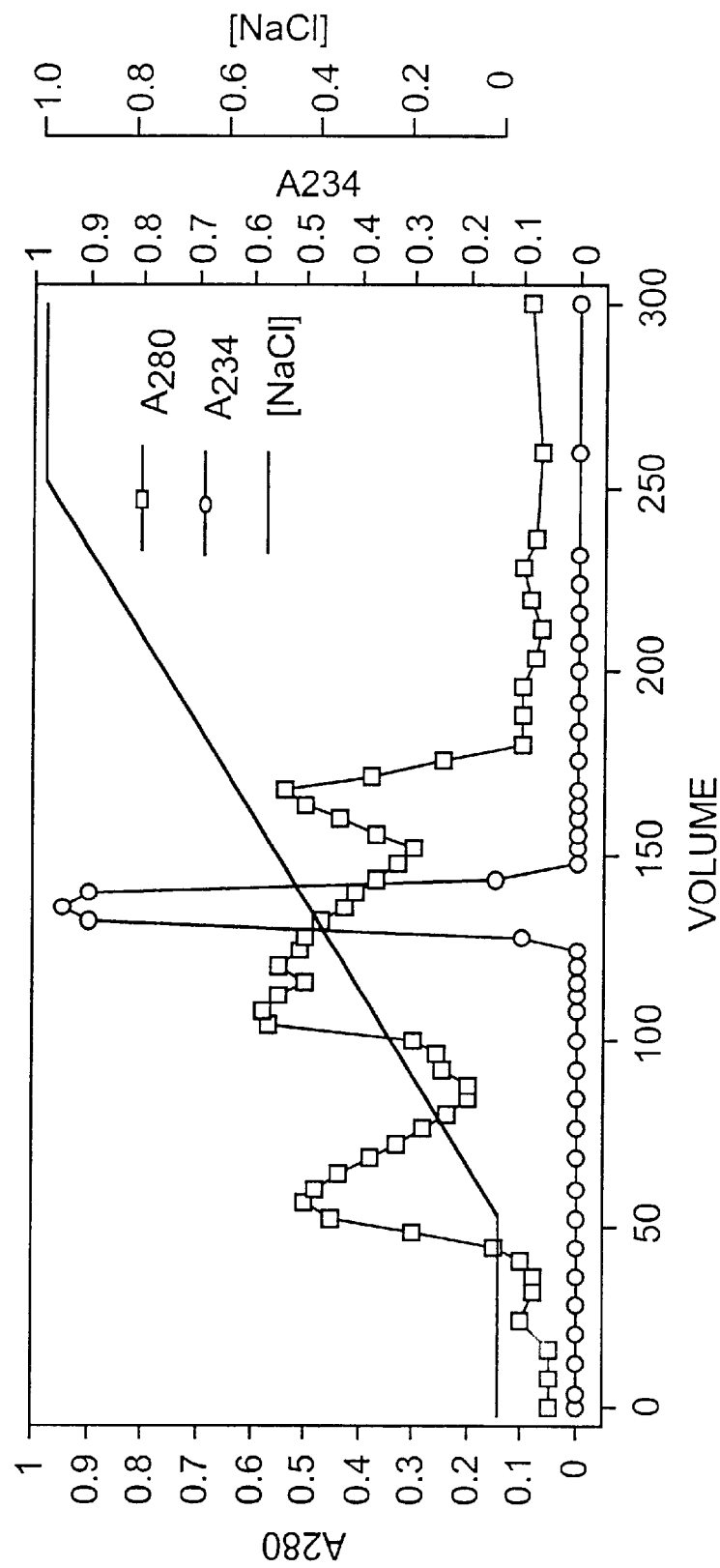
FIG. 20 is a graph illustrating DEAE ion exchange chromatography of total soluble protein from *P. acnes* ATCC 6919.
Figure 21:
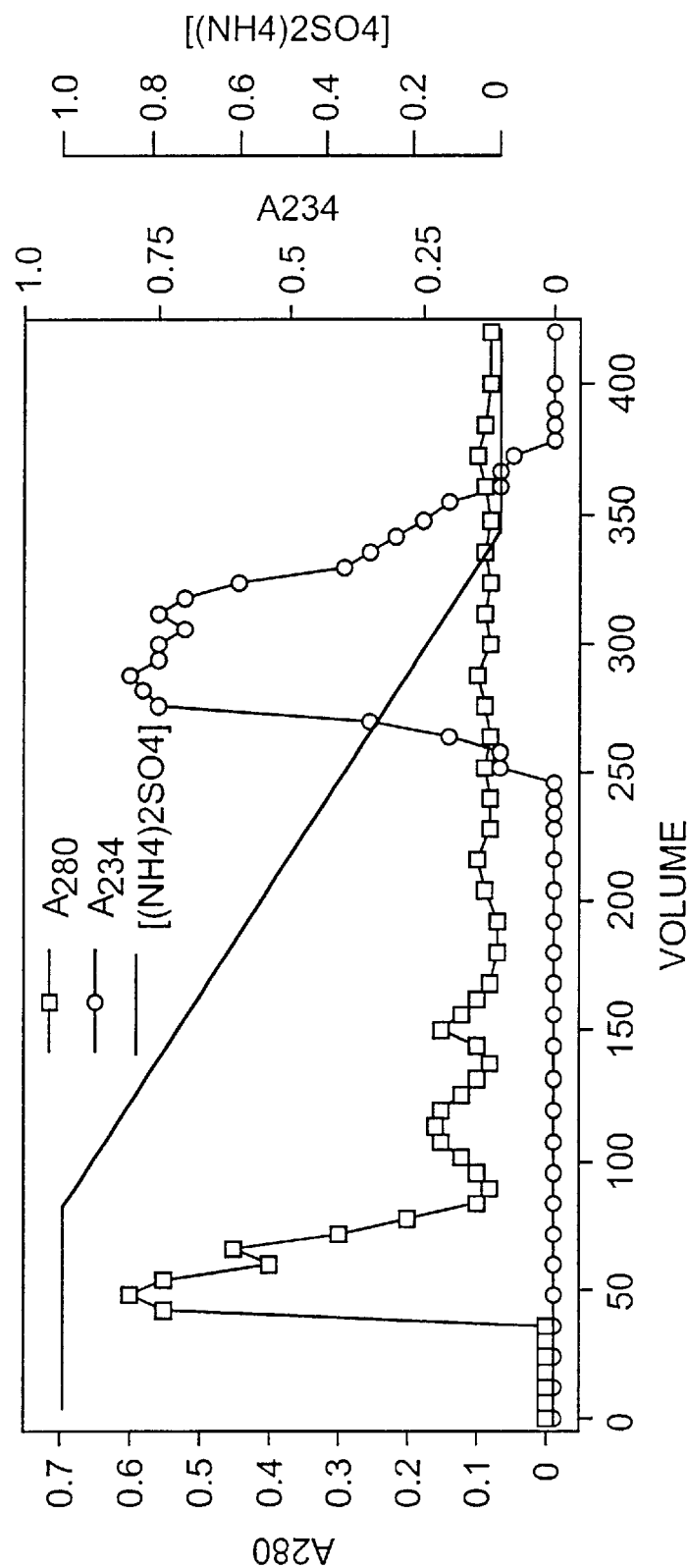
FIG. 21 is a graph illustrating hydrophobic interaction chromatography of total soluble protein from *P. acnes* ATCC 6919.

Purification of the linoleate isomerase in *P. acnes* was initiated. Following preparation of a centrifuged crude extract, samples were applied to several columns to determine applicability and suitable conditions. Typical chromatograms for some of these pilot experiments are shown in FIG. 20 and FIG. 21 for DEAE and hydrophobic interaction chromatography (HIC), respectively. The initial purification trial consisted of DEAE followed by HIC and gel filtration chromatography. After these three columns, however, multiple bands were seen on SDS PAGE.

This initial attempt at purification clearly highlighted the need to optimize separation conditions. The DEAE step was optimized further by altering the salt gradient program. Following a linear gradient to 0.175 M NaCl, the salt level was held at this level for 70 ml. The isomerase eluted at this point, after which time the gradient was continued to elute other proteins.

The isomerase binds very tightly to the phenyl HIC column, and is only released with ethylene glycol. A large number of other proteins were also released, however, with stepwise exposure to 20% ethylene glycol. The HIC chromatography step was altered by use of an ethylene glycol gradient from 5 to 30%. This resulted in a somewhat sharper elution profile for the isomerase than previously obtained (results not shown).

Following DEAE and HIC chromatography, chromatofocusing was employed. This method separates molecules on the basis of isoelectric point. Protein was applied to a weak anion exchange column at high pH, and eluted as the pH decreased by application of a lower pH "Polybuffer". Preliminary experiments showed that a pH gradient from 6.5 to 4.0 resulted in elution of the isomerase at a pH around 4.4. Clearly the isomerase is a fairly acidic protein.

Figure 22:
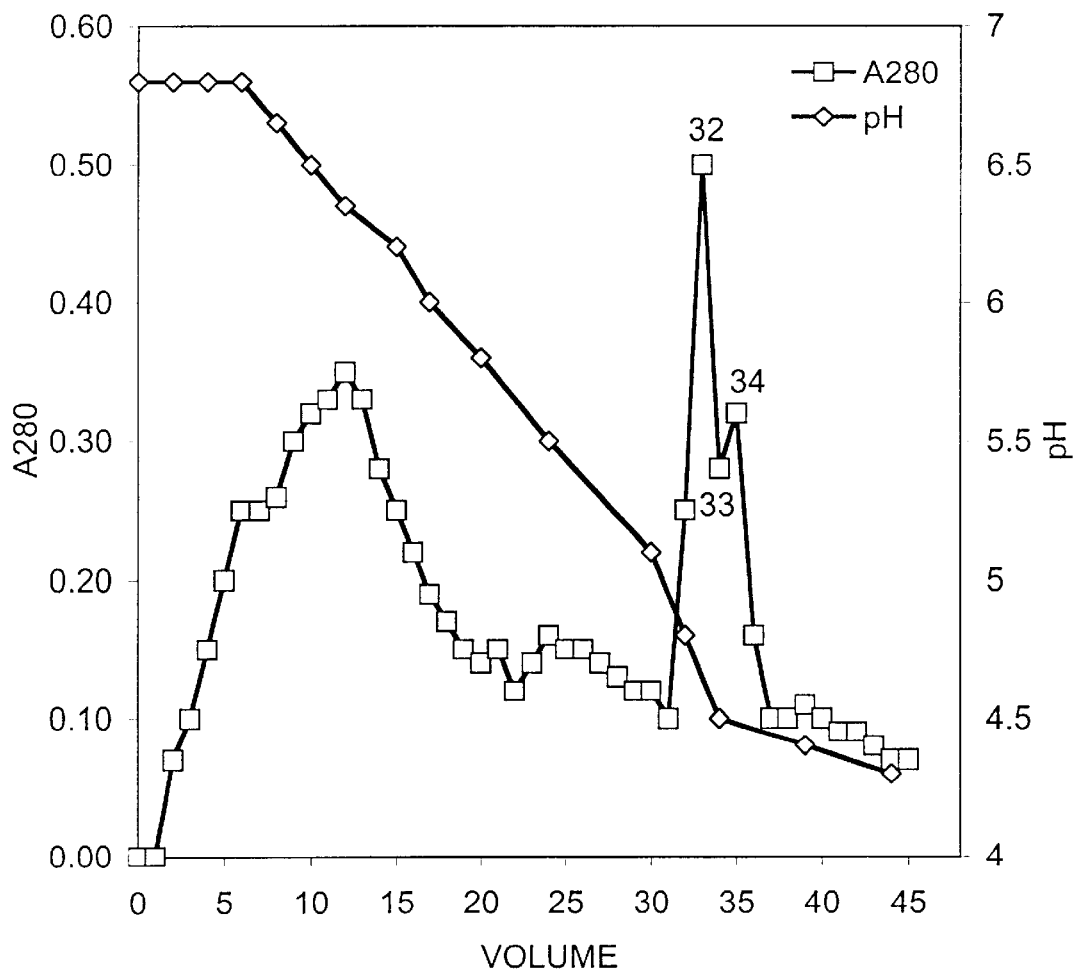
FIG. 22 is a graph illustrating chromatofocusing of isomerase activity from *P. acnes* ATCC 6919.
Figures 23A, 23B:
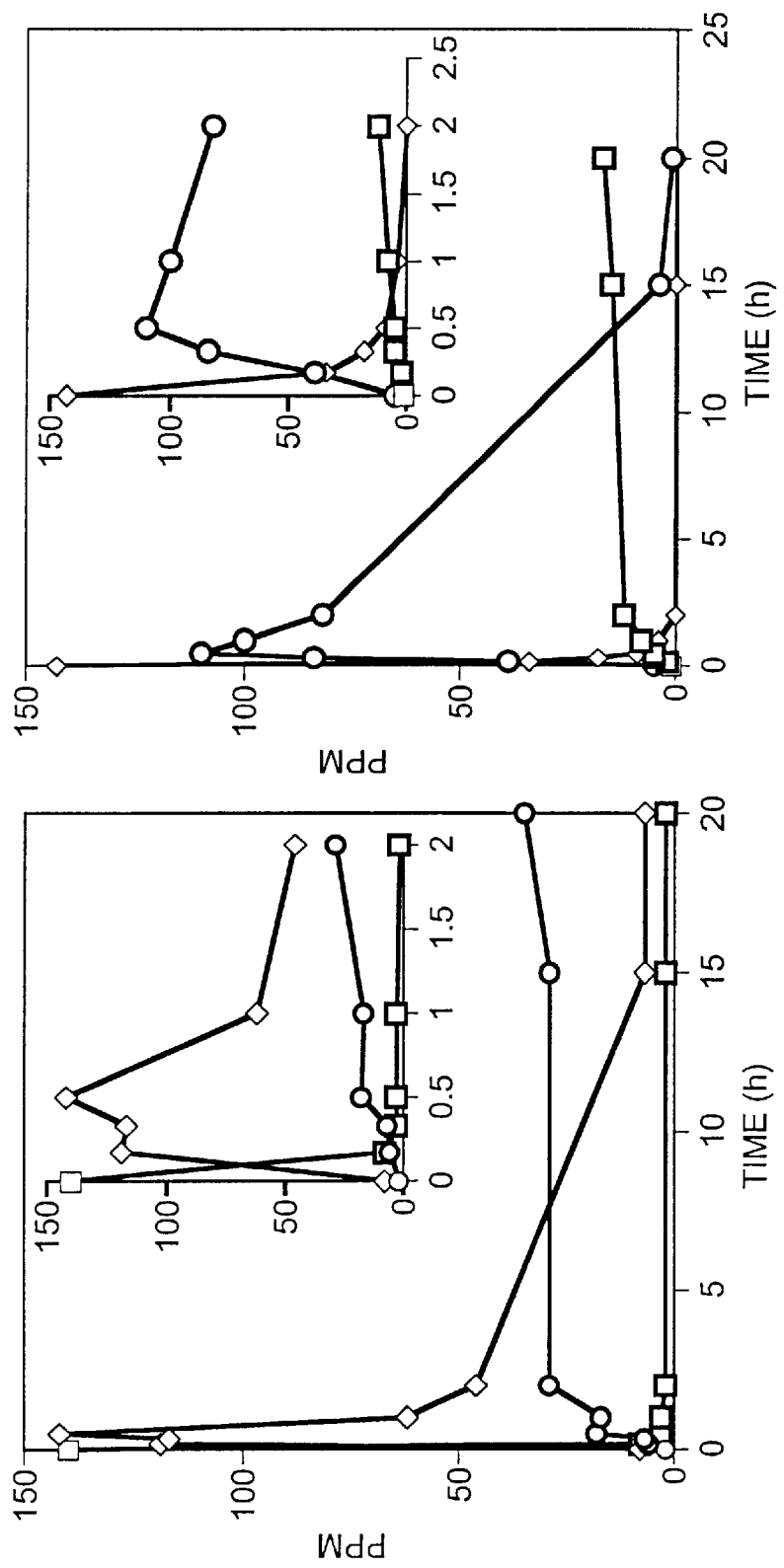
FIG. 23A is a graph showing a time course of CLA formation by *C. sporogenes* ATCC 25762 under aerobic conditions at room temperature.
FIG. 23B is a graph showing a time course of CLA formation by *C. sporogenes* ATCC 25762 under anaerobic conditions at room temperature.
Figures 23C, 23D:
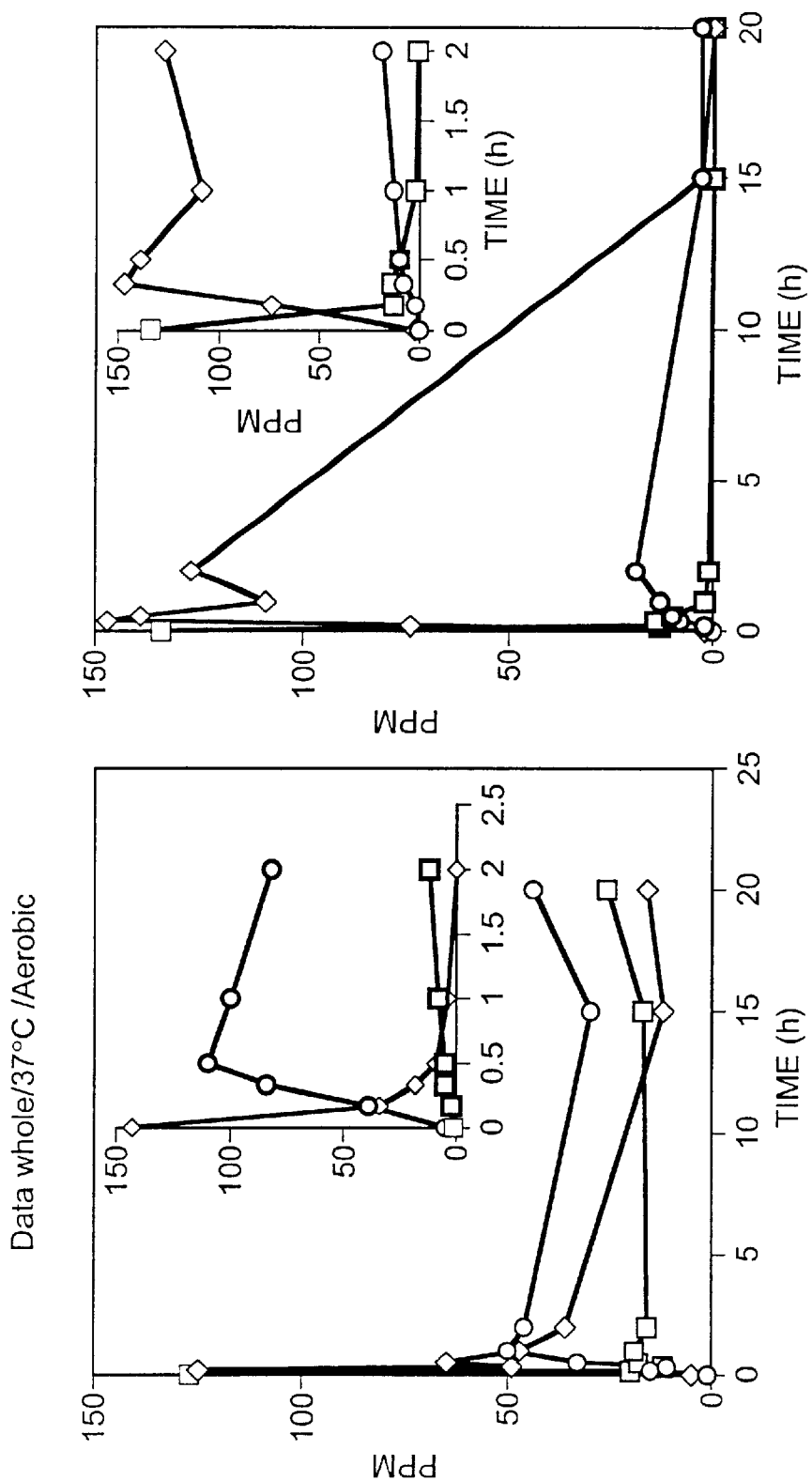
FIG. 23C is a graph showing a time course of CLA formation by *C. sporogenes* ATCC 25762 under aerobic conditions at 37° C.
FIG. 23D is a graph showing a time course of CLA formation by *C. sporogenes* ATCC 25762 under anaerobic conditions at 37° C.

Following HIC chromatography, a single fraction containing high isomerase activity was applied to a Pharmacia MonoP chromatofocusing column equilibrated with 20 mM bis-Tris (pH 6.5). The pH gradient was formed using 10% Polybuffer 74 (pH 4.0). Results are shown in FIG. 22. The isomerase activity eluted in a sharp peak around pH 4.5. The three fractions containing activity were examined for purity by SDS PAGE. Fraction 32 appeared on 12.5% and 20% gels as a single protein band with a mass of 55 kD.

The purification of the *P. acnes* 10,12-linoleate isomerase is summarized in Table 1B.

TABLE 1B

*Propionibacterium acnes*

| Step | Protein | Total Activity | Specific Activity | Yield |
|---|---|---|---|---|
| Crude extract | 419 | 1365 | 3.26 | 100 |
| DEAE | 34.8 | 774 | 22.2 | 56.7 |
| Hydrophobic interaction | 1.83 | 250 | 137 | 18.3 |
| Chromatofocusing | .107 | 51.1 | 478 | 3.75 |

Protein in milligrams. Enzyme activity units are nanomoles CLA formed per minute. Specific activity is units per milligram protein.

This material was submitted for amino acid sequencing. After running the sample on a SDS PAGE gel, the single band was transferred and N-terminal sequencing performed at the UW Medical College of Wisconsin. Surprisingly, several signals were obtained, indicating the presence of multiple peptides or that the N-terminal portion of the peptide was highly degraded (unlikely) in this apparent single band. Subsequent analysis of isomerase purified further (described below) determined that the N-terminus of the protein was blocked.

To further modify the purification scheme to obtain pure isomerase, the protocols previously used were revised and improved to enhance the purification. As before, soluble crude extract was prepared by cell disruption. This material was fractionated using DEAE chromatography. Fractions from several runs containing significant isomerase activity were pooled, dialyzed, and reapplied to the same column. The active fractions were pooled, made 1 molar in $(NH_4)_2SO_4$, and applied to a phenyl hydrophobic column in several runs. Active fractions were concentrated, if necessary, and analyzed by SDS PAGE chromatography. Fractions having high isomerase activity exhibited a large number of protein bands at this stage. Selected fractions from the HIC column were pooled, concentrated, dialyzed, and applied to a chromatofocusing column. Protein elution was accomplished with a shallower pH gradient than was previously used, from 5.5 to 4.0. The isomerase activity eluted as a sharp peak at about pH 4.2. Active fractions were examined for purity by SDS PAGE. At this point, several fractions appear to contain a single band approximately 50–55 kD in size (data not shown). Other active fractions exhibited three to four additional bands. These fractions will be applied to a gel filtration column if further purification is required. N-terminal sequencing of the P. acnes linoleate isomerase has been completed (See Example 12).

Example 12

The following example demonstrates the sequencing of the N-terminal amino acid sequence of the purified P. acnes soluble (trans,cis)-10,12-linoleate isomerase.

Linoleate isomerase was purified from P. acnes ATCC 6919 to apparent homogeneity as described in Example 11; only a single peptide band of about 55 kD could be detected on SDS PAGE stained by Coomassie Blue. The N-terminal peptide sequence (35 amino acid residues) of the purified protein was determined as follows:

SISKD SRIAI IGAGP AGLAA GMYLW QAGFX DYTIL (SEQ ID NO:42)

A protein having the sequence of SEQ ID NO:42 is referred to herein as $PPAISOM_{35}$ (formerly called $PCS-CLA_{35}$ in U.S. Provisional Application Serial No. 60/141,798, from which this application claims priority). It should be noted that since amino acid sequencing technology is not entirely error-free, SEQ ID NO:42 represents, at best, an apparent partial N-terminal amino acid sequence.

No significant homology was detected when the $PPAISOM_{35}$ amino acid sequence was initially compared to the linoleate isomerase peptide deduced from the DNA sequence cloned from L. reuteri PYR8 (SEQ ID NO:18) or of the directly determined amino acid sequence of the PYR8 isomerase (SEQ ID NO:1). We note that the L. reuteri PYR8 and P. acnes linoleate isomerases have different mass; the isomerase from L. reuteri is about 70 kD while the isomerase from P. acnes is about 55 kD. A comparison of the complete isomerase sequences from L. reuteri and P. acnes (see Example 13) will be more meaningful (See Example 13).

The N-terminal sequence of the P. acnes isomerase also showed no homology with the N-terminal peptide sequence from the putative Butyrivibrio fibrisolvens (cis,trans)-9,11-linoleate isomerase (Park et al., 1996), although, as discussed above (Background section), the present inventors consider it to be unlikely that the sequence described by Park et al. is actually a linoleate isomerase. The N-terminal peptide sequence was also analyzed against the sequences in the databases using Blastp program with standard settings. The best-matched sequence is the putative E. coli oxidoreductase, Fe—S subunit (gi887828) showing 71% identity in a region of 28 amino acid residues. However, no homology could be detected with any sequences in the data base when low complexity filtering is used in Blastp analysis. Low complexity regions commonly give spuriously high scores that reflect compositional bias rather than significant position-by-position alignment. Filtering is designed to eliminate these potentially confounding matches. Therefore, the true level of homology between P. acnes linoleate isomerase and the putative E. coli oxidoreductase Fe—S subunit remains to be determined when full-length P. acnes isomerase gene sequence is determined.

Nucleic acid sequences encoding SEQ ID NO:42 can be deduced from the amino acid sequence by those of ordinary skill in the art. Isolated nucleic acid molecules comprising such nucleic acid sequences are encompassed by the present invention.

Example 13

The following example describes the nucleic acid cloning and sequencing of a Propionibacterium acnes linoleate isomerase nucleic acid molecule of the present invention.

Peptide Sequences Determined for the Purified Isomerase.

The purified P. acnes linoleic acid isomerase, purified as described in Examples 11 and 12, was subjected to digestion with the enzyme endo LYS-C to generate peptide fragments. The resulting peptides were separated by HPLC chromatography. Peptide fragments from three different peaks were sequenced individually. None of these peptide fragments are identical, entirely or partially, to the N-terminal sequence. Therefore, these fragments represent internal peptide fragments of the P. acnes linoleate isomerase.

A sequence of 14 amino acids was determined for the peptide in HPLC peak number one and is represented herein as SEQ ID NO:44. A peptide having the sequence of SEQ ID NO:44 is referred herein as $PPAISOM_{14}$. A sequence of 9 amino acid residues was determined for the peptide in HPLC peak number two and is represented herein as SEQ ID NO:45. A peptide having the sequence of SEQ ID NO:45 is referred herein as $PPAISOM_9$. A sequence of 15 amino acid was determined for the peptide in HPLC peak number three and is represented herein as SEQ ID NO:46. A peptide having the sequence of SEQ ID NO:46 is referred herein as $PPAISOM_{15}$. It should be noted that the amino acid signals detected in this sequencing experiment were very weak. There were, therefore, alternative choices at certain positions of the sequence due to ambiguous reads. The secondary choices at ambiguous amino acid positions in SEQ ID NO:46 are presented as lowercase letters in parentheses.

Cloning the DNA Sequence Coding the N-terminal Peptide Residues.

Two sets of degenerated oligonucleotide primers were synthesized according to SEQ ID NO:42. The first oligonucleotide primer set corresponds to amino acid residues 8–14 of SEQ ID NO:42 and is designated PA05 (SEQ ID NO:47). The second oligonucleotide primer set corresponds to amino acid residues 22–28 of SEQ ID NO:42 and is designated PA011 (SEQ ID NO:48). Two known genes in the GenBank database have been previously cloned from Propionibacterium acnes: hyaluronidase (GenBank U15927) and lipase (GenBank X99255). The codon bias of these two genes was used to decrease the degeneracy at the 5' end of the primer PA05 (SEQ ID NO:47). A PCR reaction using P. acnes DNA as template generated large quantities of non-specific products of different sizes and also a product of the expected size (62 bp) in lesser amount. The PCR product of 62 bp was isolated, purified and cloned into pPCR-Script SK (+) Amp (Stratagene). Putative recombinant plasmids were analyzed by restriction digestions. Four clones were selected and sequenced. Although different primer molecules were involved in the synthesis of the PCR products, the deduced amino acid sequences of all four clones matched exactly to residues 12 through 28 of the N-terminus of the purified linoleate isomerase protein (SEQ ID NO:42), thus confirming the identity of the PCR products. The sequence of the cloned PCR product (SEQ ID NO:49) is denoted herein as nPAISOM$_{62}$. Differences in nucleotides found in the different clones of SEQ ID NO:49 are indicated in the Sequence Listing as alternate nucleotides. The deduced amino acid sequence (SEQ ID NO:50) is referred herein as PPAISOM$_{21}$.

Cloning of a Larger Portion of the Isomerase Gene by Inverse PCR.

An inverse PCR amplification approach was used to clone the DNA sequences flanking the DNA sequence nPAISOM$_{62}$. Two oligonucleotide primers, designated PA016 and PA017 (SEQ ID NO:51 and SEQ ID NO:52, respectively), were synthesized. The primer PA016 corresponded to nucleotides 7–23 of nPAISOM$_{62}$, and PA017 to nucleotides 30–47 of nPAISOM$_{62}$.

Genomic DNA from *P. acnes* was digested with the following restriction enzymes, or combinations of two enzymes that produce compatible ends: BamHI, EcoRI, HindIII, PvuII, SalI, Sau3A, BamHI/BglII, XbaI/NheI, XbaI/SpeI, XhoI/SalI. Each DNA digest was purified using a PCR purification kit (Qiagen) and circularized with T4 DNA ligase. PCR reactions were carried out with the primer pair PA016/PA017 using aliquots of the circularized DNA digests as template. A PCR product of about 570 bp was generated with the circularized BamHI digest. The PCR product was purified and cloned into the plasmid vector pCR2.1-TOPO (Invitrogen) and sequenced. With reference to the BamHI site and the sequence nPAISOM$_{62}$, the cloned DNA sequence was edited to generate a sequence of 569 bp, referred herein as nPAISOM$_{596}$ (SEQ ID NO:53). This sequence contained an open reading frame (ORF) of 104 amino acid residues, with its C-terminus still incomplete, and with the start codon occurring at positions 259–261 of SEQ ID NO:53. The deduced amino acid sequence of this incomplete ORF is denoted PPAISOM$_{104}$ (SEQ ID NO:54).

Southern Blot Analysis of *P. acnes* DNA With the Cloned Partial Isomerase Sequence, nPAISOM$_{560}$.

*P. acnes* DNA was digested with the following restriction enzymes: BglII, EcoRI, FokI, HindIII, PvuII, XhoI. The digests were analyzed on Southern Blots using the sequence nPAISOM$_{569}$ (SEQ ID NO:53) labeled with biotinylated nucleotides (NEBlot Phototope kit, New England Biolabs). With the enzymes EcoRI, HindIII, PvuI and XhoI (which do not cut the sequence nPAISOM$_{569}$), only one hybridization band was observed. This indicates that only one copy of the linoleate isomerase gene is present in the genome of *P. acnes*. As expected for DNA digested by FokI and SalI, which have unique sites in the sequence nPAISOM$_{569}$, two hybridization bands were shown on Southern blot. Similarly, two bands were observed hybridizing to nPAISOM$_{569}$ in BglII digests although additional bands of weak signal intensity and of higher molecular weight were seen on the blot (which is likely caused by a problem of incomplete DNA digestion).

Second Round of Inverse PCR to Clone the Entire Isomerase Gene and Flanking Sequences.

The XhoI digests showed one band (about 3 kb) hybridizing to nPAISOM$_{569}$ while the BglII digests showed two major hybridization bands of around 3 kb. Inverse PCR amplification and cloning of both BglII fragments would cover a sequence of about 5.5 kb in total. Therefore, two pairs of oligonucleotide primers were synthesized. The first pair of primers, designated PA021 (SEQ ID NO:55) and PA022 (SEQ ID NO:56), respectively, were synthesized for inverse PCR amplification of the upstream BglII fragment. The second pair of primers, designated PA023 (SEQ ID NO:57) and PA024 (SEQ ID NO:58), respectively, were synthesized for inverse PCR amplification of the downstream BglII fragment. As an alternative approach, *P. acnes* genomic DNA was also digested with the enzyme XhoI, circularized and used as template for inverse PCR reaction with the primer pair PA021/PA024.

No PCR product of expected size could be generated with T4 DNA ligase treated BglII digest using the primer pair PA023/PA024. One explanation for this observation is that the two ends of the downstream BglII fragment were not compatible and therefore the fragment could not be circularized. However, PCR amplification with circularized BglII digest of *P. acnes* DNA generated a PCR product of about 2.5 kb using the primer pair PA021/PA022. A PCR product of about 2.5 kb was also amplified with circularized XhoI digest using the primer pair PA021/PA024. Both PCR products were purified and cloned into pPCR-Script Amp SK (+). Both of the cloned BglII fragment and the cloned XhoI fragment were completely sequenced. The complete sequence of the BglII fragment and the XhoI fragment and the sequence nPAISOM$_{569}$ were edited to generate a sequence of about 5.3 kb (SEQ ID NO:59), which is referred herein as nPAISOM$_{5275}$.

Analysis of the Isomerase Gene and Flanking Sequences.

Figure 52:
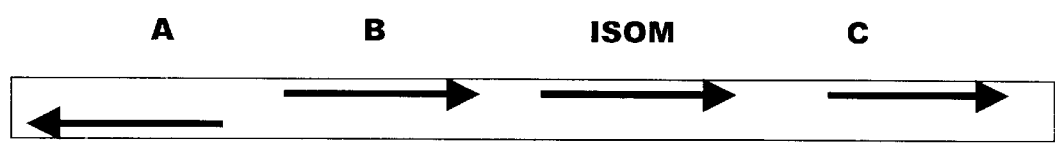
FIG. 52 is a schematic illustration of the linoleate isomerase gene and flanking open reading frames in *P. acnes*.

As schematically illustrated in FIG. 52, the sequence nPAISOM$_{5275}$ (SEQ ID NO:59) contains the entire *P. acnes* linoleate isomerase open reading frame (ISOM) as well as two ORFs (A and B) upstream and one ORF (C) downstream. The open reading frames B, C and the isomerase gene (ISOM) are coded by the same DNA strand while the ORF A is coded by the opposite DNA strand. No obvious transcription terminator or structures similar to promoter elements, common to other organisms, were found between the ORF B and the ORF for the linoleate isomerase (ISOM). At this point, it is not clear if the three open reading frames (B, C and ISOM) are transcribed as a single transcript or as multiple transcripts. RNA probing or primer extension experiments may be needed to determine the answer.

Linoleate Isomerase Open Reading Frame.

The *P. acnes* linoleate isomerase open reading frame spans from nucleotide positions 2735 to 4009 of the sequence nPAISOM$_{5275}$, and is represented by SEQ ID NO:60. A nucleic acid molecule which has a nucleic acid sequence represented by SEQ ID NO:60 is referred herein as nPAISOM$_{1275}$. nPAISOM$_{1275}$ encodes a linoleate isomerase protein of 424 amino acid residues with an amino acid sequence represented herein as SEQ ID NO:61. A protein having the amino acid sequence represented by SEQ ID NO:61 is referred herein as PPAISOM$_{424}$.

The deduced molecular weight of the isomerase protein PPAISOM$_{424}$ (SEQ ID NO:61) is about 48 kDa, which is in reasonably good agreement with the molecular weight of the purified linoleate isomerase protein (i.e., about 50–55 kDa as previously estimated by SDS-PAGE). The N-terminal peptide sequence of the purified linoleate isomerase (SEQ ID NO:42) is identical to positions 2–36 of the sequence PPAISOM$_{424}$, with the exception of two residues at positions 25 and 30, as discussed below. It appears that the methionine residue coded by the start codon of the ORF is removed after translation. The absence of additional in-frame ATG codons in the up-stream DNA sequence indicates that there is no signal peptide sequence associated with the isomerase protein. Analysis of the amino acid sequence of PPAISOM$_{424}$ (SEQ ID NO:61) shows that the unsolved residue at the position 30 of PPAISOM$_{35}$ (SEQ ID NO:42) is a histidine (H), and that residue 25 of PPAISOM$_{35}$ is a glutamate (E) in stead of a tryptophan (W). The sequences of the three internal peptide fragments resulting from endo-LYS-C digestion of the purified isomerase were also mapped within the deduced amino acid sequence PPAISOM$_{424}$. The peptide sequence of HPLC peak number one (SEQ ID NO:44) matched residues 183 through 196 of PPAISOM424. The peptide sequence of peak number three (SEQ ID NO:46) matched residues 275 through 289 of PPAISOM$_{424}$ with the only exception at position 286. The peptide sequence of peak number two (SEQ ID NO:45) matched the C-terminal residues (positions 416 through 424 of SEQ ID NO:61) of PPAISOM$_{424}$.

A ribosome binding site-like structure (AAGGAAG), referred to herein as SEQ ID NO:62, was found up-stream from the translational initiation codon of the isomerase open reading frame in nPAISOM$_{1275}$. The spacing between this putative ribosome binding site and the translation initiation codon is only 4 bases, much shorter than the usual spacing of 6–9. Although rare, a 4-base spacing was also found in other *P. acnes* genes such as the ORF B in the sequence nPAUNKA$_{783}$ (see below), and has been reported previously, for instance, in the protoporphyrinogen oxidase gene from *P. freudenreichii* (GenBank, D85417).

The (trans,cis)-10,12-linoleate isomerase open reading frame does not show a significant homology with the (cis,trans)-9,11-linoleate isomerase gene cloned from *L. reuteri* (SEQ ID NO:17), with the N-terminal sequence of the (cis,trans)-9,11-linoleate isomerase purified from *C. sporogenes* (SEQ ID NO:43), or with the N-terminal peptide sequence of a protein purified from Butyrivibrio that Park et al alleged to be a (cis,trans)-9,11-linoleate isomerase (discussed in Background Section above).

A protein pattern and profile search (ProfileScan at www.expasy.ch) was performed with the sequence PPAISOM$_{424}$ (SEQ ID NO:61) in order to detect putative functional domains in the isomerase. The results suggested that the N-terminal domain of the linoleate isomerase contained a putative NAD/FAD binding domain (PROSITE Profile No. PS50205). Specifically, this domain is located in the region spanning from amino acid residues 9–38 of SEQ ID NO:61. The NAD/FAD binding domain with the signature sequence Gly-Xaa-Gly-(Xaa)$_2$-Gly-(Xaa)$_3$-Ala-(Xaa)$_6$-Gly (positions 1 through 21 of SEQ ID NO:73, minus four additional Xaa residues from positions 14–17 of SEQ ID NO:73) is present in many different enzymes, such as dihydropyrimidine dehydrogenase (FIG. 58; SEQ ID NO:74), tryptophane monoxygenase (FIG. 58; SEQ ID NO:75), glutamate synthase (FIG. 58; SEQ ID NO:76), 6-hydroxy-L-nicotine oxidase (FIG. 58; SEQ ID NO:77), zeta-carotein desaturase (FIG. 58; SEQ ID NO:78), phytoene dehydrogenase (FIG. 58; SEQ ID NO:79) and polyamine oxidase (FIG. 58; SEQ ID NO:80). The consensus sequence is shown on the top of FIG. 58 (SEQ ID NO:73), with the position of the first residue in different enzymes shown on the left. The name of the enzymes along with their origin and GenBank Accession Nos. are given in the lower part of the figure. In addition to the characteristic signature residues, the present inventors found that a lysine residue is also conserved in this putative NAD-binding domain among the listed enzymes. The homology of the 10,12 linoleate isomerase with other enzymes extended slightly beyond the NAD-binding domain.

Interestingly, the (cis,trans)-9,11 linoleate isomerase from *Lactobacillus reuteri* (SEQ ID NO:18) also contained a putative FAD/NAD binding domain at positions 19 through 79 of SEQ ID NO:18. The putative FAD/NAD binding domain in SEQ ID NO:18 aligns with the consensus sequence of SEQ ID NO:73 as shown in FIG. 58, with a spacer of four extra amino acid residues between the consensus leucine at position 41 of SEQ ID NO:18 (position 13 of SEQ ID NO:73) and the consensus glycine at position 49 of SEQ ID NO:18 (position 21 of SEQ ID NO:73). Therefore, two different linoleate isomerases (i.e., a 9,11-linoleate isomerase and a 10,12-linoleate isomerase) share 40% identical amino acid residues over 34 residues (positions 11 through 44 of SEQ ID NO:61 and positions 27 through 41 and 46 through 63 of SEQ ID NO:18) if the 4-residue spacer at positions 42–45 of SEQ ID NO:18 is excluded. Also, the putative FAD/NAD binding domain is located near the N-terminus of both the 9,11- and the 10,12-linoleate isomerase protein sequence. Therefore, the (cis,trans)-9,11-linoleate isomerase from *Lactobacillus reuteri* and the (trans,cis)-10,12 linoleate isomerase from *Propionibacterium acnes* seem to share a putative functional domain, despite a lack of overall sequence homology between sequences.

The significance of the presence of a NAD/FAD binding site in linoleate isomerase is unclear at the present. It could play an important role in the conjugation of the double bonds even though the isomerase does not require NAD, NADP, FAD or other cofactors for its catalytic activity. The actual mechanism of the double bond isomerization of linoleic acid is currently poorly understood. This linoleate isomerase domain may be a good target for mutagenesis to study the structure/function of the isomerase. It is important to note that the (cis,trans)-9,11 linoleate isomerase is a membrane protein, with a major hydrophobic domain and some other regions of relatively weak hydrophobicity. The major hydrophobic domain located near the N-terminus seems to be the single putative transmembrane domain, which is supposed to also function as an uncleaved signal sequence for directing the protein into the membrane. In addition, this putative transmembrane domain overlaps the putative NAD-binding domain. On the other hand, the (trans,cis)-10,12 linoleate isomerase from *P. acnes* is a soluble protein with a few domains of weak hydrophobicity and the putative NAD-binding domain is located in the major hydrophobic domain at the N-terminus. The association of the (cis,trans)-9,11 linoleate isomerase with membrane and the 4-residue spacer presented in the putative NAD-binding domain may be related to a difference in positional and geometric specificity with regard to the (trans,cis)-10,12 linoleate isomerase.

A BLAST 2.0 search was performed with the sequences PPAISOM$_{424}$ using the standard parameters as set forth above. The linoleate isomerase was found to share a relatively low homology with a variety of different enzymes. In most cases, the homology was constrained to the short region of the putative NAD binding site. The isomerase shares 31% identical residues and 51% similar residues with polyamine oxidase precursor from *Zea mays* (GenBank, 064411) within a region of 115 amino acid residues (positions 8 through 122 of SEQ ID NO:61). It also shares 28% identical residues and 42% similar residues with tryptophan 2-monooxygenase from *Agrobacterium vitis* (GenBank, AAC77909.1) in an overlapping region of 167 residues (positions 8–175 of SEQ ID NO:61). The homology with the small subunit of the glutamate synthase from *Deinococcus radiodurans* (GenBank, AE001880) was 27% identical and 46% similar over an 88 amino acid sequence (positions 3–90 of SEQ ID NO:61). Another enzyme showing homology to linoleate isomerase is phytoene dehydrogenase, such as the one from *Cercospora nicotianae* (GenBank, P48537): 29% identical residues and 48% similar residues in an overlapping region of 163 amino acid residues (positions 2–165 of SEQ ID NO:61). The Fe—S subunit of the putative oxidoreductase from *E. coli* (GenBank, U28375) shares 11 contiguous identical amino acid residues with linoleate isomerase residues 12 though 22. Residues 10 through 21 of the isomerase were identical to the amino acid sequence deduced from a segment of the incompletely sequenced *Vibrio cholerae* genome (The Institute for Genomic Research, *V. cholerae* 666 1752).

The nucleotide sequence of the isomerase coding region, nPAISOM$_{1275}$ (SEQ ID NO:60), does not show any significant homology to the nucleotide sequence of the (cis,trans)-9,11-linoleate isomerase cloned from *L. reuteri* (SEQ ID NO:17). A BLAST 2.0 search was conducted with the nucleotide sequence nPAISOM$_{1275}$ (SEQ ID NO:60) using the standard parameters as set forth in the detailed description above. The isomerase gene showed no significant homology to other genes in the database (i.e., GenBank). The closest sequence sharing some homology with SEQ ID NO:60 was a phytoene dehydrogenase gene from *Cercospora nicotianae* (GenBank Accession No. U03903), which had only 30.1% similarity (i.e., not identity) with SEQ ID NO:60. The isomerase has 22 contiguous nucleotides (positions 393 through 414 of SEQ ID NO:60) identical to *Vicia faba* UDP-glucose:D-fructose-2-glucosyltransferase coding sequence (GenBank, M97551). A different stretch of 21 contiguous nucleotides of the isomerase (positions 633–653) was found in a segment of the incomplete *Sinorhizobium meliloti* genome (Stanford 382, smelil 423017E10.x1).

Example 14

The following example describes the sequencing and characterization of other open reading frames in the nucleic acid molecule nPAISOM$_{5275}$ of *P. acnes*.

The open reading frame A (ORFA) in the sequence nPAISOM$_{5275}$ (SEQ ID NO:59) spans from nucleotide positions 1 to 1073 (FIG. 52, A), and is represented by SEQ ID NO:63. A nucleic acid molecule having SEQ ID NO:63 is referred to herein as nPALPL$_{1073}$. A protein sequence of 358 amino acid residues with an incomplete C-terminus was deduced from nPALPL$_{1073}$ using the reverse complement of SEQ ID NO:63, with positions 1073–1071 (positions with regard to SEQ ID NO:63) forming the start codon. This protein showed some homology to lipases (see below) and is therefore designated LPL (lipase-like). This sequence is referred herein as PPALPL$_{358}$ (SEQ ID NO:64). The protein sequence PPALPL$_{358}$ is coded on the opposite DNA strand with respect to the open reading frame B (ORFB) and the linoleate isomerase gene. No obvious ribosome binding site could be identified with a reasonable spacing upstream from the first ATG codon of the open reading frame. Therefore, the actual translation start codon could not be determined at the present.

By BLAST 2.0 search no significant homology was found with respect to the nucleic acid sequence nPALPL$_{1073}$. A stretch of 22 contiguous nucleotides (positions 815–836 of SEQ ID NO:63) was identical to a segment of the *Bordatella pertussis* RNA polymerase sigma 80 subunit gene (Sanger 520, *B. pertussis* Contig54). The BLAST 2.0 search with the sequence PPALPL$_{358}$ showed that the protein sequence shares a low but significant homology to lipases. For example, the region spanning the positions 146–356 of SEQ ID NO:63 shares 26% identical and 42% similar amino acid residues with lipC from *Mycobacterium tuberculosis*. However, PPALPL$_{358}$ does not share significant homology to the lipase gene previously cloned from *P. acnes* (GenBank Accession No. X99255). The sequence GDSAG (positions 244–249 of SEQ ID NO:63) was conserved in many lipases and it fits the active-site serine motif (GXSXG) which is shared by various lipases, esterases and other hydrolytic enzymes.

A ProfileScan (protein pattern and profile search) was carried out with the protein sequence PPALPL$_{358}$. An esterase/lipase/thioresterase active site (PROSITE Profile No. PS50187) was found in the region 167–261 of SEQ ID NO:64. In addition, the region from the positions 213 to 268 of SEQ ID NO:64 contained a carboxylesterase type-B active site (GC0265). The sequence PPALPL$_{358}$ does not contain the exact lipase prosites (PROSITE Profile Nos. PS01173 and PS01174) that are present in the *P. acnes* lipase (GenBank Accession No. X99255). From these data, it was concluded that the open reading frame A in the sequence nPPALPL$_{1075}$ is likely to encode a lipase-like enzyme.

The open reading frame B (ORFB) (FIG. 52; B) is located up-stream to the *P. acnes* isomerase gene and is coded by the same strand as the isomerase gene. It spans the positions 1604 to 2386 of the sequence nPAISOM$_{5275}$ and is represented by SEQ ID NO:65. A nucleic acid molecule having SEQ ID NO:65 is referred herein as nPAUNK$_{783}$. This open reading frame codes an unknown protein of 260 amino acids residues and is designated PPAUNK$_{260}$ (SEQ ID NO:66). A putative ribosome binding site GAAGGAG (SEQ ID NO:67) is located up-stream from the first ATG codon, with a 4-base spacing. Therefore, this ATG codon is very likely the actual translation initiation codon of this open reading frame.

This open reading frame does not show a significant homology with any sequences in GenBank or unfinished microbial genomes. The highest BLAST score of the search with the protein sequence PPAUNK$_{260}$ was only 32 and the BLAST score for with the nucleotide sequence nPAUNK$_{783}$ was 40.

The open reading frame C (ORFC) (FIG. 52; C) is located down stream from the linoleate isomerase gene and is coded on the same DNA strand as the isomerase gene. It spans positions 4129 to 4710 in the sequence nPAISOM$_{5275}$ and is represented by SEQ ID NO:68. A nucleic acid molecule having SEQ ID NO:68 is referred to herein as nPAATL$_{582}$. This open reading frame may encode an acetyltransferase-like enzyme (ATL) of 193 amino acid residues (see below) and is denoted SEQ ID NO:69. A protein having the amino acid sequence of SEQ ID NO:69 is referred herein as PPAATL$_{193}$.

The first ATG codon of the open reading frame SEQ ID NO:68 is located 7 bases down stream from a putative ribosome binding site GGTAGGA (SEQ ID NO:70). In a BLAST 2.0 search with the nucleotide sequence nPAATL$_{582}$, no significant homology could be found with other sequences in the databases. However, the open reading frame shares 38% identical and 53% similar amino acid residues with a hypothetical protein from *Streptomyces coelicolor* (GenBank AL109732) in 56 amino acid residues overlap. It also shows a limited homology to a putative phosphoglucomutase from the plant *Arabidopsis thaliana* (GenBank AC008148) with 31% identical and 47% similar residues in 78 amino acid residues overlap.

More importantly, the protein sequence PPAATL$_{193}$ (SEQ ID NO:69) contains an acetyltransferase (GNAT) family profile (profile document PF00583). BLAST 2.0 search also shows that it has a low homology to three putative acetyltransferase genes in the database. It shares 29% identical and 35% similar amino acid residues over a region spanning positions 24–151 of SEQ ID NO:69 with the gene from *Deinococcus radiodurans* (GenBank AE001875). It shares 35% identical and 47% similar residues in 55 amino acid residues overlap with the N-terminal acetyltransferase complex, subunit ARD1 from *Methanolbacterium thermoautotrophicum* (GenBank AE000872). It shares 30% identical and 53% similar residues in 48 amino acid residues overlap with the acetyltransferase-related protein from *Thermotoga maritima* (GenBank AE001774). Therefore, the ORF C may encode an acetyltransferase-like protein.

In summary, the genomic region containing the isomerase gene, ORF B encodes an unknown protein. The other two ORFs encode enzymes related to lipases (ORF A) and acetyltransferases (ORF C), respectively. Therefore, this could be a genomic region rich in genes related to lipid/fatty acid modifications. Without being bound by theory, the present inventors believe that some of these genes could be involved in the rapid metabolism of (trans,cis)-10,12-CLA, accounting for the lack of accumulation of CLA in *P. acnes*.

Example 15

The following example describes the expression of the cloned *P. acnes* linoleate isomerase in *E. coli*.

Two oligonucleotide primers were synthesized to amplify the complete linoleate isomerase open reading frame. The primer, designated PA041-NdeI (SEQ ID NO:71) corresponds to positions 1–20 of the sequence nPAISOM$_{1275}$ (SEQ ID NO:60). This primer contains a NdeI site and 4 extra bases at the 5' end. The primer PA042-stop-XhoI (SEQ ID NO:72), is specific to the lower strand of the sequence nPAISOM$_{1275}$ and spans the position 1258–1275 of SEQ ID NO:60. It contains a XhoI site and 4 extra bases at the 5' end.

Genomic DNA prepared from *P. acnes* was used as template in a PCR reaction with the primers PA041-NdeI and PA042-Stop-XhoI. A PCR product of expected size of about 1.3 kb was generated, gel-purified and ligated with the expression vector pET24a(+) which had been digested with NdeI and XhoI. The ligation products were transferred into the *E. coli* host, One Shot TOP10 (Novagen). Potential clones carrying recombinant plasmid, designated pET-PAISOM, were analyzed by restriction digestion with NdeI and XhoI. Plasmid DNA showing the expected restriction patterns was transferred into an expression host, *E. coli* BL21 (DE3).

Figure 53:
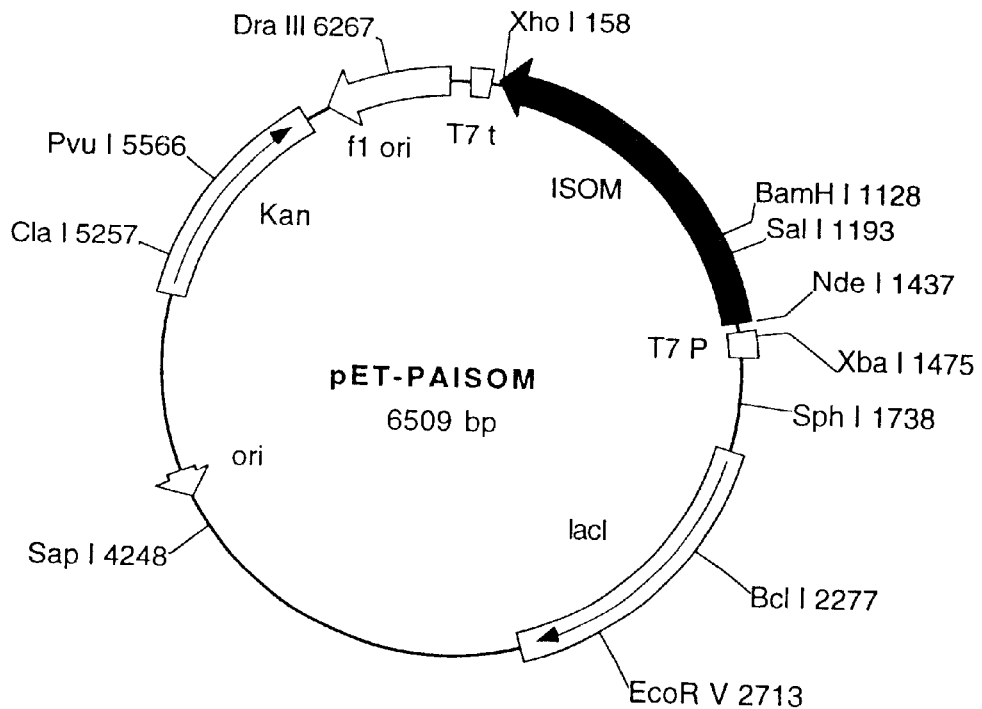
FIG. 53 is a map of the expression vector pET-PAISOM containing the complete *P. acnes* linoleate isomerase coding sequence.

In the recombinant plasmid pET-PAISOM (FIG. 53), the complete isomerase open reading frame was positioned downstream from the T7 promoter (for transcription control). The ribosome binding site with optimal spacing to the ATG codon was supplied by the vector. No extra codons or codon changes were introduced to the isomerase coding sequence.

An aliquot of a fresh overnight culture of the *E. coli* BL21 (DE3) cells containing the plasmid pET-PAISOM was used at a 1/100 ratio to inoculate 50 ml of LB medium supplemented with kanamycin at the concentration of 30 μg/ml. After a growth period of 3 hrs at 37° C., IPTG was added to the culture at the final concentration of 1 mM to induce the expression of the isomerase protein. Cells were grown for an additional period of 2 hrs after IPTG induction.

Figure 54:
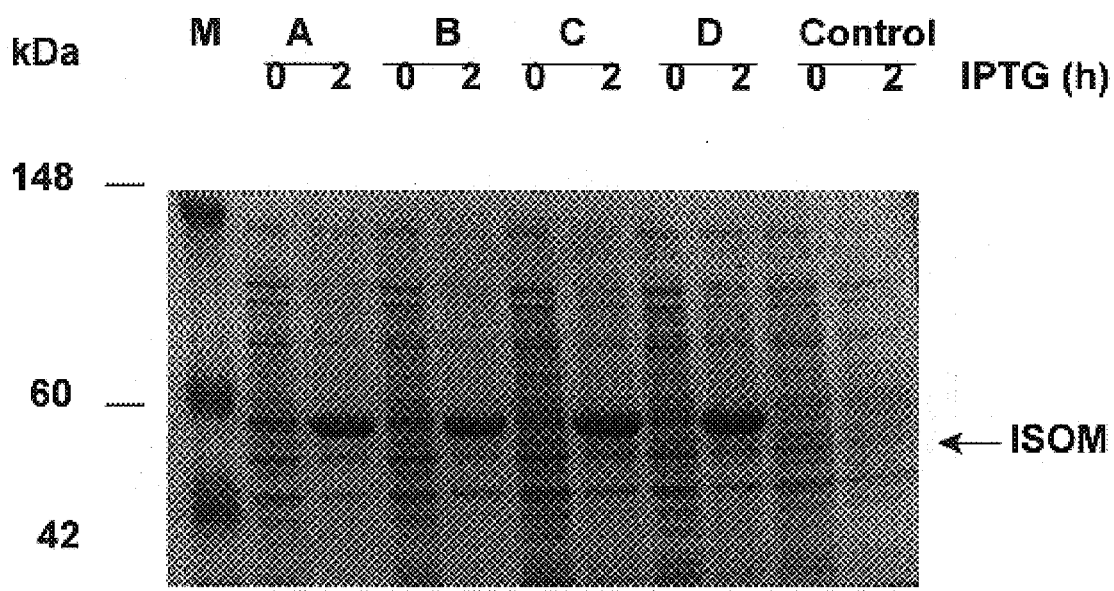
FIG. 54 is a digitized image of an SDS-PAGE showing IPTG induction of the expression of the recombinant *P. acnes* linoleate isomerase in *E. coli*.

Cells were sampled at the time of IPTG induction (0) and 2 hrs after IPTG induction (2) and the total cellular protein was analyze by SDS-PAGE. Four different clones (A–D) of plasmid pET-PAISOM were compared along with *E. coli* BL21 (DE3) cells without the isomerase gene as control. On SDS-PAGE, a peptide of about 50 kDa was seen as a predominant protein in the extract prepared from IPTG induced cells hosting pET-PAISOM (FIG. 54). This is consistent with the prediction made from the amino acid sequence and also with the size of the native linoleate isomerase purified from *P. acnes*. Without IPTG induction, the expression of the isomerase protein was very low. The 50-kDa protein band was not seen in the cell lysate of BL21 (DE3) without the isomerase gene. The data demonstrate a very high level expression in *E. coli* of the cloned linoleate isomerase protein with expected size.

Example 16

The following example describes the functional confirmation of the cloned linoleate isomerase.

Figure 55:
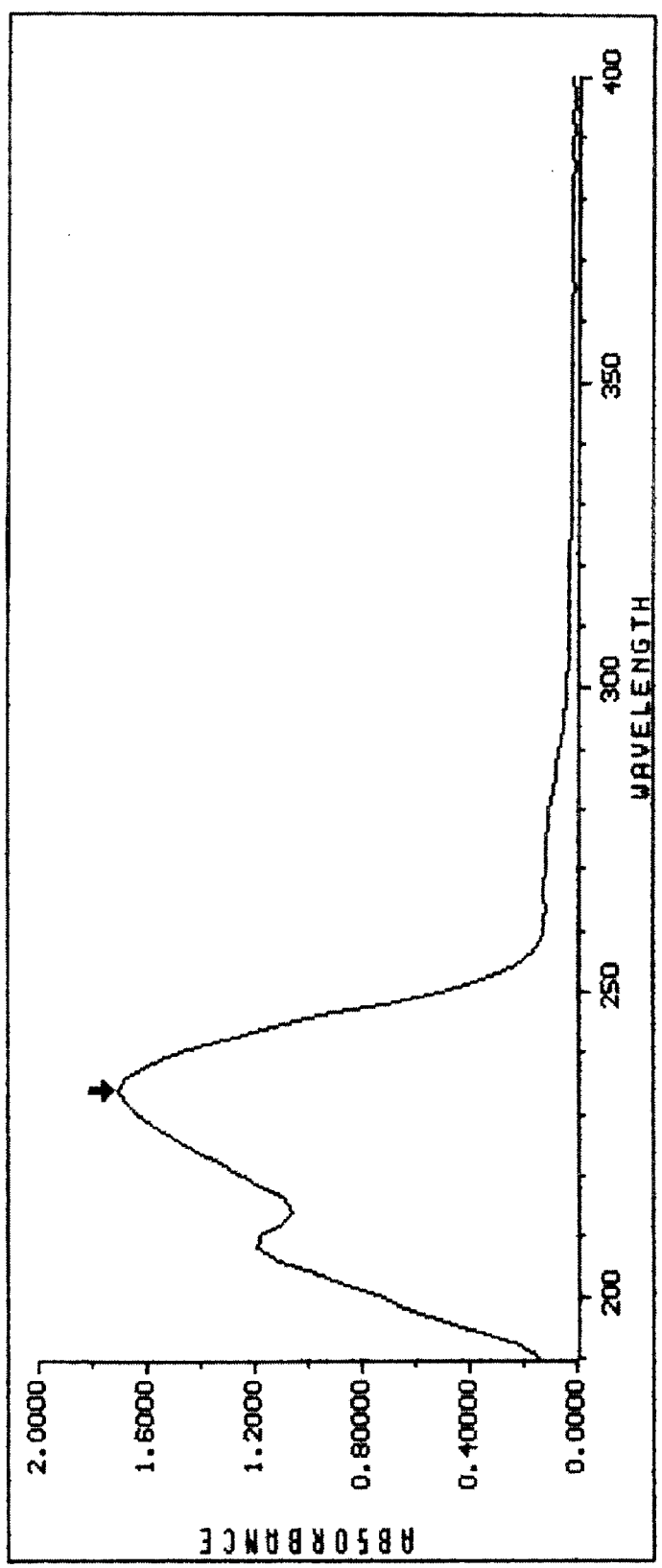
FIG. 55 is a graph showing the ultraviolet absorbence spectrum of the CLA produced by using the recombinant *P. acnes* linoleate isomerase.

To confirm the identity of the cloned isomerase gene, crude cell extracts prepared from *E. coli* cells expressing the isomerase protein were tested for isomerase enzyme activity by biotransformation of linoleic acid. The IPTG-induced culture of *E. coli* BL21 (DE3) cells hosting pET-PAISOM were harvested by centrifugation at 10,000 g at 4° C. The cell pellet was suspended into 5 ml of a lysis buffer (100 mM Tris-HCl, pH5.8; 10 mM NaCl, 10% glycerol). Cells were broken by a single pass through French Press (10,000 psi). The crude extract (cell lysate) was immediately incubated with 350 ppm of linoleic acid at room temperature with shaking at 150 rpm for one hour or overnight. Aqueous samples taken from enzyme reactions were extracted with 1 ml hexane. The hexane layer was removed and the absorbence at 234 nm was measured using a HP 8452A diode array spectrophotometer. Typically the entire spectrum in the 190–400 nm region was scanned to ensure that an actual peak at 234 nm was present. FIG. 55 shows the UV spectrum of such an extract. An absorbence peak at 234 nm was observed, as is typical of conjugated linoleic acids.

Figure 56A:
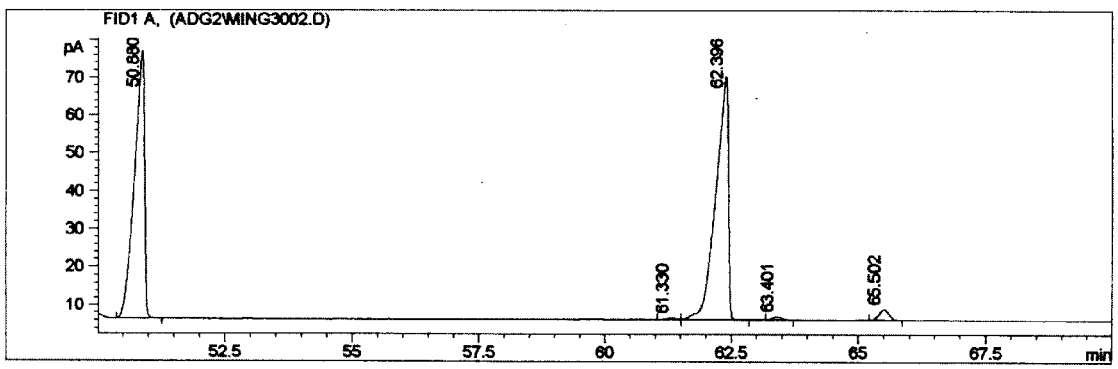
FIG. 56A is a graph showing the resolution of CLA isomers using a 100-m SP-2380 column.
Figure 56B:
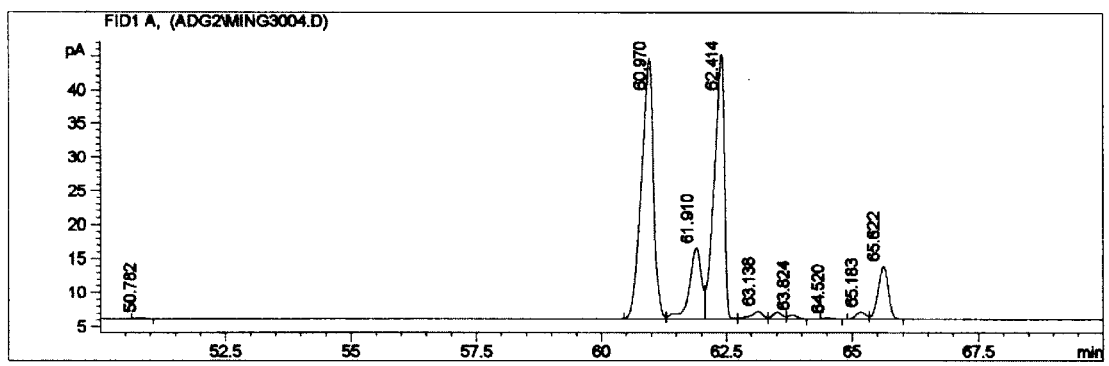
FIG. 56B is a graph showing the CLA produced by using the recombinant *P. acnes* linoleate isomerase.

In order to determine which of the CLA isomers was produced by the recombinant isomerase, methyl esters were prepared and analyzed by gas chromatography. Fatty acid methyl esters (FAMES) were formed by treatment with 4% HCl in methanol for 30 min at room temperature, followed by extraction with hexane. FAMES were analyzed by gas chromatography using a HP 6890 model chromatograph fitted with a flame ionization detector. The detector and injector were held at 250° C. After splitless injection, the column (Supelco SP-2380, 100 m, 0.25 mm ID) was held at 155° C. for 15 min, followed by an increase to 180° C. at a rate of 1° C./min. After a 30-min hold at 180° C., the temperature was increased to 220° C. at 10° C./min, and held at 220° C. for 5 min. The separation of a typical commercial CLA mixture is shown in FIG. 56A. Chemically synthesized CLA consists of a large number of structural and geometric isomers, most of which can be resolved on a 100-m column. The peak at 62.414 min represents the (trans,cis)-10,12-CLA isomer. FIG. 56B shows a typical analysis of a reaction mixture using crude cell extract containing the cloned isomerase. The only CLA peak observed elutes at essentially the same retention time as the (trans,cis)-10,12-CLA isomer.

Figure 57:
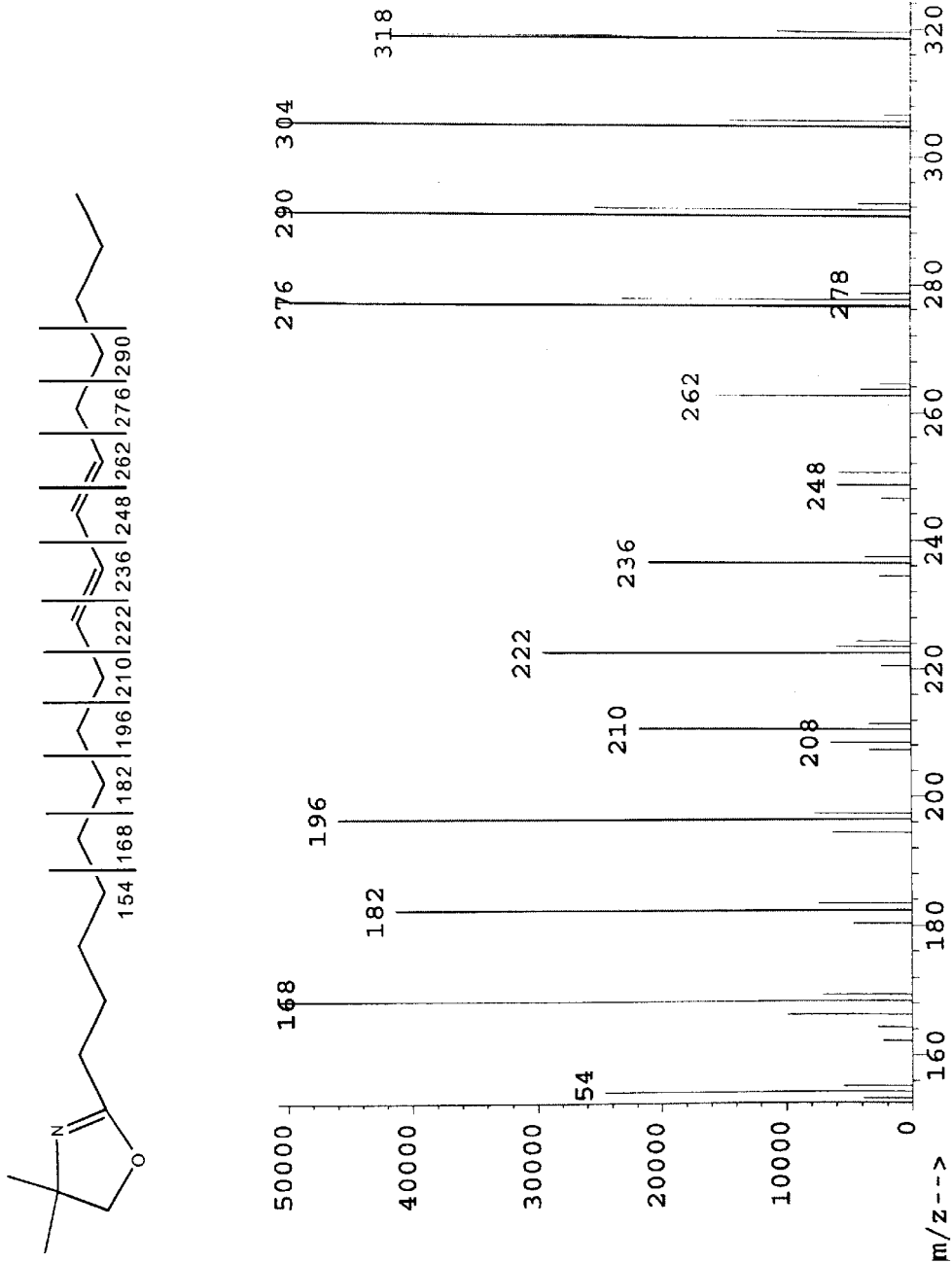
FIG. 57 is a graph of GC-MS spectrum of the DMOX derivative of the CLA produced by the recombinant *P. acnes* linoleate isomerase.

To further elucidate the double bond positions of the CLA molecules produced by the cloned isomerase, a DMOX (2-alkenyl-4,4-dimethyloxazoline) derivative was made and analyzed by gas chromatography-electron mass spectrometry. DMOX derivatives were formed by refluxing fatty acids with 500 μl 2-amino-2-methyl-1-propanol under nitrogen for 18 hrs at 160° C. After cooling, 5 ml water and 1 ml hexane were added, shaken, and the hexane layer removed for analysis. Samples were analyzed using a HP 5890A gas chromatograph fitted with a HP 5970 MS quadropole mass spectrometer. The injector and detector were held at 300° C. Splitless injection was made onto a Restec Rtx-5MS column (15 m, 0.25 mm ID). The oven temperature was initially 150° C., and was increased to 250° C. at 10° C./min with a final 10 min hold at this temperature. FIG. 57 shows the mass spectrum observed from a DMOX derivative of the putative (trans,cis)-10,12-CLA isomer formed by using the cloned isomerase. The fragmentation pattern clearly demonstrates unsaturations at positions 10 and 12, consistent with the other data already presented.

All of the biochemical data presented herein (i.e., the UV spectra, retention time on GC, and GC-MS spectra of DMOX derivative of the product of linoleic acid conversion) support the conclusion that the cloned isomerase gene from *P. acnes* indeed encodes a (trans,cis)-10,12-linoleic acid isomerase.

Example 17

The following example describes the purification and characterization of a linoleate isomerase from *Clostridium sporogenes*.

Previous work by the present inventors and by others has shown that *C. sporogenes* is capable of converting significant amounts of linoleic acid to CLA. The linoleate isomerase from *C. sporogenes* appears to have activity levels and characteristics most similar to that of *L. reuteri* PYR8. The following experiments describe the purification and characterization of the linoleate isomerase from this microorganism, with the goal to clone this isomerase gene, as has been described for *L. reuteri* in Example 5. The cloned *C. sporogenes* isomerase gene will be tested for functionality. It will also be compared to the isomerase genes cloned from *L. reuteri* and *P. acnes*.

*C. sporogenes* ATCC 25762 was grown in a Brain Heart Infusion Broth (BHI) medium under anaerobic conditions. Bacterial growth was measured with a spectrophotometer at 600 nm. When cells were grown at 37° C., pH 7.5, stationary phase was reached after 6 hours incubation. Further incubation resulted in rapid lysis of the culture. Cultures were harvested, therefore, after about 6 hours of growth. The cell pellet was washed with 0.1 M Tris, pH 6.0, containing 15 mM NaCl.

Biotransformation of linoleic acid to CLA was performed by resuspending harvested cells in fresh growth medium containing 200 ppm linoleic acid. After incubation, fatty acids were extracted with hexane and analyzed by gas chromatography using an isothermal program at 215° C. for 14 minutes. FIGS. 23A–D shows a time course of biotransformation of linoleic acid by *C. sporogenes*. Resuspended cells were grown under aerobic (FIGS. 23A & C) or anaerobic (B & D) conditions at room temperature (A & B) or at 37° C. (C & D). A rapid production of cis9,trans11-CLA with a simultaneous decrease in linoleic acid was observed within 30 minutes under all conditions tested. Similar amounts of CLA were formed under aerobic and anaerobic conditions. Upon further incubation, t9, trans11-CLA accumulated at the expense of cis9,trans11-CLA. Upon extended incubation (15–20 hours), cis9,trans11-CLA disappeared. Apparently the CLA was metabolized further.

Figure 24:
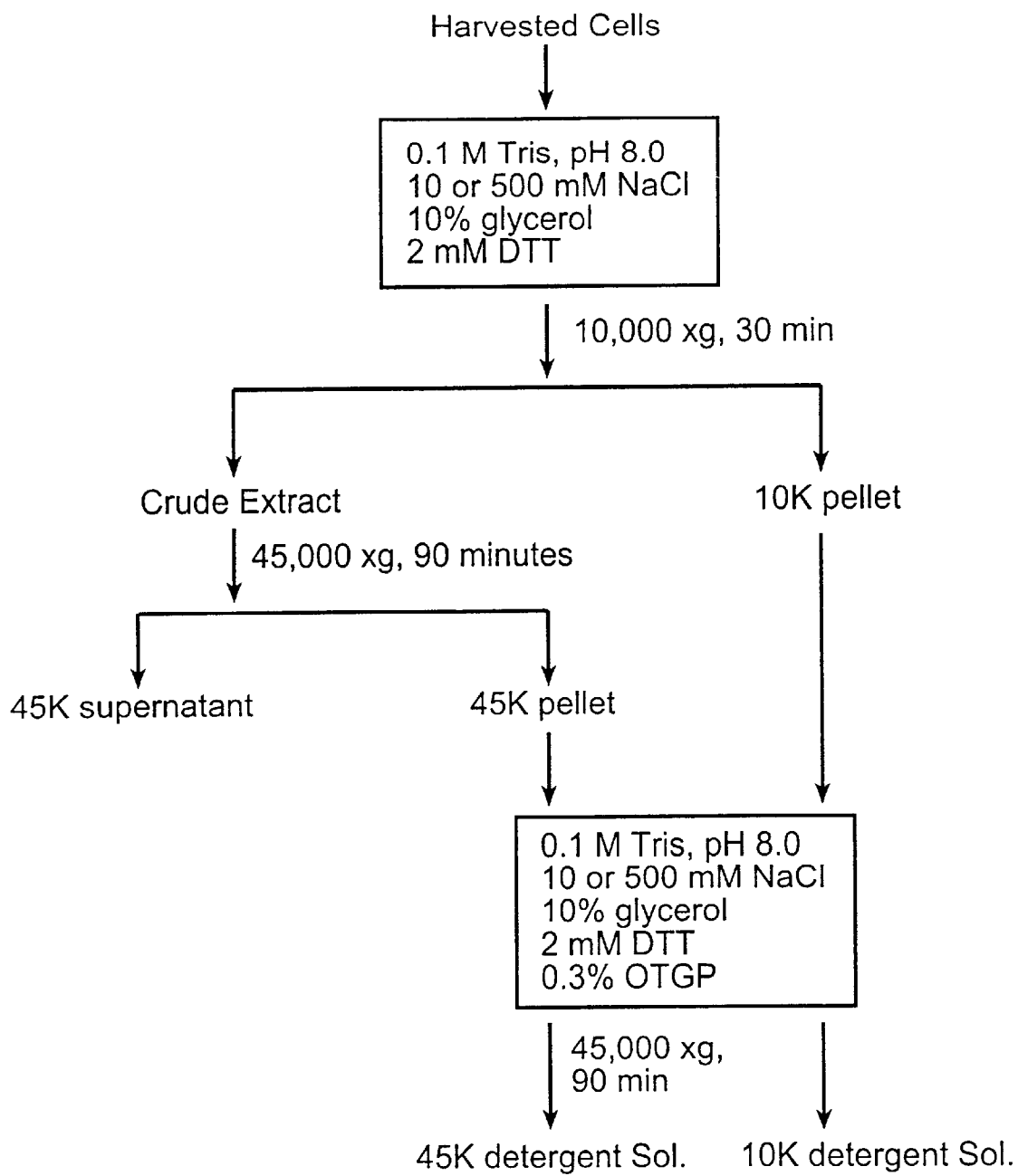
FIG. 24 is a flow diagram showing an extraction protocol for *C. sporogenes* ATCC 25762.

The cells were extracted as described in FIG. 24 to give four principal fractions. Tables 2 and 3 show the distribution of isomerase activity and protein concentration in fractions which were prepared with low salt (10 mm NaCl) from frozen cells and with high salt (500 mM NaCl) from fresh cells, respectively. Enzyme activity was detected in all fractions. The highest activity was found in the 45 k/0.3% OTGP soluble fraction. It has been reported that detergents require high concentration of salt for effective solubilization of membrane proteins. Addition of NaCl in extract buffer resulted in increasing specific activity (Table 2), indicating the effectiveness of high salt. The specific activity was at least 50-fold higher in high salt detergent soluble fractions (Table 3) than in low salt detergent soluble fractions (Table 2). Conditions under which the active cultures are stored could also affect activity. These results suggested that the *C. sporogenes* linoleate isomerase has characteristics similar to the *L. reuteri* PYR8 membrane-associated enzyme.

TABLE 2

Linoleate Isomerase Activity - Low Salt Extracts of Frozen Cells

| Fraction | Protein (mg/ml) | Total Protein (mg) | *OD$_{234}$ | Specific Activity (OD$_{234}$/60 min/mg protein) |
|---|---|---|---|---|
| Crude Extract | 6.8 | 408 | 0.26 ± 0.01 | 0.38 |
| 45K Supernatant | 4.8 | 288 | 0.12 ± 0.01 | 0.25 |
| 45K OTGP Soluble | 1.2 | 30 | 0.05 ± 0.00 | 0.41 |
| 10K OTGP Soluble | 2.9 | 73 | 0.05 ± 0.01 | 0.17 |

*OD$_{234}$ was determined in an assay using 0.1 ml of enzyme extract

TABLE 3

Linoleate Isomerase Activity - High Salt Extracts of Fresh Cells

| Fraction | Protein (mg/ml) | Total Protein (mg) | *OD$_{234}$ | Specific Activity (OD$_{234}$/60 min/mg protein) |
|---|---|---|---|---|
| Crude Extract | 6.0 | 390 | 0.66 ± 0.02 | 1.10 |
| 45K Supernatant | 6.0 | 390 | 0.31 ± 0.02 | 0.51 |

TABLE 3-continued

Linoleate Isomerase Activity - High Salt Extracts of Fresh Cells

| Fraction | Protein (mg/ml) | Total Protein (mg) | *$OD_{234}$ | Specific Activity ($OD_{234}$/60 min/mg protein) |
|---|---|---|---|---|
| 45K OTGP Soluble | 0.8 | 20 | 0.16 ± 0.01 | 20.0 |
| 10K OTGP Soluble | 2.0 | 44 | 0.25 ± 0.01 | 12.5 |

*$OD_{234}$ was determined in an assay using 0.1 ml of enzyme extract

Figure 25:
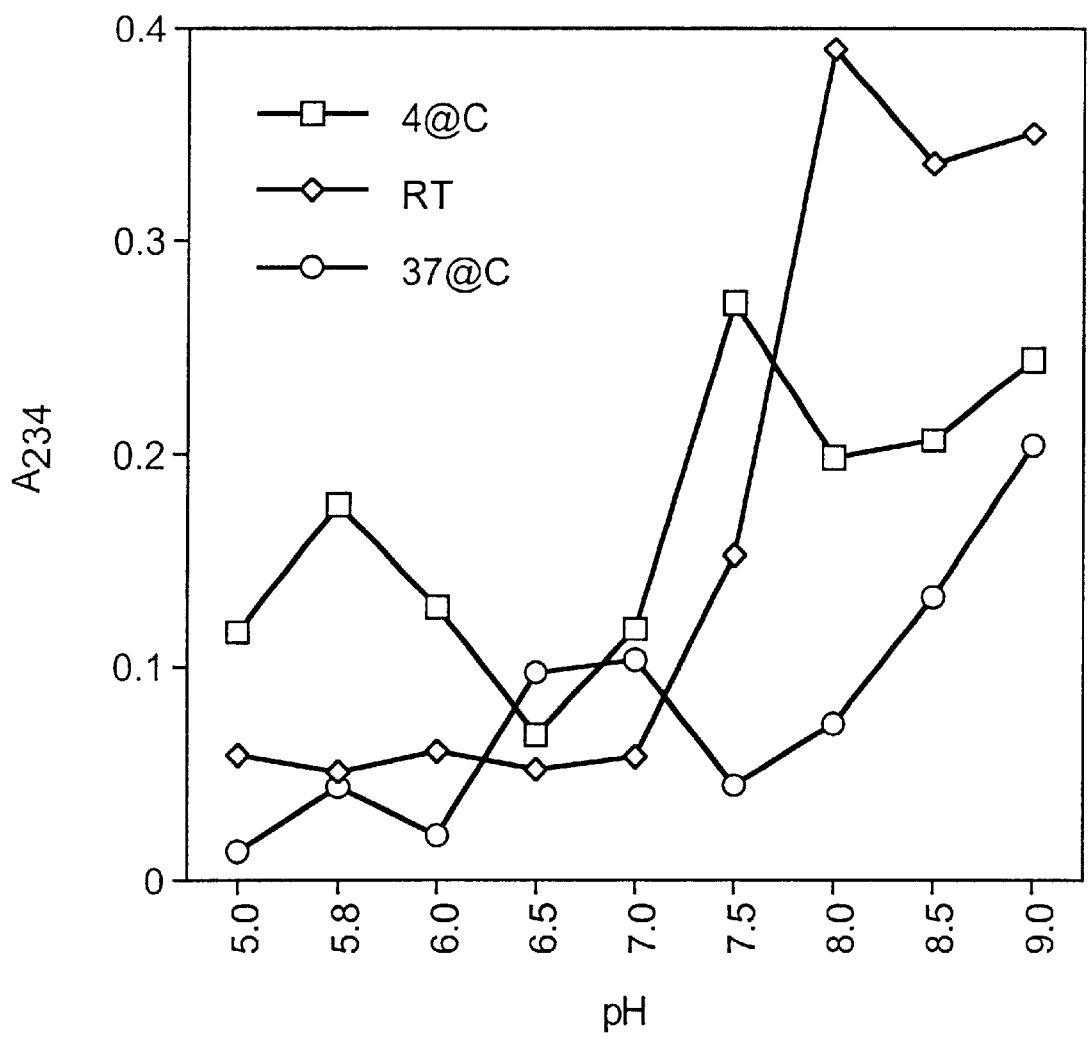
FIG. 25 is a line graph showing linoleate isomerase optimum pH and temperature in *C. sporogenes* ATCC 25762.

Temperature sensitivity of the isomerase in crude extracts was tested at 4° C., room temperature (~25° C.) and 37° C. The best temperature for the isomerase activity was room temperature (FIG. 25). The isomerase activity decreased to 73% of optimum at 4° C. and 63% of optimum at 37° C. The optimum pH was monitored by adjusting the pH from 5.0 to 9.0 using the 0.1M Tris buffer containing 10 mM NaCl, 1 mM DTT and 40 ppm linoleic acid. The optimum pH was found to be 7.5, 8.0 and 9.0 for incubating at 4° C., room temperature and 37° C., respectively (FIG. 25).

Figure 26:
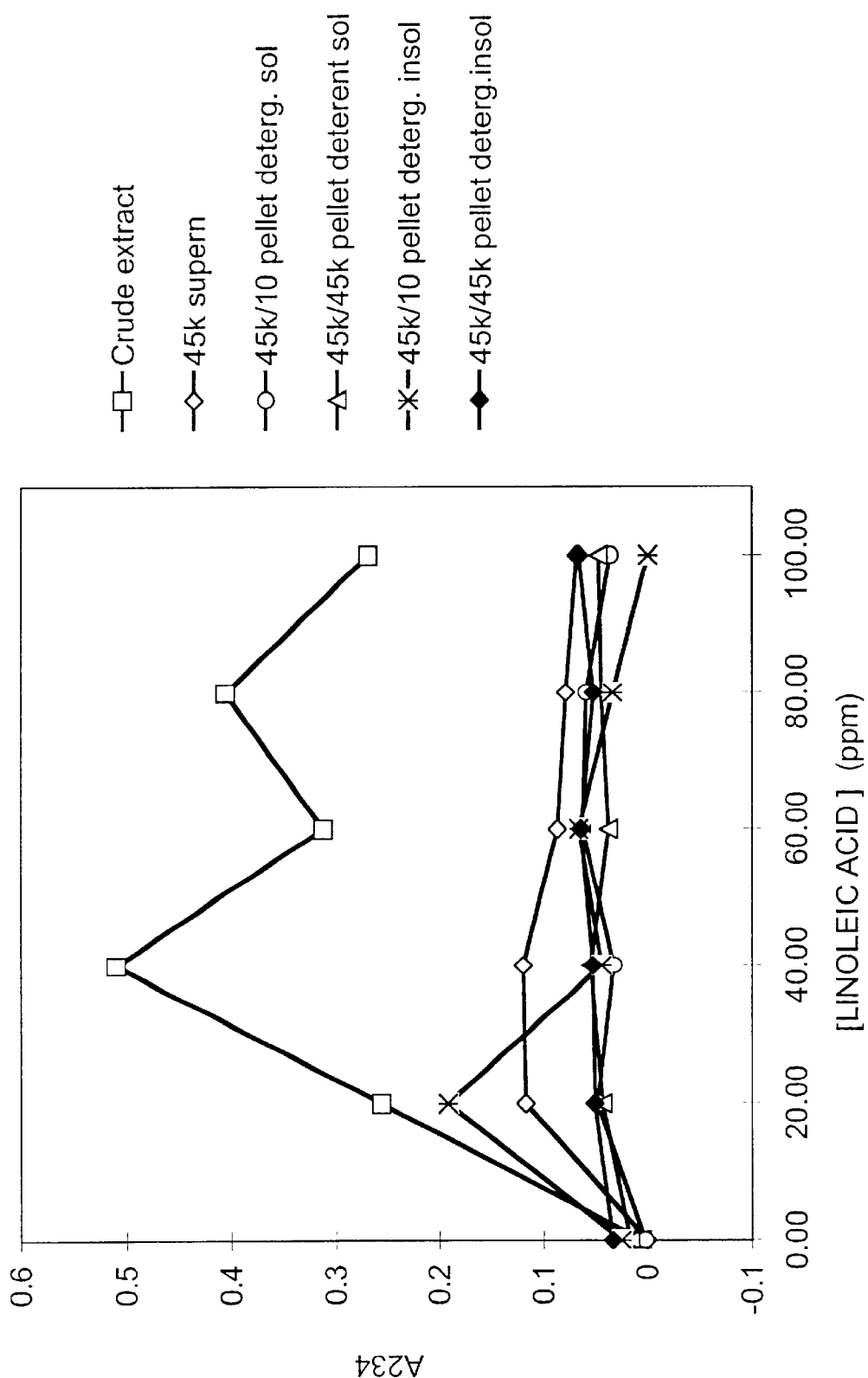
FIG. 26 is a line graph showing optimum linoleic acid concentration for *C. sporogenes* ATCC 25762 linoleate isomerase.
Figure 27:
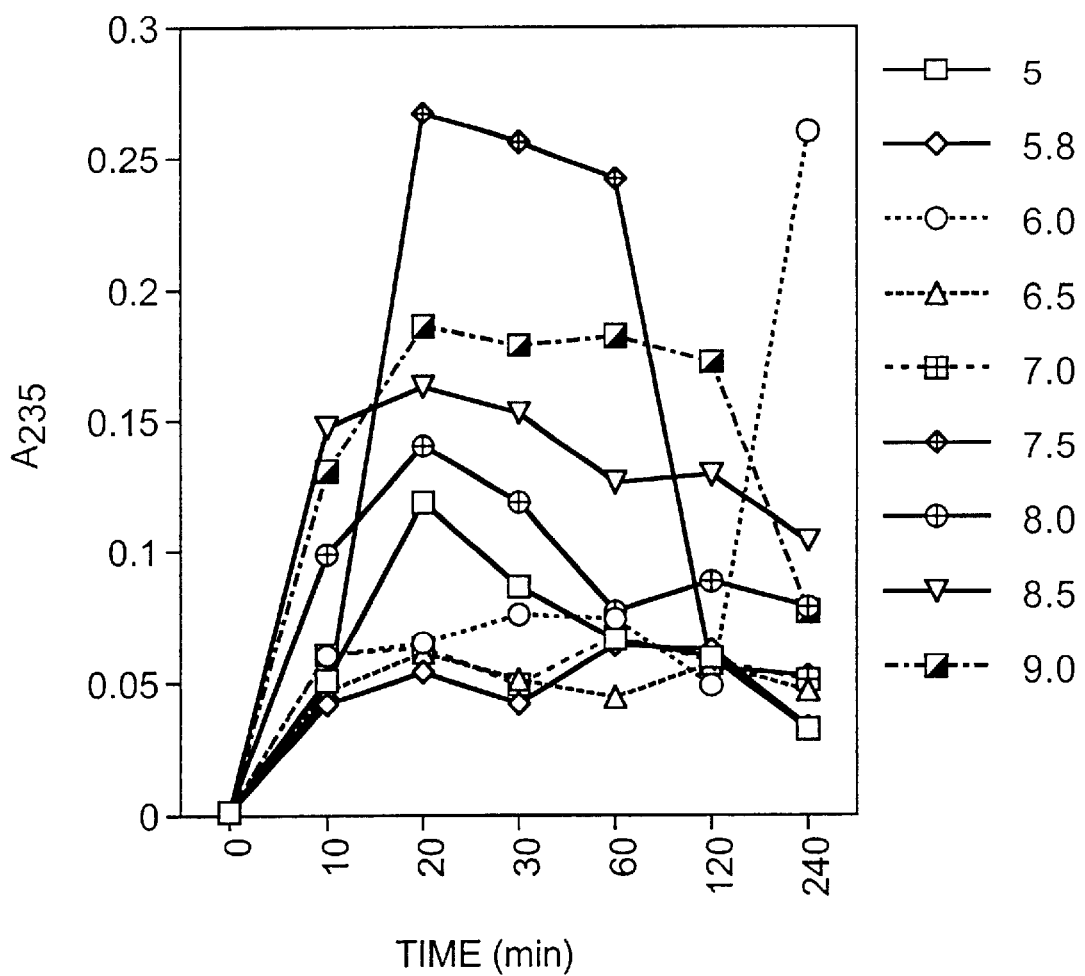
FIG. 27 is a graph showing the time course for CLA formation by *C. sporogenes* ATCC 25762 linoleate isomerase.

The concentration of linoleic acid was tested from 0 to 100 ppm (FIG. 26). The optimum concentration for linoleic acid was determined to be 40 ppm. A time course study indicated that the activity responded linearly within 20 minutes and showed a slight decrease upon 60 minutes incubation at optimum pH, temperature and substrate concentration (FIG. 27).

Figure 28:
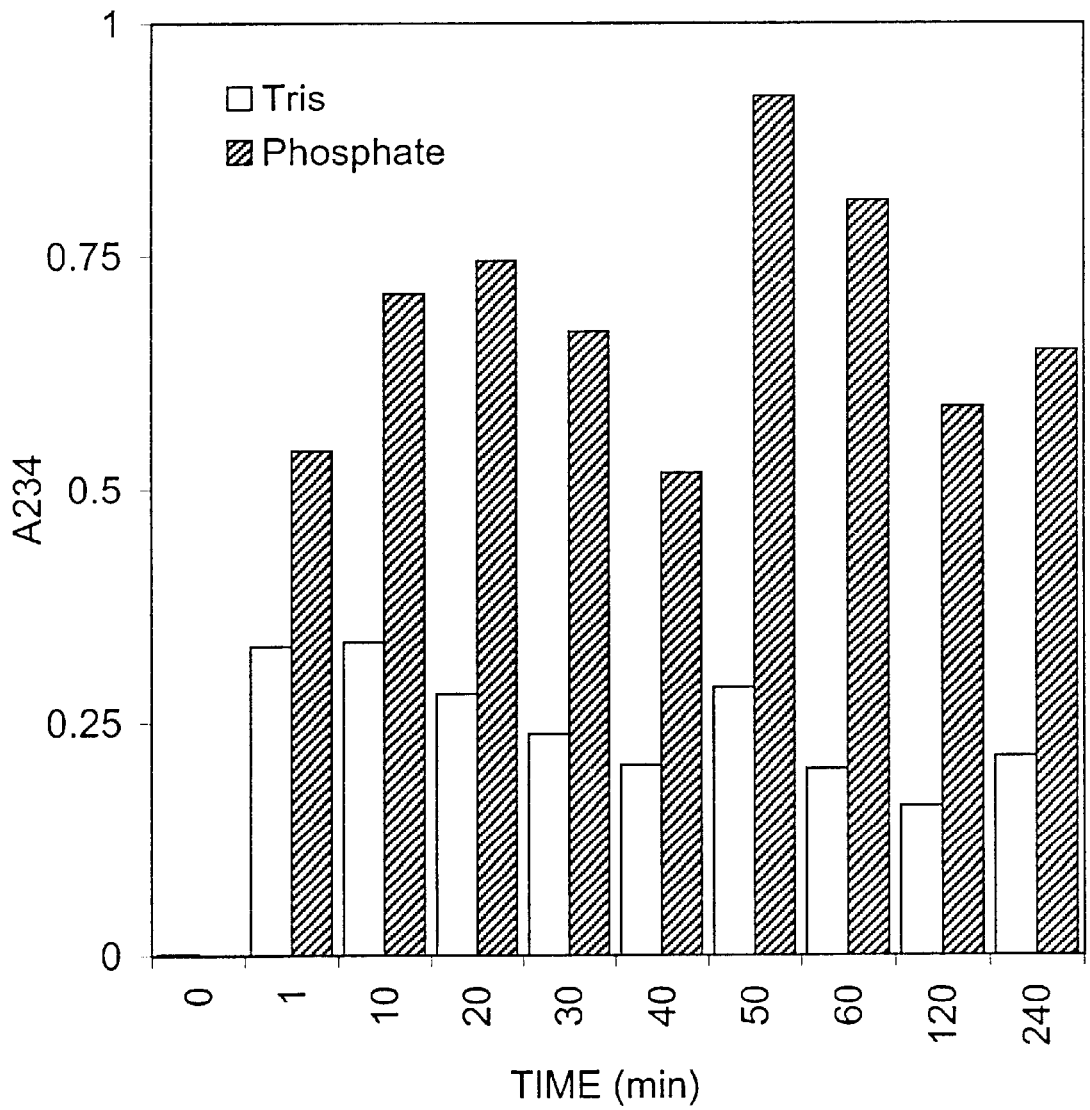
FIG. 28 is a bar graph illustrating the stability of *C. sporogenes* ATCC 25762 linoleate isomerase in Tris and phosphate buffers.

The C. sporogenes isomerase was alternatively extracted by sonication in 0.1 M Tris, pH7.5, 10 mM NaCl, 2 mM DTT and 10% glycerol. This extraction was of higher efficiency (about 20%) than that by French press. This is different from the isomerase isolated from L. reuteri, wherein it was observed that sonication resulted in a total loss of activity. Isomerase activity was higher in phosphate buffer, pH 7.5, than in Tris buffer, pH 7.5 (FIG. 28). The enzyme was most stable in phosphate buffer.

The detergent soluble fraction was further purified by Method A, B or D, infra.

Method A

Figure 29:
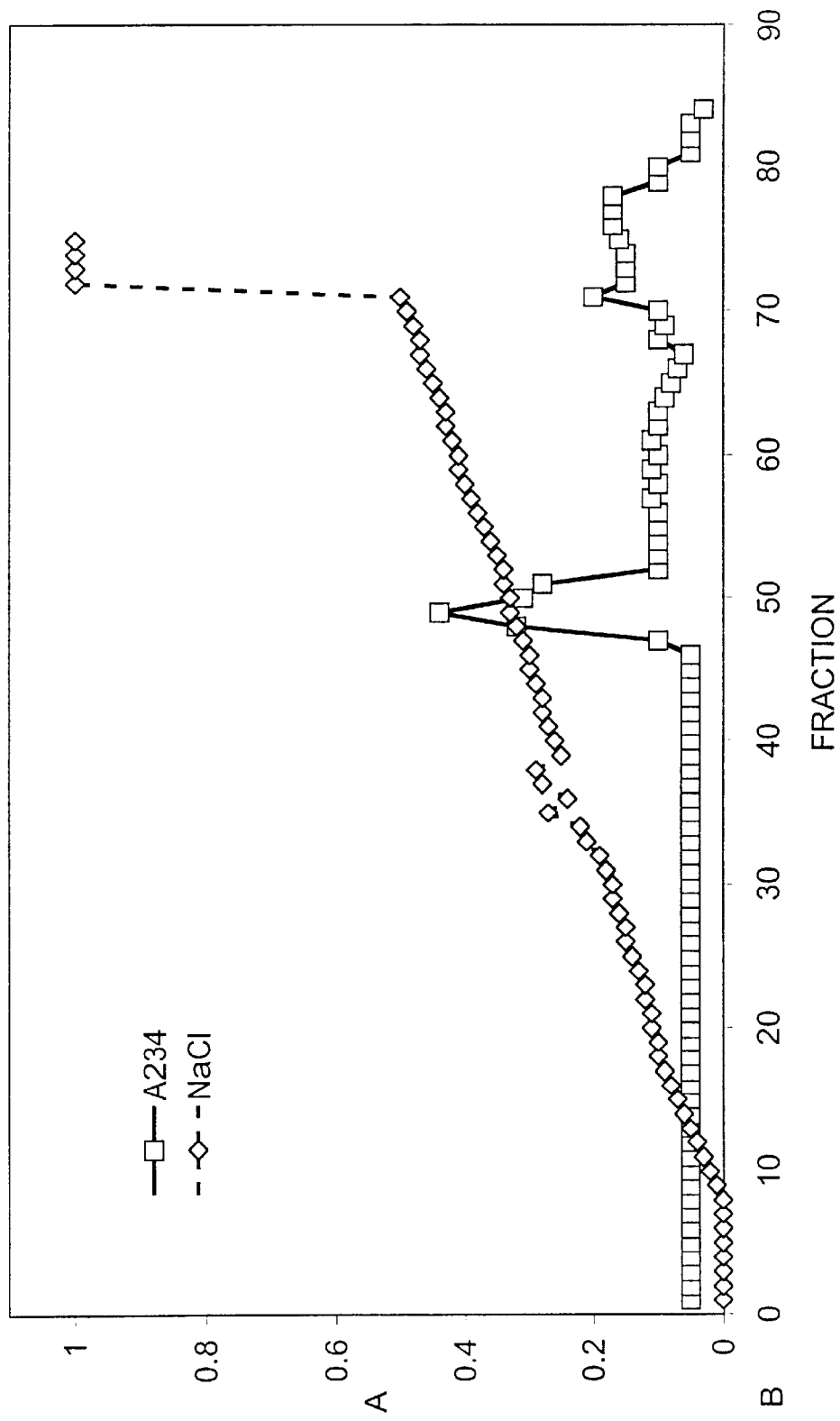
FIG. 29 is an elution profile of fresh *C. sporogenes* ATCC 25762 linoleate isomerase extracts from DEAE-5PW.

Experimental conditions for purification of the isomerase by DEAE-5PW chromatography have been established. Under these conditions, 75% of the isomerase was recovered. FIG. 29 gives an overview of the purification of the isomerase from OTGP solubilized protein. Three experiments were performed with similar results: the C. sporogenes isomerase eluted from the column by 0.5 M NaCl. The peak fractions (#48 to #51) contained 60% of the isomerase loaded on the column, resulting in a 6-fold purification to an average specific activity of 32. The column was eluted further with 1M NaCl, and putative enzyme activity was detected by UV analysis (linoleic acid (LA) was apparently converted into products with spectra identical to CLA). However, analysis of these fractions by GC showed that the major product of the conversion had a retention time of 13 minutes, while the retention time of cis9,trans11-CLA is about 10 minutes. Although this peak was minor as compared to the peak eluted by 0.5 M NaCl, this data suggested that C. sporogenes cells may have the ability to produce other isomers of CLA. It was observed that a freshly prepared extract should be used to achieve a high recovery of isomerase activity by ion-exchange chromatography, because the detergent solubilized protein tended to lose activity or it precipitated after storage at 4° C. for more than 3 days (data not shown).

A rapid spectrophotometric assay for CLA, measuring absorbence at $OD_{234}$ (detects conjugated double bonds in fatty acids as well as other UV absorbing compounds), was used to estimate CLA concentration in column eluate fractions. It was important to confirm that the $OD_{234}$ absorbing material was CLA before attempting further purification. Gas chromatography was used for this purpose. Comparison of the $OD_{234}$ data with the result obtained by gas chromatography showed good correlation, indicating that the "active" fractions collected contained the desired isomerase enzyme activity.

Isomerase was partially purified on DEAE with acceptable minimal loss of activity as described above. However, the activity of pooled enzyme fractions decreased by 50% after overnight storage at 4° C. In some experiments, no activity was detected after DEAE purification. Therefore, it would be important to maintain the enzyme activity to continue purification.

It was demonstrated that the C. sporogenes linoleate isomerase is a membrane protein. The detergent, octyl-thioglucopyranoside (OTGP), has been used successfully to solubilize isomerase. Unfortunately, OTGP (and the solubilized enzyme) precipitated slowly during purification at 4° C. A nondenaturing detergent, Triton X-100 with a high concentration of salt, is commonly used to distinguish between peripheral and integral membrane proteins. No significant difference was found in the efficiency of the solubilization between 1% Triton X-100 and 0.3% OTGP. Less total protein was solubilized with a mixture of 0.1% Triton X-100 and 0.3% OTGP. The efficiency of solubilization by 1 M NaCl alone was very low, indicating that the isomerase is an integral membrane protein.

Method B

Figure 30:
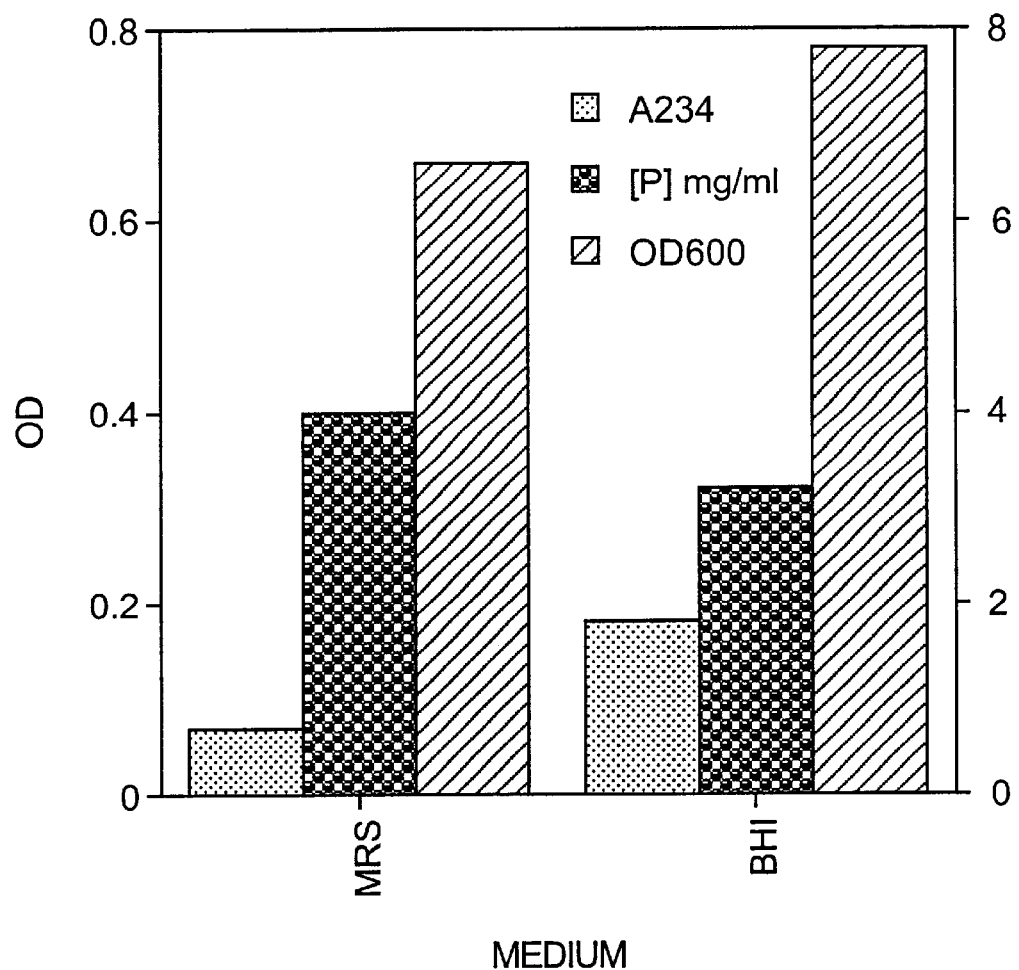
FIG. 30 is a bar graph demonstrating the effect of culture medium on *C. sporogenes* ATCC 25762 growth and linoleate isomerase activity.

It was clearly necessary to improve the activity and stability of the C. sporogenes isomerase. Two different media, BHI and MRS, were tested. Results are shown in FIG. 30. At pH 7.0, less isomerase was produced in MRS medium, although a higher total protein was obtained. There is no difference in stability of isomerase produced in either medium. Protease inhibitors, PMSF (0.1–1.0 mM), iodoacetamide (1 mM) and pepstatin A were tested for their effects on the stability of the isomerase. None provided measurable benefit.

Figure 31:
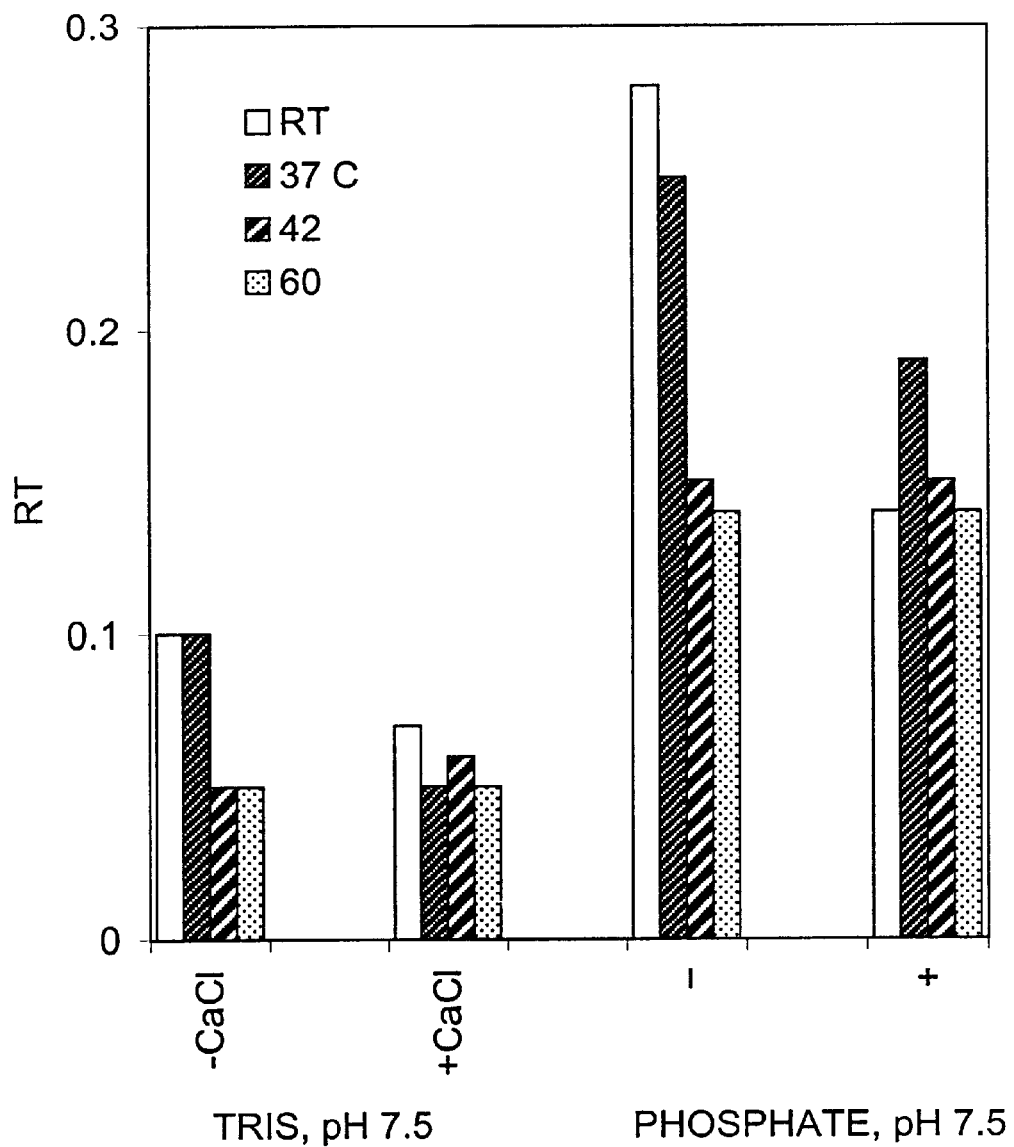
FIG. 31 is a bar graph showing the effect of $CaCl_2$ on *C. sporogenes* ATCC 25762 linoleate isomerase activity.

It has been reported that solubilization in the presence of lysophosphatidylcholine (LPC) allows higher detergent concentrations to be used, thus allowing more complete membrane protein solubilization. $CaCl_2$ can activate enzymes, such as some nucleases. Added $CaCl_2$ plus LPC has been demonstrated to stabilize detergent solubilized sodium channel membrane proteins. None of these positive effects was observed on the linoleate isomerase. Moreover, $CaCl_2$ decreased the enzyme activity in both Tris and phosphate buffer systems. At temperatures higher than 37° C., $CaCl_2$ had no effect on the activity, but the isomerase activity was reduced to 50% at the temperatures of 42° C. and 60° C. (FIG. 31).

Figure 32:
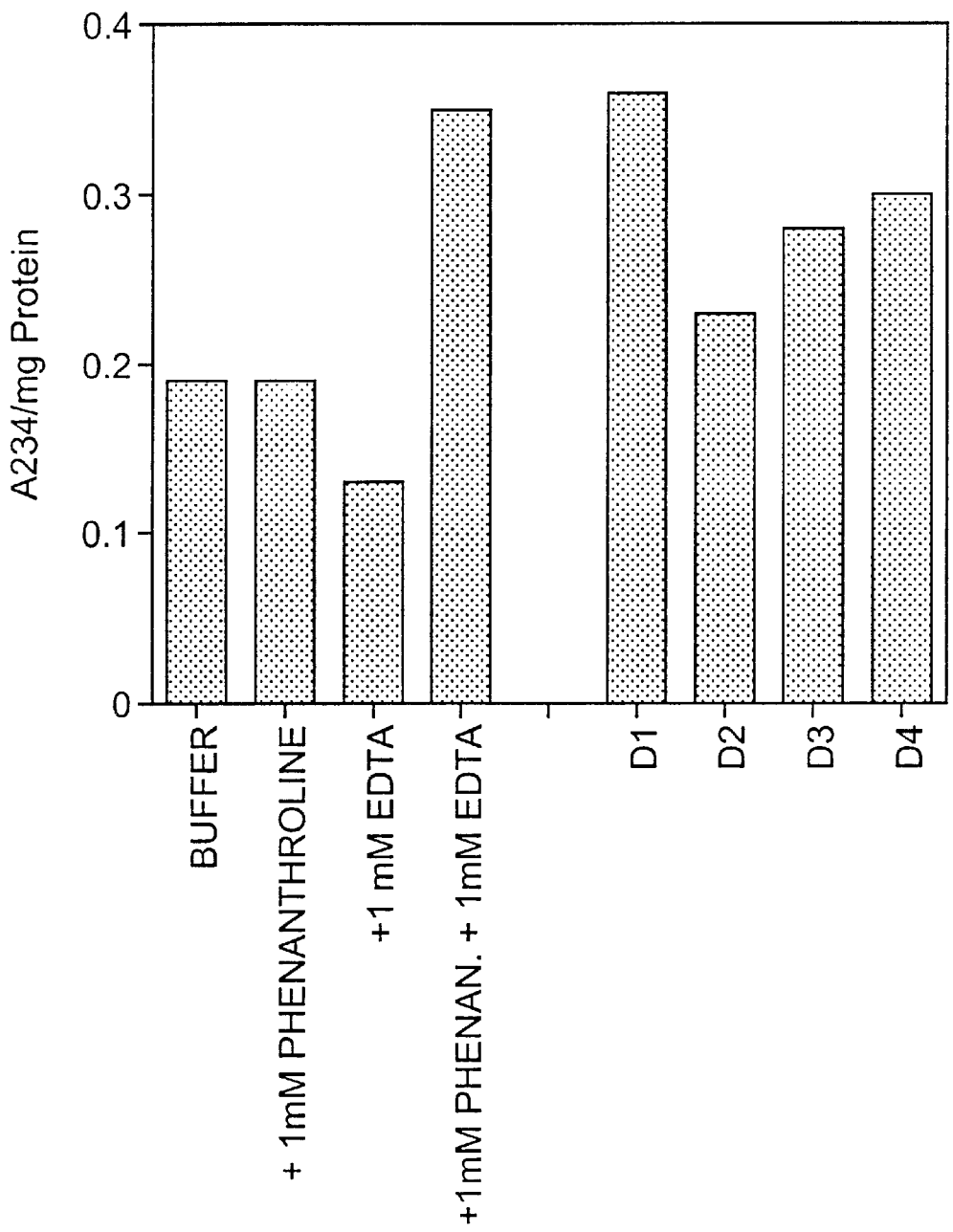
FIG. 32 is a bar graph showing the effect of chelating agents on *C. sporogenes* ATCC 25762.
Figure 33:
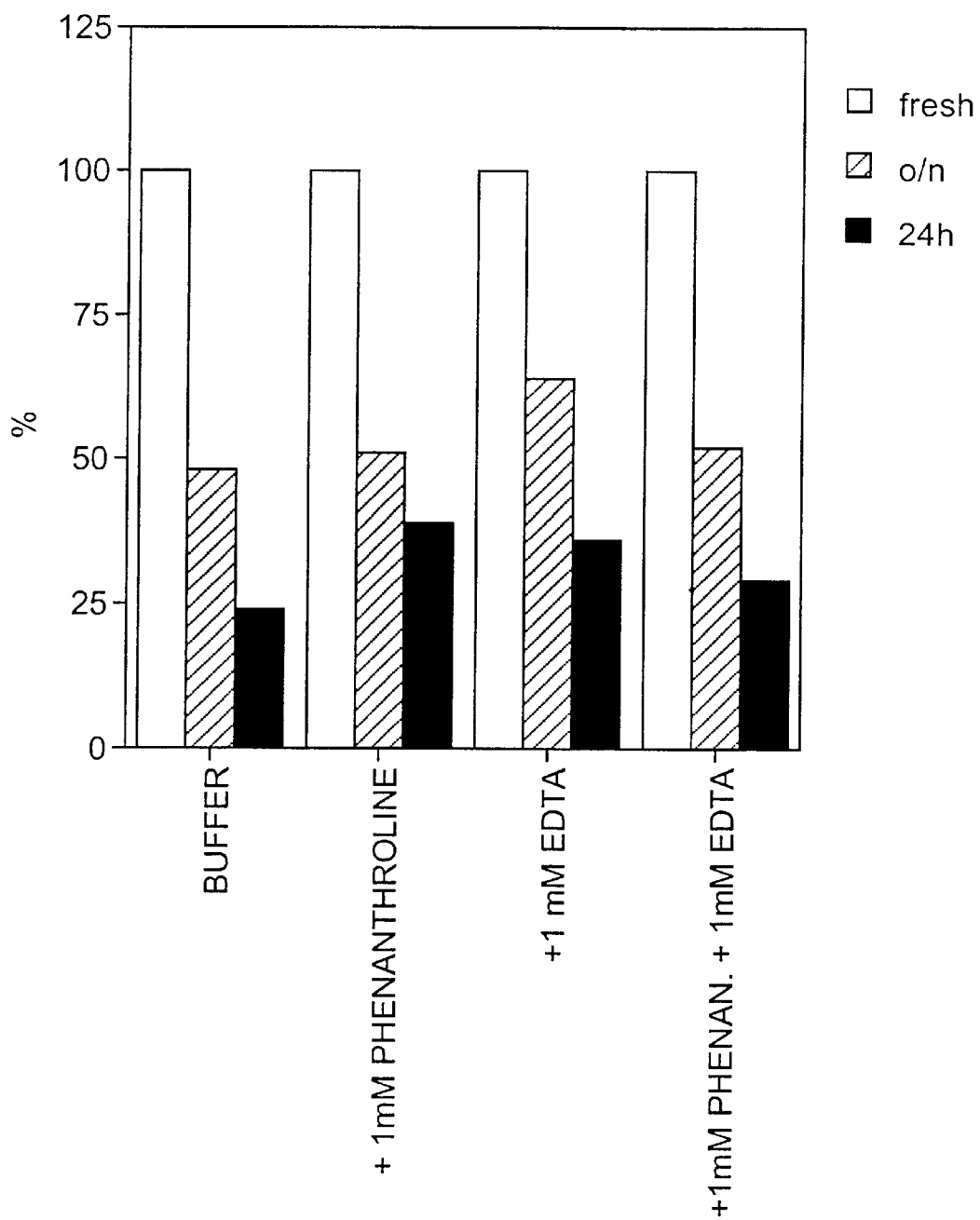
FIG. 33 is a bar graph showing the effect of chelating agents on stability of linoleate isomerase.

FIG. 32 shows the effect of the iron-chelating agents, phenanthroline and EDTA, on the enzyme activity and stability. It seems that the enzyme in crude extracts was protected by phenanthroline. This protection was more effective when 1 mM of phenanthroline was combined with 1 mM EDTA, although addition of 1 mM EDTA had a negative effect. In contrast, the addition of iron-chelating compounds to detergent buffer resulted in a loss of activity during the enzyme preparation, but a slight increase in stability (FIG. 33).

Prior to efforts to further purify the 9,11-linoleic acid isomerase from C. sporogenes, endeavors were made to increase the stability of the enzyme in crude extracts and in the detergent soluble fraction.

Figure 34:
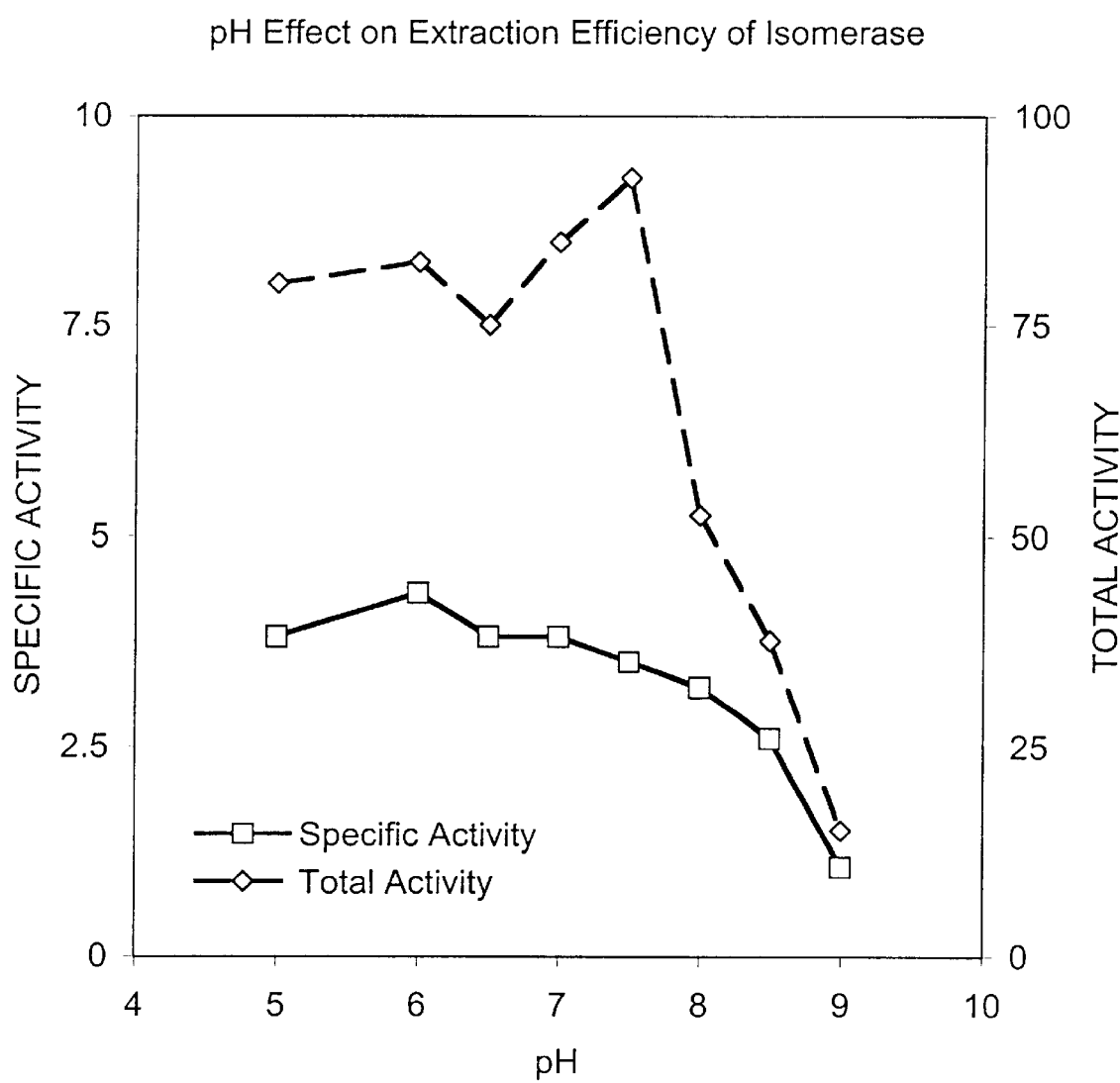
FIG. 34 is a line graph illustrating the effect of pH on extraction efficiency of linoleate isomerase in *C. sporogenes* ATCC 25762.
Figure 35:
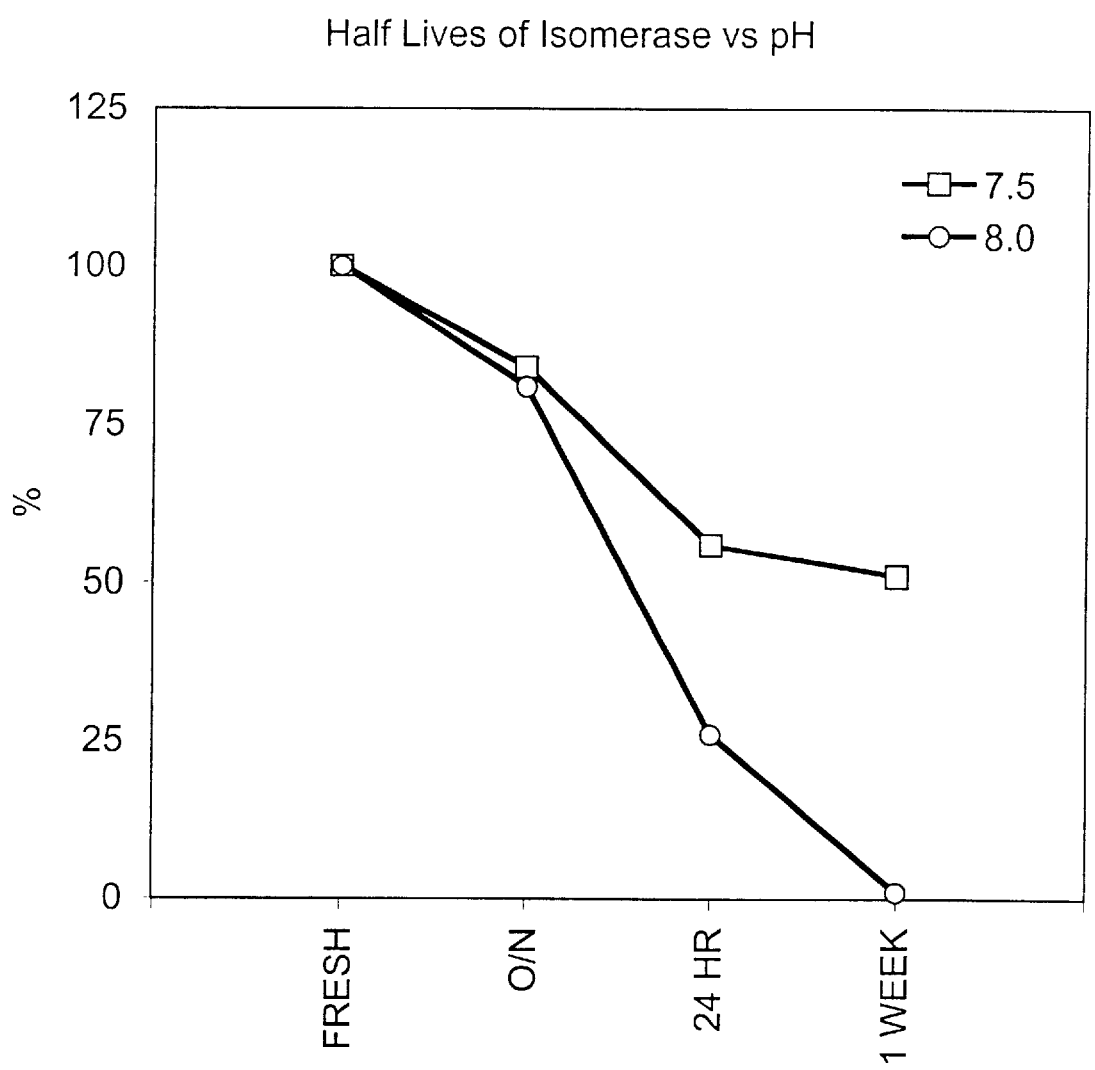
FIG. 35 is a line graph demonstrating the half lives of linoleate isomerase in *C. sporogenes* ATCC 25762 versus pH.

The effect of pH and type of buffer used during enzyme extraction, on extraction efficiency and on enzyme stability were examined. Crude extracts were prepared with 0.1 M Tris buffer at pH 5.0–9.0. The pH during extraction had a strong impact on both extraction efficiency and enzyme stability. The optimum pH for the extraction of the isomerase was 7.5 (FIG. 34), and at this pH, the half-life of isomerase was extended from one day at pH 8.0 to one week (FIG. 35).

Figure 36:
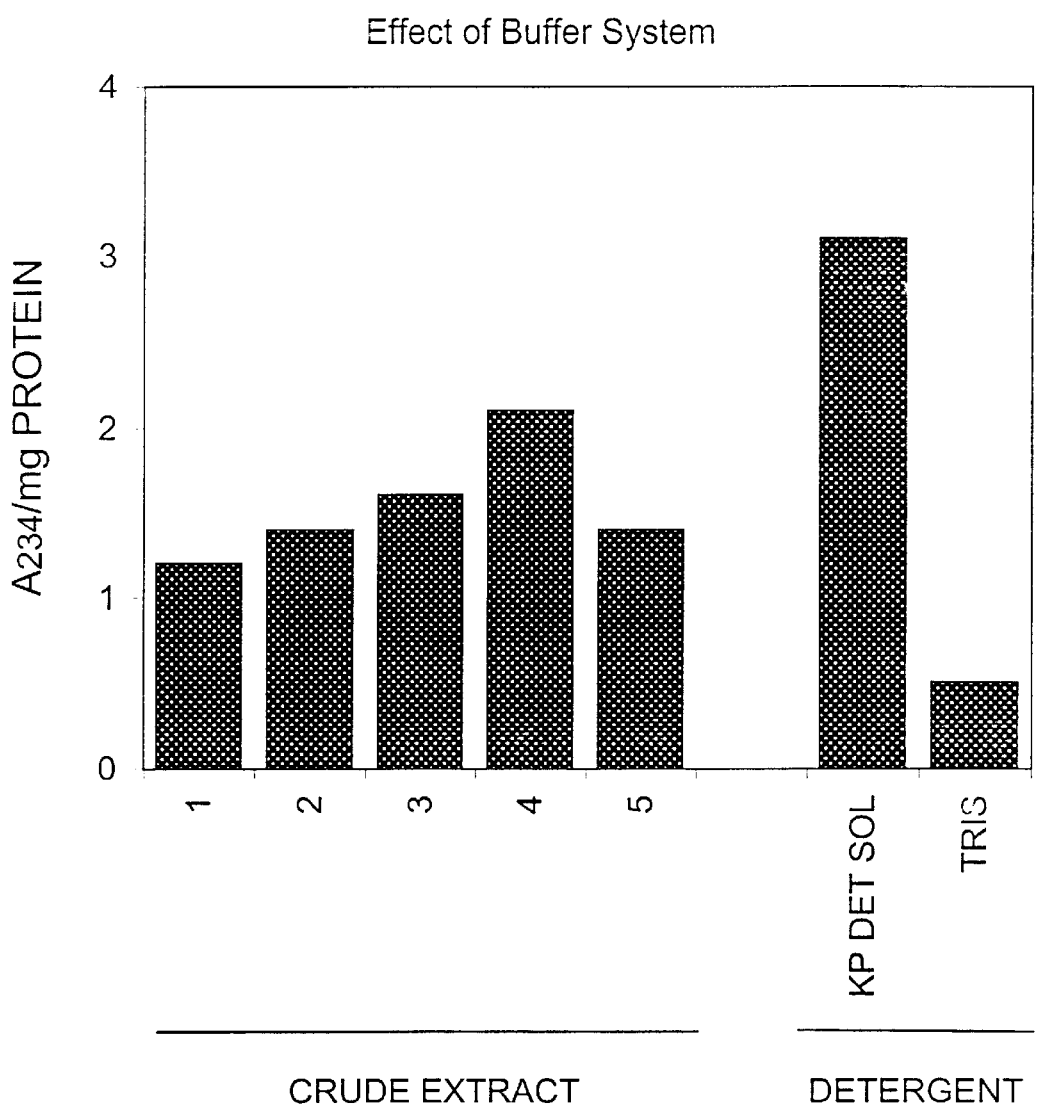
FIG. 36 is a bar graph showing the effect of buffer system on the activity of linoleate isomerase in *C. sporogenes* ATCC 25762.
Figure 37:
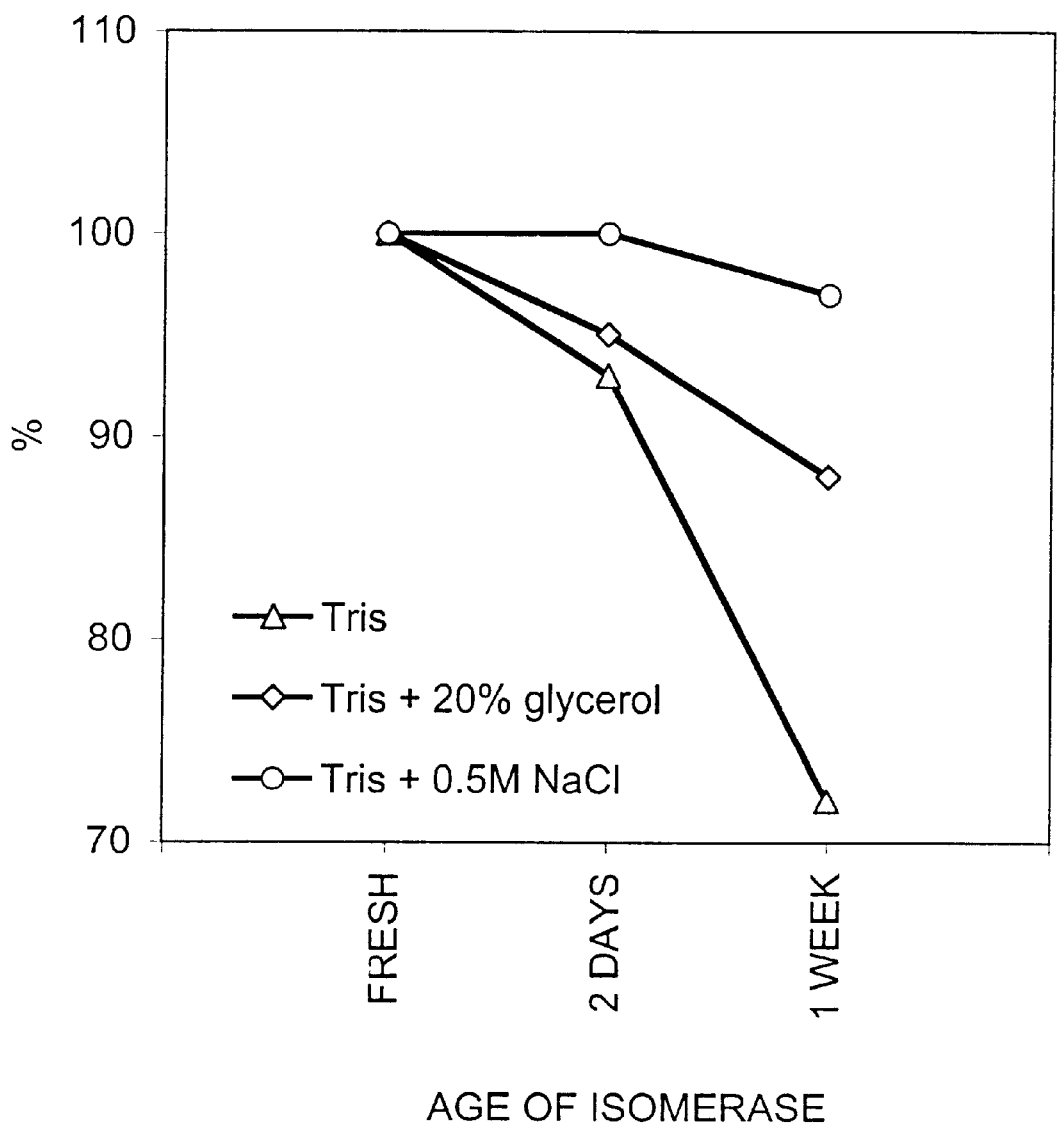
FIG. 37 is a line graph illustrating the effect of glycerol and salt concentration on the stability of crude extracts of linoleate isomerase in *C. sporogenes* ATCC 25762.

The effect of the type of buffer was also significant. Tris buffer, potassium phosphate buffer, and Hepes buffer were compared, and the results are shown in FIG. 36. Phosphate buffer was the most effective in extraction and solubilization of the isomerase. This buffer produced a distinct increase in the activity obtained. In crude extracts, activity was about double that obtained with Tris, and in detergent soluble fractions a four- to seven-fold increase was measured. Further improvements (FIG. 37) were obtained by increasing the NaCl (20% increase in activity) and glycerol concentrations (30% increase).

Figure 38:
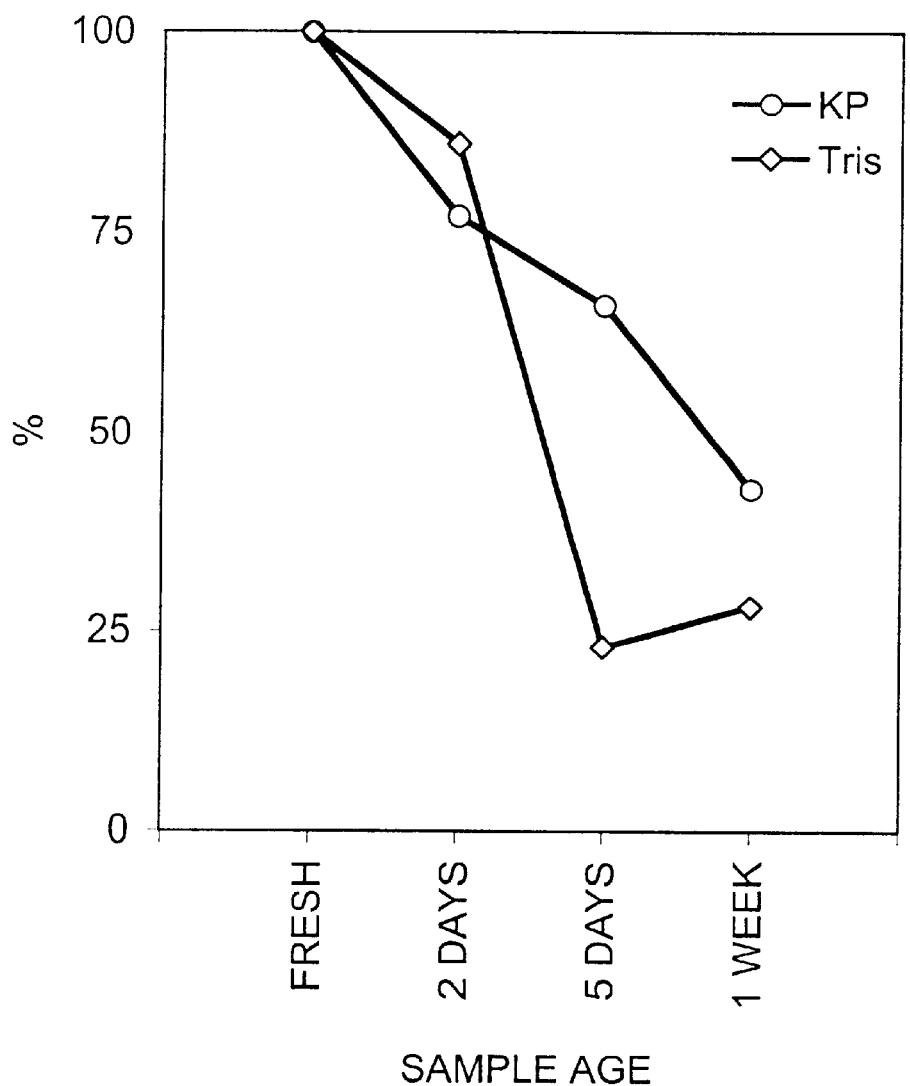
FIG. 38 is a line graph showing the stability of detergent solubilized linoleate isomerase in *C. sporogenes* ATCC 25762.

The enzyme stability was compared at pH 7.5. In general, the isomerase was more stable in crude extracts than in detergent solubilized fractions (FIG. 38). A half-life of 10, 11 and 13 days was measured in Tris, phosphate and Hepes crude extracts, respectively. Increasing glycerol and salt concentration provided major improvements on stability, resulting in near full retention of activity in crude extracts for one week. However, half-life of detergent solubilized isomerase was only three and six days in Tris and phosphate buffer, respectively.

Figure 39:
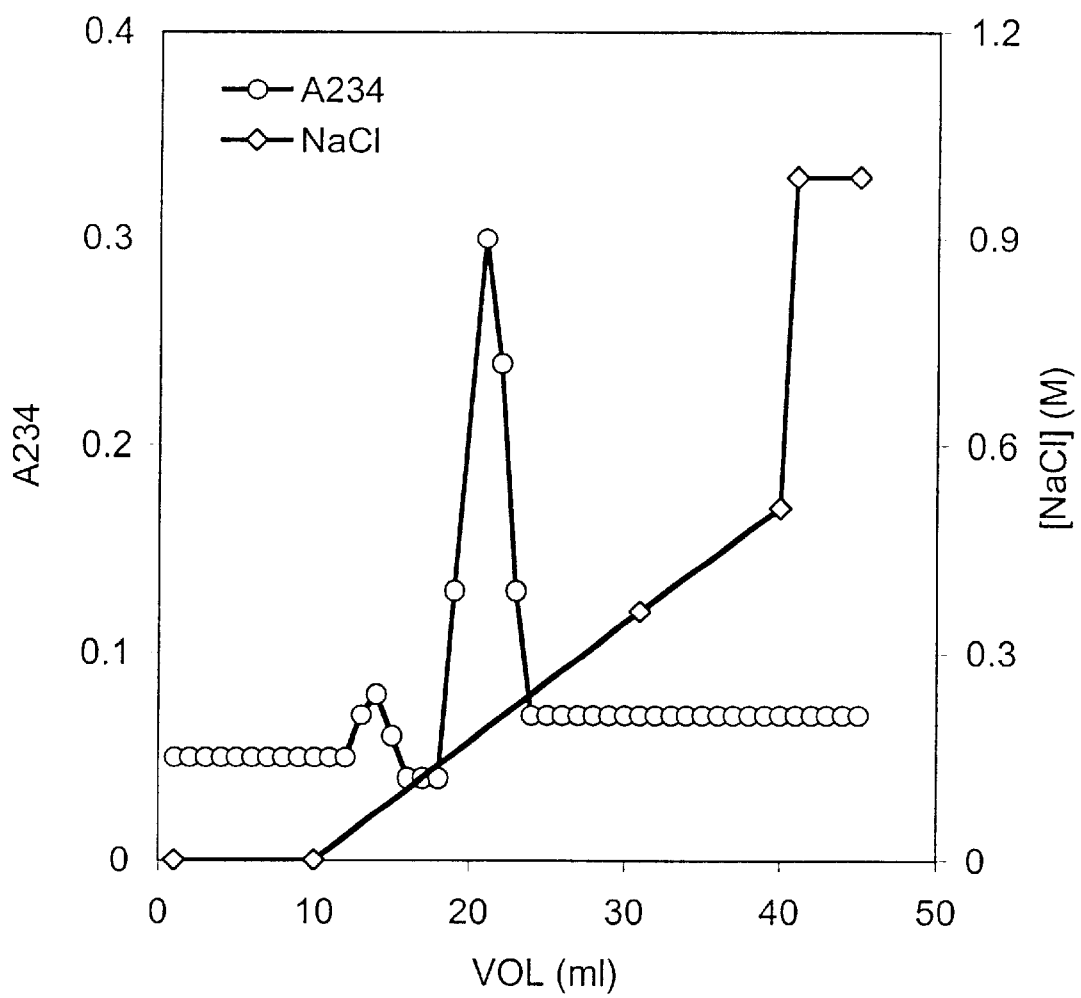
FIG. 39 is an elution profile of *C. sporogenes* ATCC 25762 linoleate isomerase on DEAE Mono Q.

A small-scale purification was performed using a Pharmacia DEAE Mono Q column with enzyme solubilized with 0.3% octyl-thioglucopyranoside (OTGP), as described above, and with phosphate buffer replacing the previously used Tris. A single peak of activity, eluting at approximately 250 mM NaCl, was obtained (FIG. 39). The specific activity after this step increased 2.5 fold. This result was reproducible. SDS-PAGE analysis of the protein from this column showed a band corresponding to a molecular weight of approximately 70 kD (data not shown). The molecular mass is similar to that of the 9,11 isomerase of L. reuteri, suggesting that the two isomerases may have similar characteristics.

OTGP has been used successfully to solubilize the isomerase. However, the detergent (and the solubilized enzyme) slowly precipitates at 4° C. This precipitation results in more than 50% loss of activity after desalting of the enzyme solution by dialysis, but more importantly, it clogs the ion exchange columns, rendering them unusable.

Therefore, detergents that could efficiently solubilize the isomerase while avoiding the precipitation problem were sought. Triton X-100 has a good performance as solubilizing agent for the isomerase, and the amount of protein solubilized increased with increasing Triton X-100 concentrations. Isomerase extraction was also enhanced at high salt concentration (500 mM NaCl). However, it was determined that enzyme activity was completely lost when the solution was dialyzed before ion exchange. The use of Triton X-100 combined with a low salt concentration resulted in lower protein extraction from the membrane pellet, but similar enzyme activity, and eliminates the requirement for the desalting step.

Extraction efficiency similar to that obtained with OTGP has been achieved using 2% Triton X-100 in 50 mM phosphate buffer. A comparison of soluble protein and specific activity in the two detergent systems is shown in Table 4. The enzyme stability is reduced in Triton with respect to OTGP, which is one remaining disadvantage of this new detergent system. However, the conditions would still give a workable time frame to purify the enzyme by multiple steps of chromatography. The continued purification scheme for the isomerase is DEAE chromatography, followed by chromatofocusing, as has been done for the isomerases described in Examples 5 and 9.

TABLE 4

Preparation of C. sporogenes 9,11 Isomerase Extracts with OTGP and Triton X-100

| Sample | Enzyme Activity (*$OD_{234}$) | Protein (mg/ml) | Specific Activity ($OD_{234}$/60 min/mg) |
|---|---|---|---|
| Crude Extract | 0.84 | 7.6 | 1.10 |
| 45K Soluble | 0.12 | 6.6 | 0.18 |
| 0.3% OTGP Soluble | 0.40 | 3.3 | 1.22 |
| 2% Triton - 50 mM NaCl | 0.42 | 2.8 | 1.50 |

*$OD_{234}$ was determined in an assay using 0.1 ml of enzyme extract

A third nonionic detergent, octyl glucoside (OG) was tested for its ability to solubilize the C. sporogenes linoleate isomerase. OG effectively solubilized the isomerase and the activity of the solubilized enzyme was stable. OG at 1.5% (2×critical micelle concentration) produced an isomerase specific activity about 20% higher than that of OTGP solubilized isomerase. No precipitation was observed in the solubilized membrane protein sample after dialysis.

Method C

While OG can be used to solubilize linoleate isomerase, this detergent is too expensive to use in large-scale isomerase purification. The protocol to solubilize linoleate isomerase was modified to initially solubilize isomerase with OG, and then keep the enzyme solubilized with OTGP during further purification. The membrane fraction was solubilized with 1.5% OG in 50 mM potassium phosphate buffer, pH7.5. OG solubilized proteins was dialyzed against 20 mM potassium phosphate buffer, pH 7.5, 10 mM NaCl, 2 mM dithiothreitol and 0.3% OTGP. After centrifugation at 45,000 g for 30 minutes, the solubilized proteins were applied to a DEAE-5PW column, equilibrated with low salt buffer (20 mM bis-Tris, pH7.5, 10 mM NaCl, 0.3% OTGP, 1 mM dithiothreitol, 1 mM EDTA and 1 $\mu$M pepstatin A) and eluted With a linear gradient of NaCl from 0 to 0.5 M at 16° C.

Figure 40:
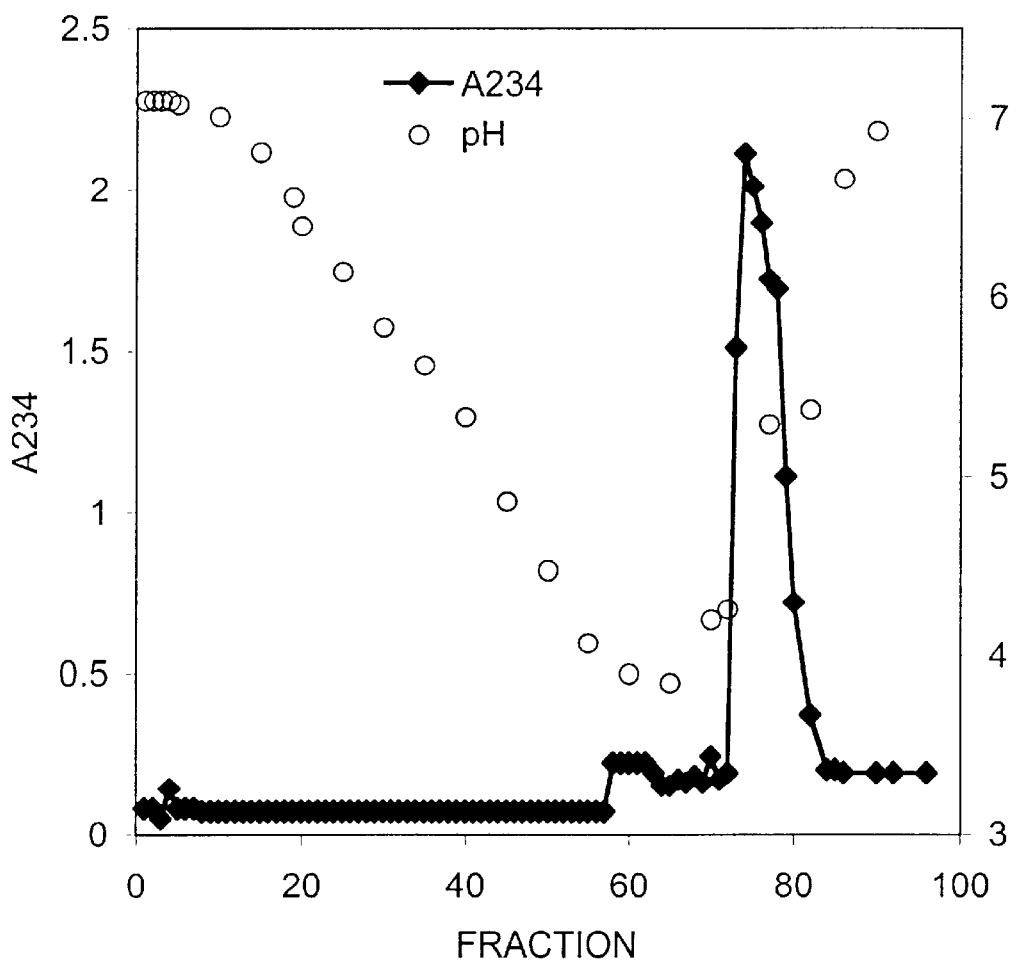
FIG. 40 is an elution profile of *C. sporogenes* ATCC 25762 detergent solubilized linoleate isomerase on DEAE-5PW column.

The DEAE-5PW column chromatography achieved a 4-fold purification. Two distinct peaks of isomerase activity were revealed (FIG. 40). Peak II, which eluted at higher ionic strength, was observed in all previous DEAE chromatography experiments. Peak I, which was eluted at lower ionic strength (0.18M NaCl), was observed for the first time. Both peaks catalyzed isomerization of linoleic acid to cis9, trans11-CLA, as determined by GC analysis of methyl ester products. Peak II was chosen for further purification.

Figure 41:
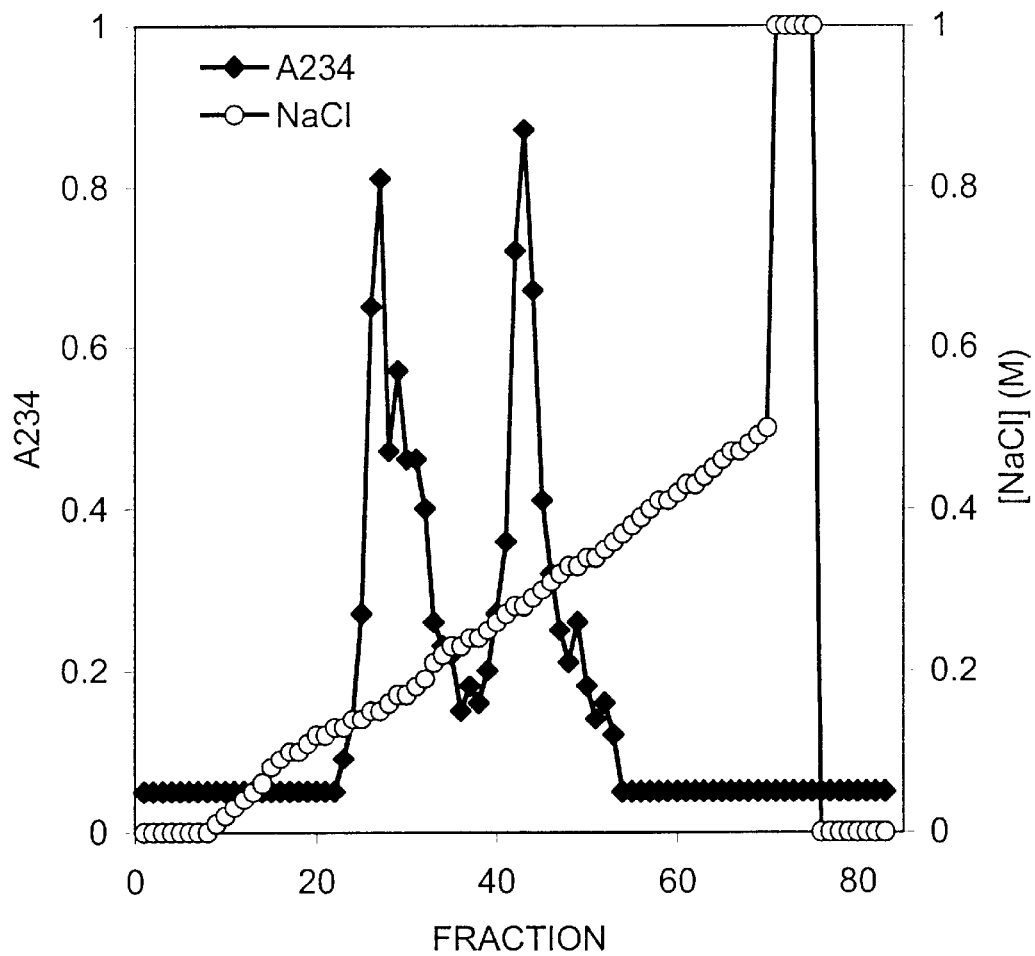
FIG. 41 is an elution profile showing separation of partially purified *C. sporogenes* ATCC 25762 linoleate isomerase by chromatofocusing.

Active fractions (fraction 43–47) from DEAE peak II were pooled, concentrated and dialyzed against 25 mM bis-Tris, pH 7.1 containing 0.3% OTGP, and then loaded on a Mono-p chromatofocusing gel column. Elution was carried out with 100 ml of 10% polybuffer74, lowering the final pH to 3.5. The isomerase activity was retained on the column. Following completion of the polybuffer74 gradient, the isomerase activity was eluted with 1 M NaCl in 50 mM bis-Tris, pH 7.1 (FIG. 41). This chromatofocusing step achieved another 2 to 6 fold purification (Table 5). Examinations by SDS PAGE of the pooled chromatofocusing fractions with high isomerase-activity revealed two major protein bands.

TABLE 5

Summary of Chromatofocusing

| Fraction | A234 | [P] (mg/ml) | Specific Activity | Fold |
|---|---|---|---|---|
| A/S* | 1.76 | 0.97 | 9 | 1 |
| F73 | 1.51 | 0.35 | 22 | 2 |
| F74 | 2.11 | 0.66 | 16 | 2 |
| F75 | 2.01 | 0.26 | 39 | 4 |
| F76 | 1.90 | 0.18 | 53 | 6 |
| F77 | 1.72 | 0.26 | 33 | 4 |
| F78 | 1.69 | 0.21 | 40 | 4 |
| F79 | 1.11 | 0.29 | 19 | 2 |
| F80 | 0.72 | 0.18 | 20 | 2 |
| F82 | 0.37 | 0.07 | 26 | 2 |
| Total loading: | A234 = 88 | | | |
| Fractions: | A235 = 75 | | | |
| Recovering = 85% | | | | |

*A/S: Applied Sample

Method D.

The pooled chromotofocusing fractions with high isomerase activity were further purified using gel filtration. This method separates the proteins by size. For isomerase purification, the gel filtration was carried out using a 1.6×55 cm Superdex-200 column. The elution buffer was composed of 100 mM K-phosphate, pH 7.5, containing 0.1–0.3 M NaCl, 013% OTGP, and 10% glycerol. Assay of isomerase activity in different fractions revealed a single peak of isomerase activity. SDS-PAGE analysis showed a single protein band after staining with Coomassie Blue of about 45 kD.

The purification of the C. sporogenes 9,11-linoleate isomerase is summarized in Table 1C.

TABLE 1C

Clostridium sporogenes

| Step | Protein | Total Activity | Specific Activity | Yield |
|---|---|---|---|---|
| Crude extract | 570 | 653 | 1.1 | 100.0 |
| OG extract | 157 | 470 | 3.0 | 72.0 |
| DEAE-5PW | 12 | 132 | 11.0 | 20.2 |
| Chromatofocusing | 0.677 | 64 | 94.6 | 9.8 |
| Gel-Filtration | 0.030 | 10.5 | 350.0 | 1.6 |

Protein in milligrams. Enzyme activity units are nanomoles CLA formed per minute. Specific activity is units per milligram protein.

Example 18

The following example describes the sequencing of the N-terminal amino acid sequence of the purified C. sporogenes integral membrane (cis,trans)-9,11-linoleate isomerase.

Clostridium isomerase was purified using multi-steps of the chromatography method (Example 17). This purified protein showed a single band of an approximate mass of 45 kD on SDS gel and was used for N-terminal sequencing. The first attempt to obtain N-terminal amino acid sequence suggested the protein was N-terminally blocked. It has been estimated that 40–70% of all proteins are N-terminally blocked either in the native form in the cell or as a result of artificial events during protein extraction and purification. To limit the possibility of an artificial N-terminal block, a protein sample that did not go through the final step of gel filtration was used. This protein sample had a very high isomerase activity and contained predominantly a 45 kD protein by SDS PAGE analysis. After blotting onto a PVDF (polyvinylidene difluoride) membrane, the 45 kD band was excised and used for sequencing. A sequence of 21 amino acid residues was determined as follows:

MFNLK NRNFL TLMDF TPXEI Q (SEQ ID NO:43)

A protein having the sequence of SEQ ID NO:43 is referred to herein as $PCLA_{21}$. It should be noted that since amino acid sequencing technology is not entirely error-free, SEQ ID NO:43 represents, at best, an apparent partial N-terminal amino acid sequence.

The sequence shows no significant homology to the linoleate isomerase cloned from L. reuteri PYR8 (SEQ ID NO:18), nor to the N-terminal sequences of 55 kD isomerase purified from P. acnes ATCC 6919 (SEQ ID NO:42) nor the putative 19 kD isomerase peptide purified from Butyrivibrio fibrisolvens (Park et al., 1996; see previous comments regarding Park et al. in Background section). The C. sporogenes isomerase N-terminal sequence was analyzed against sequences in the databases using Blastp program with standard settings. The sequence was found to share 57 to 75% identical amino acid sequences with the ornithine carbamoyltransferase isolated from 6 different organisms, including C. perfringens (gi 1321787). However, the Clostridium ornithine carbamoyltransferase is a protein of 37-kD—much smaller than the C. sporogenes, P. acnes, or the L. reuteri linoleate isomerases. The Clostridium ornithine carbamoyltransferase shares no significant sequence homology with the linoleate is isomerase peptide deduced from DNA sequence cloned from L. reuteri PYR8 or of the directly determined amino acid sequence of the PYR8 isomerase or to the N-terminal sequence of C. acnes isomerase. Therefore, the significance of the homology between the Clostridium linoleate isomerase and the enzyme involved in arginine metabolism is not clear. As discussed above with the P. acnes isomerase, comparison with the complete isomerase sequence will be necessary.

The entire C. sporogenes linoleate isomerase nucleic acid and amino acid sequence are currently being derived using standard methods in the art and as described for the P. acnes linoleate isomerase described in Example 13. Nucleic acid sequences encoding SEQ ID NO:43 can be deduced from the amino acid sequence by those of ordinary skill in the art. Isolated nucleic acid molecules comprising such nucleic acid sequences are encompassed by the present invention.

Example 19

The following example demonstrates the enzyme activity of the C. sporogenes linoleate isomerase.

Figure 43:
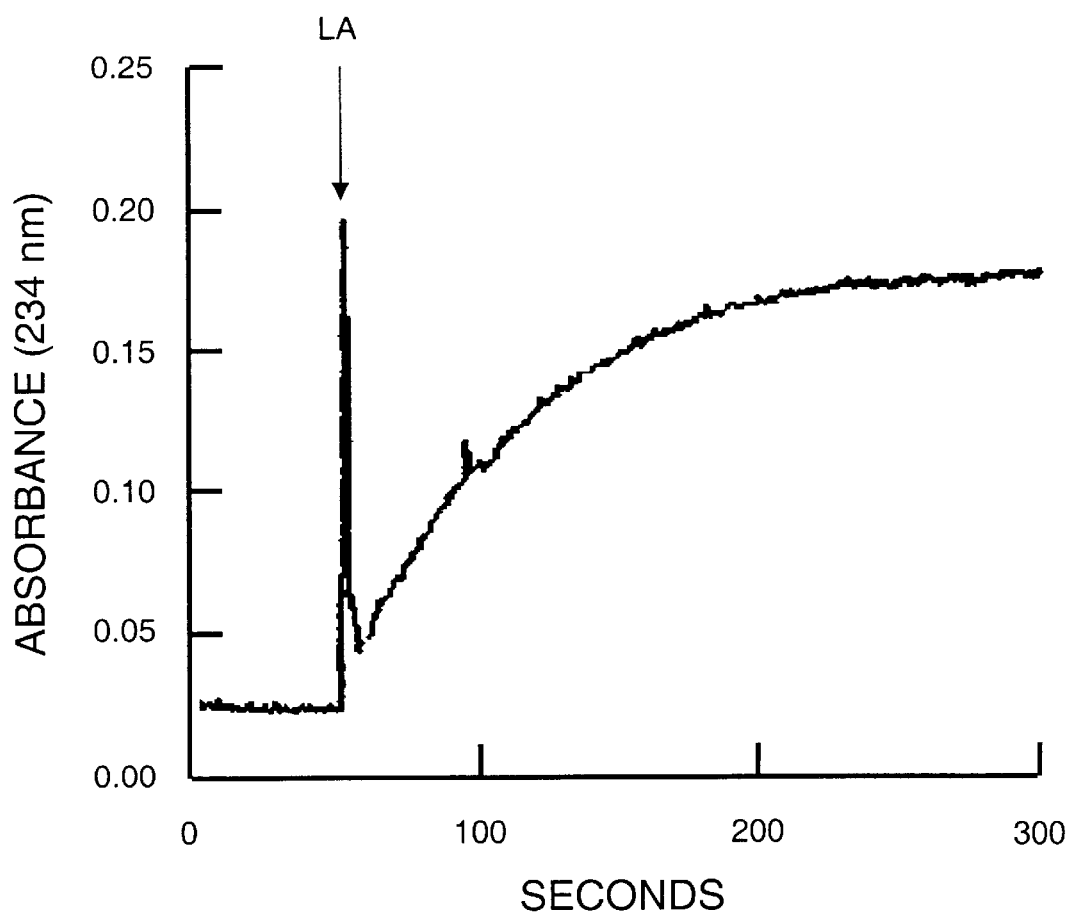
FIG. 43 is an absorbence profile showing the time course of isomerization of linoleic acid.

Similar kinetic data have been developed for L. reuteri (Example 4). In this experiment, all kinetic experiments were performed in a quartz cuvette (1-cm light-path with a magnetic stirrer) at room temperature using a HP 8452A diode array spectrophotometer. The cuvette was filled with 1 ml of incubation buffer containing 50 μg protein, 0.1 M potassium phosphate, pH7.5, 10 mM NaCl and 10% 1,2-propane diol. The isomerization was initiated by adding a small aliquot (1–2 μl) of freshly diluted substrate stock (~20

μM linoleic acid) in 1,2-propane diol at 50 seconds. The increase in absorbence at 234 nm was monitored and recorded. FIG. 43 shows a typical progress curve for the enzymatic catalyzed conversion of linoleic acid to CLA versus time. The amount of product formed was calculated based on a molar extinction coefficient of 24,000.

Using partially purified enzyme (a mixture of DEAE active fractions), the following *C. sporogenes* linoleate isomerase kinetic parameters were characterized: substrate specificity, inhibitors of the enzyme activity, pH, cofactors, and the effect of various fatty acids and their derivatives on catalysis.

pH Dependence of the Isomerization

Figure 44:
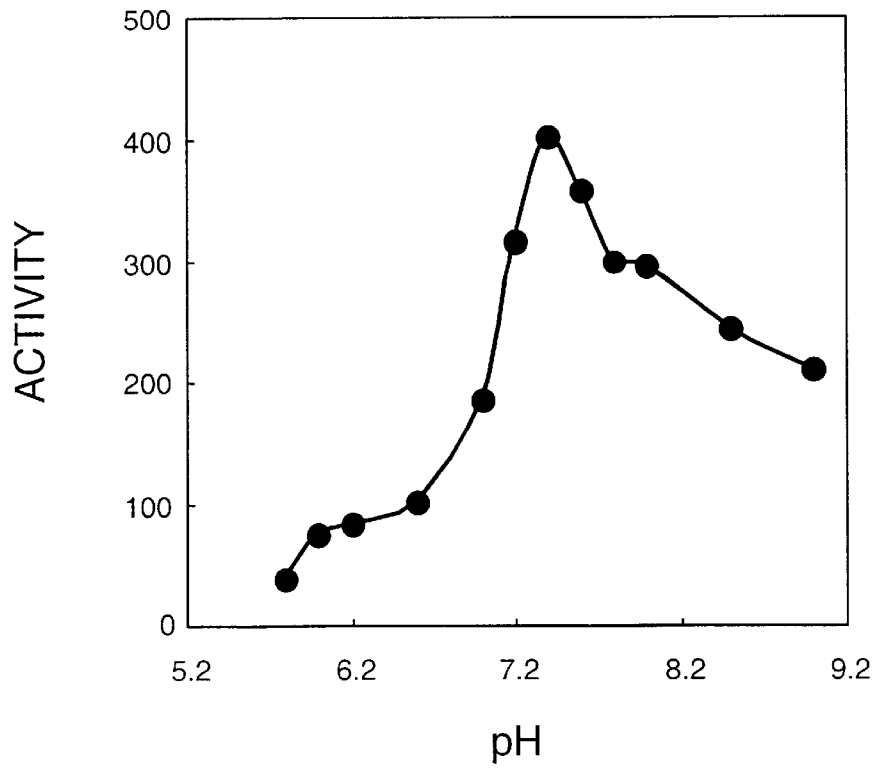
FIG. 44 is a line graph illustrating the effect of pH on isomerization of linoleic acid to CLA by *C. sporogenes* ATCC 25762 linoleate isomerase.

The effect of pH on the isomerase activity was determined using a series of potassium phosphate buffers (0.1 M) at different pH values. A plot of isomerization versus pH for *C. sporogenes* linoleate isomerase is shown in FIG. 44. The optimum pH for isomerization is about pH 7.5, which was also the optimum for the *L. reuteri* PYR8 isomerase. Therefore, pH7.5 buffer was used for all kinetic analyses.

co-workers with *Butyrivibrio fibrisolvens* isomerase and in our studies with the *L. reuteri* PLR8 and *P. acnes* 6919 isomerases.

Affinity to Substrates

Since the *C. sporogenes* linoleate isomerase showed a high specificity for "Z" double bond compounds with a chain length of 18 carbons, the affinity of the enzyme for similar compounds (linoleic acid, linolenic acid, r-linolenic acid and (cis,cis,cis,cis)-6,9,12,15 octadecatetraenoic acid) was investigated.

Figure 45:
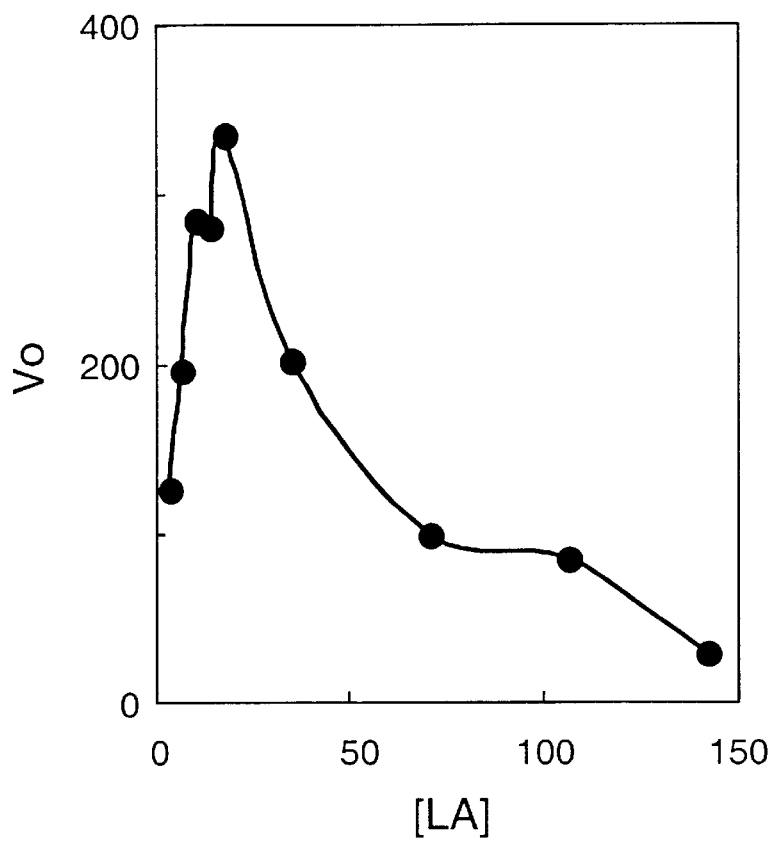
FIG. 45 is a line graph showing the effect of substrate concentration on the rate of linoleic acid isomerization.

Kinetic analysis of the substrate concentration dependency of isomerization (FIG. 45) provided evidence that:

1. The reaction velocity is strongly dependent on substrate concentration; and,
2. The substrate has an inhibitory effect at concentrations above 20, 40, 15 and 120 μM for linoleic acid, linolenic

TABLE 6

Substrate specificity of the linoleate isomerase from *Clostridium sporogenes*‡

| SUBSTRATE | RELATIVE ACTIVITY % |
|---|---|
| (cis,cis)-9,12-octadecadienoic acid (18:2) (linoleic acid) | 100 |
| (cis,cis,cis)-9,12,15 octadecatrienoic acid (18:3) (linolenic acid) | 84 |
| (cis,cis,cis)-6,9,12-octadecatrienoic acid (18:3) (γ-linolenic acid) | 77 |
| (cis,cis,cis,cis)-6,9,12,15 octadecatetraenoic acid (18:4) (stearidonic acid) | 60 |
| (cis,cis)-11,14 eicosadienoic acid (20:2) | 20 |
| (cis,cis,cis)-8,11,14 eicosatrienoic acid (20:3) | 0 |
| (cis,cis)-13,16 docosadienoic acid (22:2) | 0 |
| (cis,cis)-9,12-octadecadien-1-ol (18:2) (linoleyl alcohol) | 0 |
| (cis,cis)-linoleic acid methyl ester (18:2) (methyl linoleate) | 0 |
| (cis,cis)-11,14 eicosadienoic acid methyl ester (20:2) | 0 |
| (trans,trans)-9,12-octadecadienoic acid (18:2) (linolelaidic acid) | 0 |
| (cis)-9:10-epoxyoctadecanoic (18:0) (epoxystearic acid; oleic acid oxide) | 0 |
| (cis)-13-docosaenoic acid (18:1) (erucic acid) | 0 |
| (cis)-9 octadecenoic acid (18:1) (oleic acid) | 0 |
| (cis)-9 hexadecenoic acid (16:1) (palmitoleic acid) | 0 |

‡Isomerase activity was determined with the individual substrate concentrations fixed at 10 PPM. The activity determined with linoleic acid (LA) alone is set as 100%. The data determined with other substrates are presented as relative activity (percent of the isomerase activity determined with linoleic acid as substrate).

Substrate Specificity

The substrate specificity of *C. sporogenes* linoleate isomerase was studied using a number of unsaturated fatty acids and their esterified or alcoholized derivatives as substrate. Substrate specificity trends are summarized in Table 6. The isomerase shows a definite preference towards substrates containing "Z" double bonds at the 9, 12 position of C18 fatty acids. Compounds that possess additional double bonds are also good substrates, but the turnover rate decreased with increasing number of double bonds. Among the other dienoic acids tested (C18–C22), only (cis,cis)-11, 14-eicosadienoic acid was isomerised. This suggests that the isomerase uses C18 and C20 unsaturated fatty acids having nine carbon atom after the first double-bond position.

The isomerase was also incubated with linoleyl alcohol and methyl linoleate. As shown in Table 6, alcoholized linoleic acid and esterified linoleic acid do not serve as substrates. It is clear that the isomerase only uses compounds that contain a free carboxyl group. This is in agreement with the results obtained by Kepler and his acid, r-linolenic acid and (cis,cis,cis,cis)-6,9,12,15 octadecatetraenoic acid, respectively.

Figure 46:
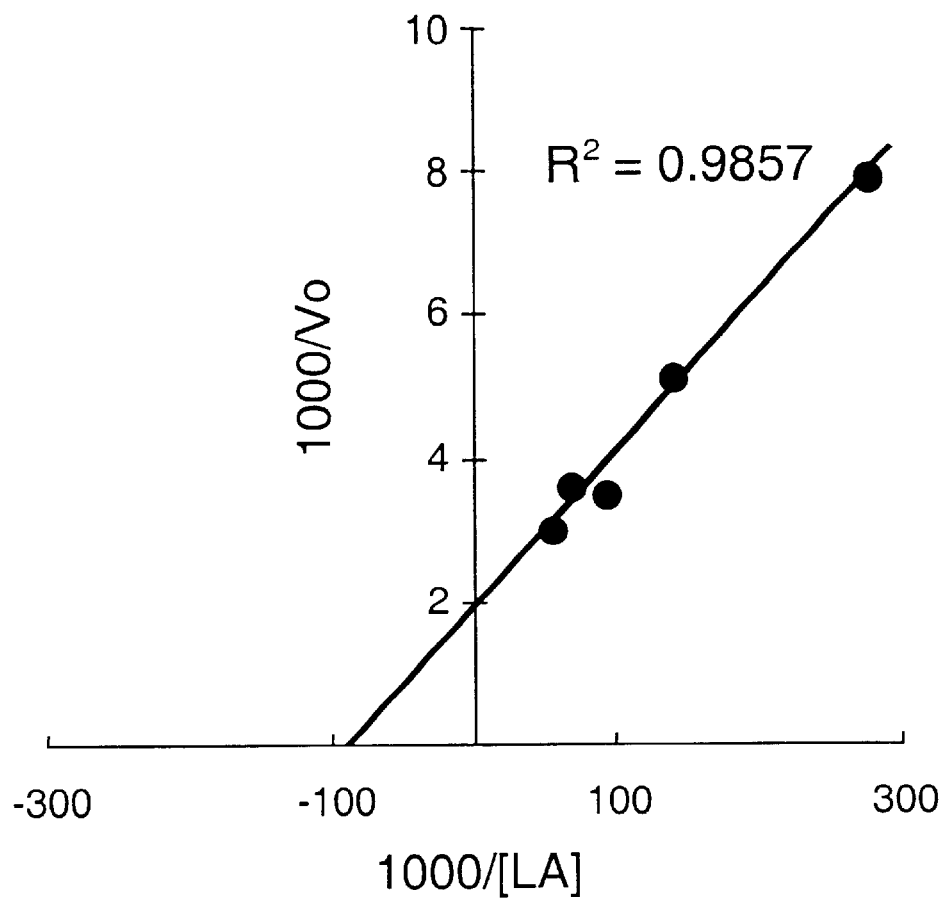
FIG. 46 is a Lineweaver-Burke plot of reaction kinetics of *C. sporogenes* ATCC 25762 linoleate isomerase.

FIG. 46 shows a Lineweaver-Burke plot of 1/v versus 1/[S]. Calculation from this plot yielded a Km of 11.3 μM and a maximal velocity (Vmax) of 350 μmol CLA/min/mg protein for linoleic acid. The values of Km and Vmax determinated using other C18 unsaturated fatty acids are shown in Table 7A. All of the substrates tested showed a normal Michaelis-Menten behavior over the range of concentrations tested. The Km value increased with increasing number of double bonds in substrates. The enzyme had similar Km values for the isomers with three double bonds: linolenic acid and r-linolenic acid. From a comparison of Km, linoleic acid is clearly the best substrate for the *C. sporogenes* linoleate isomerase.

Table 7A compares key kinetic parameters of linoleate isomerases from *L. reuteri* PYR8, and *C. sporogenes* 23272, all isolated by the present inventors, and the *B. fibrisolvens* A-38 linoleate isomerase (Kepler and Tove, 1967, *J. Biochem.* 242:5686–5692).

TABLE 7A

Comparison of kinetic constants for linoleate isomerases from different organisms

| Organism | Vmax (nmole/min/mg protein) | | | | Km ($\mu$M) | | | |
|---|---|---|---|---|---|---|---|---|
| | LA* | LnA‡ | $\gamma$-LnA# | $\Delta$-LA$^f$ | LA* | LnA‡ | $\gamma$-LnA# | $\Delta$-LA$^f$ |
| C. sporogenes 27232 | 350 | 811 | 236 | 204 | 11.3 | 22.5 | 23.8 | 18.9 |
| L. reuteri PYR8 | 880 | ND | ND | ND | 8.1 | ND | ND | ND |
| B. fibrisolvens A-38† | 55 | 130 | ND | ND | 12.0 | 23.0 | ND | ND |

*(cis,cis)-9,12-octadecadienoic acid (18:2) (linoleic acid)
‡(cis,cis,cis)-9,12,15 octadecatrienoic acid (18:3) (linolenic acid)
(cis,cis,cis)-6,9,12-octadecatrienoic acid (18:3) ($\gamma$-linolenic acid)
$^f$(cis,cis,cis,cis)-6,9,12,15 octadecatetraenoic acid (18:4) (stearidonic acid)
†Kepler and Tove (1967) J. Biol. Chem. 242: 5686–5692
U $\mu$mole CLA/min
ND Not determined As seen in Table 7A, the kinetic data for the *C. sporogenes* linoleate isomerase is qualitatively similar to other linoleate isomerases. However, the rates of isomerization are much higher than those reported by Kepler for unpurified *Butyrivibrio fibrisolvens* isomerase (See Kepler and Tove, 1967, ibid.).

Table 7B is a summary of the kinetic data and characterization of linoleate isomerases from *P. acnes* (crude extract prior to DEAE purification as in Example 11, except that the Vmax was determined using enzyme purified through the chromatofocusing step as in Example 11), *L. reuteri* (enzyme purified through the gel filtration step as in Example 3), and *C. sporogenes* (enzyme purified through the gel filtration step as in Example 17), all isolated by the present inventors, and the *B. fibrisolvens* A-38 linoleate isomerase (crude extract; Kepler and Tove, 1967, *J. Biochem.* 242:5686–5692). The substrate in these experiments was linoleic acid.

TABLE 7B

Linoleate Isomerase Characterization

| Organism | CLA Isomer[1] | Optimal pH | Km ($\mu$M) | Vmax (nmol/min/mg) | Enzyme Solubility[2] |
|---|---|---|---|---|---|
| P. acnes | 10, 12 | 7.3 | 17.2[4] | 478[5] | S |
| L. reuteri | 9, 11 | 7.5 | 8.1[5] | 880[5] | M |
| C. sporogenes | 9, 11 | 7.5 | 11.3[5] | 350[5] | M |
| B. fibrisolvens[3] | 9, 11 | 7.2 | 12.4[4] | 55[4] | M |

[1]CLA isomer produced. 10, 12 = t10, c12-CLA; 9, 11 = c9, t11-CLA
[2]Enzyme solubility. S = soluble; M = integral membrane protein
[3]Kepler & Tove 1969 = Kepler, Carol R., and S.B. Tove. 1969, Linoleate $\Delta^{12}$-cis,$\Delta^{11}$transisomerase. Methods Enzymol. 14: 105–110.
[4]Crude extract
[5]Purified enzyme Effect of Cofactors on Isomerase Activity Two substrates, linoleic acid (LA) and (cis,cis,cis,cis)-6,9,12,15 octadecatetraenoic acid (tetra LA), were used to test the effect of cofactors. The reaction mixtures contained 10 PPM (LA) or 20 PPM (tetra LA) substrate, and one or more of the following cofactors or additions: 1 mM DTT, 50 $\mu$M ATP, ADP, NAD, NADH, NADPH and CoA. As seen in Table 8 and Table 9, none of the cofactors or additions has a strong effect on the isomerase activity, suggesting the isomerization does not require the addition of external cofactors or energy.

TABLE 8

Effect of cofactors on the isomerization of linoleic acid by the linoleate isomerase from *C. sporogenes* 23272

| Cofactor | Activity (nmol/min) | (%) |
|---|---|---|
| None | 10.6 ± 2.3 | 100 |
| ATP | 11.1 ± 1.4 | 105 |
| ADP | 11.1 ± 1.7 | 105 |
| NAD | 10.8 ± 1.3 | 102 |
| NADH | 10.5 ± 1.0 | 99 |
| NADPH | 11.1 ± 1.5 | 105 |
| DTT | 12.8 ± 3.8 | 121 |

TABLE 9

Effect of cofactors on the isomerization of (cis,cis,cis,cis)-6,9,12,15 octadecatetraenoic acid

| Cofactor | Activity (nmol/min) | (%) |
|---|---|---|
| None | 6.2 | 100 |
| CoA | 6.5 | 105 |
| ATP | 6.1 | 98 |
| ADP | 5.7 | 92 |
| NAD | 5.6 | 90 |
| NADH | 6.4 | 103 |
| NADPH | 6.3 | 102 |
| DTT | 5.9 | 95 |
| DTT + ATP | 6.2 | 100 |

Effect of Fatty Acids and Their Derivatives on Linoleic Acid Isomerization

The effect of fatty acids and their derivatives was investigated. The concentration of fatty acids was fixed at 35 $\mu$M. Table 10 shows the summary of the data. The results demonstrated that:

1. The saturated fatty acids tested apparently do not affect activity of the *C. sporogenes* linoleate isomerase;

2. Isomerase activity is strongly inhibited by all of the unsaturated fatty acids studied; and, 3. Ester derivatives of linoleic acid carboxyl group, methyl linoleate and linoleyl alcohol are also inhibitors of the *C. sporogenes* linoleate isomerase.

TABLE 10

Effect of fatty acids and derivatives on the isomerization of linoleic acid[a] catalyzed by *C. sporogenes* linoleate isomerase

| ADDITION[b] | RELATIVE ACTIVITY[c] (%) |
|---|---|
| none | 100 |
| octadecanoic acid (18:0) (stearic acid) | 107 |
| hexadecanoic acid (16:0) (palmitic acid) | 93 |
| (cis,cis)-9,12-octadecadien-1-ol (18:2) (linoleyl alcohol) | 81 |
| (cis,cis)-linoleic acid methyl ester (18:2) (methyl linoleate) | 69 |
| (cis)-9-hexadecenoic acid (16:1) (palmitoleic acid) | 27 |
| (cis)-9-octadecenoic acid (18:1) (oleic acid) | 25 |
| (trans,trans)-9,12-octadecadienoic acid (18:2) (linolelaidic acid) | 19 |
| (cis,cis) -11,14 ecosadienoic acid (20:2) | 0 |

[a] the reaction mixture contained 35 $\mu$M substrate (LA),50 mg partially purified protein, 100 mM potassium phosphate buffer, pH 7.5, 10%, 1,2 propane diol and 10 mM NaCl
[b] compounds were added to the reaction mixture at a concentration of 35 $\mu$M
[c] the activity determined with linoleic acid (LA) alone is set as 100%. The effect of addition of specific compounds on isomerase activity is presented as relative activity (percent of the isomerase activity determined with linoleic acid as substrate).

Inhibitory Effect of Oleic Acid and Palmitoleic Acid

Figure 47:
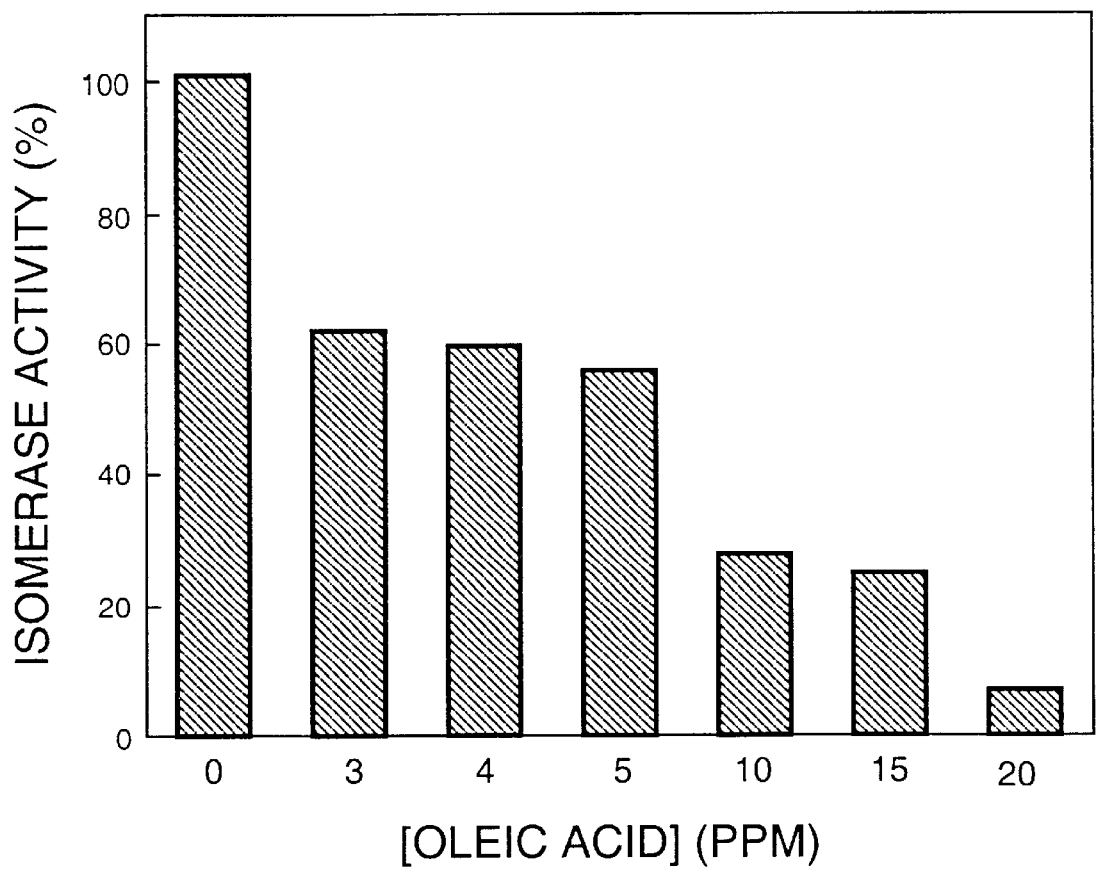
FIG. 47 is a bar graph showing the effect of oleic acid on isomerase activity.
Figure 48:
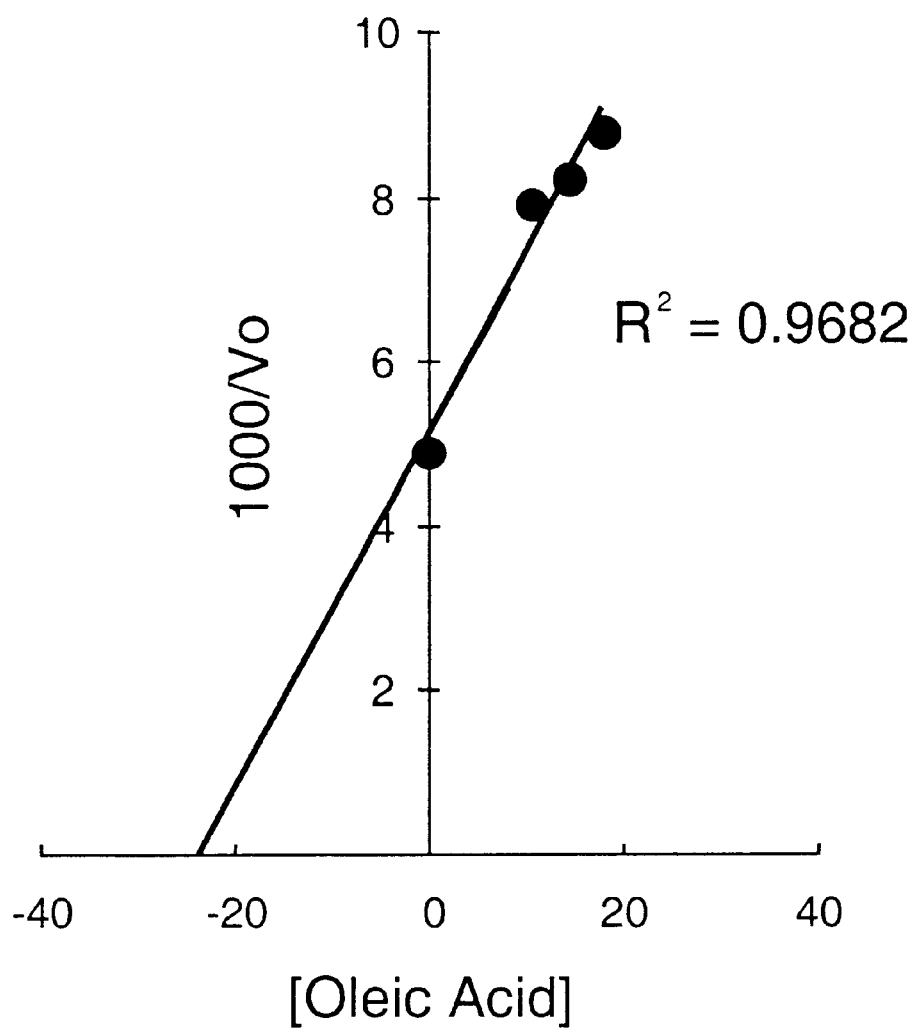
FIG. 48 is a secondary plot of oleic acid inhibition.
Figure 49:
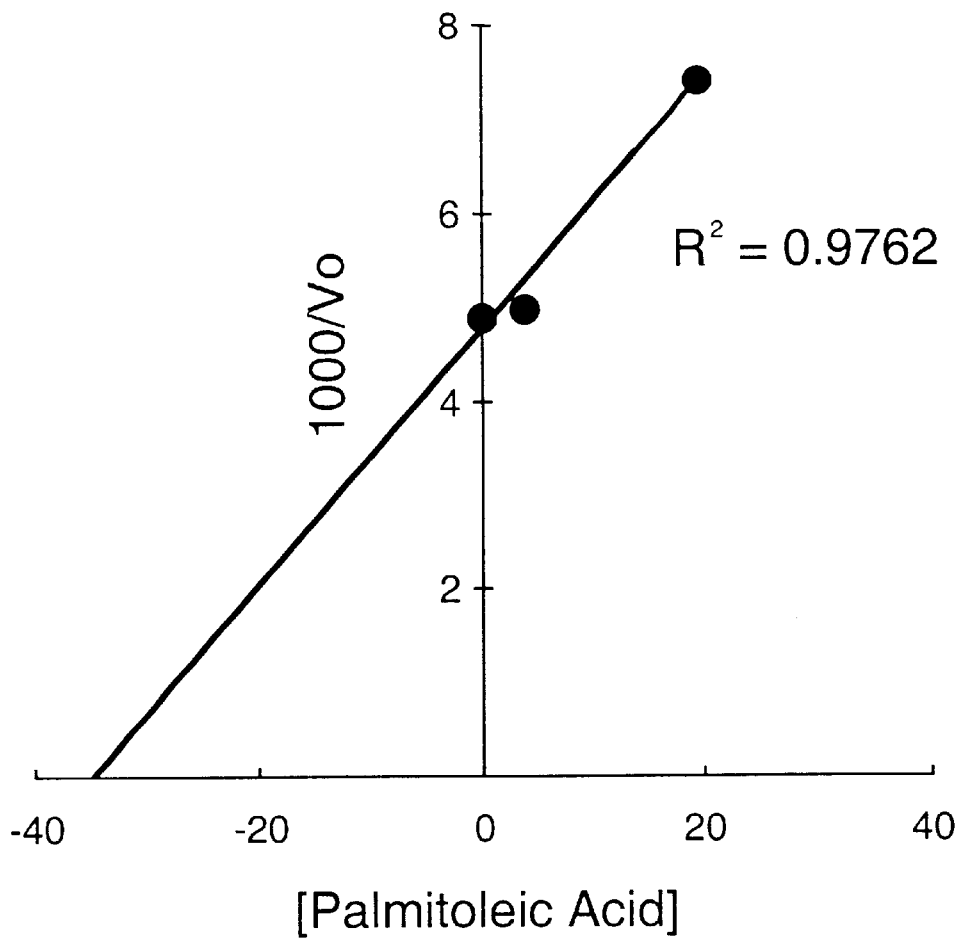
FIG. 49 is a secondary plot of palmitoleic acid inhibition.

The inhibitory effect of oleic acid and palmitoleic acid was further characterized:

1. Both C18 and C16 unsaturated fatty acids containing a cis double bound at the 9 carbon (counting from carboxyl end) inhibited isomerization of linoleic acid;
2. The isomerase activity was dramatically reduced with increasing concentration of oleic acid (FIG. 47); in the presence of 70 $\mu$M oleic acid (20 PPM), the isomerase activity was almost completely lost; and,
3. The inhibition constants (Ki) for oleic acid and palmitoleic acid, calculated from secondary plots (1/v Vs [S]), are 23.8 and 33.1 $\mu$M, respectively (FIGS. 48 and 49).

Figure 50:
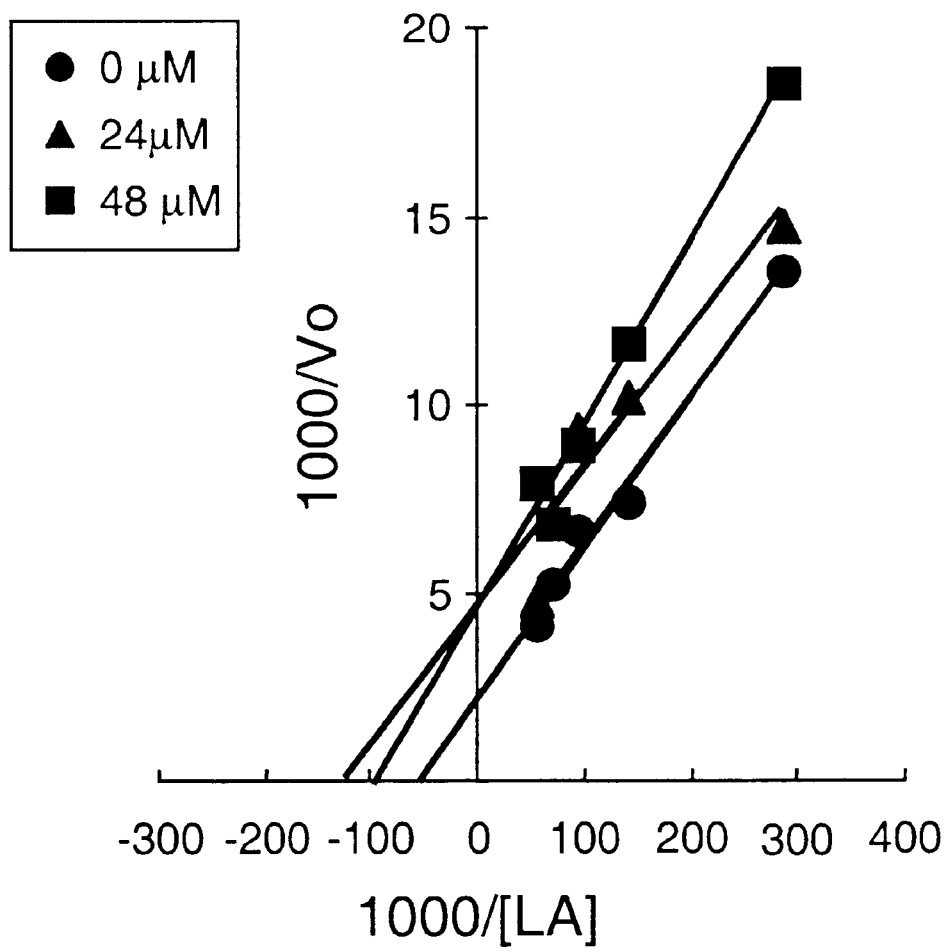
FIG. 50 is a Lineweaver-Burke plot of linoleic acid isomerization kinetics in the presence of absence of oleic acid.
Figure 51:
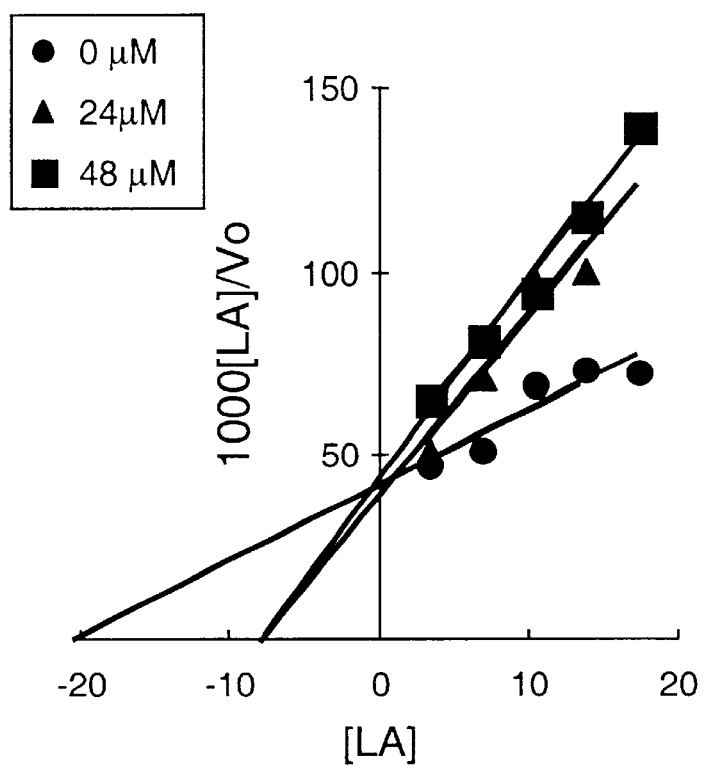
FIG. 51 is a Hanes-Woolf plot of oleic acid inhibition of linoleic acid.

Kepler and Tove and co-workers reported that oleic acid competitively inhibited isomerization of linoleic acid to CLA (Kepler and Tove, 1967, ibid.). To determine whether oleic acid is a competitive inhibitor of the *C. sporogenes* linoleate isomerase, the inhibitory effect of oleic acid was further investigated using Lineweaver-Burke (1/V versus 1/[S]) and Hanes-Woolf ([S]/V versus [S]) plots. The kinetic analyses were performed in the presence of 0, 24 and 48 $\mu$M oleic acid with varied concentration of linoleic acid. Parallel lines in a Lineweaver-Burke plot (FIG. 50) and a common intercept in the Hanes-Woolf plot (FIG. 51) were obtained. These data are consistent with oleic acid being an uncompetitive inhibitor of the *C. sporogenes* linoleate isomerase. Similar results were obtained with the *L. reuteri* PYR8 (cis,trans)-9,11-linoleate isomerase. These results contrast with the competitive inhibition by oleic acid reported for the *B. fibrisolvens* (cis,trans)-9,11-linoleate isomerase.

Example 20

The following example describes the optimization of growth conditions for *L. reuteri* PYR8.

Fermentation work was concentrated on the optimization of growth conditions for *L. reuteri* PYR8. A fermentation medium that could consistently support cell growth well and isomerase production, thus eliminating the variability previously observed was pursued.

Working with MRS medium, it was determined that the linoleate isomerase activity was variable, mainly due to the medium composition and sterilization procedures that had some effect on cell growth. The number of inoculum stages and the inoculum size did not affect final cell concentration. Mixed versus static growth, suspected to affect the gas balance in the medium, did not appear to be a significant variable. Given the medium richness, toxic concentrations of some compounds were suspected as a possible reason for the variability. However, it was determined that different dilutions of MRS resulted in proportional lower cell densities (data not shown) indicating a nutritional limitation in the medium. Additionally, high variability was observed when using two batches of the same medium.

Experiments performed in one and ten-liter fermentors indicated that a different medium (AV) with composition similar to MRS, but with higher yeast extract, peptone and acetate concentration, and without beef extract, gave consistently better results in fermentors than MRS with respect to both cell growth and isomerase activity. We adopted this medium as our base medium for further work. Its composition is shown in Table 11.

TABLE 11

Composition of AV Medium

| Component | Concentration |
|---|---|
| Yeast Extract | 10 g/l |
| Proteose Peptone #3 (Difco) | 20 g/l |
| Sodium Acetate | 10 g/l |
| Glucose | 20 g/l |
| Tween 80 | 1 ml/l |
| MgSO4 | 0.028 g/l |
| MnSO4.2H2O | 0.012 g/l |
| FeSO4.7H2O | 0.0034 g/l |
| Vitamin Mixture | 10 ml/l |

The vitamin mixture contained riboflavin, pantothenic acid, pyridoxal, nicotinic acid, folic acid, choline chloride, biotin and thiamine.

A full factorial experiment was run in bottles, dividing this medium into seven categories (yeast extract, peptone, acetate, glucose, Tween 80, salts and vitamins), and studying the impact of two concentrations of the components in each category as follows: 2.5 and 10 g/l yeast extract, 10 and 20 g/ll peptone, 10 and 20 g/l glucose, 5 and 10 g/l acetate, 0.5 and 1 ml/l Tween 80, 0.5x and 1xsalts concentration and no addition vs. addition of vitamins. This study demonstrated clearly that yeast extract concentration had the most significant impact on growth, followed by glucose and the combined effect of glucose and yeast extract. Peptone effect was marginal and the other components did not affect growth. The concentration of Tween 80 seemed to affect isomerase activity, as measured by conversion of linoleic acid to CLA.

Difco yeast extract was successfully replaced by KAT yeast extract, and several industrial type nitrogen sources were tested as replacements for Peptone #3. These are summarized in Table 12.

TABLE 12

Nitrogen Sources Evaluated as Medium Components

| Nitrogen Source Name | Type | Manufacturer |
| --- | --- | --- |
| N—Z-Amine A | Enzyme Hydrolysate of Casein | Quest |
| N—Z-Amine YT | Enzyme Hydrolysate of Casein | Quest |
| Pepticase | Enzyme Hydrolysate of Casein | Quest |
| Amicase | Acid Hydrolysate of Casein | Quest |
| Edamin K | Enzyme Hydrolysate of Lactalbumin | Quest |
| Amisoy | Acid Hydrolysate of Soy | Quest |
| Hy-soy | Enzyme Hydrolysate of Soy | Quest |
| Primatone RL | Enzyme Hydrolysate of Meat | Quest |
| Primatone HS | Enzyme Hydrolysate of Meat | Quest |
| Primagen | Enzyme Hydrolysate of Animal Tissue | Quest |
| Pancase | Pancreatic Digest of Casein | Red Star |
| Amberferm 2000 | Proteolyzed Dairy Protein | Red Star |
| Amberferm 2234 | Proteolyzed Dairy Protein | Red Star |
| Amberferm 4000 | Acid Hydrolyzed Vegetable Protein | Red Star |
| Amberferm 4002 | Acid Hydrolyzed Vegetable Protein Blend | Red Star |
| Amberferm 4015G | Enzyme Hydrolyzed Soy Protein | Red Star |
| Amberferm 4016 | Enzyme Hydrolyzed Soy | Red Star |
| Whey Protein Concentrate | Corn Steep Liquor | Roquette |
| Nutrisoy Soy Flour | Hydrolyze in the Lab with Neutrase | ADM |
| Nutrisoy Soy Flour with Added Oils | Hydrolyze in the Lab with Neutrase | ADM |
| Pharmamedia | Cottonseed Flour | Traders |

Most of these nitrogen sources supported growth of *L. reuteri* PYR8, but isomerase activity was not always detected. The most promising ones, N-Z-Amine A, Amberferm 2234, Amberferm 4015, Amisoy and Hy-Soy were further tested in fermentors. Hy-soy was determined not just to be a good replacement for peptone, but to actually improve growth over peptone.

Lactose, fructose and galactose were compared to glucose as possible carbon sources. The organism did not grow on fructose and lactose, and galactose did not offer any advantage over glucose.

Fermentations performed with peptone and increasing levels of yeast extract up to 20 g/l indicated that yeast extract concentrations above 10 g/l were still beneficial. Further optimization proceeded with a full factorial experiment in fermentors where the effects two levels of yeast extract (20 and 30 g/l), Hy-Soy (10 and 20 g/l) and glucose (20 and 30 g/l) were compared. pH control at 4.8 was adopted to avoid low pH inhibition due to the higher acid production from the higher glucose concentrations. The growth results from these fermentations showed that even though there was not a statistically significant difference between conditions, higher yeast extract fermentors resulted in slightly higher optical density (data not shown). The culture in the medium with high level of the three components grew faster and reached a higher cell density.

The medium with 30 g/l yeast extract, 10 g/l Hy-Soy and 30 g/l glucose was chosen for further optimizations steps.

The effects of growth temperature and Tween 80 concentration were studied. Fermentations were performed at 11 and 1.5 ml/l Tween 80 and 37° C., 40° C. and 43° C. Medium with Hy-Soy at 20 g/l was also compared at 37° C. and 43° C. The growth and conversion results indicated clearly that higher temperatures were beneficial for growth and isomerase activity (data not shown). The increase in Tween 80 concentration did not seem to impact linoleic acid conversion significantly, although a higher conversion rate was observed at 43° C. with higher Tween 80 concentration.

A temperature of 40° C. was adopted as the preferred growth temperature and the medium containing 30 g/l yeast extract, 10 g/l Hy-Soy, 30 g/l glucose and 1.5 ml/l Tween, as the new base medium. In another set of fermentations, the reproducibility of the process was tested in triplicate fermentors. Higher concentrations of yeast extract, Hy-Soy and glucose were also compared at 40° C. The results showed that good reproducibility can be obtained with this medium and growing conditions, with respect to final cell density and isomerase activity (data not shown). Further increases in the concentrations of the main components favored cell growth. An optical density above 10 units was obtained with 40 g/l yeast extract, 20 g/l Hy-Soy and 40 g/l glucose. The specific enzyme activity and activity per cell was similar under all these different conditions. Therefore, an increase in cell density resulted in increased isomerase activity.

The medium with 30 g/l yeast extract, 10 g/l Hy-Soy and 30 g/l glucose plus the additional components of the AV medium described above, resulted in cell densities (measured by OD and DCW) twice as high as those obtained with MRS, and a much more reliable performance. With these conditions, the fermentation performed consistently better in fermentors than in static bottles. The cultures were harvested at 24 and 30 hours to determine isomerase activity as a function of culture age. No difference was found in the rate of conversion of linoleic acid to CLA between cells of different age for any of the media tested. The shorter fermentation time is due to the faster growth in this medium and at the higher temperature. At 24 hours, the culture had already reached stationary phase.

Several substances were tested as possible inducers of the 9,11 linoleate isomerase. The materials tested included: lauric acid, myristic acid, palmitic acid, palmitoleic acid, oleic acid, linoleic acid, linolenic acid, oleic acid stearyl ester, linoleyl alcohol, linoleic acid methyl ester, linoleic acid ethyl ester, stearic acid and linoleic acid methyl ester. They were added to the growth medium at a 100 mg/l level. No positive effect was found with any of the compounds, and some of them were detrimental to the expression and/or activity of the isomerase. The determination of the existence of a positive effect may be obscured by the required presence of Tween 80, which may be an inducer in itself, but which cannot be eliminated because it is required for growth.

Example 21

The following example describes the determination of conditions to improve enzyme stability and performance and on testing the limitations of the biotransformation process. Whole cells of *L. reuteri* PYR8 were used in all biotransformation experiments described below.

One aspect of the preservation of the enzyme activity is the handling of the cells immediately after harvesting and the determination of suitable storage conditions. The preservation of activity in cells' maintained in different buffers was investigated, and it was determined that reduced buffers such as TKM/EDTA/NaCl (50 mM Tris.HCl, 25 mM KCl, 5 mM $MgCl_2$, 1.25 mM EDTA, 0.1 mM NaCl, pH 7.5) with 20 mM cysteine or 20 mM DTT preserved isomerase activity much better than other buffers or culture medium. Cells maintained in 100 mM Bis-Tris pH 5.8 with 10 mM NaCl, 10% glycerol and 2 mM DTT (breakage buffer) did not lose any activity in 48 hours. It was also determined that the biotransformation rate measured in this buffer was very similar to that measured in the culture medium (MRS) which had been used as the preferred medium to perform the reaction.

Isomerase activity could also be preserved by freezing the cell paste. The cell paste was frozen immediately after harvesting with and without washing with either MRS or breakage buffer. No differences were observed. Some interesting results were also obtained when the cells were directly preserved in the culture broth with or without harvesting. A comparison was made between activity in cells immediately after harvest, cells that were harvested and maintained as a cell paste (no washing) at 4° C. for 24 hours, cells that were kept without harvesting in the culture broth at 4° C. for 24 hours, and cells from culture broth that were kept at room temperature for 24 hours. The conversion of linoleic acid to CLA was very similar in every case, with only a slight decrease observed in those cells that had been maintained at room temperature for a day.

In another experiment, the isomerase activity was followed in cells that were handled in different ways after harvesting. Cells were resuspended in either MRS, breakage buffer or culture supernatant (pH adjusted to 5.8). Isomerase activity, compared as conversion of 1000 ppm linoleic acid, was measured in the cells immediately after harvesting, after being held for 24 hours at 4° C. and after a four hour period at 22° C. followed by 20 hours at 4° C. The results from these different experiments indicated that the enzyme activity is better preserved when the cells are maintained under strictly non-growing conditions (data not shown). In several repeat experiments, cells resuspended in MRS gave more variable results than cells resuspended in breakage buffer. When cells in MRS were kept at room temperature, the deterioration was even more marked. Breakage buffer was selected as the medium of choice to perform the biotransformation because of the better enzyme stability. Cells can also be preserved prior to harvesting in the culture broth at the low pH reached at the end of the fermentation.

Another aspect of the biotransformation investigated was the possible presence of mass transfer limitations between the oil, the water phase and the membrane bound enzyme. Experiments were done using different methods of addition of the linoleic acid and performing the isomerization reaction in stirred jars at different agitation rates.

Linoleic acid was added as 99% LA, dissolved in propyleneglycol (100 mg/ml solution) or emulsified with 0.5, 5 or 30% lecithin. The emulsion was prepared by blending the linoleic acid and the lecithin with the reaction medium before the addition of the cells. Linoleic acid was added at 1000 and 2000 ppm. The results indicated that there was no significant difference between adding the pure acid or the propyleneglycol solution, and that the reaction was slightly faster with both than when the acid was emulsified with lecithin (data not shown). High levels of lecithin seemed to negatively affect the final conversion.

Two biotransformation reactions were performed in stirred jars with 300 ml of reaction medium. Cells were concentrated 10-fold with respect to the original culture density. The reaction was run between 6° C. and 8° C., in MRS, and linoleic acid was added dissolved in propyleneglycol. 1000 ppm were added at time 0 and another 1000 ppm at two hours. Agitation was kept at 200 rpm in one reactor and 1000 rpm in the other. Results showed that no significant difference was found between the two conditions. These experiments indicated that mass transfer limitations are not a major problem when working with this enzyme.

The effect of substrate and product on the enzyme performance was also investigated, as well as the possibility of recycling the cells. The effect of CLA on the reaction was studied by adding different concentrations of either a mixture of isomers (Sigma material, approximately 41% 9,11 isomer and 48% 10,12 CLA), or just 9,11 CLA (Matreya material, approximately 77% 9,11 CLA). Concentrations from 500 to 3000 ppm were tested. Some experiments were also performed recycling the broth from a previous biotransformation reaction with *L. reuteri* PYR8, resulting in an initial CLA concentration around 700 ppm. In every case, 1000 ppm linoleic acid were added. With both the Sigma and the Matreya CLA, the reaction was completely inhibited even at the lowest concentration tested, and linoleic acid and CLA remained constant over the four-hour period that the reaction was followed. In the same period, almost complete conversion of the linoleic acid was obtained in the control without exogenous CLA. However, the effect was not detected when the CLA present came from recycled reaction broth. In this case, there was no difference in conversion rate between no CLA presence and 700 ppm. The results may indicate that some of the impurities present in the chemically produced CLA may be stronger coinhibitors of the 9,11 isomerase than the product itself.

Three separate experiments were performed where the cells were recycled after a first biotransformation step. In the first experiment, a biotransformation step with 1000 ppm linoleic acid was completed in three hours in both MRS and breakage buffer. 98–99% of the linoleic acid was isomerized to 9,11 CLA. Cells were recovered by centrifugation, resuspended in the same medium, 1000 ppm linoleic acid were added, and the reaction proceeded for another three hours. Very good conversions were obtained in every case (data not shown).

In the second experiment, cell recycle was studied with cells that have performed the biotransformation at different levels of linoleic acid. Cells were harvested, resuspended in breakage buffer at a 10-fold concentration, and linoleic acid was added at 1000, 1500, 2000, 2500 and 3000 ppm level. Given the higher linoleic acid concentration, the reaction was allowed to proceed for six hours. At that time, the cells were recovered by centrifugation, washed with buffer to remove (at least partially) non reacted linoleic acid and CLA, and to place all the cells under comparable conditions. 1000 ppm linoleic acid were added and the reaction was followed for four hours. The conversions and CLA concentrations obtained during the first stage indicated that with cells with good activity, no substrate inhibition was detected up to 3000 ppm linoleic acid. The reactions at higher linoleic acid did not reach completion in seven hours, but the rate of formation of CLA was very similar at the different substrate concentrations. However, when the cells were recycled and supplied with linoleic acid in a second stage, the reaction did not take place and isomerase activity was not detected in any of the cells, regardless of the linoleic acid level to which they had been exposed. Cells from the same lot that were not exposed to linoleic acid maintained full activity after 24 hours.

These results prompted the need to investigate the length of exposure to the reaction mix in relation to the loss of activity observed. Since it was clear that the activity was not lost in cells which had not performed the reaction, either the substrate, or more likely the product, might interact with the enzyme and affect its activity.

In the third recycle experiment, cells were concentrated as usual and the reaction was started at 2000 ppm. Aliquots were taken while the reaction proceeded, every two hours up to eight hours with one final sample at 25 hours. The cells from each aliquot were recovered by centrifugation and resuspended in buffer. 1000 ppm linoleic acid was added. The reaction was then followed for three hours. The results clearly indicated that the activity was slowly being lost in the cells. The reaction slowed down over time in the first stage and the activity was not recovered when the cells were placed in fresh reaction medium. While cells recycled after two hours had very good activity and could quickly transform the 1000 ppm linoleic acid to CLA, cells recycled after eight hours had no activity. Once again, full activity was preserved in the control (no reaction) after 25 hours.

This experiment provided a clear demonstration that the enzyme is either inactivated or becomes inaccessible to the substrate during the reaction. The reason is not clear, but an interaction with the product is suggested, as the activity seems to be lost as the product accumulates. It is not clear at this time the nature of this interaction or if it is directly related to the enzyme or the physical conditions of the cells. Studies will be required with immobilized enzyme to better understand this effect.

Example 22

The following example describes a preferred biotransformation protocol.

Cells of *Lactobacillus reuteri* (or another organism carrying the linoleate isomerase gene) are grown in modified AV medium with 40 g/l yeast extract, 20 g/l Hy-soy and 40 g/l glucose (or other appropriate medium for other organisms) to a cell density of about 3–4 g/l dry cell weight. When the cells reach stationary phase, they are harvested and resuspended in breakage buffer at a concentration between 5 and 20 g dry cell weight per liter. The biotransformation reaction should be preferably carried out at a temperature between 4° C. and 8° C. to maintain the enzyme activity. The linoleic acid can be added as a 99% oil, as a component of another oil, as an oil phase, or dissolved in a cosolvent such as propylene glycol. It can be added at concentrations between 0.5 and 4 g/l. The addition should preferably be done in several steps of smaller amounts. To obtain higher CLA concentrations, it is also possible to add the cells in successive steps while the reaction proceeds. Under these conditions, and at these linoleic acid concentrations, conversion of linoleic acid to CLA between 80% and 100% is expected within 2 to 8 hours.

Example 23

The following example describes the biotransformation of linoleic acid to 10,12 CLA with *P. acnes* whole cells.

The objective of these studies was to begin the characterization of the behavior of the 10,12 linoleic acid isomerase and to determine the conditions to enhance its performance.

*P. acnes* is a strict anaerobe for which growth in the medium currently used is very poor. Some previous experiments suggested that *P. acnes* was able to further metabolize 10,12 CLA. The new experiments also indicated this to be the case, but it seems to be a slow process which may depend on the conditions of the reaction. It must be noted that with the current cell concentration achieved in the culture, and the same bioconversion protocol used in the production of the 9,11 CLA isomer (10-fold concentration of the cells, resuspension in buffer, addition of linoleic acid dissolved in propyleneglycol), the reaction proceeds at a much lower rate than that of the 9,11 isomerase, and much lower conversions are achieved.

The reaction was compared in culture medium vs. breakage buffer, at different temperatures and in the presence and absence of air. Temperature had a strong effect on the reaction rate. The reaction proceed very slowly at 4° C. and the rate increased with temperature, from room temperature to 37° C. No significant difference in conversion was found between the use of growth medium or a buffer, or the presence or absence of oxygen during the time frame allowed for the reaction to proceed (30 hours) (data not shown).

Further experiments with different cell and substrate concentrations had shown an apparent decrease in the CLA concentration when the reaction proceeded more than 48 hours, while the formation of CLA from linoleic acid seemed to stop at that time.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. An isolated nucleic acid molecule comprising a nucleic acid sequence selected from the group consisting of:
   a) a nucleic acid sequence encoding a protein comprising an amino acid sequence of SEQ ID NO:61;
   b) a nucleic acid sequence encoding a protein that is at least about 70% identical to SEQ ID NO:61, wherein said protein has 10,12-linoleate isomerase activity;
   c) a nucleic acid sequence encoding an enzymatically active fragment of SEQ ID NO:61; and,
   d) a nucleic acid sequence that is fully complementary to any of said nucleic acid sequences of (a), (b) or (c).

2. The isolated nucleic acid molecule of claim 1, wherein said nucleic acid molecule comprises a nucleic acid sequence selected from the group consisting of:
   a) a nucleic acid sequence encoding a protein comprising an amino acid sequence of SEQ ID NO:61;
   b) a nucleic acid sequence encoding a protein that is at least about 70% identical to SEQ ID NO:61, wherein said protein has 10,12-linoleate isomerase activity; and
   c) a nucleic acid sequence encoding an enzymatically active fragment of SEQ ID NO:61.

3. The isolated nucleic acid molecule of claim 1, wherein said nucleic acid molecule comprises a nucleic acid sequence encoding an enzymatically active fragment of SEQ ID NO:61.

4. The isolated nucleic acid molecule of claim 1, wherein said nucleic acid molecule comprises a nucleic acid sequence encoding a protein having an amino acid sequence of SEQ ID NO:61.

5. The isolated nucleic acid molecule of claim 1, wherein said nucleic acid molecule comprises a nucleic acid sequence selected from the group consisting of SEQ ID NO:59 and SEQ ID NO:60.

6. The isolated nucleic acid molecule of claim 1, wherein said nucleic acid molecule comprises nucleic acid sequence SEQ ID NO:60.

7. The isolated nucleic acid molecule of claim 1, wherein said nucleic acid molecule is selected from the group consisting of *Propionibacterium acnes, Propionibacterium acidipropionici* and *Propionibacterium freudenreichii* linoleate isomerase nucleic acid molecules.

8. The isolated nucleic acid molecule of claim 1, wherein said nucleic acid molecule comprises a *Propionibacterium acnes* nucleic acid molecule.

9. A recombinant nucleic acid molecule comprising an isolated nucleic acid molecule as set forth in claim 2 operatively linked to a transcription control sequence.

10. A recombinant virus comprising an isolated nucleic acid molecule as set forth in claim 2.

11. A recombinant cell comprising an isolated nucleic acid molecule as set forth in claim 2, wherein said cell expresses said nucleic acid molecule.

12. The recombinant cell of claim 11, wherein said cell is selected from the group consisting of bacterial, fungal, microalgal, insect, plant and mammalian cells.

13. The recombinant cell of claim 11, wherein said cell is a yeast cell.

14. The recombinant cell of claim 11, wherein said cell is a bacterial cell.

15. The recombinant cell of claim 11, wherein said cell is a bacterial cell selected from the group consisting of Propionibacterium, Escherichia and Bacillus cells.

16. The recombinant cell of claim 11, wherein said cell is a microorganism selected from the group consisting of *Propionibacterium acnes, Propionibacterium freudenreichii, Propionibacterium acidipropionici, Escherichia coli, Bacillus subtilis,* and *Bacillus licheniformis.*

17. The recombinant cell of claim 11, wherein said cell is a microorganism selected from the group consisting of *Escherichia coli, Bacillus subtilis* and *Bacillus licheniformis.*

18. An oligonucleotide comprising at least about 24 contiguous nucleotides of SEQ ID NO:60.

19. The oligonucleotide of claim 18, comprising at least about 45 contiguous nucleotides of SEQ ID NO:60.

20. The oligonucleotide of claim 18, comprising at least about 90 contiguous nucleotides of SEQ ID NO:60.

21. The oligonucleotide of claim 18, comprising at least about 180 contiguous nucleotides of SEQ ID NO:60.

22. A method to produce linoleate isomerase, comprising culturing a recombinant cell under conditions whereby said linoleate isomerase is produced, wherein said recombinant cell is transfected with an isolated nucleic acid molecule of comprising a nucleic acid sequence selected from the group consisting of:
   a) a nucleic acid sequence encoding a protein comprising an amino acid sequence of SEQ ID NO:61;
   b) a nucleic acid sequence encoding a protein that is at least about 70% identical to SEQ ID NO:61, wherein said protein has 10,12-linoleate isomerase activity; and
   c) a nucleic acid sequence encoding an enzymatically active fragment of SEQ ID NO:61.

23. The method of claim 22, wherein said nucleic acid molecule comprises a nucleic acid sequence encoding an enzymatically active fragment of SEQ ID NO:61.

24. The method of claim 22, wherein said nucleic acid molecule comprises a nucleic acid sequence encoding a protein having an amino acid sequence of SEQ ID NO:61.

25. The method of claim 22, wherein said nucleic acid molecule comprises a nucleic acid sequence selected from the group consisting of SEQ ID NO:59 and SEQ ID NO:60.

26. The method of claim 22, wherein said recombinant cell is from a microorganism selected from the group consisting of *Propionibacterium acnes, Propionibacterium freudenreichii, Propionibacterium acidipropionici, Escherichia coli, Bacillus subtilis* and *Bacillus licheniformis.*

27. The method of claim 22, wherein said recombinant cell is from a microorganism selected from the group consisting of *Escherichia coli, Bacillus subtilis* and *Bacillus licheniformis.*

28. An immobilized cell or immobilized homogenate thereof, wherein said cell is transfected with a recombinant nucleic acid molecule comprising a nucleic acid sequence selected from the group consisting of:
  a) a nucleic acid sequence encoding a protein comprising an amino acid sequence of SEQ ID NO:61;
  b) a nucleic acid sequence encoding a protein that is at least about 70% identical to SEQ ID NO:61, wherein said protein has 10,12-linoleate isomerase activity; and
  c) a nucleic acid sequence encoding an enzymatically active fragment of SEQ ID NO:61;
wherein said nucleic acid sequence is operatively linked to a transcription control sequence.

29. The immobilized cell or immobilized homogenate thereof of claim 28, wherein said recombinant nucleic acid molecule comprises a nucleic acid sequence encoding an enzymatically active fragment of SEQ ID NO:61.

30. The immobilized cell or immobilized homogenate thereof of claim 28, wherein said recombinant nucleic acid molecule comprises a nucleic acid sequence encoding a protein having an amino acid sequence of SEQ ID NO:61.

31. The immobilized cell or immobilized homogenate thereof of claim 28, wherein said recombinant nucleic acid molecule comprises a nucleic acid sequence selected from the group consisting of SEQ ID NO:59 and SEQ ID NO:60.

32. The immobilized cell or immobilized homogenate thereof of claim 28, wherein said recombinant nucleic acid molecule is integrated into the genome of said cell.

33. The immobilized cell or immobilized homogenate thereof of claim 28, wherein said recombinant nucleic acid molecule is a plasmid.

34. The immobilized cell or immobilized homogenate thereof of claim 28, wherein said cell is selected from the group consisting of a bacterial cell, a fungal cell, a microalgal cell, an insect cell, a plant cell and a mammalian cell.

35. The immobilized cell or immobilized homogenate thereof of claim 28, wherein said cell is a bacterial cell.

36. The immobilized cell or immobilized homogenate thereof of claim 28, wherein said cell is a bacterial cell selected from the group consisting of Propionibacterium, Escherichia and Bacillus cells.

37. The immobilized cell or immobilized homogenate thereof of claim 28, wherein said cell is a yeast cell.

38. The immobilized cell or immobilized homogenate thereof of claim 28, wherein said transfected cell has been lysed to form said homogenate.

39. The immobilized cell or immobilized homogenate thereof of claim 28, wherein said cell or homogenate has been immobilized by crosslinking with a bifunctional or multifunctional crosslinking agent.

40. The immobilized cell or immobilized homogenate thereof of claim 39, wherein said crosslinking agent is glutaraldehyde.

41. A method for producing CLA (conjugated linoleic acid or conjugated linolenic acid) or a derivative thereof, comprising contacting an oil, said oil comprising a fatty acid selected from the group consisting linoleic acid, linolenic acid, and a derivative thereof, with an immobilized cell of claim 24.

42. The method of claim 41, wherein said fatty acid is in the form of a triglyceride and wherein said method further comprises contacting said oil with a hydrolysis enzyme to convert at least a portion of said triglycerides to free fatty acids.

43. The method of claim 42, wherein said hydrolysis enzyme is selected from the group consisting of lipases, phospholipases and esterases.

44. The method of claim 41, further comprising the step of recovering said CLA or derivative thereof.

45. The method of claim 44, wherein said CLA is (trans, cis)-10,12-linoleic acid.

46. The method of claim 41, wherein said oil is selected from the group consisting of sunflower oil, safflower oil, corn oil, linseed oil, palm oil, rapeseed oil, sardine oil, herring oil, mustard seed oil, peanut oil, sesame oil, perilla oil, cottonseed oil, soybean oil, dehydrated castor oil and walnut.

47. The method of claim 41, wherein said step of producing said CLA from said oil provides at least about 50% conversion of said oil to said CLA or derivative thereof.

48. The method of claim 41, wherein said cell is a bacterial cell.

49. The method of claim 48, wherein said bacterial cell is *Escherichia coli.*

50. The method of claim 48, wherein said bacterial cell is *Bacillus subtilis.*

51. The method of claim 48, wherein said bacterial cell is *Bacillus licheniformis.*

* * * * *

SEQUENCE LISTING

```
<160> NUMBER OF SEQ ID NOS: 80

<210> SEQ ID NO 1
<211> LENGTH: 35
<212> TYPE: PRT
<213> ORGANISM: Lactobacillus reuteri
<220> FEATURE:
<221> NAME/KEY: UNSURE
```

```
<222> LOCATION: (30)
<223> OTHER INFORMATION: Xaa = any amino acid

<400> SEQUENCE: 1

Met Tyr Tyr Ser Asn Gly Asn Tyr Glu Ala Phe Ala Arg Pro Lys Lys
 1               5                  10                  15

Pro Ala Gly Val Asp Lys Lys His Ala Tyr Ile Val Gly Xaa Gly Leu
            20                  25                  30

Ala Ser Leu
        35

<210> SEQ ID NO 2
<211> LENGTH: 29
<212> TYPE: DNA
<213> ORGANISM: Lactobacillus reuteri
<220> FEATURE:
<221> NAME/KEY: unsure
<222> LOCATION: (1)..(29)
<223> OTHER INFORMATION: n = a, c, g, or t

<400> SEQUENCE: 2
cgtgaattca tgtaytayws naayggnaa                                    29

<210> SEQ ID NO 3
<211> LENGTH: 27
<212> TYPE: DNA
<213> ORGANISM: Lactobacillus reuteri
<220> FEATURE:
<221> NAME/KEY: unsure
<222> LOCATION: (1)..(27)
<223> OTHER INFORMATION: n = a, c, g, or t

<400> SEQUENCE: 3
actggatccn acdatratng crtgytt                                      27

<210> SEQ ID NO 4
<211> LENGTH: 87
<212> TYPE: DNA
<213> ORGANISM: Lactobacillus reuteri
<220> FEATURE:
<221> NAME/KEY: CDS
<222> LOCATION: (1)..(87)

<400> SEQUENCE: 4 atg tat tat tcg aac gga aat tat gaa gcc ttt gct cga cca aag aag   48
Met Tyr Tyr Ser Asn Gly Asn Tyr Glu Ala Phe Ala Arg Pro Lys Lys
 1               5                  10                  15 cct gct ggc gtt gat aag aaa cac gcc tac ata gtc gga               87
Pro Ala Gly Val Asp Lys Lys His Ala Tyr Ile Val Gly
            20                  25

<210> SEQ ID NO 5
<211> LENGTH: 29
<212> TYPE: PRT
<213> ORGANISM: Lactobacillus reuteri

<400> SEQUENCE: 5

Met Tyr Tyr Ser Asn Gly Asn Tyr Glu Ala Phe Ala Arg Pro Lys Lys
 1               5                  10                  15

Pro Ala Gly Val Asp Lys Lys His Ala Tyr Ile Val Gly
            20                  25

<210> SEQ ID NO 6
<211> LENGTH: 17
<212> TYPE: DNA
```

<213> ORGANISM: Lactobacillus reuteri

<400> SEQUENCE: 6
ggtcgagcaa aggcttc                                                      17

<210> SEQ ID NO 7
<211> LENGTH: 17
<212> TYPE: DNA
<213> ORGANISM: Lactobacillus reuteri

<400> SEQUENCE: 7
aagcctgctg gcgttga                                                      17

<210> SEQ ID NO 8
<211> LENGTH: 596
<212> TYPE: DNA
<213> ORGANISM: Lactobacillus reuteri
<220> FEATURE:
<221> NAME/KEY: CDS
<222> LOCATION: (122)..(595)

<400> SEQUENCE: 8

```
aaaaattatt tagaattaat ttataagttc attgtgttta ataaaattga cactttcaac        60
cgctttcact aaaattaagg tagttatgat gcacttgttt actgagaagg gagtcgtcaa       120 a atg tat tat tca aac ggg aat tat gaa gcc ttt gct cga cca aag aag       169
  Met Tyr Tyr Ser Asn Gly Asn Tyr Glu Ala Phe Ala Arg Pro Lys Lys
  1               5                  10                  15 cct gct ggc gtt gat aag aaa cat gcc tac att gtc ggt ggt ggt tta        217
Pro Ala Gly Val Asp Lys Lys His Ala Tyr Ile Val Gly Gly Gly Leu
            20                  25                  30 gct ggt tta tcg gcc gcc gtg ttt tta att cgt gat gcc caa atg ccg        265
Ala Gly Leu Ser Ala Ala Val Phe Leu Ile Arg Asp Ala Gln Met Pro
        35                  40                  45 ggt gag aat atc cat att tta gag gaa tta ccg gtt gcc ggt ggt tct        313
Gly Glu Asn Ile His Ile Leu Glu Glu Leu Pro Val Ala Gly Gly Ser
    50                  55                  60 ctt gat ggt gaa gat cgt cct gga att ggt ttt gtt act cgt gga ggc        361
Leu Asp Gly Glu Asp Arg Pro Gly Ile Gly Phe Val Thr Arg Gly Gly
65                  70                  75                  80 cgg gaa atg gag aac cat ttc gag tgt atg tgg gac atg tat cgt tca        409
Arg Glu Met Glu Asn His Phe Glu Cys Met Trp Asp Met Tyr Arg Ser
                85                  90                  95 att cca tca ctt gaa atc cca ggt gct tcc tac ctt gat gaa tac tac        457
Ile Pro Ser Leu Glu Ile Pro Gly Ala Ser Tyr Leu Asp Glu Tyr Tyr
            100                 105                 110 tgg tta gat aag gaa gat cca aac agt tct aat tgt cgt tta acc tat        505
Trp Leu Asp Lys Glu Asp Pro Asn Ser Ser Asn Cys Arg Leu Thr Tyr
        115                 120                 125 aag cgg gga aat gaa gtt cca tcg gac ggt aaa tat ggt tta agt aaa        553
Lys Arg Gly Asn Glu Val Pro Ser Asp Gly Lys Tyr Gly Leu Ser Lys
    130                 135                 140 aag gca atc aaa gag ctg act aag cta att atg acc cct aaa g              596
Lys Ala Ile Lys Glu Leu Thr Lys Leu Ile Met Thr Pro Lys
145                 150                 155
```

<210> SEQ ID NO 9
<211> LENGTH: 158
<212> TYPE: PRT
<213> ORGANISM: Lactobacillus reuteri

<400> SEQUENCE: 9

```
Met Tyr Tyr Ser Asn Gly Asn Tyr Glu Ala Phe Ala Arg Pro Lys Lys
  1               5                  10                  15

Pro Ala Gly Val Asp Lys Lys His Ala Tyr Ile Val Gly Gly Leu
             20                  25                  30

Ala Gly Leu Ser Ala Ala Val Phe Leu Ile Arg Asp Ala Gln Met Pro
         35                  40                  45

Gly Glu Asn Ile His Ile Leu Glu Glu Leu Pro Val Ala Gly Gly Ser
     50                  55                  60

Leu Asp Gly Glu Asp Arg Pro Gly Ile Gly Phe Val Thr Arg Gly Gly
 65                  70                  75                  80

Arg Glu Met Glu Asn His Phe Glu Cys Met Trp Asp Met Tyr Arg Ser
                 85                  90                  95

Ile Pro Ser Leu Glu Ile Pro Gly Ala Ser Tyr Leu Asp Glu Tyr Tyr
             100                 105                 110

Trp Leu Asp Lys Glu Asp Pro Asn Ser Ser Asn Cys Arg Leu Thr Tyr
             115                 120                 125

Lys Arg Gly Asn Glu Val Pro Ser Asp Gly Lys Tyr Gly Leu Ser Lys
 130                 135                 140

Lys Ala Ile Lys Glu Leu Thr Lys Leu Ile Met Thr Pro Lys
145                 150                 155
```

<210> SEQ ID NO 10
<211> LENGTH: 1709
<212> TYPE: DNA
<213> ORGANISM: Lactobacillus reuteri

<400> SEQUENCE: 10

| | | | | | |
|---|---|---|---|---|---|
| cggaaggcat | caaaatccca | atgaattccc | accaaactta | gtgcataggg | caagaagggt | 60 |
| gtcccgcgat | tggtatgcat | ggattggaac | ccgcctttaa | gattaatgcg | cctgaaggaa | 120 |
| gccagctggt | cgccaatccg | tagcaccatt | ccctgggcaa | ttcggctttt | atattgaccg | 180 |
| agttgtcctg | tttaaccagg | catcaccttg | ccacgcccct | ccttgacggt | caagatgatt | 240 |
| tacagcatag | ggtgcacttg | caatcttagc | gttaagattt | gtttggttat | tattgataat | 300 |
| aaacgcaccg | gctttgttcc | aggtaattga | aatgccaagt | tgttggcgaa | cagccggagt | 360 |
| taagactgaa | ttagcctgtt | cctgagttgg | cggtaatgtt | tttttgatcg | ttgtgactgg | 420 |
| ttttcttcca | ataagcaatt | ttactaatat | ggtttaacga | agcatttgtt | agctgaggtt | 480 |
| gctggataac | tccagtaact | actaataaac | cagcaagagc | aaataaaagg | tgatagaggc | 540 |
| gtttcttaag | tttcataaat | tcactccatt | tctaataatt | ccaaagtcta | ttttactagt | 600 |
| ttgaacatac | gtttggaata | attatttaga | attaatttat | aagttcattg | tgtttaataa | 660 |
| aattgacact | ttcaaccgct | ttcactaaaa | ttaaggtagt | tatgatgcac | ttgtttactg | 720 |
| agaagggagt | cgtcaaaatg | tattattcaa | acgggaatta | tgaagccttt | gctcgaccaa | 780 |
| agaagcctgc | tggcgttgat | aagaaacatg | cctacattgt | cggtggtggt | ttagctggtt | 840 |
| tatcggccgc | cgtgttttta | attcgtgatg | cccaaatgcc | gggtgagaat | atccatattt | 900 |
| tagaggaatt | accggttgcc | ggtggttctc | ttgatggtga | agatcgtcct | ggaattggtt | 960 |
| ttgttactcg | tggaggccgg | gaaatggaga | accatttcga | gtgtatgtgg | acatgtatc | 1020 |
| gttcaattcc | atcacttgaa | atcccaggtg | cttcctacct | tgatgaatac | tactggttag | 1080 |
| ataaggaaga | tccaaacagt | tctaattgtc | gtttaaccta | taagcgggga | aatgaagttc | 1140 |
| catcggacgg | taaatatggt | ttaagtaaaa | aggcaatcaa | agagctgact | aagctaatta | 1200 |
| tgacccctga | agaaaaattg | ggaagggaga | ctattggtga | atacttctct | gatgatttct | 1260 |

-continued

```
ttgaaagcaa tttctggatt tattggtcaa caatgtttgc gtttgaacgg tggcactctc    1320
tagctgaaat gcgtcgttat atgatgcggt ttattcacca tattgatggt ttaccggatt    1380
tcactgcact gaagtttaat aagtataacc aatatgaatc aatgaccaag ccgctattgg    1440
cctacctgaa agatcatcat gtcaagattg agtacgatac ccaggtaaag aatgttattg    1500
ttgatactca tgggcggcaa aagcacgcta agcgaatctt attaactcaa gccggtaaag    1560
ataaagttgt tgagttaacg gacaatgacc ttgtctttgt cacaaacggt tcaattacag    1620
aaagttctac ttacggcagt caccatcaag ccagctcgac caacgcagca cttggtgggt    1680
agttggaaac tgtgggaaaa ccttgctcc                                       1709
```

<210> SEQ ID NO 11
<211> LENGTH: 324
<212> TYPE: PRT
<213> ORGANISM: Lactobacillus reuteri
<220> FEATURE:
<221> NAME/KEY: UNSURE
<222> LOCATION: (315)
<223> OTHER INFORMATION: Xaa = any amino acid

<400> SEQUENCE: 11

```
Met Tyr Tyr Ser Asn Gly Asn Tyr Glu Ala Phe Ala Arg Pro Lys Lys
  1               5                  10                  15

Pro Ala Gly Val Asp Lys Lys His Ala Tyr Ile Val Gly Gly Gly Leu
             20                  25                  30

Ala Gly Leu Ser Ala Ala Val Phe Leu Ile Arg Asp Ala Gln Met Pro
         35                  40                  45

Gly Glu Asn Ile His Ile Leu Glu Glu Leu Pro Val Ala Gly Gly Ser
     50                  55                  60

Leu Asp Gly Glu Asp Arg Pro Gly Ile Gly Phe Val Thr Arg Gly Gly
 65                  70                  75                  80

Arg Glu Met Glu Asn His Phe Glu Cys Met Trp Asp Met Tyr Arg Ser
                 85                  90                  95

Ile Pro Ser Leu Glu Ile Pro Gly Ala Ser Tyr Leu Asp Glu Tyr Tyr
            100                 105                 110

Trp Leu Asp Lys Glu Asp Pro Asn Ser Ser Asn Cys Arg Leu Thr Tyr
        115                 120                 125

Lys Arg Gly Asn Glu Val Pro Ser Asp Gly Lys Tyr Gly Leu Ser Lys
    130                 135                 140

Lys Ala Ile Lys Glu Leu Thr Lys Leu Ile Met Thr Pro Glu Glu Lys
145                 150                 155                 160

Leu Gly Arg Glu Thr Ile Gly Glu Tyr Phe Ser Asp Asp Phe Phe Glu
                165                 170                 175

Ser Asn Phe Trp Ile Tyr Trp Ser Thr Met Phe Ala Phe Glu Arg Trp
            180                 185                 190

His Ser Leu Ala Glu Met Arg Arg Tyr Met Met Arg Phe Ile His His
        195                 200                 205

Ile Asp Gly Leu Pro Asp Phe Thr Ala Leu Lys Phe Asn Lys Tyr Asn
    210                 215                 220

Gln Tyr Glu Ser Met Thr Lys Pro Leu Leu Ala Tyr Leu Lys Asp His
225                 230                 235                 240

His Val Lys Ile Glu Tyr Asp Thr Gln Val Lys Asn Val Ile Val Asp
                245                 250                 255

Thr His Gly Arg Gln Lys His Ala Lys Arg Ile Leu Leu Thr Gln Ala
            260                 265                 270
```

Gly Lys Asp Lys Val Val Glu Leu Thr Asp Asn Asp Leu Val Phe Val
            275                 280                 285

Thr Asn Gly Ser Ile Thr Glu Ser Ser Thr Tyr Gly Ser His His Gln
    290                 295                 300

Ala Ser Ser Thr Asn Ala Ala Leu Gly Gly Xaa Leu Glu Thr Val Gly
305                 310                 315                 320

Lys Pro Cys Ser

<210> SEQ ID NO 12
<211> LENGTH: 17
<212> TYPE: DNA
<213> ORGANISM: Lactobacillus reuteri

<400> SEQUENCE: 12
ccaattccag gacgatc                                                        17

<210> SEQ ID NO 13
<211> LENGTH: 19
<212> TYPE: DNA
<213> ORGANISM: Lactobacillus reuteri

<400> SEQUENCE: 13
acatgtatcg ttcaattcc                                                      19

<210> SEQ ID NO 14
<211> LENGTH: 1165
<212> TYPE: DNA
<213> ORGANISM: Lactobacillus reuteri

<400> SEQUENCE: 14
aagcctgctg gcgttgataa gaaacatgcc tacattgtcg gtggtggttt agctggttta        60
tcggccgccg tgtttttaat tcgtgatgcc caaatgccgg tgagaatat ccatatttta       120
gaggaattac cggttgaata attaatggta atgtttcttt ggacattcgg aacaaagaca       180
ttgtattcta gagaaccatc actagattta gcttcgatat gagcacctgc cggaacgata       240
ttattaccgt cataaatatt ggtaactcgg tagcgaactt gcttattctg atctaatgct       300
tttctcacca gaccttcgta gtaattttgc cctgttgagt tcttacttcg tgcttcattt       360
gcccaggcag tttgcgtggc aatattagat ggatttgatt cggatgcatc aaatccatga       420
atacccacca actagtgcat agggcaagaa ggtgtccgcg atcgtatgca tgattgtacc       480
cgcctttaag attatgcgcc tgaaaggaag ccagctggtc gccaatccgt agcaccattc       540
cctgggcaat tcggcttta tattgaccga gttgtcctgt ttaaccaggc atcaccttgc       600
cacgcccttc cttgacggtc aagatgattt acagcatagg gtgcacttgc aatcttagcg       660
ttaagatttg tttggttatt attgataata acgcaccgg cttgttccaa ggtaattgaa       720
atgccaagtt gttggcgaac agccggagtt aagactgaat tagcctgttc ctgagttggc       780
ggtaatgttt ttttgatcgt tgtgactggt tttcttccaa taagcaattt tactaatatg       840
gtttaacgaa gcatttgtta gctgaggttg ctggataact ccagtaacta ctaataaacc       900
agcaagagca aataaaaggt gatagaggcg tttcttaagt ttcataaatt cactccattt       960
ctaataattc caaagtctat tttactagtt tgaacatacg tttggaataa ttatttagaa      1020
ttaatttata agttcattgt gtttaataaa attgacactt tcaaccgctt tcactaaaat      1080
taaggtagtt atgatgcact tgtttactga gaagggagtc gtcaaaatgt attattcaaa      1140
cgggaattat gaagcctttg ctcga                                             1165

<210> SEQ ID NO 15
<211> LENGTH: 2319
<212> TYPE: DNA
<213> ORGANISM: Lactobacillus reuteri

<400> SEQUENCE: 15

```
ccaattccag gacgatcttc accatcaaga gaaccaccgg caaccggtcc cttaccgcta      60
tcctgatctt tctttccttc ctcaacttgc ttttgagctg cctttactag gttcatagta     120
aagaagggct tcaatactgg cttaaaatcc tttttaaagt ggtcagtaag gttttggtat     180
aagcggacat cattgtcaaa taccaatact tcttcaaatt gatttcggtg agcatcaaat     240
gaagcttcgt ctaaatctac actcccaaga atcacacggg aatcatgagt agttgaacta     300
cttaacaagt aaaacttaga atggataacc tgagtaggcg cgattgatac gcgaaaaaga     360
ttatttaaga cgttcgtttg gttgtcactg gttaacgctg agaagagttt agcagcttct     420
ttatttgctg aactaaggag agcattggta agtgcaacct ttgtcaccat ctcatcagca     480
cttaattcac tagttgattg ggagcttaac gctacattaa tactgataaa attactaagg     540
tatttattaa tgaagtcagc agtaattttc ccagttactg cgattaactg atcgtatttt     600
tgtgaatcaa ataattgatg gatctttaat ggtggtgttt cttgaccatc aaaaacaata     660
tgaattttc ttataccagc agtttctgtc atgaccataa tcctttacta tcaataaata     720
tattagtttt attttcgact atttaatccc tttttgcaag tggttccccg ataagctata     780
taaaaaaga agccggaaat ttccagcttc tttcatcttt atagtaagtg ctgttgctcc     840
attaattcac caatccacgt tccttggagt ttctttaata atggcttttc aacaatcttt     900
ggaattggca agtccatgtc ttttaacggc ttcttatcat tcatgtaata cattgcccgc     960
attaactctc gaagatcata aatagagtta aagacttctg gaactccccg atcaacatct    1020
aatagagtgt agacggcttc cattgcggtc cgtactgaat attccgtggt aaatacggta    1080
tctcgacttg gagattcagc aaagttacca ataaatgcca agttagcgga tccttctgga    1140
acaacgtctg gacggtcgcc cttaactcgt ggcataaagt agctagtgat aaatggcata    1200
tatactggaa cagtattaat tgaactctcc ttagccaaat cgtcaattaa cggcttctgg    1260
aaccccaga tggatagcca ttctttagta atctcttcac cagtacaatc aacgatccgt    1320
ttcttaatat agtttccctt tgtattagag tacagaccgt aaatccaaac aatggtttca    1380
ttttctttt gtttcttgaa gtgcggttga cggtgaattg tccaggaaag catccaatta    1440
gagtcagtga ccgtaatgat tccaccagta ttaactttgc catcatggag atctcgcttg    1500
gttaagcgtt caatgtatgg ttcaacttgc gggttcttaa cggttgcagt agcggaaatg    1560
aaccagcttc tccctggaag attcttgcaa aagacatcag gatgaccaaa atcagctgac    1620
tgccgagcaa ggttttccca cagtttccaa ctaccaccaa gtgctgcgtt ggtcgagctg    1680
cttgatggtg actgccgtaa gtagaacttt ctgtaattga accgtttgtg acaaagacaa    1740
ggtcattgtc cgttaactca acaactttat ctttaccggc ttgagttaat aagattcgct    1800
tagcgtgctt ttgccgccca tgagtatcaa caataacatt cttttacctgg gtatcgtact    1860
caatcttgac atgatgatct ttcaggtagg ccaatagcgg cttggtcatt gattcatatt    1920
ggttatactt attaaacttc agtgcagtga atccggtaa accatcaata tggtgaataa    1980
accgcatcat ataacgacgc atttcagcta gagagtgcca ccgttcaaac gcaaacattg    2040
ttgaccaata aatccagaaa ttgctttcaa agaaatcatc agagaagtat tcaccaatag    2100
```

-continued

| | | |
|---|---|---|
| tctcccttcc caattttct tcaggggtca taattagctt agtcagctct ttgattgcct | 2160 |
| ttttacttaa accatattta ccgtccgatg gaacttcatt tccccgctta taggttaaac | 2220 |
| gacaattaga actgtttgga tcttccttat ctaaccagta gtattcatca aggtaggaag | 2280 |
| cacctgggat ttcaagtgat ggaattgaac gatacatgt | 2319 |

<210> SEQ ID NO 16
<211> LENGTH: 3551
<212> TYPE: DNA
<213> ORGANISM: Lactobacillus reuteri

<400> SEQUENCE: 16

| | | |
|---|---|---|
| accggttgaa taattaatgg taatgtttct ttggacattc ggaacaaaga cattgtattc | 60 |
| tagagaacca tcactagatt tagcttcgat atgagcacct gccggaacga tattattacc | 120 |
| gtcataaata ttggtaactc ggtagcgaac ttgcttattc tgatctaatg cttttctcac | 180 |
| cagaccttcg tagtaatttt gccctgttga gttcttactt cgtgcttcat ttgcccaggc | 240 |
| agtttgcgtg gcaatattag atggatttga ttcggatgca tcaaatccat gaataccacc | 300 |
| aactagtgca taggcaagaa ggtgtccgcg atcgtatgca tgattgtacc cgcctttaag | 360 |
| attatgcgcc tgaaaggaag ccagctggtc gccaatccgt agcaccattc cctgtggcaa | 420 |
| atttcggctt ttatattgac cgagttgtcc tgtttaacca ggcatcacct tgccacgccc | 480 |
| ttccttgacg gtcaagatga tttacagcat agggtgcact tgcaatctta gcgttaagat | 540 |
| ttgtttggtt attattgata taaacgcac cggctttgtt ccaggtaatt gaaatgccaa | 600 |
| gttgttggcg aacagccgga gttaagacta aattagcctg ttcctgagtt ggcggtaatg | 660 |
| ttttttttgat cgttgtgact ggttttcttc caataagcaa ttttactaat atggtttaac | 720 |
| gaagcatttg ttagctgagg ttgctggata actccagtaa ctactaataa accagcaaga | 780 |
| gcaaataaaa ggtgatagag gcgttcctta agtttcataa attcactcca tttctaataa | 840 |
| ttccaaagtc tattttacta gtttgaacat acgtttggaa taattattta gaattaattt | 900 |
| ataagttcat tgtgttaat aaaattgaca ctttcaaccg ctttcactaa aattaaggta | 960 |
| gttatgatgc acttgtttac tgagaaggga gtcgtcaaaa tgtattattc aaacgggaat | 1020 |
| tatgaagcct ttgctcgacc aaagaagcct gctggcgttg ataagaaaca tgcctacatt | 1080 |
| gtcggtggtg gtttagctgg tttatcggcc gccgtgtttt taattcgtga tgcccaaatg | 1140 |
| ccgggtgaga atatccatat tttagaggaa ttaccggttg ccgtggttc tcttgatggt | 1200 |
| gaagatcgtc ctggaattgg ttttgttact cgtggaggcc gggaaatgga gaaccatttc | 1260 |
| gagtgtatgt gggacatgta tcgttcaatt ccatcacttg aaatcccagg tgcttcctac | 1320 |
| cttgatgaat actactggtt agataaggaa gatccaaaca gttctaattg tcgtttaacc | 1380 |
| tataagcggg gaaatgaagt tccatcggac ggtaaatatg gtttaagtaa aaaggcaatc | 1440 |
| aaagagctga ctaagctaat tatgacccct gaagaaaaat tgggaaggga gactattggt | 1500 |
| gaatacttct ctgatgattt ctttgaaagc aatttctgga tttattggtc aacaatgttt | 1560 |
| gcgtttgaac ggtggcactc tctagctgaa atgcgtcgtt atatgatgcg gtttattcac | 1620 |
| catattgatg gttaccgga tttcactgca ctgaagttta ataagtataa ccaatatgaa | 1680 |
| tcaatgacca agccgctatt ggcctacctg aaagatcatc atgtcaagat tgagtacgat | 1740 |
| acccaggtaa agaatgttat tgttgatact catgggcggc aaaagcacgc taagcgaatc | 1800 |
| ttattaactc aagccggtaa agataaagtt gttgagttaa cggacaatga ccttgtcttt | 1860 |
| gtcacaaacg gttcaattac agaaagttct acttacggca gtcaccatca agcagctcga | 1920 |

-continued

```
ccaacgcaag cacttggtgg tagttggaaa ctgtgggaaa accttgctcg gcagtcagct    1980
gattttggtc atcctgatgt cttttgcaag aatcttccag ggagaagctg gttcatttcc    2040
gctactgcaa ccgttaagaa cccgcaagtt gaaccataca ttgaacgctt aaccaagcga    2100
gatctccatg atggcaaagt taatactggt ggaatcatta cggtcactga ctctaattgg    2160
atgctttcct ggacaattca ccgtcaaccg cacttcaaga aacaaagaa aaatgaaacc     2220
attgtttgga tttacggtct gtactctaat acaaagggaa actatattaa gaacggatc    2280
gttgattgta ctggtgaaga gattactaaa gaatggctat ccatctgggg gttccagaag    2340
ccgttaattg acgatttggc taaggagagt tcaattaata ctgttccagt atatatgcca    2400
tttatcacta gctactttat gccacgagtt aagggcgacc gtccagacgt tgttccagaa    2460
ggatccgcta acttggcatt tattggtaac tttgctgaat ctccaagtcg agataccgta    2520
tttaccacgg aatattcagt acggaccgca atggaagccg tctacactct attagatgtt    2580
gatcggggag ttccagaagt ctttaactct atttatgatc ttcgagagtt aatgcgggca    2640
atgtattaca tgaatgataa gaagccgtta aaagacatgg acttgccaat tccaaagatt    2700
gttgaaaagc cattattaaa gaaactccaa ggaacgtgga ttggtgaatt aatggagcaa    2760
cagcacttac tataaagatg aaagaagctg gaaatttccg gcttcttttt ttatatagct    2820
tatcggggaa ccacttgcaa aaagggatta aatagtcgaa aataaaacta atatatttat    2880
tgatagtaaa ggattatggt catgacagaa actgctggta taagaaaaat tcatattgtt    2940
tttgatggtc aagaaacacc accattaaag atccatcaat tatttgattc acaaaaatac    3000
gatcagttaa tcgcagtaac tgggaaaatt actgctgact tcattaataa ataccttagt    3060
aattttatca gtattaatgt agcgttaagc tcccaatcaa ctagtgaatt aagtgctgat    3120
gagatggtga caaaggttgc acttaccaat gctctcctta gttcagcaaa taagaagct    3180
gctaaactct tctcagcgtt aaccagtgac aaccaaacga acgtcttaaa taatctttt    3240
cgcgtatcaa tcgcgcctac tcaggttatc cattctaagt tttacttgtt aagtagttca    3300
actactcatg attcccgtgt gattcttggg agtgtagatt tagacgaagc ttcatttgat    3360
gctcaccgaa atcaatttga agaagtattg gtatttgaca atgatgtccg cttataccaa    3420
aaccttactg accactttaa aaaggatttt aagccagtat tgaagccctt ctttactatg    3480
aacctagtaa aggcagctca aaagcaagtt gaggaaggaa agaaagatca ggatagcggt    3540
aagggaccgg t                                                          3551
```

<210> SEQ ID NO 17
<211> LENGTH: 1776
<212> TYPE: DNA
<213> ORGANISM: Lactobacillus reuteri
<220> FEATURE:
<221> NAME/KEY: CDS
<222> LOCATION: (1)..(1776)

<400> SEQUENCE: 17

```
atg tat tat tca aac ggg aat tat gaa gcc ttt gct cga cca aag aag      48
Met Tyr Tyr Ser Asn Gly Asn Tyr Glu Ala Phe Ala Arg Pro Lys Lys
 1               5                  10                  15 cct gct ggc gtt gat aag aaa cat gcc tac att gtc ggt ggt ggt tta     96
Pro Ala Gly Val Asp Lys Lys His Ala Tyr Ile Val Gly Gly Gly Leu
             20                  25                  30 gct ggt tta tcg gcc gcc gtg ttt tta att cgt gat gcc caa atg ccg    144
Ala Gly Leu Ser Ala Ala Val Phe Leu Ile Arg Asp Ala Gln Met Pro
         35                  40                  45
```

-continued

| | |
|---|---|
| ggt gag aat atc cat att tta gag gaa tta ccg gtt gcc ggt ggt tct<br>Gly Glu Asn Ile His Ile Leu Glu Glu Leu Pro Val Ala Gly Gly Ser<br>50                 55               60 | 192 |
| ctt gat ggt gaa gat cgt cct gga att ggt ttt gtt act cgt gga ggc<br>Leu Asp Gly Glu Asp Arg Pro Gly Ile Gly Phe Val Thr Arg Gly Gly<br>65              70              75              80 | 240 |
| cgg gaa atg gag aac cat ttc gag tgt atg tgg gac atg tat cgt tca<br>Arg Glu Met Glu Asn His Phe Glu Cys Met Trp Asp Met Tyr Arg Ser<br>              85              90              95 | 288 |
| att cca tca ctt gaa atc cca ggt gct tcc tac ctt gat gaa tac tac<br>Ile Pro Ser Leu Glu Ile Pro Gly Ala Ser Tyr Leu Asp Glu Tyr Tyr<br>        100              105             110 | 336 |
| tgg tta gat aag gaa gat cca aac agt tct aat tgt cgt tta acc tat<br>Trp Leu Asp Lys Glu Asp Pro Asn Ser Ser Asn Cys Arg Leu Thr Tyr<br>        115              120             125 | 384 |
| aag cgg gga aat gaa gtt cca tcg gac ggt aaa tat ggt tta agt aaa<br>Lys Arg Gly Asn Glu Val Pro Ser Asp Gly Lys Tyr Gly Leu Ser Lys<br>130                 135              140 | 432 |
| aag gca atc aaa gag ctg act aag cta att atg acc cct gaa gaa aaa<br>Lys Ala Ile Lys Glu Leu Thr Lys Leu Ile Met Thr Pro Glu Glu Lys<br>145                 150              155              160 | 480 |
| ttg gga agg gag act att ggt gaa tac ttc tct gat gat ttc ttt gaa<br>Leu Gly Arg Glu Thr Ile Gly Glu Tyr Phe Ser Asp Asp Phe Phe Glu<br>        165              170             175 | 528 |
| agc aat ttc tgg att tat tgg tca aca atg ttt gcg ttt gaa cgg tgg<br>Ser Asn Phe Trp Ile Tyr Trp Ser Thr Met Phe Ala Phe Glu Arg Trp<br>        180              185             190 | 576 |
| cac tct cta gct gaa atg cgt cgt tat atg atg cgg ttt att cac cat<br>His Ser Leu Ala Glu Met Arg Arg Tyr Met Met Arg Phe Ile His His<br>        195              200             205 | 624 |
| att gat ggt tta ccg gat ttc act gca ctg aag ttt aat aag tat aac<br>Ile Asp Gly Leu Pro Asp Phe Thr Ala Leu Lys Phe Asn Lys Tyr Asn<br>210                 215              220 | 672 |
| caa tat gaa tca atg acc aag ccg cta ttg gcc tac ctg aaa gat cat<br>Gln Tyr Glu Ser Met Thr Lys Pro Leu Leu Ala Tyr Leu Lys Asp His<br>225                 230              235              240 | 720 |
| cat gtc aag att gag tac gat acc cag gta aag aat gtt att gtt gat<br>His Val Lys Ile Glu Tyr Asp Thr Gln Val Lys Asn Val Ile Val Asp<br>        245              250             255 | 768 |
| act cat ggg cgg caa aag cac gct aag cga atc tta tta act caa gcc<br>Thr His Gly Arg Gln Lys His Ala Lys Arg Ile Leu Leu Thr Gln Ala<br>        260              265             270 | 816 |
| ggt aaa gat aaa gtt gtt gag tta acg gac aat gac ctt gtc ttt gtc<br>Gly Lys Asp Lys Val Val Glu Leu Thr Asp Asn Asp Leu Val Phe Val<br>275                 280              285 | 864 |
| aca aac ggt tca att aca gaa agt tct act tac ggc agt cac cat caa<br>Thr Asn Gly Ser Ile Thr Glu Ser Ser Thr Tyr Gly Ser His His Gln<br>290                 295              300 | 912 |
| gca gct cga cca acg caa gca ctt ggt ggt agt tgg aaa ctg tgg gaa<br>Ala Ala Arg Pro Thr Gln Ala Leu Gly Gly Ser Trp Lys Leu Trp Glu<br>305                 310              315              320 | 960 |
| aac ctt gct cgg cag tca gct gat ttt ggt cat cct gat gtc ttt tgc<br>Asn Leu Ala Arg Gln Ser Ala Asp Phe Gly His Pro Asp Val Phe Cys<br>        325              330             335 | 1008 |
| aag aat ctt cca ggg aga agc tgg ttc att tcc gct act gca acc gtt<br>Lys Asn Leu Pro Gly Arg Ser Trp Phe Ile Ser Ala Thr Ala Thr Val<br>        340              345             350 | 1056 |
| aag aac ccg caa gtt gaa cca tac att gaa cgc tta acc aag cga gat<br>Lys Asn Pro Gln Val Glu Pro Tyr Ile Glu Arg Leu Thr Lys Arg Asp | 1104 |

```
                355                 360                 365
ctc cat gat ggc aaa gtt aat act ggt gga atc att acg gtc act gac    1152
Leu His Asp Gly Lys Val Asn Thr Gly Gly Ile Ile Thr Val Thr Asp
    370                 375                 380 tct aat tgg atg ctt tcc tgg aca att cac cgt caa ccg cac ttc aag    1200
Ser Asn Trp Met Leu Ser Trp Thr Ile His Arg Gln Pro His Phe Lys
385                 390                 395                 400 aaa caa aag aaa aat gaa acc att gtt tgg att tac ggt ctg tac tct    1248
Lys Gln Lys Lys Asn Glu Thr Ile Val Trp Ile Tyr Gly Leu Tyr Ser
                405                 410                 415 aat aca aag gga aac tat att aag aaa cgg atc gtt gat tgt act ggt    1296
Asn Thr Lys Gly Asn Tyr Ile Lys Lys Arg Ile Val Asp Cys Thr Gly
            420                 425                 430 gaa gag att act aaa gaa tgg cta tcc atc tgg ggg ttc cag aag ccg    1344
Glu Glu Ile Thr Lys Glu Trp Leu Ser Ile Trp Gly Phe Gln Lys Pro
        435                 440                 445 tta att gac gat ttg gct aag gag agt tca att aat act gtt cca gta    1392
Leu Ile Asp Asp Leu Ala Lys Glu Ser Ser Ile Asn Thr Val Pro Val
    450                 455                 460 tat atg cca ttt atc act agc tac ttt atg cca cga gtt aag ggc gac    1440
Tyr Met Pro Phe Ile Thr Ser Tyr Phe Met Pro Arg Val Lys Gly Asp
465                 470                 475                 480 cgt cca gac gtt gtt cca gaa gga tcc gct aac ttg gca ttt att ggt    1488
Arg Pro Asp Val Val Pro Glu Gly Ser Ala Asn Leu Ala Phe Ile Gly
                485                 490                 495 aac ttt gct gaa tct cca agt cga gat acc gta ttt acc acg gaa tat    1536
Asn Phe Ala Glu Ser Pro Ser Arg Asp Thr Val Phe Thr Thr Glu Tyr
            500                 505                 510 tca gta cgg acc gca atg gaa gcc gtc tac act cta tta gat gtt gat    1584
Ser Val Arg Thr Ala Met Glu Ala Val Tyr Thr Leu Leu Asp Val Asp
        515                 520                 525 cgg gga gtt cca gaa gtc ttt aac tct att tat gat ctt cga gag tta    1632
Arg Gly Val Pro Glu Val Phe Asn Ser Ile Tyr Asp Leu Arg Glu Leu
    530                 535                 540 atg cgg gca atg tat tac atg aat gat aag aag ccg tta aaa gac atg    1680
Met Arg Ala Met Tyr Tyr Met Asn Asp Lys Lys Pro Leu Lys Asp Met
545                 550                 555                 560 gac ttg cca att cca aag att gtt gaa aag cca tta tta aag aaa ctc    1728
Asp Leu Pro Ile Pro Lys Ile Val Glu Lys Pro Leu Leu Lys Lys Leu
                565                 570                 575 caa gga acg tgg att ggt gaa tta atg gag caa cag cac tta cta taa    1776
Gln Gly Thr Trp Ile Gly Glu Leu Met Glu Gln Gln His Leu Leu
            580                 585                 590
```

<210> SEQ ID NO 18
<211> LENGTH: 591
<212> TYPE: PRT
<213> ORGANISM: Lactobacillus reuteri

<400> SEQUENCE: 18

```
Met Tyr Tyr Ser Asn Gly Asn Tyr Glu Ala Phe Ala Arg Pro Lys Lys
 1               5                  10                  15

Pro Ala Gly Val Asp Lys Lys His Ala Tyr Ile Val Gly Gly Gly Leu
                20                  25                  30

Ala Gly Leu Ser Ala Ala Val Phe Leu Ile Arg Asp Ala Gln Met Pro
            35                  40                  45

Gly Glu Asn Ile His Ile Leu Glu Glu Leu Pro Val Ala Gly Gly Ser
        50                  55                  60

Leu Asp Gly Glu Asp Arg Pro Gly Ile Gly Phe Val Thr Arg Gly Gly
```

```
       65                  70                  75                  80
Arg Glu Met Glu Asn His Phe Glu Cys Met Trp Asp Met Tyr Arg Ser
                    85                  90                  95
Ile Pro Ser Leu Glu Ile Pro Gly Ala Ser Tyr Leu Asp Glu Tyr Tyr
                100                 105                 110
Trp Leu Asp Lys Glu Asp Pro Asn Ser Ser Asn Cys Arg Leu Thr Tyr
            115                 120                 125
Lys Arg Gly Asn Glu Val Pro Ser Asp Gly Lys Tyr Gly Leu Ser Lys
130                 135                 140
Lys Ala Ile Lys Glu Leu Thr Lys Leu Ile Met Thr Pro Glu Glu Lys
145                 150                 155                 160
Leu Gly Arg Glu Thr Ile Gly Glu Tyr Phe Ser Asp Asp Phe Phe Glu
                165                 170                 175
Ser Asn Phe Trp Ile Tyr Trp Ser Thr Met Phe Ala Phe Glu Arg Trp
                180                 185                 190
His Ser Leu Ala Glu Met Arg Arg Tyr Met Met Arg Phe Ile His His
            195                 200                 205
Ile Asp Gly Leu Pro Asp Phe Thr Ala Leu Lys Phe Asn Lys Tyr Asn
    210                 215                 220
Gln Tyr Glu Ser Met Thr Lys Pro Leu Leu Ala Tyr Leu Lys Asp His
225                 230                 235                 240
His Val Lys Ile Glu Tyr Asp Thr Gln Val Lys Asn Val Ile Val Asp
                245                 250                 255
Thr His Gly Arg Gln Lys His Ala Lys Arg Ile Leu Leu Thr Gln Ala
                260                 265                 270
Gly Lys Asp Lys Val Val Glu Leu Thr Asp Asn Asp Leu Val Phe Val
            275                 280                 285
Thr Asn Gly Ser Ile Thr Glu Ser Ser Thr Tyr Gly Ser His His Gln
290                 295                 300
Ala Ala Arg Pro Thr Gln Ala Leu Gly Gly Ser Trp Lys Leu Trp Glu
305                 310                 315                 320
Asn Leu Ala Arg Gln Ser Ala Asp Phe Gly His Pro Asp Val Phe Cys
                325                 330                 335
Lys Asn Leu Pro Gly Arg Ser Trp Phe Ile Ser Ala Thr Ala Thr Val
                340                 345                 350
Lys Asn Pro Gln Val Glu Pro Tyr Ile Glu Arg Leu Thr Lys Arg Asp
            355                 360                 365
Leu His Asp Gly Lys Val Asn Thr Gly Gly Ile Ile Thr Val Thr Asp
370                 375                 380
Ser Asn Trp Met Leu Ser Trp Thr Ile His Arg Gln Pro His Phe Lys
385                 390                 395                 400
Lys Gln Lys Lys Asn Glu Thr Ile Val Trp Ile Tyr Gly Leu Tyr Ser
                405                 410                 415
Asn Thr Lys Gly Asn Tyr Ile Lys Lys Arg Ile Val Asp Cys Thr Gly
            420                 425                 430
Glu Glu Ile Thr Lys Glu Trp Leu Ser Ile Trp Gly Phe Gln Lys Pro
            435                 440                 445
Leu Ile Asp Asp Leu Ala Lys Glu Ser Ser Ile Asn Thr Val Pro Val
        450                 455                 460
Tyr Met Pro Phe Ile Thr Ser Tyr Phe Met Pro Arg Val Lys Gly Asp
465                 470                 475                 480
Arg Pro Asp Val Val Pro Glu Gly Ser Ala Asn Leu Ala Phe Ile Gly
            485                 490                 495
```

```
Asn Phe Ala Glu Ser Pro Ser Arg Asp Thr Val Phe Thr Thr Glu Tyr
            500                 505                 510

Ser Val Arg Thr Ala Met Glu Ala Val Tyr Thr Leu Leu Asp Val Asp
        515                 520                 525

Arg Gly Val Pro Glu Val Phe Asn Ser Ile Tyr Asp Leu Arg Glu Leu
    530                 535                 540

Met Arg Ala Met Tyr Tyr Met Asn Asp Lys Lys Pro Leu Lys Asp Met
545                 550                 555                 560

Asp Leu Pro Ile Pro Lys Ile Val Glu Lys Pro Leu Leu Lys Lys Leu
                565                 570                 575

Gln Gly Thr Trp Ile Gly Glu Leu Met Glu Gln Gln His Leu Leu
            580                 585                 590

<210> SEQ ID NO 19
<211> LENGTH: 656
<212> TYPE: DNA
<213> ORGANISM: Lactobacillus reuteri
<220> FEATURE:
<221> NAME/KEY: CDS
<222> LOCATION: (1)..(654)

<400> SEQUENCE: 19 atg gtc atg aca gaa act gct ggt ata aga aaa att cat att gtt ttt        48
Met Val Met Thr Glu Thr Ala Gly Ile Arg Lys Ile His Ile Val Phe
 1               5                  10                  15 gat ggt caa gaa aca cca cca tta aag atc cat caa tta ttt gat tca        96
Asp Gly Gln Glu Thr Pro Pro Leu Lys Ile His Gln Leu Phe Asp Ser
             20                  25                  30 caa aaa tac gat cag tta atc gca gta act ggg aaa att act gct gac       144
Gln Lys Tyr Asp Gln Leu Ile Ala Val Thr Gly Lys Ile Thr Ala Asp
         35                  40                  45 ttc att aat aaa tac ctt agt aat ttt atc agt att aat gta gcg tta       192
Phe Ile Asn Lys Tyr Leu Ser Asn Phe Ile Ser Ile Asn Val Ala Leu
     50                  55                  60 agc tcc caa tca act agt gaa tta agt gct gat gag atg gtg aca aag       240
Ser Ser Gln Ser Thr Ser Glu Leu Ser Ala Asp Glu Met Val Thr Lys
 65                  70                  75                  80 gtt gca ctt acc aat gct ctc ctt agt tca gca aat aaa gaa gct gct       288
Val Ala Leu Thr Asn Ala Leu Leu Ser Ser Ala Asn Lys Glu Ala Ala
                 85                  90                  95 aaa ctc ttc tca gcg tta acc agt gac aac caa acg aac gtc tta aat       336
Lys Leu Phe Ser Ala Leu Thr Ser Asp Asn Gln Thr Asn Val Leu Asn
            100                 105                 110 aat ctt ttt cgc gta tca atc gcg cct act cag gtt atc cat tct aag       384
Asn Leu Phe Arg Val Ser Ile Ala Pro Thr Gln Val Ile His Ser Lys
        115                 120                 125 ttt tac ttg tta agt agt tca act act cat gat tcc cgt gtg att ctt       432
Phe Tyr Leu Leu Ser Ser Ser Thr Thr His Asp Ser Arg Val Ile Leu
    130                 135                 140 ggg agt gta gat tta gac gaa gct tca ttt gat gct cac cga aat caa       480
Gly Ser Val Asp Leu Asp Glu Ala Ser Phe Asp Ala His Arg Asn Gln
145                 150                 155                 160 ttt gaa gaa gta ttg gta ttt gac aat gat gtc cgc tta tac caa aac       528
Phe Glu Glu Val Leu Val Phe Asp Asn Asp Val Arg Leu Tyr Gln Asn
                165                 170                 175 ctt act gac cac ttt aaa aag gat ttt aag cca gta ttg aag ccc ttc       576
Leu Thr Asp His Phe Lys Lys Asp Phe Lys Pro Val Leu Lys Pro Phe
            180                 185                 190 ttt act atg aac cta gta aag gca gct caa aag caa gtt gag gaa gga       624
```

```
Phe Thr Met Asn Leu Val Lys Ala Ala Gln Lys Gln Val Glu Glu Gly
        195                 200                 205 aag aaa gat cag gat agc ggt aag gga ccg gt                              656
Lys Lys Asp Gln Asp Ser Gly Lys Gly Pro
    210                 215

<210> SEQ ID NO 20
<211> LENGTH: 218
<212> TYPE: PRT
<213> ORGANISM: Lactobacillus reuteri

<400> SEQUENCE: 20

Met Val Met Thr Glu Thr Ala Gly Ile Arg Lys Ile His Ile Val Phe
  1               5                  10                  15

Asp Gly Gln Glu Thr Pro Pro Leu Lys Ile His Gln Leu Phe Asp Ser
               20                  25                  30

Gln Lys Tyr Asp Gln Leu Ile Ala Val Thr Gly Lys Ile Thr Ala Asp
           35                  40                  45

Phe Ile Asn Lys Tyr Leu Ser Asn Phe Ile Ser Ile Asn Val Ala Leu
       50                  55                  60

Ser Ser Gln Ser Thr Ser Glu Leu Ser Ala Asp Glu Met Val Thr Lys
 65                  70                  75                  80

Val Ala Leu Thr Asn Ala Leu Leu Ser Ser Ala Asn Lys Glu Ala Ala
                 85                  90                  95

Lys Leu Phe Ser Ala Leu Thr Ser Asp Asn Gln Thr Asn Val Leu Asn
            100                 105                 110

Asn Leu Phe Arg Val Ser Ile Ala Pro Thr Gln Val Ile His Ser Lys
        115                 120                 125

Phe Tyr Leu Leu Ser Ser Ser Thr Thr His Asp Ser Arg Val Ile Leu
    130                 135                 140

Gly Ser Val Asp Leu Asp Glu Ala Ser Phe Asp Ala His Arg Asn Gln
145                 150                 155                 160

Phe Glu Glu Val Leu Val Phe Asp Asn Asp Val Arg Leu Tyr Gln Asn
                165                 170                 175

Leu Thr Asp His Phe Lys Lys Asp Phe Lys Pro Val Leu Lys Pro Phe
            180                 185                 190

Phe Thr Met Asn Leu Val Lys Ala Ala Gln Lys Gln Val Glu Glu Gly
        195                 200                 205

Lys Lys Asp Gln Asp Ser Gly Lys Gly Pro
    210                 215

<210> SEQ ID NO 21
<211> LENGTH: 726
<212> TYPE: DNA
<213> ORGANISM: Lactobacillus reuteri
<220> FEATURE:
<221> NAME/KEY: CDS
<222> LOCATION: (1)..(726)
<221> NAME/KEY: unsure
<222> LOCATION: (1)..(726)
<223> OTHER INFORMATION: n = a, c, g, or t

<400> SEQUENCE: 21 atg ctt cgt tan acc ata tta gta aaa ttg ctt att gga aga aaa cca       48
Met Leu Arg Xaa Thr Ile Leu Val Lys Leu Leu Ile Gly Arg Lys Pro
  1               5                  10                  15 gtc aca acg atc aaa aaa aca tta ccg cca act cag gaa cag gct aat       96
Val Thr Thr Ile Lys Lys Thr Leu Pro Pro Thr Gln Glu Gln Ala Asn
               20                  25                  30
```

```
tca gtc tta act ccg gct gtt cgc caa caa ctt ggc att tca att acc    144
Ser Val Leu Thr Pro Ala Val Arg Gln Gln Leu Gly Ile Ser Ile Thr
        35                  40                  45 tgg aac aaa gcc ggt gcg ttt att atc aat aat aac caa aca aat ctt    192
Trp Asn Lys Ala Gly Ala Phe Ile Ile Asn Asn Asn Gln Thr Asn Leu
 50                  55                  60 aac gct aag att gca agt gca ccc tat gct gta aat cat ctt gac cgt    240
Asn Ala Lys Ile Ala Ser Ala Pro Tyr Ala Val Asn His Leu Asp Arg
 65                  70                  75                  80 caa gga agg gcg tgg caa ggt gat gcc tgg tta aac agg aca act cgg    288
Gln Gly Arg Ala Trp Gln Gly Asp Ala Trp Leu Asn Arg Thr Thr Arg
             85                  90                  95 tca ata tan aag ccg aaa ttt gcc aca ggg aat ggt gct acg gat tgg    336
Ser Ile Xaa Lys Pro Lys Phe Ala Thr Gly Asn Gly Ala Thr Asp Trp
            100                 105                 110 cga cca gct ggc ttc ctt cag gcg cat aat ctt aaa ggc ggg tac aat    384
Arg Pro Ala Gly Phe Leu Gln Ala His Asn Leu Lys Gly Gly Tyr Asn
            115                 120                 125 cat gca tac gat cgc gga cac ctt ctt gcc tat gca cta gtt ggt ggt    432
His Ala Tyr Asp Arg Gly His Leu Leu Ala Tyr Ala Leu Val Gly Gly
            130                 135                 140 att cat gga ttt gat gca tcc gaa tca aat cca tct aat att gcc acg    480
Ile His Gly Phe Asp Ala Ser Glu Ser Asn Pro Ser Asn Ile Ala Thr
145                 150                 155                 160 caa act gcc tgg gca aat gaa gca cga agt aag aac tca aca ggg caa    528
Gln Thr Ala Trp Ala Asn Glu Ala Arg Ser Lys Asn Ser Thr Gly Gln
                165                 170                 175 aat tac tac gaa ggt ctg gtg aga aaa gca tta gat cag aat aag caa    576
Asn Tyr Tyr Glu Gly Leu Val Arg Lys Ala Leu Asp Gln Asn Lys Gln
                180                 185                 190 gtt cgc tac cga gtt acc aat att tat gac ggt aat aat atc gtt ccg    624
Val Arg Tyr Arg Val Thr Asn Ile Tyr Asp Gly Asn Asn Ile Val Pro
                195                 200                 205 gca ggt gct cat atc gaa gct aaa tct agt gat ggt tct cta gaa tac    672
Ala Gly Ala His Ile Glu Ala Lys Ser Ser Asp Gly Ser Leu Glu Tyr
            210                 215                 220 aat gtc ttt gtt ccg aat gtc caa aga aac att acc att aat tat tca    720
Asn Val Phe Val Pro Asn Val Gln Arg Asn Ile Thr Ile Asn Tyr Ser
225                 230                 235                 240 acc ggt                                                            726
Thr Gly

<210> SEQ ID NO 22
<211> LENGTH: 242
<212> TYPE: PRT
<213> ORGANISM: Lactobacillus reuteri
<220> FEATURE:
<221> NAME/KEY: UNSURE
<222> LOCATION: (1)..(242)
<223> OTHER INFORMATION: Xaa = Tyr or stop

<400> SEQUENCE: 22

Met Leu Arg Xaa Thr Ile Leu Val Lys Leu Leu Ile Gly Arg Lys Pro
 1               5                  10                  15

Val Thr Thr Ile Lys Lys Thr Leu Pro Pro Thr Gln Glu Gln Ala Asn
            20                  25                  30

Ser Val Leu Thr Pro Ala Val Arg Gln Gln Leu Gly Ile Ser Ile Thr
        35                  40                  45

Trp Asn Lys Ala Gly Ala Phe Ile Ile Asn Asn Asn Gln Thr Asn Leu
 50                  55                  60
```

```
Asn Ala Lys Ile Ala Ser Ala Pro Tyr Ala Val Asn His Leu Asp Arg
 65                  70                  75                  80

Gln Gly Arg Ala Trp Gln Gly Asp Ala Trp Leu Asn Arg Thr Thr Arg
                 85                  90                  95

Ser Ile Xaa Lys Pro Lys Phe Ala Thr Gly Asn Gly Ala Thr Asp Trp
            100                 105                 110

Arg Pro Ala Gly Phe Leu Gln Ala His Asn Leu Lys Gly Gly Tyr Asn
        115                 120                 125

His Ala Tyr Asp Arg Gly His Leu Leu Ala Tyr Ala Leu Val Gly Gly
    130                 135                 140

Ile His Gly Phe Asp Ala Ser Glu Ser Asn Pro Ser Asn Ile Ala Thr
145                 150                 155                 160

Gln Thr Ala Trp Ala Asn Glu Ala Arg Ser Lys Asn Ser Thr Gly Gln
                165                 170                 175

Asn Tyr Tyr Glu Gly Leu Val Arg Lys Ala Leu Asp Gln Asn Lys Gln
            180                 185                 190

Val Arg Tyr Arg Val Thr Asn Ile Tyr Asp Gly Asn Asn Ile Val Pro
        195                 200                 205

Ala Gly Ala His Ile Glu Ala Lys Ser Ser Asp Gly Ser Leu Glu Tyr
    210                 215                 220

Asn Val Phe Val Pro Asn Val Gln Arg Asn Ile Thr Ile Asn Tyr Ser
225                 230                 235                 240

Thr Gly

<210> SEQ ID NO 23
<211> LENGTH: 18
<212> TYPE: DNA
<213> ORGANISM: Lactobacillus reuteri

<400> SEQUENCE: 23
aatctagtga tggttctc                                              18

<210> SEQ ID NO 24
<211> LENGTH: 18
<212> TYPE: DNA
<213> ORGANISM: Lactobacillus reuteri

<400> SEQUENCE: 24
caagttgagg aaggaaag                                              18

<210> SEQ ID NO 25
<211> LENGTH: 3684
<212> TYPE: DNA
<213> ORGANISM: Lactobacillus reuteri

<400> SEQUENCE: 25
caagttgagg aaggaaagaa agatcaggat agcggtaagg gaccggttat ccttgataat      60
gaaacaacag ataagatcgc tgaaacagac atggtggatc tgttgaagca tgaccttcag     120
catgatattg accataatct tgttcctgaa atgatcacaa agtcaatgcg tgatattacc     180
ataaatcgtt ctcaagcaaa ggagaaaatt gctaagcagg ttaagcaaca tgatacgatt     240
tatactttgc aaaagaagc ggtctctcct cgggcagcta agccaaaact aaagactcga     300
gaaaaaatta ccaagcaggt tcaggatgct tgatcagtg aatgtcacc acagcaacgg     360 gatgctgaga aaagtacac gacttttctg tacgatcggc aatggaacg aaacattgcg     420 aataacaata gtggcctata cgttcctaat gatacgggaa ctcacccaat cccatttggt     480
```

-continued

| | |
|---|---|
| aaaattgcaa ctatttctga aattcgtgac ggtttaaaga gcattgatgc tgttatgaag | 540 |
| ggctatcagc agtttgtcgt tgattatgat gctgactacg ggaagcggtt ctttgaagca | 600 |
| attttgtata gttttactgc accgttttta tgggaaattc gttctaaagc tagcctgaac | 660 |
| cctgaagatg ggaatgatgt tcctaatttc ctaatcctag gggcaacggc tggttccgga | 720 |
| aagtctaccc ttcttcggat tattaatcag ctcacgtgga acactgatcg ctcgttgatt | 780 |
| gactttggaa cgatctaccc gtcgcaaact cctcaaaaga aggcaaagac tgttgaggcg | 840 |
| atggaacatt atatgaaact tggtagttca tacccggttt tgttagatga aattgaaccg | 900 |
| tacttcttcc agcaagatca atatagtcga ctggagttct ggtttgctat gattaaggtt | 960 |
| gttacgatta ttgcaatgat tattcttggt ttactggtta tcgttcttgg gttaggtaat | 1020 |
| aactggcacc cagttgggat ttctaatttg tggtctcatg gcggattctt taccggtggc | 1080 |
| tttatgggct ttatgttctc gctatctgtg attgctggtt cttatcaggg aattgagtta | 1140 |
| ttgggaatca ctgctggtga agctgaatca ccacgtcatg cgattgtgaa atcagttaag | 1200 |
| tccgttatct ggcggatctt aatcttctat attggtgcaa ttttcgtcat tgtttctatt | 1260 |
| tacccatgga acgaattgaa gtccgttggc tcaccattcg ttgaaacctt cacgaaggtt | 1320 |
| ggaattactg gagcagccgg aatcattaac tttgttgttt tgacggcagc tctttctgga | 1380 |
| gctaactctg gaatttacag tgctagtcgg atgttgttca gctttctgt tgatggggaa | 1440 |
| gtaccaaagt tctttagtaa gctttccaag cgcgttgttc ctaatgttgc aatcctcacg | 1500 |
| atttcttcct ggatcttcct tggctttgta attaatgaat aatgtcgat ttttagttct | 1560 |
| gctgctcaaa atattttcgt cattgtatat agttccagtg ttcttccagg gatggtacca | 1620 |
| tggtttatca ttctcttgtc agaacttcac ttcagaaaag aacaccctga acagcttaaa | 1680 |
| gatcatccat tcaagatgcc gctttacccg gcttataact actttagttt gattgccttg | 1740 |
| actgtgatct tgatcttcat gttctttaac ccagatactc gagtttcagt atcagttggt | 1800 |
| gttatcttct tgattatcat gagtattatt tatcgtgttc gtgttcatga aggaaaagaa | 1860 |
| aagtaaatat atagctaaag cagctttgta atcctgcgt acaataccc ttagggttga | 1920 |
| cactttaaat aataaagtg tgaatcctag ggggtgtttt gcattgtaag ttattcaact | 1980 |
| attgaaaagc ttaaattact tcatgattat cagaaatcgg attatggttt aacggtgtac | 2040 |
| tccgattacc atggtgtccg accagcaaac atgagtaagt ggattaagca attcctactc | 2100 |
| gctggattgg cgggattaat tagacctaag cataatcaga agtactcatt agagactaag | 2160 |
| ttaactgctg taaaagctta tctttctggc aagtatacta atcaagcaat tctccagcag | 2220 |
| tatcaaatta gaaatatttc tcaactacat caatgggtta tcagttacaa taatgacaaa | 2280 |
| ctccgagtta atcagacaac gagaaagcga gtcagaaaaa tgggacgaaa agtaaccttt | 2340 |
| gatgaaaaga ggcagattgt ccgatggaca attgaacata caataacta taaagcggct | 2400 |
| gcagagaagt atgatattag ttaccaacga gtttattctt gggtacggaa gtaccgagta | 2460 |
| aatagcgact gggaagtact aaaagataac cgtgggcgta ataaaggaaa agagcccact | 2520 |
| aatgaactag aaaaactaag gaaacgagtt cgtgagctag aagatcgtga ccgtgaacgg | 2580 |
| gagctgcaaa tcgctttcgc aaaaaaatta gtcgaaatac gcaatcggga ggtgaaacga | 2640 |
| ccggacgata tcaagcgatt caagaaatga acaatgaagg ttattccatt agtgaattgg | 2700 |
| ccaaggtcgc tggaattact agacaggctt actacaaatg gttgaaacat gaaccgacta | 2760 |
| aatatgagat tgaagaatcg gagattctcc aattgattaa acagttagaa aatgaacata | 2820 |
| agcaaagcgt tggttatgac aaaatgacta ggttaatcaa gttaagtcag cagatctctt | 2880 |

-continued

| | |
|---|---|
| ataccgttaa taagaaacga gtcattcgta ttatgaaagg ccatagtatc aaggccgact | 2940 |
| atcgtcagcc aaccgacaaa cgtattcaag cccagcaaac ttatgaagct gaaatattc | 3000 |
| ttaaccgaca atttgaccaa actgcagcta accaagtttg ggttacggat acgacggaac | 3060 |
| tgaattacgg aatctggctt aataaagttc gtctacatat agtattagat ttatatggtc | 3120 |
| aatacccagt aagctggtta attacaccta cagaaaccgc tgaaggagta gttcaagtgt | 3180 |
| tcgagcaagc acggatgaaa gaaggagcac tagctccgtt aattcatact gatcgtggtg | 3240 |
| cggcgtatac ttccaaagca tttaatcagt atttagtagt taatggtgcc caacacagtt | 3300 |
| attcagcacc agggacaccg gctgacaatg ccgtaataga acattggtgg gcagatttta | 3360 |
| aggctatttg gatcgcacat ctacctaaag cacaaacatt attagaacta gaagaacaag | 3420 |
| ttagagaagg aattacctat ttcactgaaa aatttatctc agcgaagaga atgaccttaa | 3480 |
| ccgcagcgga ataccgcttt ggcaaggcca actaattttt attatttaat gtgtaaactt | 3540 |
| gacagggcac agtaccctgt ttgaggggac tcacaaagct gcttttttag ttttgtttta | 3600 |
| ctgcaccggt gaataatta atggtaatgt ttctttggac attcggaaca aagacattgt | 3660 |
| attctagaga accatcacta gatt | 3684 |

<210> SEQ ID NO 26
<211> LENGTH: 7113
<212> TYPE: DNA
<213> ORGANISM: Lactobacillus reuteri
<220> FEATURE:
<221> NAME/KEY: unsure
<222> LOCATION: (1)..(7113)
<223> OTHER INFORMATION: n = a, c, g, or t

<400> SEQUENCE: 26

| | |
|---|---|
| gtcgactgga gttctggttt gctatgatta aggttgttac gattattgca atgattattc | 60 |
| ttggtttact ggttatcgtt cttgggttag gtaataactg gcacccagtt gggatttcta | 120 |
| atttgtggtc tcatggcgga ttcttttaccg gtggctttat gggctttatg ttctcgctat | 180 |
| ctgtgattgc tggttcttat cagggaattg agttattggg aatcactgct ggtgaagctg | 240 |
| aatcaccacg tcatgcgatt gtgaaatcag ttaagtccgt tatctggcgg atcttaatct | 300 |
| tctatattgg tgcaattttc gtcattgttt ctatttaccc atggaacgaa ttgaagtccg | 360 |
| ttggctcacc attcgttgaa accttcacga aggttggaat tactggagca gccggaatca | 420 |
| ttaactttgt tgttttgacg gcagctcttt ctggagctaa ctctggaatt tacagtgcta | 480 |
| gtcggatgtt gttcaagctt tctgttgatg gggaagtacc aaagttcttt agtaagcttt | 540 |
| ccaagcgcgt tgttcctaat gttgcaatcc tcacgatttc ttcctggatc ttccttggct | 600 |
| ttgtaattaa tgaattaatg tcgattttta gttctgctgc tcaaaatatt ttcgtcattg | 660 |
| tatatagttc cagtgttctt ccagggatgg taccatggtt tatcattctc ttgtcagaac | 720 |
| ttcacttcag aaaagaacac cctgaacagc ttaaagatca tccattcaag atgccgcttt | 780 |
| acccggctta taactacttt agtttgattg ccttgactgt gatcttgatc ttcatgttct | 840 |
| ttaacccaga tactcgagtt tcagtatcag ttggtgttat cttcttgatt atcatgagta | 900 |
| ttatttatcg tgttcgtgtt catgaaggaa aagaaaagta aatatatagc taaagcagct | 960 |
| ttgtaaatcc tgcgtacaat accccttagg gttgacactt taaataataa agtgtgaat | 1020 |
| cctaggggt gtttttgcatt gtaagttatt caactattga aaagcttaaa ttacttcatg | 1080 |
| attatcagaa atcggattat ggtttaacgg tgtactccga ttaccatggt gtccgaccag | 1140 |

```
caaacatgag taagtggatt aagcaattcc tactcgctgg attggcggga ttaattagac    1200
ctaagcataa tcagaagtac tcattagaga ctaagttaac tgctgtaaaa gcttatcttt    1260
ctggcaagta tactaatcaa gcaattctcc agcagtatca aattagaaat atttctcaac    1320
tacatcaatg ggttatcagt tacaataatg acaaactccg agttaatcag acaacgagaa    1380
agcgagtcag aaaaatggga cgaaaagtaa cctttgatga aaagaggcag attgtccgat    1440
ggacaattga acataacaat aactataaag cggctgcaga gaagtatgat attagttacc    1500
aacgagttta ttcttgggta cggaagtacc gagtaaatag cgactgggaa gtactaaaag    1560
ataaccgtgg gcgtaataaa ggaaaagagc ccactaatga actagaaaaa ctaaggaaac    1620
gagttcgtga gctagaagat cgtgaccgtg aacgggagct gcaaatcgct ttcgcaaaaa    1680
aattagtcga aatacgcaat cgggaggtga aacgaccgga cgatatcaag cgattcaaga    1740
aatgaacaat gaaggttatt ccattagtga attggccaag gtcgctggaa ttactagaca    1800
ggcttactac aaatggttga aacatgaacc gactaaatat gagattgaag aatcggagat    1860
tctccaattg attaaacagt tagaaaatga acataagcaa agcgttggtt atgacaaaat    1920
gactaggtta atcaagttaa gtcagcagat ctcttatacc gttaataaga aacgagtcat    1980
tcgtattatg aaaggccata gtatcaaggc cgactatcgt cagccaaccg acaaacgtat    2040
tcaagcccag caaacttatg aagctgaaaa tattcttaac cgacaatttg accaaactgc    2100
agctaaccaa gtttgggtta cggatacgac ggaactgaat tacggaatct ggcttaataa    2160
agttcgtcta catatagtat tagatttata tggtcaatac ccagtaagct ggttaattac    2220
acctacagaa accgctgaag gagtagttca agtgttcgag caagcacgga tgaaagaagg    2280
agcactagct ccgttaattc atactgatcg tggtgcggcg tatacttcca aagcatttaa    2340
tcagtattta gtagttaatg gtgcccaaca cagttattca gcaccaggga caccggctga    2400
caatgccgta atagaacatt ggtgggcaga ttttaaggct atttggatcg cacatctacc    2460
taaagcacaa acattattag aactagaaga acaagttaga gaaggaatta cctatttcac    2520
tgaaaaattt atctcagcga agagaaatga ccttaccgca gcggaatacc gctttggcaa    2580
ggccaactaa tttttattat ttaatgtgta aacttgacag ggcacagtac cctgtttgag    2640
gggactcaca aagctgcttt tttagttttg ttttactgca ccggttgaat aattaatggt    2700
aatgtttctt tggacattcg gaacaaagac attgtattct agagaaccat cactagattt    2760
agcttcgata tgagcacctg ccggaacgat attattaccg tcataaatat tggtaactcg    2820
gtagcgaact tgcttattct gatctaatgc ttttctcacc agaccttcgt agtaattttg    2880
ccctgttgag ttcttacttc gtgcttcatt tgcccaggca gtttgcgtgg caatattaga    2940
tggatttgat tcggatgcat caaatccatg aataccacca actagtgcat aggcaagaag    3000
gtgtccgcga tcgtatgcat gattgtaccc gcctttaaga ttatgcgcct gaaggaagcc    3060
agctggtcgc caatccgtag caccattccc tgtggcaaat ttcggcttnt atattgaccg    3120
agttgtcctg tttaaccagg catcaccttg ccacgcccct ccttgacggt caagatgatt    3180
tacagcatag ggtgcacttg caatcttagc gttaagattt gtttggttat tattgataat    3240
aaacgcaccg gctttgttcc aggtaattga aatgccaagt tgttggcgaa cagccggagt    3300
taagactgaa ttagcctgtt cctgagttgg cggtaatgtt tttttgatcg ttgtgactgg    3360
ttttcttcca ataagcaatt ttactaatat ggtntaacga agcatttgtt agctgaggtt    3420
gctggataac tccagtaact actaataaac cagcaagagc aaataaaagg tgatagaggc    3480
gtttcttaag tttcataaat tcactccatt tctaataatt ccaaagtcta ttttactagt    3540
```

-continued

```
ttgaacatac gtttggaata attatttaga attaatttat aagttcattg tgtttaataa    3600
aattgacact ttcaaccgct ttcactaaaa ttaaggtagt tatgatgcac ttgtttactg    3660
agaagggagt cgtcaaaatg tattattcaa acgggaatta tgaagccttt gctcgaccaa    3720
agaagcctgc tggcgttgat aagaaacatg cctacattgt cggtggtggt ttagctggtt    3780
tatcggccgc cgtgttttta attcgtgatg cccaaatgcc gggtgagaat atccatattt    3840
tagaggaatt accggttgcc ggtggttctc ttgatggtga agatcgtcct ggaattggtt    3900
ttgttactcg tggaggccgg gaaatggaga accatttcga gtgtatgtgg gacatgtatc    3960
gttcaattcc atcacttgaa atcccaggtg cttcctacct tgatgaatac tactggttag    4020
ataaggaaga tccaaacagt tctaattgtc gtttaaccta taagcgggga aatgaagttc    4080
catcggacgg taaatatggt ttaagtaaaa aggcaatcaa agagctgact aagctaatta    4140
tgacccctga agaaaaattg ggaagggaga ctattggtga atacttctct gatgatttct    4200
ttgaaagcaa tttctggatt tattggtcaa caatgtttgc gtttgaacgg tggcactctc    4260
tagctgaaat gcgtcgttat atgatgcggt ttattcacca tattgatggt ttaccggatt    4320
tcactgcact gaagtttaat aagtataacc aatatgaatc aatgaccaag ccgctattgg    4380
cctacctgaa agatcatcat gtcaagattg agtacgatac ccaggtaaag aatgttattg    4440
ttgatactca tgggcggcaa aagcacgcta agcgaatctt attaactcaa gccggtaaag    4500
ataaagttgt tgagttaacg gacaatgacc ttgtctttgt cacaaacggt tcaattacag    4560
aaagttctac ttacggcagt caccatcaag cagctcgacc aacgcaagca cttggtggta    4620
gttgaaaact gtgggaaaac cttgctcggc agtcagctga ttttggtcat cctgatgtct    4680
tttgcaagaa tcttccaggg agaagctggt tcatttccgc tactgcaacc gttaagaacc    4740
cgcaagttga accatacatt gaacgcttaa ccaagcgaga tctccatgat ggcaaagtta    4800
atactggtgg aatcattacg gtcactgact ctaattggat gctttcctgg acaattcacc    4860
gtcaaccgca cttcaagaaa caaaagaaaa atgaaaccat tgtttggatt tacggtctgt    4920
actctaatac aaagggaaac tatattaaga aacggatcgt tgattgtact ggtgaagaga    4980
ttactaaaga atggctatcc atctgggggt tccagaagcc gttaattgac gatttggcta    5040
aggagagttc aattaatact gttccagtat atatgccatt tatcactagc tactttatgc    5100
cacgagttaa gggcgaccgt ccagacgttg ttccagaagg atccgctaac ttggcattta    5160
ttggtaactt tgctgaatct ccaagtcgag ataccgtatt taccacggaa tattcagtac    5220
ggaccgcaat ggaagccgtc tacactctat tagatgttga tcggggagtt ccagaagtct    5280
ttaactctat ttatgatctt cgagagttaa tgcgggcaat gtattacatg aatgataaga    5340
agccgttaaa agacatggac ttgccaattc caaagattgt tgaaaagcca ttattaaaga    5400
aactccaagg aacgtggatt ggtgaattaa tggagcaaca gcacttacta taaagatgaa    5460
agaagctgga aatttccggc ttctttttt atatagctta tcggggaacc acttgcaaaa    5520
agggattaaa tagtcgaaaa taaaactaat atatttattg atagtaaagg attatggtca    5580
tgacagaaac tgctggtata agaaaaattc atattgtttt tgatggtcaa gaaacaccac    5640
cattaaagat ccatcaatta tttgattcac aaaaatacga tcagttaatc gcagtaactg    5700
ggaaaattac tgctgacttc attaataaat accttagtaa ttttatcagt attaatgtag    5760
cgttaagctc ccaatcaact agtgaattaa gtgctgatga gatggtgaca aaggttgcac    5820
ttaccaatgc tctccttagt tcagcaaata agaagctgc taaactcttc tcagcgttaa    5880
```

-continued

```
ccagtgacaa ccaaacgaac gtcttaaata atctttttcg cgtatcaatc gcgcctactc    5940
aggttatcca ttctaagttt tacttgttaa gtagttcaac tactcatgat tcccgtgtga    6000
ttcttgggag tgtagattta gacgaagctt catttgatgc tcaccgaaat caatttgaag    6060
aagtattggt atttgacaat gatgtccgct tataccaaaa ccttactgac cactttaaaa    6120
aggattttaa gccagtattg aagcccttct ttactatgaa cctagtaaag gcagctcaaa    6180
agcaagttga ggaaggaaag aaagatcagg atagcggtaa gggaccggtt atccttgata    6240
atgaaacaac agataagatc gctgaaacag acatggtgga tctgttgaag catgaccttc    6300
agcatgatat tgaccataat cttgttcctg aaatgatcac aaagtcaatg cgtgatatta    6360
ccataaatcg ttctcaagca aaggagaaaa ttgctaagca ggttaagcaa catgatacga    6420
tttatacttt gcaaaaagaa gcggtctctc ctcgggcagc taagccaaaa ctaaagactc    6480
gagaaaaaat taccaagcag gttcaggatg ctttgatcag tggaatgtca ccacagcaac    6540
gggatgctga gaaaaagtac acgactttc tgtacgatcg gccaatggaa cgaaacattg    6600
cgaataacaa tagtggccta tacgttccta atgatacggg aactcaccca atcccatttg    6660
gtaaaattgc aactatttct gaaattcgtg acggtttaaa gagcattgat gctgttatga    6720
agggctatca gcagtttgtc gttgattatg atgctgacta cgggaagcgg ttctttgaag    6780
caattttgta tagttttact gcaccgtttt tatgggaaat tcgttctaaa gctagcctga    6840
accctgaaga tgggaatgat gttcctaatt tcctaatcct aggggcaacg gctggttccg    6900
gaaagtctac ccttcttcgg attattaatc agctcacgtg gaacactgat cgctcgttga    6960
ttgactttgg aacgatctac ccgtcgcaaa ctcctcaaaa gaaggcaaag actgttgagg    7020
cgatggaaca ttatatgaaa cttggtagtt catacccggt tttgttagat gaaattgaac    7080
cgtacttctt ccagcaagat caatatagtc gac                                 7113
```

<210> SEQ ID NO 27
<211> LENGTH: 941
<212> TYPE: DNA
<213> ORGANISM: Lactobacillus reuteri
<220> FEATURE:
<221> NAME/KEY: CDS
<222> LOCATION: (3)..(941)

<400> SEQUENCE: 27

```
gt cga ctg gag ttc tgg ttt gct atg att aag gtt gtt acg att att       47
   Arg Leu Glu Phe Trp Phe Ala Met Ile Lys Val Val Thr Ile Ile
     1               5                  10                  15
gca atg att att ctt ggt tta ctg gtt atc gtt ctt ggg tta ggt aat      95
Ala Met Ile Ile Leu Gly Leu Leu Val Ile Val Leu Gly Leu Gly Asn
             20                  25                  30
aac tgg cac cca gtt ggg att tct aat ttg tgg tct cat ggc gga ttc     143
Asn Trp His Pro Val Gly Ile Ser Asn Leu Trp Ser His Gly Gly Phe
         35                  40                  45
ttt acc ggt ggc ttt atg ggc ttt atg ttc tcg cta tct gtg att gct     191
Phe Thr Gly Gly Phe Met Gly Phe Met Phe Ser Leu Ser Val Ile Ala
     50                  55                  60
ggt tct tat cag gga att gag tta ttg gga atc act gct ggt gaa gct     239
Gly Ser Tyr Gln Gly Ile Glu Leu Leu Gly Ile Thr Ala Gly Glu Ala
 65                  70                  75
gaa tca cca cgt cat gcg att gtg aaa tca gtt aag tcc gtt atc tgg     287
Glu Ser Pro Arg His Ala Ile Val Lys Ser Val Lys Ser Val Ile Trp
 80                  85                  90                  95
cgg atc tta atc ttc tat att ggt gca att ttc gtc att gtt tct att     335
Arg Ile Leu Ile Phe Tyr Ile Gly Ala Ile Phe Val Ile Val Ser Ile
                100                 105                 110
tac cca tgg aac gaa ttg aag tcc gtt ggc tca cca ttc gtt gaa acc     383
Tyr Pro Trp Asn Glu Leu Lys Ser Val Gly Ser Pro Phe Val Glu Thr
            115                 120                 125
ttc acg aag gtt gga att act gga gca gcc gga atc att aac ttt gtt     431
Phe Thr Lys Val Gly Ile Thr Gly Ala Ala Gly Ile Ile Asn Phe Val
```

```
                    130                 135                 140
gtt ttg acg gca gct ctt tct gga gct aac tct gga att tac agt gct        479
Val Leu Thr Ala Ala Leu Ser Gly Ala Asn Ser Gly Ile Tyr Ser Ala
145                 150                 155
agt cgg atg ttg ttc aag ctt tct gtt gat ggg gaa gta cca aag ttc        527
Ser Arg Met Leu Phe Lys Leu Ser Val Asp Gly Glu Val Pro Lys Phe
160                 165                 170                 175
ttt agt aag ctt tcc aag cgc gtt gtt cct aat gtt gca atc ctc acg        575
Phe Ser Lys Leu Ser Lys Arg Val Val Pro Asn Val Ala Ile Leu Thr
                    180                 185                 190
att tct tcc tgg atc ttc ctt ggc ttt gta att aat gaa tta atg tcg        623
Ile Ser Ser Trp Ile Phe Leu Gly Phe Val Ile Asn Glu Leu Met Ser
                195                 200                 205
att ttt agt tct gct gct caa aat att ttc gtc att gta tat agt tcc        671
Ile Phe Ser Ser Ala Ala Gln Asn Ile Phe Val Ile Val Tyr Ser Ser
            210                 215                 220
agt gtt ctt cca ggg atg gta cca tgg ttt atc att ctc ttg tca gaa        719
Ser Val Leu Pro Gly Met Val Pro Trp Phe Ile Ile Leu Leu Ser Glu
225                 230                 235
ctt cac ttc aga aaa gaa cac cct gaa cag ctt aaa gat cat cca ttc        767
Leu His Phe Arg Lys Glu His Pro Glu Gln Leu Lys Asp His Pro Phe
240                 245                 250                 255
aag atg ccg ctt tac ccg gct tat aac tac ttt agt ttg att gcc ttg        815
Lys Met Pro Leu Tyr Pro Ala Tyr Asn Tyr Phe Ser Leu Ile Ala Leu
                    260                 265                 270
act gtg atc ttg atc ttc atg ttc ttt aac cca gat act cga gtt tca        863
Thr Val Ile Leu Ile Phe Met Phe Phe Asn Pro Asp Thr Arg Val Ser
                275                 280                 285
gta tca gtt ggt gtt atc ttc ttg att atc atg agt att att tat cgt        911
Val Ser Val Gly Val Ile Phe Leu Ile Ile Met Ser Ile Ile Tyr Arg
            290                 295                 300
gtt cgt gtt cat gaa gga aaa gaa aag taa                                941
Val Arg Val His Glu Gly Lys Glu Lys
305                 310
```

<210> SEQ ID NO 28
<211> LENGTH: 312
<212> TYPE: PRT
<213> ORGANISM: Lactobacillus reuteri

<400> SEQUENCE: 28

```
Arg Leu Glu Phe Trp Phe Ala Met Ile Lys Val Val Thr Ile Ile Ala
 1               5                  10                  15

Met Ile Ile Leu Gly Leu Leu Val Ile Val Leu Gly Leu Gly Asn Asn
            20                  25                  30

Trp His Pro Val Gly Ile Ser Asn Leu Trp Ser His Gly Gly Phe Phe
        35                  40                  45

Thr Gly Gly Phe Met Gly Phe Met Phe Ser Leu Ser Val Ile Ala Gly
    50                  55                  60

Ser Tyr Gln Gly Ile Glu Leu Leu Gly Ile Thr Ala Gly Glu Ala Glu
65                  70                  75                  80

Ser Pro Arg His Ala Ile Val Lys Ser Val Lys Ser Val Ile Trp Arg
                85                  90                  95

Ile Leu Ile Phe Tyr Ile Gly Ala Ile Phe Val Ile Val Ser Ile Tyr
            100                 105                 110

Pro Trp Asn Glu Leu Lys Ser Val Gly Ser Pro Phe Val Glu Thr Phe
        115                 120                 125

Thr Lys Val Gly Ile Thr Gly Ala Ala Gly Ile Ile Asn Phe Val Val
    130                 135                 140

Leu Thr Ala Ala Leu Ser Gly Ala Asn Ser Gly Ile Tyr Ser Ala Ser
145                 150                 155                 160

Arg Met Leu Phe Lys Leu Ser Val Asp Gly Glu Val Pro Lys Phe Phe
                165                 170                 175

Ser Lys Leu Ser Lys Arg Val Val Pro Asn Val Ala Ile Leu Thr Ile
            180                 185                 190
```

-continued

```
Ser Ser Trp Ile Phe Leu Gly Phe Val Ile Asn Glu Leu Met Ser Ile
        195                 200                 205
Phe Ser Ser Ala Ala Gln Asn Ile Phe Val Ile Val Tyr Ser Ser Ser
    210                 215                 220
Val Leu Pro Gly Met Val Pro Trp Phe Ile Ile Leu Leu Ser Glu Leu
225                 230                 235                 240
His Phe Arg Lys Glu His Pro Glu Gln Leu Lys Asp His Pro Phe Lys
                245                 250                 255
Met Pro Leu Tyr Pro Ala Tyr Asn Tyr Phe Ser Leu Ile Ala Leu Thr
                260                 265                 270
Val Ile Leu Ile Phe Met Phe Phe Asn Pro Asp Thr Arg Val Ser Val
            275                 280                 285
Ser Val Gly Val Ile Phe Leu Ile Ile Met Ser Ile Ile Tyr Arg Val
        290                 295                 300
Arg Val His Glu Gly Lys Glu Lys
305                 310
```

<210> SEQ ID NO 29
<211> LENGTH: 600
<212> TYPE: DNA
<213> ORGANISM: Lactobacillus reuteri
<220> FEATURE:
<221> NAME/KEY: CDS
<222> LOCATION: (1)..(597)

<400> SEQUENCE: 29

```
atg agt aag tgg att aag caa ttc cta ctc gct gga ttg gcg gga tta      48
Met Ser Lys Trp Ile Lys Gln Phe Leu Leu Ala Gly Leu Ala Gly Leu
  1               5                  10                  15 att aga cct aag cat aat cag aag tac tca tta gag act aag tta act      96
Ile Arg Pro Lys His Asn Gln Lys Tyr Ser Leu Glu Thr Lys Leu Thr
             20                  25                  30 gct gta aaa gct tat ctt tct ggc aag tat act aat caa gca att ctc     144
Ala Val Lys Ala Tyr Leu Ser Gly Lys Tyr Thr Asn Gln Ala Ile Leu
         35                  40                  45 cag cag tat caa att aga aat att tct caa cta cat caa tgg gtt atc     192
Gln Gln Tyr Gln Ile Arg Asn Ile Ser Gln Leu His Gln Trp Val Ile
     50                  55                  60 agt tac aat aat gac aaa ctc cga gtt aat cag aca acg aga aag cga     240
Ser Tyr Asn Asn Asp Lys Leu Arg Val Asn Gln Thr Thr Arg Lys Arg
 65                  70                  75                  80 gtc aga aaa atg gga cga aaa gta acc ttt gat gaa aag agg cag att     288
Val Arg Lys Met Gly Arg Lys Val Thr Phe Asp Glu Lys Arg Gln Ile
                 85                  90                  95 gtc cga tgg aca att gaa cat aac aat aac tat aaa gcg gct gca gag     336
Val Arg Trp Thr Ile Glu His Asn Asn Asn Tyr Lys Ala Ala Ala Glu
            100                 105                 110 aag tat gat att agt tac caa cga gtt tat tct tgg gta cgg aag tac     384
Lys Tyr Asp Ile Ser Tyr Gln Arg Val Tyr Ser Trp Val Arg Lys Tyr
        115                 120                 125 cga gta aat agc gac tgg gaa gta cta aaa gat aac cgt ggg cgt aat     432
Arg Val Asn Ser Asp Trp Glu Val Leu Lys Asp Asn Arg Gly Arg Asn
    130                 135                 140 aaa gga aaa gag ccc act aat gaa cta gaa aaa cta agg aaa cga gtt     480
Lys Gly Lys Glu Pro Thr Asn Glu Leu Glu Lys Leu Arg Lys Arg Val
145                 150                 155                 160 cgt gag cta gaa gat cgt gac cgt gaa cgg gag ctg caa atc gct ttc     528
Arg Glu Leu Glu Asp Arg Asp Arg Glu Arg Glu Leu Gln Ile Ala Phe
                165                 170                 175
```

```
gca aaa aaa tta gtc gaa ata cgc aat cgg gag gtg aaa cga ccg gac    576
Ala Lys Lys Leu Val Glu Ile Arg Asn Arg Glu Val Lys Arg Pro Asp
            180                 185                 190 gat atc aag cga ttc aag aaa tga                                    600
Asp Ile Lys Arg Phe Lys Lys
        195

<210> SEQ ID NO 30
<211> LENGTH: 199
<212> TYPE: PRT
<213> ORGANISM: Lactobacillus reuteri

<400> SEQUENCE: 30

Met Ser Lys Trp Ile Lys Gln Phe Leu Leu Ala Gly Leu Ala Gly Leu
 1               5                  10                  15

Ile Arg Pro Lys His Asn Gln Lys Tyr Ser Leu Glu Thr Lys Leu Thr
            20                  25                  30

Ala Val Lys Ala Tyr Leu Ser Gly Lys Tyr Thr Asn Gln Ala Ile Leu
        35                  40                  45

Gln Gln Tyr Gln Ile Arg Asn Ile Ser Gln Leu His Gln Trp Val Ile
    50                  55                  60

Ser Tyr Asn Asn Asp Lys Leu Arg Val Asn Gln Thr Thr Arg Lys Arg
65                  70                  75                  80

Val Arg Lys Met Gly Arg Lys Val Thr Phe Asp Glu Lys Arg Gln Ile
                85                  90                  95

Val Arg Trp Thr Ile Glu His Asn Asn Tyr Lys Ala Ala Ala Glu
            100                 105                 110

Lys Tyr Asp Ile Ser Tyr Gln Arg Val Tyr Ser Trp Val Arg Lys Tyr
        115                 120                 125

Arg Val Asn Ser Asp Trp Glu Val Leu Lys Asp Asn Arg Gly Arg Asn
    130                 135                 140

Lys Gly Lys Glu Pro Thr Asn Glu Leu Glu Lys Leu Arg Lys Arg Val
145                 150                 155                 160

Arg Glu Leu Glu Asp Arg Asp Arg Glu Arg Glu Leu Gln Ile Ala Phe
                165                 170                 175

Ala Lys Lys Leu Val Glu Ile Arg Asn Arg Glu Val Lys Arg Pro Asp
            180                 185                 190

Asp Ile Lys Arg Phe Lys Lys
        195

<210> SEQ ID NO 31
<211> LENGTH: 849
<212> TYPE: DNA
<213> ORGANISM: Lactobacillus reuteri
<220> FEATURE:
<221> NAME/KEY: CDS
<222> LOCATION: (1)..(849)

<400> SEQUENCE: 31 atg aac aat gaa ggt tat tcc att agt gaa ttg gcc aag gtc gct gga    48
Met Asn Asn Glu Gly Tyr Ser Ile Ser Glu Leu Ala Lys Val Ala Gly
 1               5                  10                  15 att act aga cag gct tac tac aaa tgg ttg aaa cat gaa ccg act aaa    96
Ile Thr Arg Gln Ala Tyr Tyr Lys Trp Leu Lys His Glu Pro Thr Lys
            20                  25                  30 tat gag att gaa gaa tcg gag att ctc caa ttg att aaa cag tta gaa   144
Tyr Glu Ile Glu Glu Ser Glu Ile Leu Gln Leu Ile Lys Gln Leu Glu
        35                  40                  45 aat gaa cat aag caa agc gtt ggt tat gac aaa atg act agg tta atc   192
```

```
Asn Glu His Lys Gln Ser Val Gly Tyr Asp Lys Met Thr Arg Leu Ile
        50                  55                  60 aag tta agt cag cag atc tct tat acc gtt aat aag aaa cga gtc att    240
Lys Leu Ser Gln Gln Ile Ser Tyr Thr Val Asn Lys Lys Arg Val Ile
 65                  70                  75                  80 cgt att atg aaa ggc cat agt atc aag gcc gac tat cgt cag cca acc    288
Arg Ile Met Lys Gly His Ser Ile Lys Ala Asp Tyr Arg Gln Pro Thr
                 85                  90                  95 gac aaa cgt att caa gcc cag caa act tat gaa gct gaa aat att ctt    336
Asp Lys Arg Ile Gln Ala Gln Gln Thr Tyr Glu Ala Glu Asn Ile Leu
            100                 105                 110 aac cga caa ttt gac caa act gca gct aac caa gtt tgg gtt acg gat    384
Asn Arg Gln Phe Asp Gln Thr Ala Ala Asn Gln Val Trp Val Thr Asp
        115                 120                 125 acg acg gaa ctg aat tac gga atc tgg ctt aat aaa gtt cgt cta cat    432
Thr Thr Glu Leu Asn Tyr Gly Ile Trp Leu Asn Lys Val Arg Leu His
130                 135                 140 ata gta tta gat tta tat ggt caa tac cca gta agc tgg tta att aca    480
Ile Val Leu Asp Leu Tyr Gly Gln Tyr Pro Val Ser Trp Leu Ile Thr
145                 150                 155                 160 cct aca gaa acc gct gaa gga gta gtt caa gtg ttc gag caa gca cgg    528
Pro Thr Glu Thr Ala Glu Gly Val Val Gln Val Phe Glu Gln Ala Arg
                165                 170                 175 atg aaa gaa gga gca cta gct ccg tta att cat act gat cgt ggt gcg    576
Met Lys Glu Gly Ala Leu Ala Pro Leu Ile His Thr Asp Arg Gly Ala
            180                 185                 190 gcg tat act tcc aaa gca ttt aat cag tat tta gta gtt aat ggt gcc    624
Ala Tyr Thr Ser Lys Ala Phe Asn Gln Tyr Leu Val Val Asn Gly Ala
        195                 200                 205 caa cac agt tat tca gca cca ggg aca ccg gct gac aat gcc gta ata    672
Gln His Ser Tyr Ser Ala Pro Gly Thr Pro Ala Asp Asn Ala Val Ile
    210                 215                 220 gaa cat tgg tgg gca gat ttt aag gct att tgg atc gca cat cta cct    720
Glu His Trp Trp Ala Asp Phe Lys Ala Ile Trp Ile Ala His Leu Pro
225                 230                 235                 240 aaa gca caa aca tta tta gaa cta gaa gaa caa gtt aga gaa gga att    768
Lys Ala Gln Thr Leu Leu Glu Leu Glu Glu Gln Val Arg Glu Gly Ile
                245                 250                 255 acc tat ttc act gaa aaa ttt atc tca gcg aag aga aat gac ctt acc    816
Thr Tyr Phe Thr Glu Lys Phe Ile Ser Ala Lys Arg Asn Asp Leu Thr
            260                 265                 270 gca gcg gaa tac cgc ttt ggc aag gcc aac taa                         849
Ala Ala Glu Tyr Arg Phe Gly Lys Ala Asn
        275                 280
```

<210> SEQ ID NO 32
<211> LENGTH: 282
<212> TYPE: PRT
<213> ORGANISM: Lactobacillus reuteri

<400> SEQUENCE: 32

```
Met Asn Asn Glu Gly Tyr Ser Ile Ser Glu Leu Ala Lys Val Ala Gly
 1               5                  10                  15

Ile Thr Arg Gln Ala Tyr Tyr Lys Trp Leu Lys His Glu Pro Thr Lys
                20                  25                  30

Tyr Glu Ile Glu Glu Ser Glu Ile Leu Gln Leu Ile Lys Gln Leu Glu
            35                  40                  45

Asn Glu His Lys Gln Ser Val Gly Tyr Asp Lys Met Thr Arg Leu Ile
        50                  55                  60
```

```
Lys Leu Ser Gln Gln Ile Ser Tyr Thr Val Asn Lys Lys Arg Val Ile
 65                  70                  75                  80

Arg Ile Met Lys Gly His Ser Ile Lys Ala Asp Tyr Arg Gln Pro Thr
                 85                  90                  95

Asp Lys Arg Ile Gln Ala Gln Gln Thr Tyr Glu Ala Glu Asn Ile Leu
            100                 105                 110

Asn Arg Gln Phe Asp Gln Thr Ala Ala Asn Gln Val Trp Val Thr Asp
            115                 120                 125

Thr Thr Glu Leu Asn Tyr Gly Ile Trp Leu Asn Lys Val Arg Leu His
        130                 135                 140

Ile Val Leu Asp Leu Tyr Gly Gln Tyr Pro Val Ser Trp Leu Ile Thr
145                 150                 155                 160

Pro Thr Glu Thr Ala Glu Gly Val Val Gln Val Phe Glu Gln Ala Arg
                165                 170                 175

Met Lys Glu Gly Ala Leu Ala Pro Leu Ile His Thr Asp Arg Gly Ala
            180                 185                 190

Ala Tyr Thr Ser Lys Ala Phe Asn Gln Tyr Leu Val Val Asn Gly Ala
            195                 200                 205

Gln His Ser Tyr Ser Ala Pro Gly Thr Pro Ala Asp Asn Ala Val Ile
        210                 215                 220

Glu His Trp Trp Ala Asp Phe Lys Ala Ile Trp Ile Ala His Leu Pro
225                 230                 235                 240

Lys Ala Gln Thr Leu Leu Glu Leu Glu Glu Gln Val Arg Glu Gly Ile
                245                 250                 255

Thr Tyr Phe Thr Glu Lys Phe Ile Ser Ala Lys Arg Asn Asp Leu Thr
            260                 265                 270

Ala Ala Glu Tyr Arg Phe Gly Lys Ala Asn
            275                 280

<210> SEQ ID NO 33
<211> LENGTH: 744
<212> TYPE: DNA
<213> ORGANISM: Lactobacillus reuteri
<220> FEATURE:
<221> NAME/KEY: CDS
<222> LOCATION: (1)..(744)
<221> NAME/KEY: unsure
<222> LOCATION: (1)..(744)
<223> OTHER INFORMATION: n = a, c, g, or t

<400> SEQUENCE: 33 atg ctt cgt tan acc ata tta gta aaa ttg ctt att gga aga aaa cca       48
Met Leu Arg Xaa Thr Ile Leu Val Lys Leu Leu Ile Gly Arg Lys Pro
 1               5                  10                  15 gtc aca acg atc aaa aaa aca tta ccg cca act cag gaa cag gct aat       96
Val Thr Thr Ile Lys Lys Thr Leu Pro Pro Thr Gln Glu Gln Ala Asn
                20                  25                  30 tca gtc tta act ccg gct gtt cgc caa caa ctt ggc att tca att acc      144
Ser Val Leu Thr Pro Ala Val Arg Gln Gln Leu Gly Ile Ser Ile Thr
            35                  40                  45 tgg aac aaa gcc ggt gcg ttt att atc aat aat aac caa aca aat ctt      192
Trp Asn Lys Ala Gly Ala Phe Ile Ile Asn Asn Asn Gln Thr Asn Leu
        50                  55                  60 aac gct aag att gca agt gca ccc tat gct gta aat cat ctt gac cgt      240
Asn Ala Lys Ile Ala Ser Ala Pro Tyr Ala Val Asn His Leu Asp Arg
 65                 70                  75                  80 caa gga agg gcg tgg caa ggt gat gcc tgg tta aac agg aca act cgg      288
Gln Gly Arg Ala Trp Gln Gly Asp Ala Trp Leu Asn Arg Thr Thr Arg
                85                  90                  95
```

```
tca ata tan aag ccg aaa ttt gcc aca ggg aat ggt gct acg gat tgg    336
Ser Ile Xaa Lys Pro Lys Phe Ala Thr Gly Asn Gly Ala Thr Asp Trp
            100                 105                 110 cga cca gct ggc ttc ctt cag gcg cat aat ctt aaa ggc ggg tac aat    384
Arg Pro Ala Gly Phe Leu Gln Ala His Asn Leu Lys Gly Gly Tyr Asn
        115                 120                 125 cat gca tac gat cgc gga cac ctt ctt gcc tat gca cta gtt ggt ggt    432
His Ala Tyr Asp Arg Gly His Leu Leu Ala Tyr Ala Leu Val Gly Gly
    130                 135                 140 att cat gga ttt gat gca tcc gaa tca aat cca tct aat att gcc acg    480
Ile His Gly Phe Asp Ala Ser Glu Ser Asn Pro Ser Asn Ile Ala Thr
145                 150                 155                 160 caa act gcc tgg gca aat gaa gca cga agt aag aac tca aca ggg caa    528
Gln Thr Ala Trp Ala Asn Glu Ala Arg Ser Lys Asn Ser Thr Gly Gln
                165                 170                 175 aat tac tac gaa ggt ctg gtg aga aaa gca tta gat cag aat aag caa    576
Asn Tyr Tyr Glu Gly Leu Val Arg Lys Ala Leu Asp Gln Asn Lys Gln
            180                 185                 190 gtt cgc tac cga gtt acc aat att tat gac ggt aat aat atc gtt ccg    624
Val Arg Tyr Arg Val Thr Asn Ile Tyr Asp Gly Asn Asn Ile Val Pro
        195                 200                 205 gca ggt gct cat atc gaa gct aaa tct agt gat ggt tct cta gaa tac    672
Ala Gly Ala His Ile Glu Ala Lys Ser Ser Asp Gly Ser Leu Glu Tyr
    210                 215                 220 aat gtc ttt gtt ccg aat gtc caa aga aac att acc att aat tat tca    720
Asn Val Phe Val Pro Asn Val Gln Arg Asn Ile Thr Ile Asn Tyr Ser
225                 230                 235                 240 acc ggt gca gta aaa caa aac taa                                    744
Thr Gly Ala Val Lys Gln Asn
                245

<210> SEQ ID NO 34
<211> LENGTH: 247
<212> TYPE: PRT
<213> ORGANISM: Lactobacillus reuteri
<220> FEATURE:
<221> NAME/KEY: UNSURE
<222> LOCATION: (1)..(247)
<223> OTHER INFORMATION: Xaa = Tyr or stop

<400> SEQUENCE: 34

Met Leu Arg Xaa Thr Ile Leu Val Lys Leu Leu Ile Gly Arg Lys Pro
1               5                   10                  15

Val Thr Thr Ile Lys Lys Thr Leu Pro Pro Thr Gln Glu Gln Ala Asn
            20                  25                  30

Ser Val Leu Thr Pro Ala Val Arg Gln Gln Leu Gly Ile Ser Ile Thr
        35                  40                  45

Trp Asn Lys Ala Gly Ala Phe Ile Ile Asn Asn Gln Thr Asn Leu
    50                  55                  60

Asn Ala Lys Ile Ala Ser Ala Pro Tyr Ala Val Asn His Leu Asp Arg
65                  70                  75                  80

Gln Gly Arg Ala Trp Gln Gly Asp Ala Trp Leu Asn Arg Thr Arg
                85                  90                  95

Ser Ile Xaa Lys Pro Lys Phe Ala Thr Gly Asn Gly Ala Thr Asp Trp
            100                 105                 110

Arg Pro Ala Gly Phe Leu Gln Ala His Asn Leu Lys Gly Gly Tyr Asn
        115                 120                 125

His Ala Tyr Asp Arg Gly His Leu Leu Ala Tyr Ala Leu Val Gly Gly
    130                 135                 140
```

```
Ile His Gly Phe Asp Ala Ser Glu Ser Asn Pro Ser Asn Ile Ala Thr
145                 150                 155                 160

Gln Thr Ala Trp Ala Asn Glu Ala Arg Ser Lys Asn Ser Thr Gly Gln
            165                 170                 175

Asn Tyr Tyr Glu Gly Leu Val Arg Lys Ala Leu Asp Gln Asn Lys Gln
            180                 185                 190

Val Arg Tyr Arg Val Thr Asn Ile Tyr Asp Gly Asn Asn Ile Val Pro
            195                 200                 205

Ala Gly Ala His Ile Glu Ala Lys Ser Ser Asp Gly Ser Leu Glu Tyr
            210                 215                 220

Asn Val Phe Val Pro Asn Val Gln Arg Asn Ile Thr Ile Asn Tyr Ser
225                 230                 235                 240

Thr Gly Ala Val Lys Gln Asn
                245
```

<210> SEQ ID NO 35
<211> LENGTH: 1540
<212> TYPE: DNA
<213> ORGANISM: Lactobacillus reuteri
<220> FEATURE:
<221> NAME/KEY: CDS
<222> LOCATION: (1)..(1539)

<400> SEQUENCE: 35

```
atg gtc atg aca gaa act gct ggt ata aga aaa att cat att gtt ttt      48
Met Val Met Thr Glu Thr Ala Gly Ile Arg Lys Ile His Ile Val Phe
  1               5                  10                  15 gat ggt caa gaa aca cca cca tta aag atc cat caa tta ttt gat tca      96
Asp Gly Gln Glu Thr Pro Pro Leu Lys Ile His Gln Leu Phe Asp Ser
             20                  25                  30 caa aaa tac gat cag tta atc gca gta act ggg aaa att act gct gac     144
Gln Lys Tyr Asp Gln Leu Ile Ala Val Thr Gly Lys Ile Thr Ala Asp
         35                  40                  45 ttc att aat aaa tac ctt agt aat ttt atc agt att aat gta gcg tta     192
Phe Ile Asn Lys Tyr Leu Ser Asn Phe Ile Ser Ile Asn Val Ala Leu
     50                  55                  60 agc tcc caa tca act agt gaa tta agt gct gat gag atg gta aca aag     240
Ser Ser Gln Ser Thr Ser Glu Leu Ser Ala Asp Glu Met Val Thr Lys
 65                  70                  75                  80 gtt gca ctt acc aat gct ctc ctt agt tca gca aat aaa gaa gct gct     288
Val Ala Leu Thr Asn Ala Leu Leu Ser Ser Ala Asn Lys Glu Ala Ala
                 85                  90                  95 aaa ctc ttc tca gcg tta acc agt gac aac caa acg aac gtc tta aat     336
Lys Leu Phe Ser Ala Leu Thr Ser Asp Asn Gln Thr Asn Val Leu Asn
            100                 105                 110 aat ctt ttt cgc gta tca atc gcg cct act cag gtt atc cat tct aag     384
Asn Leu Phe Arg Val Ser Ile Ala Pro Thr Gln Val Ile His Ser Lys
        115                 120                 125 ttt tac ttg tta agt agt tca act act cat gat tcc cgt gtg att ctt     432
Phe Tyr Leu Leu Ser Ser Ser Thr Thr His Asp Ser Arg Val Ile Leu
    130                 135                 140 ggg agt gta gat tta gac gaa gct tca ttt gat gct cac cga aat caa     480
Gly Ser Val Asp Leu Asp Glu Ala Ser Phe Asp Ala His Arg Asn Gln
145                 150                 155                 160 ttt gaa gaa gta ttg gta ttt gac aat gat gtc cgc tta tac caa aac     528
Phe Glu Glu Val Leu Val Phe Asp Asn Asp Val Arg Leu Tyr Gln Asn
                165                 170                 175 ctt act gac cac ttt aaa aag gat ttt aag cca gta ttg aag ccc ttc     576
Leu Thr Asp His Phe Lys Lys Asp Phe Lys Pro Val Leu Lys Pro Phe
```

```
                    180                     185                     190
ttt act atg aac cta gta aag gca gct caa aag caa gtt gag gaa gga          624
Phe Thr Met Asn Leu Val Lys Ala Ala Gln Lys Gln Val Glu Glu Gly
            195                     200                     205 aag aaa gat cag gat agc ggt aag gga ccg gtt atc ctt gat aat gaa          672
Lys Lys Asp Gln Asp Ser Gly Lys Gly Pro Val Ile Leu Asp Asn Glu
        210                     215                     220 aca aca gat aag atc gct gaa aca gac atg gtg gat ctg ttg aag cat          720
Thr Thr Asp Lys Ile Ala Glu Thr Asp Met Val Asp Leu Leu Lys His
225                     230                     235                 240 gac ctt cag cat gat att gac cat aat ctt gtt cct gaa atg atc aca          768
Asp Leu Gln His Asp Ile Asp His Asn Leu Val Pro Glu Met Ile Thr
                245                     250                     255 aag tca atg cgt gat att acc ata aat cgt tct caa gca aag gag aaa          816
Lys Ser Met Arg Asp Ile Thr Ile Asn Arg Ser Gln Ala Lys Glu Lys
            260                     265                     270 att gct aag cag gtt aag caa cat gat acg att tat act ttg caa aaa          864
Ile Ala Lys Gln Val Lys Gln His Asp Thr Ile Tyr Thr Leu Gln Lys
        275                     280                     285 gaa gcg gtc tct cct cgg gca gct aag cca aaa cta aag act cga gaa          912
Glu Ala Val Ser Pro Arg Ala Ala Lys Pro Lys Leu Lys Thr Arg Glu
    290                     295                     300 aaa att acc aag cag gtt cag gat gct ttg atc agt gga atg tca cca          960
Lys Ile Thr Lys Gln Val Gln Asp Ala Leu Ile Ser Gly Met Ser Pro
305                     310                     315                 320 cag caa cgg gat gct gag aaa aag tac acg act ttt ctg tac gat cgg         1008
Gln Gln Arg Asp Ala Glu Lys Lys Tyr Thr Thr Phe Leu Tyr Asp Arg
                325                     330                     335 cca atg gaa cga aac att gcg aat aac aat agt ggc cta tac gtt cct         1056
Pro Met Glu Arg Asn Ile Ala Asn Asn Asn Ser Gly Leu Tyr Val Pro
            340                     345                     350 aat gat acg gga act cac cca atc cca ttt ggt aaa att gca act att         1104
Asn Asp Thr Gly Thr His Pro Ile Pro Phe Gly Lys Ile Ala Thr Ile
        355                     360                     365 tct gaa att cgt gac ggt tta aag agc att gat gct gtt atg aag ggc         1152
Ser Glu Ile Arg Asp Gly Leu Lys Ser Ile Asp Ala Val Met Lys Gly
    370                     375                     380 tat cag cag ttt gtc gtt gat tat gat gct gac tac ggg aag cgg ttc         1200
Tyr Gln Gln Phe Val Val Asp Tyr Asp Ala Asp Tyr Gly Lys Arg Phe
385                     390                     395                 400 ttt gaa gca att ttg tat agt ttt act gca ccg ttt tta tgg gaa att         1248
Phe Glu Ala Ile Leu Tyr Ser Phe Thr Ala Pro Phe Leu Trp Glu Ile
                405                     410                     415 cgt tct aaa gct agc ctg aac cct gaa gat ggg aat gat gtt cct aat         1296
Arg Ser Lys Ala Ser Leu Asn Pro Glu Asp Gly Asn Asp Val Pro Asn
            420                     425                     430 ttc cta atc cta ggg gca acg gct ggt tcc gga aag tct acc ctt ctt         1344
Phe Leu Ile Leu Gly Ala Thr Ala Gly Ser Gly Lys Ser Thr Leu Leu
        435                     440                     445 cgg att att aat cag ctc acg tgg aac act gat cgc tcg ttg att gac         1392
Arg Ile Ile Asn Gln Leu Thr Trp Asn Thr Asp Arg Ser Leu Ile Asp
    450                     455                     460 ttt gga acg atc tac ccg tcg caa act cct caa aag aag gca aag act         1440
Phe Gly Thr Ile Tyr Pro Ser Gln Thr Pro Gln Lys Lys Ala Lys Thr
465                     470                     475                 480 gtt gag gcg atg gaa cat tat atg aaa ctt ggt agt tca tac ccg gtt         1488
Val Glu Ala Met Glu His Tyr Met Lys Leu Gly Ser Ser Tyr Pro Val
                485                     490                     495 ttg tta gat gaa att gaa ccg tac ttc ttc cag caa gat caa tat agt         1536
```

```
Leu Leu Asp Glu Ile Glu Pro Tyr Phe Phe Gln Gln Asp Gln Tyr Ser
            500                 505                 510
cga c                                                                    1540
Arg
```

<210> SEQ ID NO 36
<211> LENGTH: 513
<212> TYPE: PRT
<213> ORGANISM: Lactobacillus reuteri

<400> SEQUENCE: 36

```
Met Val Met Thr Glu Thr Ala Gly Ile Arg Lys Ile His Ile Val Phe
  1               5                  10                  15

Asp Gly Gln Glu Thr Pro Leu Lys Ile His Gln Leu Phe Asp Ser
                 20                  25                  30

Gln Lys Tyr Asp Gln Leu Ile Ala Val Thr Gly Lys Ile Thr Ala Asp
             35                  40                  45

Phe Ile Asn Lys Tyr Leu Ser Asn Phe Ile Ser Ile Asn Val Ala Leu
     50                  55                  60

Ser Ser Gln Ser Thr Ser Glu Leu Ser Ala Asp Glu Met Val Thr Lys
 65                  70                  75                  80

Val Ala Leu Thr Asn Ala Leu Leu Ser Ser Ala Asn Lys Glu Ala Ala
                 85                  90                  95

Lys Leu Phe Ser Ala Leu Thr Ser Asp Asn Gln Thr Asn Val Leu Asn
            100                 105                 110

Asn Leu Phe Arg Val Ser Ile Ala Pro Thr Gln Val Ile His Ser Lys
        115                 120                 125

Phe Tyr Leu Leu Ser Ser Thr Thr His Asp Ser Arg Val Ile Leu
    130                 135                 140

Gly Ser Val Asp Leu Asp Glu Ala Ser Phe Asp Ala His Arg Asn Gln
145                 150                 155                 160

Phe Glu Glu Val Leu Val Phe Asp Asn Asp Val Arg Leu Tyr Gln Asn
                165                 170                 175

Leu Thr Asp His Phe Lys Lys Asp Phe Lys Pro Val Leu Lys Pro Phe
            180                 185                 190

Phe Thr Met Asn Leu Val Lys Ala Ala Gln Lys Gln Val Glu Glu Gly
        195                 200                 205

Lys Lys Asp Gln Asp Ser Gly Lys Gly Pro Val Ile Leu Asp Asn Glu
    210                 215                 220

Thr Thr Asp Lys Ile Ala Glu Thr Asp Met Val Asp Leu Leu Lys His
225                 230                 235                 240

Asp Leu Gln His Asp Ile Asp His Asn Leu Val Pro Glu Met Ile Thr
                245                 250                 255

Lys Ser Met Arg Asp Ile Thr Ile Asn Arg Ser Gln Ala Lys Glu Lys
            260                 265                 270

Ile Ala Lys Gln Val Lys Gln His Asp Thr Ile Tyr Thr Leu Gln Lys
        275                 280                 285

Glu Ala Val Ser Pro Arg Ala Lys Pro Lys Leu Lys Thr Arg Glu
    290                 295                 300

Lys Ile Thr Lys Gln Val Gln Asp Ala Leu Ile Ser Gly Met Ser Pro
305                 310                 315                 320

Gln Gln Arg Asp Ala Glu Lys Lys Tyr Thr Thr Phe Leu Tyr Asp Arg
                325                 330                 335

Pro Met Glu Arg Asn Ile Ala Asn Asn Asn Ser Gly Leu Tyr Val Pro
            340                 345                 350
```

Asn Asp Thr Gly Thr His Pro Ile Pro Phe Gly Lys Ile Ala Thr Ile
          355                 360                 365

Ser Glu Ile Arg Asp Gly Leu Lys Ser Ile Asp Ala Val Met Lys Gly
        370                 375                 380

Tyr Gln Gln Phe Val Val Asp Tyr Asp Ala Asp Tyr Gly Lys Arg Phe
385                 390                 395                 400

Phe Glu Ala Ile Leu Tyr Ser Phe Thr Ala Pro Phe Leu Trp Glu Ile
                405                 410                 415

Arg Ser Lys Ala Ser Leu Asn Pro Glu Asp Gly Asn Asp Val Pro Asn
            420                 425                 430

Phe Leu Ile Leu Gly Ala Thr Ala Gly Ser Gly Lys Ser Thr Leu Leu
        435                 440                 445

Arg Ile Ile Asn Gln Leu Thr Trp Asn Thr Asp Arg Ser Leu Ile Asp
    450                 455                 460

Phe Gly Thr Ile Tyr Pro Ser Gln Thr Pro Gln Lys Lys Ala Lys Thr
465                 470                 475                 480

Val Glu Ala Met Glu His Tyr Met Lys Leu Gly Ser Ser Tyr Pro Val
                485                 490                 495

Leu Leu Asp Glu Ile Glu Pro Tyr Phe Phe Gln Gln Asp Gln Tyr Ser
            500                 505                 510

Arg

<210> SEQ ID NO 37
<211> LENGTH: 26
<212> TYPE: DNA
<213> ORGANISM: Lactobacillus reuteri
<220> FEATURE:
<221> NAME/KEY: terminator
<222> LOCATION: (1)..(26)

<400> SEQUENCE: 37
aaagaagctg aaatttcggc ttcttt                                      26

<210> SEQ ID NO 38
<211> LENGTH: 28
<212> TYPE: DNA
<213> ORGANISM: Lactobacillus reuteri

<400> SEQUENCE: 38
gcagtcgacg gagttaagac tgaattag                                    28

<210> SEQ ID NO 39
<211> LENGTH: 26
<212> TYPE: DNA
<213> ORGANISM: Lactobacillus reuteri

<400> SEQUENCE: 39
ctagtcgacg cagtttctgt catgac                                      26

<210> SEQ ID NO 40
<211> LENGTH: 32
<212> TYPE: DNA
<213> ORGANISM: Lactobacillus reuteri

<400> SEQUENCE: 40
catatgtatt attcaaacgg gaattatgaa gc                               32

<210> SEQ ID NO 41
<211> LENGTH: 30

```
<212> TYPE: DNA
<213> ORGANISM: Lactobacillus reuteri

<400> SEQUENCE: 41
tgatcatcta taccagcagt ttctgtcatg                                          30

<210> SEQ ID NO 42
<211> LENGTH: 35
<212> TYPE: PRT
<213> ORGANISM: Propionibacterium acnes
<220> FEATURE:
<221> NAME/KEY: UNSURE
<222> LOCATION: (30)
<223> OTHER INFORMATION: Xaa = any amino acid

<400> SEQUENCE: 42

Ser Ile Ser Lys Asp Ser Arg Ile Ala Ile Ile Gly Ala Gly Pro Ala
  1               5                  10                  15

Gly Leu Ala Ala Gly Met Tyr Leu Trp Gln Ala Gly Phe Xaa Asp Tyr
             20                  25                  30

Thr Ile Leu
         35

<210> SEQ ID NO 43
<211> LENGTH: 21
<212> TYPE: PRT
<213> ORGANISM: Clostridium sporogenes
<220> FEATURE:
<221> NAME/KEY: UNSURE
<222> LOCATION: (18)
<223> OTHER INFORMATION: Xaa = any amino acid

<400> SEQUENCE: 43

Met Phe Asn Leu Lys Asn Arg Asn Phe Leu Thr Leu Met Asp Phe Thr
  1               5                  10                  15

Pro Xaa Glu Ile Gln
             20

<210> SEQ ID NO 44
<211> LENGTH: 14
<212> TYPE: PRT
<213> ORGANISM: Propionibacterium acnes

<400> SEQUENCE: 44

Lys Tyr Leu Asp Phe Val Thr Met Met Ser Phe Ala Lys Gly
  1               5                  10

<210> SEQ ID NO 45
<211> LENGTH: 9
<212> TYPE: PRT
<213> ORGANISM: Propionibacterium acnes

<400> SEQUENCE: 45

Lys Asp Leu Val Thr Arg Phe Phe Val
  1               5

<210> SEQ ID NO 46
<211> LENGTH: 15
<212> TYPE: PRT
<213> ORGANISM: Propionibacterium acnes
<220> FEATURE:
<221> NAME/KEY: UNSURE
<222> LOCATION: (2)
<223> OTHER INFORMATION: Xaa = Ile or Ser
<221> NAME/KEY: UNSURE
<222> LOCATION: (4)
```

```
<223> OTHER INFORMATION: Xaa = His or Phe
<221> NAME/KEY: UNSURE
<222> LOCATION: (6)
<223> OTHER INFORMATION: Xaa = Glu or Gln
<221> NAME/KEY: UNSURE
<222> LOCATION: (10)
<223> OTHER INFORMATION: Xaa = Asp or Thr
<221> NAME/KEY: UNSURE
<222> LOCATION: (12)
<223> OTHER INFORMATION: Xaa = Gly or Ser

<400> SEQUENCE: 46

Lys Xaa Ile Xaa Gln Xaa Tyr Met Val Xaa Ala Xaa Leu Val Lys
  1               5                  10                  15

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:primer
<221> NAME/KEY: unsure
<222> LOCATION: (1)..(20)
<223> OTHER INFORMATION: n = a, c, g, or t

<400> SEQUENCE: 47
atcgcgatna tnggngcngg                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:primer
<221> NAME/KEY: unsure
<222> LOCATION: (1)..(20)
<223> OTHER INFORMATION: n = a, c, g, or t

<400> SEQUENCE: 48
ccngcytgcc anarrtacat                                               20

<210> SEQ ID NO 49
<211> LENGTH: 62
<212> TYPE: DNA
<213> ORGANISM: Propionibacterium acnes

<400> SEQUENCE: 49
atcgagatva trggggctgg cccggccggg ctggctgccg gaatgtacct ctggcargcs   60
gg                                                                 62

<210> SEQ ID NO 50
<211> LENGTH: 21
<212> TYPE: PRT
<213> ORGANISM: Propionibacterium acnes
<220> FEATURE:
<221> NAME/KEY: UNSURE
<222> LOCATION: (2)
<223> OTHER INFORMATION: xaa = ala or glu
<221> NAME/KEY: UNSURE
<222> LOCATION: (3)..(4)
<223> OTHER INFORMATION: xaa = ile or met

<400> SEQUENCE: 50

Ile Xaa Xaa Xaa Gly Ala Gly Pro Ala Gly Leu Ala Ala Gly Met Tyr
  1               5                  10                  15

Leu Trp Gln Ala Gly
           20
```

<210> SEQ ID NO 51
<211> LENGTH: 17
<212> TYPE: DNA
<213> ORGANISM: Artificial Sequence
<220> FEATURE:
<223> OTHER INFORMATION: Description of Artificial Sequence:primer
<221> NAME/KEY: unsure
<222> LOCATION: (1)..(17)
<223> OTHER INFORMATION: n = a, c, g, or t

<400> SEQUENCE: 51
gggccagccc cyatnat                                                    17

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 52
gctggctgcc ggaatgta                                                   18

<210> SEQ ID NO 53
<211> LENGTH: 569
<212> TYPE: DNA
<213> ORGANISM: Propionibacterium acnes

<400> SEQUENCE: 53
ggatcccaac tggccgcctg ccccggggga ggagtaccac gccgacatcg aaggcaacaa      60
tgcccgtaac gggtggaccg aggacacccc ggccgtcaat gatgcccagg ccgagcggcg     120
ggccaaggag ctggcagcac atctcgatga gatggcacgt ggtcggcgaa ctgcccgctg     180
agatgtttcg cgacctatac cattaccgac cccattcatc gccgaactta ttcaccacta     240
catcgacaag gaagaacgat gtccatctcg aaggattcac gtatcgccat catcggggct     300
ggcccggccg gctggctgc cggaatgtac ctcgaacagg ccggatttca cgactacacg      360
atcctggaac gcaccgacca cgtcggaggc aagtgccact caccgaacta ccacggccgt     420
cgttatgaga tgggggccat catgggcgtc cccagttacg acaccatcca ggagatcatg     480
gatcgcactg gcgacaaggt cgacgggccg aaactgcgtc gcgagttcct gcacgaggac     540
ggcgagatct acgtcccgga aaaggatcc                                      569

<210> SEQ ID NO 54
<211> LENGTH: 104
<212> TYPE: PRT
<213> ORGANISM: Propionibacterium acnes

<400> SEQUENCE: 54

Met Ser Ile Ser Lys Asp Ser Arg Ile Ala Ile Ile Gly Ala Gly Pro
 1               5                  10                  15

Ala Gly Leu Ala Ala Gly Met Tyr Leu Glu Gln Ala Gly Phe His Asp
            20                  25                  30

Tyr Thr Ile Leu Glu Arg Thr Asp His Val Gly Gly Lys Cys His Ser
        35                  40                  45

Pro Asn Tyr His Gly Arg Arg Tyr Glu Met Gly Ala Ile Met Gly Val
    50                  55                  60

Pro Ser Tyr Asp Thr Ile Gln Glu Ile Met Asp Arg Thr Gly Asp Lys
65                  70                  75                  80

Val Asp Gly Pro Lys Leu Arg Arg Glu Phe Leu His Glu Asp Gly Glu

```
                85                  90                  95
Ile Tyr Val Pro Glu Lys Asp Pro
                100
```

<210> SEQ ID NO 55
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 55
cgatgtcggc gtggtac                                                    17

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 56
tcacgtatcg ccatcatc                                                   18

<210> SEQ ID NO 57
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 57
aatccggcct gttcgag                                                    17

<210> SEQ ID NO 58
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 58
aggacggcga gatctac                                                    17

<210> SEQ ID NO 59
<211> LENGTH: 5275
<212> TYPE: DNA
<213> ORGANISM: Propionibacterium acnes

<400> SEQUENCE: 59
gccgggcggg cacgattgac gaatttccgc acactggatg gcggaacaaa ggtgtcgtga      60
tttccctgga tcaccattgt tggtggtgcc tgaggagtga tccaggtgga actgttgaca     120
gcgcgataac ggtcggggaa ttgcttgggg gtgccaccga tatacatttt ggcggcattg     180
cccgcgctca gtgtggtgac cgactcgacg gtaccgacat ccaccgttgg atagagggcg     240
aggactgact tcggggcccg tattgagccg caggaactct tcaactttcc actggcggcg     300
ccgtaggcga gattaatggc cattccacca ccagcggaat cacccatgat cgatacctgt     360
gaagggtcgc caccgagttc tttcacgtgg acaggctcc aggcccaggc acatgcgacc     420
tgttttgggg cggtattcca ggtggggtgg ccctgggtgg ccaggtgta cgaggggcga     480 atgactaacc agccatgatc ggaaaaccat ctcaacgtgg cgggcatggt ggcgtcggtg     540

-continued

| | | | | |
|---|---|---|---|---|
| ctccatcctt | caccatgaat | gtcgacaagt | accggggcat | tgtggttatg ggcacggtag | 600 |
| atctgggccg | tctcgtcagg | gccggatcca | taccggaccg | tttcgtcagg gtggtcggac | 660 |
| atcgacgaca | ccgcagctgc | cgagacgacg | ttgatacgtc | caccggggcg gtccgtgatc | 720 |
| cacgccgtcg | tcgccgttgc | cgccactggc | acgatgaggg | ccatcaccga aagacaacg | 780 |
| gccaccactc | gcagaccacc | tcgtcccaaa | agagcgagga | cgaaggcgat gacggcgatg | 840 |
| accagagccg | gtacagccaa | cgatcccacc | agaacggagg | agatgaaggt gagggcattg | 900 |
| tgtgagggga | ggatcgcggc | cactgaccac | gccagtaccg | gcagggtcag gatcagcccg | 960 |
| acgagaccgg | aagtgatgcg | tagccaggaa | tgacgggagg | ttttcgtgtc agccacgcgt | 1020 |
| ccaccgtact | cacgggacat | ggtcgatagg | atcttcgcgc | aggagggacc catggctatc | 1080 |
| aggatcagac | aggttgctac | cgaagacagg | ccggccgtcg | cgcggatgtc ccacggcgag | 1140 |
| tatgtttggc | tggctgtcga | caccgagtca | gtcgttgatg | gccttctcta ggtcttcgga | 1200 |
| ttcgcctggg | ccggggtgca | ccttgacgaa | cctactccgc | tggaactgga aagtctctac | 1260 |
| gtccgttctc | gtctgtacgg | caccgggctc | ggccaggccc | tcatgaatac cgtcatcggc | 1320 |
| gattcccggg | cctatgtcat | ggtctatccc | gacaacaccc | aggccaaggc attctaccgc | 1380 |
| cgtaacggat | tctctcccga | tggtcatctc | gacgattacc | gcgacgagga tccggcctac | 1440 |
| gtcctggagt | gctggattcg | ctgaatcccc | ttggttcttg | ctcgcgacaa gctaggataa | 1500 |
| attaaattta | tttatttctt | gtgtcgatgc | gccacgacga | cgtagtggga ccggctcagg | 1560 |
| ggatgacgac | ccggtcccgg | gccgtgagtc | acgaaggagt | gccatgtcca taacaccacg | 1620 |
| aaagtgcaag | gctgccgccc | ttgccacagc | gccggtggcc | gctgccctcg gtgcttacgg | 1680 |
| atttcttaaa | ggggcgacga | agttctattc | cagccaggtt | aacggaactc ccgagcagta | 1740 |
| caagatgacc | cttcctggtg | acgacctcgt | cccggaaggt | tcgccgcgct tcaagcgcct | 1800 |
| cacccatgtg | gaggatctcg | acgcccctg | cgacgaggtc | tggaagcacg tctaccagct | 1860 |
| caacaccacg | accgccggct | tctactcctt | caccttcttc | gagaagatgt tcggactgtc | 1920 |
| ggtcgacaac | accttcatgg | tggaacaggc | ttggcaggcc | ccggactact acaagcccgg | 1980 |
| tgacatgttc | tgttggagtt | acgccggttt | cggtgccgag | gtcgccgaca tggtccccgg | 2040 |
| caagtatctg | gtgtggttcg | ctgacacccg | tgacggcacc | aggacaccgg gcgcaagttt | 2100 |
| cctgctaccg | cctggaatgc | cgtggaaccg | ctggagttgg | gtcatcgccc tggaaccct | 2160 |
| cgacagtggc | aaccggacgc | gcatctactc | cggtggaac | atctcggcct ccgaggagtc | 2220 |
| cagtccgatc | tcggtcttcc | tcatggatct | ggtcatgatg | gacggcggcg gcatggtgaa | 2280 |
| ccgtcggatg | ttccaaggc | tggagaaggc | tgccgtcgga | actgctcgca agaacatcgt | 2340 |
| tcctgcgcgc | ctatcagcgg | ttcatgggca | agtcctacgg | cactgacgac gacctgcagt | 2400 |
| accgcgttcc | gtacccggag | atccgctggt | ccgcgactt | ccctcgagtg gccagcgaac | 2460 |
| gggcctcctt | caccgaggat | cccaactggc | cgcctgcccc | ggggaggag taccacgccg | 2520 |
| acatcgaagg | caacaatgcc | cgtaacgggt | ggaccgagga | caccccggcc gtcaatgatg | 2580 |
| cccaggccga | gcggcgggcc | aaggagctgg | cagcacatct | cgatgagatg gcacgtggtc | 2640 |
| ggcgaactgc | ccgctgagat | gtttcgcgac | ctataccatt | accgacccca ttcatcgccg | 2700 |
| aacttattca | ccactacatc | gacaaggaag | aacgatgtcc | atctcgaagg attcacgtat | 2760 |
| cgccatcatc | ggggctggcc | cggccgggct | ggctgccgga | atgtacctcg aacaggccgg | 2820 |
| atttcacgac | tacacgatcc | tggaacgcac | cgaccacgtc | ggaggcaagt gccactcacc | 2880 |
| gaactaccac | ggccgtcgtt | atgagatggg | ggccatcatg | ggcgtcccca gttacgacac | 2940 |

```
catccaggag atcatggatc gcactggcga caaggtcgac gggccgaaac tgcgtcgcga    3000
gttcctgcac gaggacggcg agatctacgt cccggaaaag gatccagtgc gtggtccgca    3060
ggtcatggca gcagtgcaga agctgggcca gttgctcgcg acgaagtacc agggatatga    3120
cgccaacggc cactacaaca aggttcacga ggacctcatg ctgcccttcg acgagttcct    3180
cgccctcaac gggtgcgagg ccgcccgaga cctgtggatc aaccccttca cggccttcgg    3240
ctacgggcac ttcgacaacg tcccggccgc ctacgtgctg aagtacctcg acttcgtcac    3300
catgatgtcc tttgccaagg gagatctgtg gacgtgggcc gacggcaccc aggcgatgtt    3360
cgagcacctc aacgccaccc tggagcaccc ggccgaacgc aacgttgaca tcactcgcat    3420
cacccgcgag gacggcaagg tccacattca caccacggac tgggatcgcg agtccgacgt    3480
cctcgtcctc accgtcccgc tggaaaagtt cctcgactac tccgacgcgg acgatgacga    3540
gcgggagtac ttctcgaaga tcatccacca gcagtacatg gtggatgcct gcctggtgaa    3600
ggagtacccg accatctccg ggtacgtccc cgacaacatg aggcccgaac gtctcgggca    3660
cgtcatggtt tactaccacc gctgggctga tgatccgcac cagatcatca cgacctacct    3720
gctacgtaac catccggact acgcggacaa gactcaggag gagtgccgcc agatggtcct    3780
cgacgacatg gagaccttcg gtcatccggt cgagaagatc atcgaggagc agacctggta    3840
ctacttcccg cacgttagct cggaggacta caaggccggg tggtacgaga aggtcgaggg    3900
aatgcagggt cgtcgcaaca ccttctacgc cggagaaatt atgagtttcg gtaatttcga    3960
cgaggtgtgc cactactcga aggacctggt gacgcggttc ttcgtgtgag gtgtattccc    4020
gcattgctgc ggggatgaga atgggggggtg gtaccgggtt cggtaccacc ccccatcgac    4080
cgtcgcgaac cgggcctctg tgaggcttcg ggccggtagg atcaggttat ggatacttca    4140
gtcaatgtcg acacgtcgtc aagaccggcg cacgaaccgg ccaccgctcc cggtcgtttc    4200
gtcgtcagag atgcctgtca cgaggacctg cctgaagccg cggctgttca ggccgtgtgc    4260
gtccgagaga tcgccagggg ggtgatccct aatgacgtcc ttaccgaggt cactggcccc    4320
ggtatcgtcc acaccaccat tgagcagtgg aaccacttta tggatgatgg tgcgatcttc    4380
aagatccttg ttgatcgcct cgatatgagg actgtcgggg ttgccatggc ccgggtctct    4440
acaagttctg atgctcccac accgtgggag atcgcgaccc tccatgtact gccagaggcg    4500
cgaaactgcg gagcgtcaga caacctcctc gatgcttgta tcgggaaccg gtcggcctat    4560
gtgtgggtct ttgccgataa tgctcgcgcc atttcgttct accaacgcca tgggttccac    4620
gtcgacgcgg ccgacggtgc cgttgacgat tccctcggcg gggtagagct gcagcggctg    4680
atccgcgagg acatcatcga gtcgcagtga tgatggatgg gtagctcccg tggctcgtcg    4740
gcatgccagc acataggtct agcgctgcct cagccgacga tggtcctcac acatgggacg    4800
agagcttggt ggtgtcatcc tgaatatgca gggcgacttg cttgagcttg tcttcgtggg    4860
ctcgggcatg gtgcgcgcag aaaaggagct cgccaccgtt gcgcagcgtg atgcgcacat    4920
aggcttgtgc gccgcaacga tcacaacggt ccgcagtggt aagggcttgg tgttcgatca    4980
tcgtggtgct catgacaacc tcctccatct gaatcatcgg atcacctact agacaaccta    5040
cgctatcgtc ggaatgttct catacgtatc gaaagatgga tggctggggg cgaacacggt    5100
gccgggattc cgtgtcgtcg gctgtcgata agctgccacc gtgaccatgg acaacatctc    5160
gacctcatca gccaacagct cggaaacgcc acgtggtaag ggcgataccg tgcgcacggc    5220
gtcgactagc cgggagtacg gcgccaagaa tttattggtg ttggaggggc tcgag         5275
```

<210> SEQ ID NO 60
<211> LENGTH: 1275
<212> TYPE: DNA
<213> ORGANISM: Propionibacterium acnes
<220> FEATURE:
<221> NAME/KEY: CDS
<222> LOCATION: (1)..(1272)

<400> SEQUENCE: 60

| | | | | | | | | | | | | | | | | |
|---|---|---|---|---|---|---|---|---|---|---|---|---|---|---|---|---|
| atg | tcc | atc | tcg | aag | gat | tca | cgt | atc | gcc | atc | atc | ggg | gct | ggc | ccg | 48 |
| Met | Ser | Ile | Ser | Lys | Asp | Ser | Arg | Ile | Ala | Ile | Ile | Gly | Ala | Gly | Pro | |
| 1 | | | | 5 | | | | | 10 | | | | | 15 | | |
| gcc | ggg | ctg | gct | gcc | gga | atg | tac | ctc | gaa | cag | gcc | gga | ttt | cac | gac | 96 |
| Ala | Gly | Leu | Ala | Ala | Gly | Met | Tyr | Leu | Glu | Gln | Ala | Gly | Phe | His | Asp | |
| | | | 20 | | | | | 25 | | | | | 30 | | | |
| tac | acg | atc | ctg | gaa | cgc | acc | gac | cac | gtc | gga | ggc | aag | tgc | cac | tca | 144 |
| Tyr | Thr | Ile | Leu | Glu | Arg | Thr | Asp | His | Val | Gly | Gly | Lys | Cys | His | Ser | |
| | | 35 | | | | | 40 | | | | | 45 | | | | |
| ccg | aac | tac | cac | ggc | cgt | cgt | tat | gag | atg | ggg | gcc | atc | atg | ggc | gtc | 192 |
| Pro | Asn | Tyr | His | Gly | Arg | Arg | Tyr | Glu | Met | Gly | Ala | Ile | Met | Gly | Val | |
| | 50 | | | | | 55 | | | | | 60 | | | | | |
| ccc | agt | tac | gac | acc | atc | cag | gag | atc | atg | gat | cgc | act | ggc | gac | aag | 240 |
| Pro | Ser | Tyr | Asp | Thr | Ile | Gln | Glu | Ile | Met | Asp | Arg | Thr | Gly | Asp | Lys | |
| 65 | | | | | 70 | | | | | 75 | | | | | 80 | |
| gtc | gac | ggg | ccg | aaa | ctg | cgt | cgc | gag | ttc | ctg | cac | gag | gac | ggc | gag | 288 |
| Val | Asp | Gly | Pro | Lys | Leu | Arg | Arg | Glu | Phe | Leu | His | Glu | Asp | Gly | Glu | |
| | | | | 85 | | | | | 90 | | | | | 95 | | |
| atc | tac | gtc | ccg | gaa | aag | gat | cca | gtg | cgt | ggt | ccg | cag | gtc | atg | gca | 336 |
| Ile | Tyr | Val | Pro | Glu | Lys | Asp | Pro | Val | Arg | Gly | Pro | Gln | Val | Met | Ala | |
| | | | 100 | | | | | 105 | | | | | 110 | | | |
| gca | gtg | cag | aag | ctg | ggc | cag | ttg | ctc | gcg | acg | aag | tac | cag | gga | tat | 384 |
| Ala | Val | Gln | Lys | Leu | Gly | Gln | Leu | Leu | Ala | Thr | Lys | Tyr | Gln | Gly | Tyr | |
| | | 115 | | | | | 120 | | | | | 125 | | | | |
| gac | gcc | aac | ggc | cac | tac | aac | aag | gtt | cac | gag | gac | ctc | atg | ctg | ccc | 432 |
| Asp | Ala | Asn | Gly | His | Tyr | Asn | Lys | Val | His | Glu | Asp | Leu | Met | Leu | Pro | |
| | 130 | | | | | 135 | | | | | 140 | | | | | |
| ttc | gac | gag | ttc | ctc | gcc | ctc | aac | ggg | tgc | gag | gcc | gcc | cga | gac | ctg | 480 |
| Phe | Asp | Glu | Phe | Leu | Ala | Leu | Asn | Gly | Cys | Glu | Ala | Ala | Arg | Asp | Leu | |
| 145 | | | | | 150 | | | | | 155 | | | | | 160 | |
| tgg | atc | aac | ccc | ttc | acg | gcc | ttc | ggc | tac | ggg | cac | ttc | gac | aac | gtc | 528 |
| Trp | Ile | Asn | Pro | Phe | Thr | Ala | Phe | Gly | Tyr | Gly | His | Phe | Asp | Asn | Val | |
| | | | | 165 | | | | | 170 | | | | | 175 | | |
| ccg | gcc | gcc | tac | gtg | ctg | aag | tac | ctc | gac | ttc | gtc | acc | atg | atg | tcc | 576 |
| Pro | Ala | Ala | Tyr | Val | Leu | Lys | Tyr | Leu | Asp | Phe | Val | Thr | Met | Met | Ser | |
| | | | 180 | | | | | 185 | | | | | 190 | | | |
| ttt | gcc | aag | gga | gat | ctg | tgg | acg | tgg | gcc | gac | ggc | acc | cag | gcg | atg | 624 |
| Phe | Ala | Lys | Gly | Asp | Leu | Trp | Thr | Trp | Ala | Asp | Gly | Thr | Gln | Ala | Met | |
| | | 195 | | | | | 200 | | | | | 205 | | | | |
| ttc | gag | cac | ctc | aac | gcc | acc | ctg | gag | cac | ccg | gcc | gaa | cgc | aac | gtt | 672 |
| Phe | Glu | His | Leu | Asn | Ala | Thr | Leu | Glu | His | Pro | Ala | Glu | Arg | Asn | Val | |
| | 210 | | | | | 215 | | | | | 220 | | | | | |
| gac | atc | act | cgc | atc | acc | cgc | gag | gac | ggc | aag | gtc | cac | att | cac | acc | 720 |
| Asp | Ile | Thr | Arg | Ile | Thr | Arg | Glu | Asp | Gly | Lys | Val | His | Ile | His | Thr | |
| 225 | | | | | 230 | | | | | 235 | | | | | 240 | |
| acg | gac | tgg | gat | cgc | gag | tcc | gac | gtc | ctc | gtc | ctc | acc | gtc | ccg | ctg | 768 |
| Thr | Asp | Trp | Asp | Arg | Glu | Ser | Asp | Val | Leu | Val | Leu | Thr | Val | Pro | Leu | |
| | | | | 245 | | | | | 250 | | | | | 255 | | |
| gaa | aag | ttc | ctc | gac | tac | tcc | gac | gcg | gac | gat | gac | gag | cgg | gag | tac | 816 |
| Glu | Lys | Phe | Leu | Asp | Tyr | Ser | Asp | Ala | Asp | Asp | Asp | Glu | Arg | Glu | Tyr | |
| | | | 260 | | | | | 265 | | | | | 270 | | | |

-continued

```
ttc tcg aag atc atc cac cag cag tac atg gtg gat gcc tgc ctg gtg     864
Phe Ser Lys Ile Ile His Gln Gln Tyr Met Val Asp Ala Cys Leu Val
        275                 280                 285 aag gag tac ccg acc atc tcc ggg tac gtc ccc gac aac atg agg ccc     912
Lys Glu Tyr Pro Thr Ile Ser Gly Tyr Val Pro Asp Asn Met Arg Pro
290                 295                 300 gaa cgt ctc ggg cac gtc atg gtt tac tac cac cgc tgg gct gat gat     960
Glu Arg Leu Gly His Val Met Val Tyr Tyr His Arg Trp Ala Asp Asp
305                 310                 315                 320 ccg cac cag atc atc acg acc tac ctg cta cgt aac cat ccg gac tac    1008
Pro His Gln Ile Ile Thr Thr Tyr Leu Leu Arg Asn His Pro Asp Tyr
                325                 330                 335 gcg gac aag act cag gag gag tgc cgc cag atg gtc ctc gac gac atg    1056
Ala Asp Lys Thr Gln Glu Glu Cys Arg Gln Met Val Leu Asp Asp Met
            340                 345                 350 gag acc ttc ggt cat ccg gtc gag aag atc atc gag gag cag acc tgg    1104
Glu Thr Phe Gly His Pro Val Glu Lys Ile Ile Glu Glu Gln Thr Trp
        355                 360                 365 tac tac ttc ccg cac gtt agc tcg gag gac tac aag gcc ggg tgg tac    1152
Tyr Tyr Phe Pro His Val Ser Ser Glu Asp Tyr Lys Ala Gly Trp Tyr
370                 375                 380 gag aag gtc gag gga atg cag ggt cgt cgc aac acc ttc tac gcc gga    1200
Glu Lys Val Glu Gly Met Gln Gly Arg Arg Asn Thr Phe Tyr Ala Gly
385                 390                 395                 400 gaa att atg agt ttc ggt aat ttc gac gag gtg tgc cac tac tcg aag    1248
Glu Ile Met Ser Phe Gly Asn Phe Asp Glu Val Cys His Tyr Ser Lys
                405                 410                 415 gac ctg gtg acg cgg ttc ttc gtg tga                                1275
Asp Leu Val Thr Arg Phe Phe Val
            420
```

<210> SEQ ID NO 61
<211> LENGTH: 424
<212> TYPE: PRT
<213> ORGANISM: Propionibacterium acnes

<400> SEQUENCE: 61

```
Met Ser Ile Ser Lys Asp Ser Arg Ile Ala Ile Ile Gly Ala Gly Pro
1               5                   10                  15

Ala Gly Leu Ala Ala Gly Met Tyr Leu Glu Gln Ala Gly Phe His Asp
            20                  25                  30

Tyr Thr Ile Leu Glu Arg Thr Asp His Val Gly Gly Lys Cys His Ser
        35                  40                  45

Pro Asn Tyr His Gly Arg Arg Tyr Glu Met Gly Ala Ile Met Gly Val
    50                  55                  60

Pro Ser Tyr Asp Thr Ile Gln Glu Ile Met Asp Arg Thr Gly Asp Lys
65                  70                  75                  80

Val Asp Gly Pro Lys Leu Arg Arg Glu Phe Leu His Glu Asp Gly Glu
                85                  90                  95

Ile Tyr Val Pro Glu Lys Asp Pro Val Arg Gly Pro Gln Val Met Ala
            100                 105                 110

Ala Val Gln Lys Leu Gly Gln Leu Leu Ala Thr Lys Tyr Gln Gly Tyr
        115                 120                 125

Asp Ala Asn Gly His Tyr Asn Lys Val His Glu Asp Leu Met Leu Pro
    130                 135                 140

Phe Asp Glu Phe Leu Ala Leu Asn Gly Cys Glu Ala Ala Arg Asp Leu
145                 150                 155                 160

Trp Ile Asn Pro Phe Thr Ala Phe Gly Tyr Gly His Phe Asp Asn Val
```

165                 170                 175
Pro Ala Ala Tyr Val Leu Lys Tyr Leu Asp Phe Val Thr Met Met Ser
                180                 185                 190

Phe Ala Lys Gly Asp Leu Trp Thr Trp Ala Asp Gly Thr Gln Ala Met
            195                 200                 205

Phe Glu His Leu Asn Ala Thr Leu Glu His Pro Ala Glu Arg Asn Val
210                 215                 220

Asp Ile Thr Arg Ile Thr Arg Glu Asp Gly Lys Val His Ile His Thr
225                 230                 235                 240

Thr Asp Trp Asp Arg Glu Ser Asp Val Leu Val Leu Thr Val Pro Leu
                245                 250                 255

Glu Lys Phe Leu Asp Tyr Ser Asp Ala Asp Asp Glu Arg Glu Tyr
            260                 265                 270

Phe Ser Lys Ile Ile His Gln Gln Tyr Met Val Asp Ala Cys Leu Val
        275                 280                 285

Lys Glu Tyr Pro Thr Ile Ser Gly Tyr Val Pro Asp Asn Met Arg Pro
    290                 295                 300

Glu Arg Leu Gly His Val Met Val Tyr Tyr His Arg Trp Ala Asp Asp
305                 310                 315                 320

Pro His Gln Ile Ile Thr Thr Tyr Leu Leu Arg Asn His Pro Asp Tyr
                325                 330                 335

Ala Asp Lys Thr Gln Glu Glu Cys Arg Gln Met Val Leu Asp Asp Met
            340                 345                 350

Glu Thr Phe Gly His Pro Val Glu Lys Ile Ile Glu Glu Gln Thr Trp
        355                 360                 365

Tyr Tyr Phe Pro His Val Ser Ser Glu Asp Tyr Lys Ala Gly Trp Tyr
    370                 375                 380

Glu Lys Val Glu Gly Met Gln Gly Arg Arg Asn Thr Phe Tyr Ala Gly
385                 390                 395                 400

Glu Ile Met Ser Phe Gly Asn Phe Asp Glu Val Cys His Tyr Ser Lys
                405                 410                 415

Asp Leu Val Thr Arg Phe Phe Val
            420

<210> SEQ ID NO 62
<211> LENGTH: 7
<212> TYPE: DNA
<213> ORGANISM: Propionibacterium acnes
<220> FEATURE:
<221> NAME/KEY: RBS
<222> LOCATION: (1)..(7)

<400> SEQUENCE: 62 aaggaag                                                              7

<210> SEQ ID NO 63
<211> LENGTH: 1073
<212> TYPE: DNA
<213> ORGANISM: Propionibacterium acnes

<400> SEQUENCE: 63
gccgggcggg cacgattgac gaatttccgc acactggatg gcggaacaaa ggtgtcgtga      60
tttccctgga tcaccattgt tggtggtgcc tgaggagtga tccaggtgga actgttgaca     120
gcgcgataac ggtcggggaa ttgcttgggg gtgccaccga tatacatttt ggcggcattg     180
cccgcgctca gtgtggtgac cgactcgacg gtaccgacat ccaccgttgg atagagggcg     240

-continued

```
aggactgact tcggggcccg tattgagccg caggaactct tcaactttcc actggcggcg    300
ccgtaggcga gattaatggc cattccacca ccagcggaat cacccatgat cgatacctgt    360
gaagggtcgc caccgagttc tttcacgtgg acaggctcc aggcccaggc acatgcgacc    420
tgttttgggg cggtattcca ggtggggtgg ccctgggtgg ccaggtgta cgagggcga     480
atgactaacc agccatgatc ggaaaaccat ctcaacgtgg cgggcatggt ggcgtcggtg    540
ctccatcctt caccatgaat gtcgacaagt accggggcat tgtggttatg ggcacggtag    600
atctgggccg tctcgtcagg gccggatcca taccggaccg tttcgtcagg gtggtcggac    660
atcgacgaca ccgcagctgc cgagacgacg ttgatacgtc caccggggcg gtccgtgatc    720
cacgccgtcg tcgccgttgc cgccactggc acgatgaggg ccatcaccga aagacaacg     780
gccaccactc gcagaccacc tcgtcccaaa agagcgagga cgaaggcgat gacggcgatg    840
accagagccg gtacagccaa cgatcccacc agaacgagg agatgaaggt gagggcattg     900
tgtgagggga ggatcgcggc cactgaccac gccagtaccg gcaggtcag gatcagcccg     960
acgagaccgg aagtgatgcg tagccaggaa tgacgggagg ttttcgtgtc agccacgcgt    1020
ccaccgtact cacgggacat ggtcgatagg atcttcgcgc aggagggacc cat           1073
```

<210> SEQ ID NO 64
<211> LENGTH: 358
<212> TYPE: PRT
<213> ORGANISM: Propionibacterium acnes

<400> SEQUENCE: 64

```
Met Gly Pro Ser Cys Ala Lys Ile Leu Ser Thr Met Ser Arg Glu Tyr
 1               5                  10                  15

Gly Gly Arg Val Ala Asp Thr Lys Thr Ser Arg His Ser Trp Leu Arg
            20                  25                  30

Ile Thr Ser Gly Leu Val Gly Leu Ile Leu Thr Leu Pro Val Leu Ala
        35                  40                  45

Trp Ser Val Ala Ala Ile Leu Pro Ser His Asn Ala Leu Thr Phe Ile
    50                  55                  60

Ser Ser Val Leu Val Gly Ser Leu Ala Val Pro Ala Leu Val Ile Ala
65                  70                  75                  80

Val Ile Ala Phe Val Leu Ala Leu Leu Gly Arg Gly Gly Leu Arg Val
                85                  90                  95

Val Ala Val Phe Ser Val Met Ala Leu Ile Val Pro Val Ala Ala
            100                 105                 110

Thr Ala Thr Thr Ala Trp Ile Thr Asp Arg Pro Gly Gly Arg Ile Asn
        115                 120                 125

Val Val Ser Ala Ala Ala Val Ser Ser Met Ser Asp His Pro Asp Glu
130                 135                 140

Thr Val Arg Tyr Gly Ser Gly Pro Asp Glu Thr Ala Gln Ile Tyr Arg
145                 150                 155                 160

Ala His Asn His Asn Ala Pro Val Leu Val Asp Ile His Gly Glu Gly
                165                 170                 175

Trp Ser Thr Asp Ala Thr Met Pro Ala Thr Leu Arg Trp Phe Ser Asp
            180                 185                 190

His Gly Trp Leu Val Ile Arg Pro Ser Tyr Thr Leu Ala Thr Gln Gly
        195                 200                 205

His Pro Thr Trp Asn Thr Ala Pro Lys Gln Val Ala Cys Ala Trp Ala
    210                 215                 220

Trp Ser Leu Ser His Val Lys Glu Leu Gly Gly Asp Pro Ser Gln Val
```

-continued

```
                225                 230                 235                 240
        Ser Ile Met Gly Asp Ser Ala Gly Gly Met Ala Ile Asn Leu Ala
                        245                 250                 255

Tyr Gly Ala Ala Ser Gly Lys Leu Lys Ser Ser Cys Gly Ser Ile Arg
                        260                 265                 270

Ala Pro Lys Ser Val Leu Ala Leu Tyr Pro Thr Val Asp Val Gly Thr
                        275                 280                 285

Val Glu Ser Val Thr Thr Leu Ser Ala Gly Asn Ala Ala Lys Met Tyr
                        290                 295                 300

Ile Gly Gly Thr Pro Lys Gln Phe Pro Asp Arg Tyr Arg Ala Val Asn
        305                 310                 315                 320

Ser Ser Thr Trp Ile Thr Pro Gln Ala Pro Pro Thr Met Val Ile Gln
                        325                 330                 335

Gly Asn His Asp Thr Phe Val Pro Pro Ser Ser Val Arg Lys Phe Val
                        340                 345                 350

Asn Arg Ala Arg Pro Ala
                        355

<210> SEQ ID NO 65
<211> LENGTH: 783
<212> TYPE: DNA
<213> ORGANISM: Propionibacterium acnes
<220> FEATURE:
<221> NAME/KEY: CDS
<222> LOCATION: (1)..(783)

<400> SEQUENCE: 65 atg tcc ata aca cca cga aag tgc aag gct gcc gcc ctt gcc aca gcg        48
Met Ser Ile Thr Pro Arg Lys Cys Lys Ala Ala Ala Leu Ala Thr Ala
1               5                   10                  15 ccg gtg gcc gct gcc ctc ggt gct tac gga ttt ctt aaa ggg gcg acg        96
Pro Val Ala Ala Ala Leu Gly Ala Tyr Gly Phe Leu Lys Gly Ala Thr
                20                  25                  30 aag ttc tat tcc agc cag gtt aac gga act ccc gag cag tac aag atg       144
Lys Phe Tyr Ser Ser Gln Val Asn Gly Thr Pro Glu Gln Tyr Lys Met
            35                  40                  45 acc ctt cct ggt gac gac ctc gtc ccg gaa ggt tcg ccg cgc ttc aag       192
Thr Leu Pro Gly Asp Asp Leu Val Pro Glu Gly Ser Pro Arg Phe Lys
        50                  55                  60 cgc ctc acc cat gtg gag gat ctc gac gcc ccc tgc gac gag gtc tgg       240
Arg Leu Thr His Val Glu Asp Leu Asp Ala Pro Cys Asp Glu Val Trp
65                  70                  75                  80 aag cac gtc tac cag ctc aac acc acg gcc ggc ttc tac tcc ttc           288
Lys His Val Tyr Gln Leu Asn Thr Thr Thr Ala Gly Phe Tyr Ser Phe
                85                  90                  95 acc ttc ttc gag aag atg ttc gga ctg tcg gtc gac aac acc ttc atg       336
Thr Phe Phe Glu Lys Met Phe Gly Leu Ser Val Asp Asn Thr Phe Met
            100                 105                 110 gtg gaa cag gct tgg cag gcc ccg gac tac tac aag ccc ggt gac atg       384
Val Glu Gln Ala Trp Gln Ala Pro Asp Tyr Tyr Lys Pro Gly Asp Met
        115                 120                 125 ttc tgt tgg agt tac gcc ggt ttc ggt gcc gag gtc gcc gac atg gtc       432
Phe Cys Trp Ser Tyr Ala Gly Phe Gly Ala Glu Val Ala Asp Met Val
    130                 135                 140 ccc ggc aag tat ctg gtg tgg ttc gct gac acc cgt gac ggc acc agg       480
Pro Gly Lys Tyr Leu Val Trp Phe Ala Asp Thr Arg Asp Gly Thr Arg
145                 150                 155                 160 aca ccg ggc gca agt ttc ctg cta ccg cct gga atg ccg tgg aac cgc       528
Thr Pro Gly Ala Ser Phe Leu Leu Pro Pro Gly Met Pro Trp Asn Arg
```

```
                    165                 170                 175
tgg agt tgg gtc atc gcc ctg gaa ccc ctc gac agt ggc aac cgg acg      576
Trp Ser Trp Val Ile Ala Leu Glu Pro Leu Asp Ser Gly Asn Arg Thr
            180                 185                 190 cgc atc tac tcc cgg tgg aac atc tcg gcc tcc gag gag tcc agt ccg      624
Arg Ile Tyr Ser Arg Trp Asn Ile Ser Ala Ser Glu Glu Ser Ser Pro
        195                 200                 205 atc tcg gtc ttc ctc atg gat ctg gtc atg atg gac ggc ggc ggc atg      672
Ile Ser Val Phe Leu Met Asp Leu Val Met Met Asp Gly Gly Gly Met
210                 215                 220 gtg aac cgt cgg atg ttc caa ggg ctg gag aag gct gcc gtc gga act      720
Val Asn Arg Arg Met Phe Gln Gly Leu Glu Lys Ala Ala Val Gly Thr
225                 230                 235                 240 gct cgc aag aac atc gtt cct gcg cgc cta tca gcg gtt cat ggg caa      768
Ala Arg Lys Asn Ile Val Pro Ala Arg Leu Ser Ala Val His Gly Gln
                245                 250                 255 gtc cta cgg cac tga                                                  783
Val Leu Arg His
            260

<210> SEQ ID NO 66
<211> LENGTH: 260
<212> TYPE: PRT
<213> ORGANISM: Propionibacterium acnes

<400> SEQUENCE: 66

Met Ser Ile Thr Pro Arg Lys Cys Lys Ala Ala Ala Leu Ala Thr Ala
1               5                   10                  15

Pro Val Ala Ala Ala Leu Gly Ala Tyr Gly Phe Leu Lys Gly Ala Thr
            20                  25                  30

Lys Phe Tyr Ser Ser Gln Val Asn Gly Thr Pro Glu Gln Tyr Lys Met
        35                  40                  45

Thr Leu Pro Gly Asp Asp Leu Val Pro Glu Gly Ser Pro Arg Phe Lys
    50                  55                  60

Arg Leu Thr His Val Glu Asp Leu Asp Ala Pro Cys Asp Glu Val Trp
65                  70                  75                  80

Lys His Val Tyr Gln Leu Asn Thr Thr Ala Gly Phe Tyr Ser Phe
                85                  90                  95

Thr Phe Phe Glu Lys Met Phe Gly Leu Ser Val Asp Asn Thr Phe Met
            100                 105                 110

Val Glu Gln Ala Trp Gln Ala Pro Asp Tyr Tyr Lys Pro Gly Asp Met
        115                 120                 125

Phe Cys Trp Ser Tyr Ala Gly Phe Gly Ala Glu Val Ala Asp Met Val
    130                 135                 140

Pro Gly Lys Tyr Leu Val Trp Phe Ala Asp Thr Arg Asp Gly Thr Arg
145                 150                 155                 160

Thr Pro Gly Ala Ser Phe Leu Leu Pro Pro Gly Met Pro Trp Asn Arg
                165                 170                 175

Trp Ser Trp Val Ile Ala Leu Glu Pro Leu Asp Ser Gly Asn Arg Thr
            180                 185                 190

Arg Ile Tyr Ser Arg Trp Asn Ile Ser Ala Ser Glu Glu Ser Ser Pro
        195                 200                 205

Ile Ser Val Phe Leu Met Asp Leu Val Met Met Asp Gly Gly Gly Met
    210                 215                 220

Val Asn Arg Arg Met Phe Gln Gly Leu Glu Lys Ala Ala Val Gly Thr
225                 230                 235                 240
```

```
Ala Arg Lys Asn Ile Val Pro Ala Arg Leu Ser Ala Val His Gly Gln
                245                 250                 255

Val Leu Arg His
            260

<210> SEQ ID NO 67
<211> LENGTH: 7
<212> TYPE: DNA
<213> ORGANISM: Propionibacterium acnes
<220> FEATURE:
<221> NAME/KEY: RBS
<222> LOCATION: (1)..(7)

<400> SEQUENCE: 67 gaaggag                                                              7

<210> SEQ ID NO 68
<211> LENGTH: 582
<212> TYPE: DNA
<213> ORGANISM: Propionibacterium acnes
<220> FEATURE:
<221> NAME/KEY: CDS
<222> LOCATION: (1)..(582)

<400> SEQUENCE: 68 atg gat act tca gtc aat gtc gac acg tcg tca aga ccg gcg cac gaa    48
Met Asp Thr Ser Val Asn Val Asp Thr Ser Ser Arg Pro Ala His Glu
  1               5                  10                  15 ccg gcc acc gct ccc ggt cgt ttc gtc gtc aga gat gcc tgt cac gag    96
Pro Ala Thr Ala Pro Gly Arg Phe Val Val Arg Asp Ala Cys His Glu
             20                  25                  30 gac ctg cct gaa gcc gcg gct gtt cag gcc gtg tgc gtc cga gag atc   144
Asp Leu Pro Glu Ala Ala Ala Val Gln Ala Val Cys Val Arg Glu Ile
         35                  40                  45 ggc cag ggg gtg atc cct aat gac gtc ctt acc gag gtc act ggc ccc   192
Gly Gln Gly Val Ile Pro Asn Asp Val Leu Thr Glu Val Thr Gly Pro
     50                  55                  60 ggt atc gtc cac acc acc att gag cag tgg aac cac ttt atg gat gat   240
Gly Ile Val His Thr Thr Ile Glu Gln Trp Asn His Phe Met Asp Asp
 65                  70                  75                  80 ggt gcg atc ttc aag atc ctt gtt gat cgc ctc gat atg agg act gtc   288
Gly Ala Ile Phe Lys Ile Leu Val Asp Arg Leu Asp Met Arg Thr Val
                 85                  90                  95 ggg gtt gcc atg gcc cgg gtc tct aca agt tct gat gct ccc aca ccg   336
Gly Val Ala Met Ala Arg Val Ser Thr Ser Ser Asp Ala Pro Thr Pro
            100                 105                 110 tgg gag atc gcg acc ctc cat gta ctg cca gag gcg cga aac tgc gga   384
Trp Glu Ile Ala Thr Leu His Val Leu Pro Glu Ala Arg Asn Cys Gly
        115                 120                 125 gcg tca gac aac ctc ctc gat gct tgt atc ggg aac cgg tcg gcc tat   432
Ala Ser Asp Asn Leu Leu Asp Ala Cys Ile Gly Asn Arg Ser Ala Tyr
    130                 135                 140 gtg tgg gtc ttt gcc gat aat gct cgc gcc att tcg ttc tac caa cgc   480
Val Trp Val Phe Ala Asp Asn Ala Arg Ala Ile Ser Phe Tyr Gln Arg
145                 150                 155                 160 cat ggg ttc cac gtc gac gcg gcc gac ggt gcc gtt gac gat tcc ctc   528
His Gly Phe His Val Asp Ala Ala Asp Gly Ala Val Asp Asp Ser Leu
                165                 170                 175 ggc ggg gta gag ctg cag cgg ctg atc cgc gag gac atc atc gag tcg   576
Gly Gly Val Glu Leu Gln Arg Leu Ile Arg Glu Asp Ile Ile Glu Ser
            180                 185                 190 cag tga                                                            582
```

Gln

<210> SEQ ID NO 69
<211> LENGTH: 193
<212> TYPE: PRT
<213> ORGANISM: Propionibacterium acnes

<400> SEQUENCE: 69

Met Asp Thr Ser Val Asn Val Asp Thr Ser Ser Arg Pro Ala His Glu
1               5                   10                  15

Pro Ala Thr Ala Pro Gly Arg Phe Val Val Arg Asp Ala Cys His Glu
            20                  25                  30

Asp Leu Pro Glu Ala Ala Ala Val Gln Ala Val Cys Val Arg Glu Ile
        35                  40                  45

Gly Gln Gly Val Ile Pro Asn Asp Val Leu Thr Glu Val Thr Gly Pro
    50                  55                  60

Gly Ile Val His Thr Thr Ile Glu Gln Trp Asn His Phe Met Asp Asp
65                  70                  75                  80

Gly Ala Ile Phe Lys Ile Leu Val Asp Arg Leu Asp Met Arg Thr Val
                85                  90                  95

Gly Val Ala Met Ala Arg Val Ser Thr Ser Ser Asp Ala Pro Thr Pro
            100                 105                 110

Trp Glu Ile Ala Thr Leu His Val Leu Pro Glu Ala Arg Asn Cys Gly
        115                 120                 125

Ala Ser Asp Asn Leu Leu Asp Ala Cys Ile Gly Asn Arg Ser Ala Tyr
    130                 135                 140

Val Trp Val Phe Ala Asp Asn Ala Arg Ala Ile Ser Phe Tyr Gln Arg
145                 150                 155                 160

His Gly Phe His Val Asp Ala Ala Asp Gly Ala Val Asp Asp Ser Leu
                165                 170                 175

Gly Gly Val Glu Leu Gln Arg Leu Ile Arg Glu Asp Ile Ile Glu Ser
            180                 185                 190

Gln

<210> SEQ ID NO 70
<211> LENGTH: 7
<212> TYPE: DNA
<213> ORGANISM: Propionibacterium acnes
<220> FEATURE:
<221> NAME/KEY: RBS
<222> LOCATION: (1)..(7)

<400> SEQUENCE: 70 ggtagga                                                         7

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 71
cagacatatg tccatctcga aggattc                                   27

<210> SEQ ID NO 72
<211> LENGTH: 29
<212> TYPE: DNA
<213> ORGANISM: Artificial Sequence
<220> FEATURE:

<223> OTHER INFORMATION: Description of Artificial Sequence:primer

<400> SEQUENCE: 72
ctatctcgag tcacacgaag aaccgcgtc                                29

<210> SEQ ID NO 73
<211> LENGTH: 53
<212> TYPE: PRT
<213> ORGANISM: Artificial Sequence
<220> FEATURE:
<223> OTHER INFORMATION: Description of Artificial Sequence:consensus
<221> NAME/KEY: UNSURE
<222> LOCATION: (1)..(53)
<223> OTHER INFORMATION: Xaa = any amino acid

<400> SEQUENCE: 73

Gly Xaa Gly Xaa Xaa Gly Xaa Xaa Xaa Ala Xaa Xaa Leu Xaa Xaa Xaa
 1               5                  10                  15

Xaa Xaa Xaa Xaa Gly Xaa Xaa Xaa Xaa Xaa Xaa Glu Xaa Xaa Xaa
             20                  25                  30

Xaa Xaa Gly Gly Xaa Xaa Xaa Xaa Xaa Xaa Xaa Xaa Gly Xaa Xaa
         35                  40                  45

Xaa Xaa Xaa Xaa Gly
     50

<210> SEQ ID NO 74
<211> LENGTH: 43
<212> TYPE: PRT
<213> ORGANISM: Homo sapiens

<400> SEQUENCE: 74

Ser Glu Ala Tyr Ser Ala Lys Ile Ala Leu Phe Gly Ala Gly Pro Ala
 1               5                  10                  15

Ser Ile Ser Cys Ala Ser Phe Leu Ala Arg Leu Gly Tyr Ser Asp Ile
             20                  25                  30

Thr Ile Phe Glu Lys Gln Glu Tyr Val Gly Gly
         35                  40

<210> SEQ ID NO 75
<211> LENGTH: 41
<212> TYPE: PRT
<213> ORGANISM: Agrobacterium vitis

<400> SEQUENCE: 75

Lys Val Ala Ile Val Gly Ala Gly Leu Ser Gly Leu Val Val Ala Ser
 1               5                  10                  15

Glu Leu Leu His Ala Gly Ile Asp Asp Val Thr Leu Tyr Glu Ala Ser
             20                  25                  30

Asp Arg Ile Gly Gly Lys Leu Trp Ser
         35                  40

<210> SEQ ID NO 76
<211> LENGTH: 45
<212> TYPE: PRT
<213> ORGANISM: Deinococcus radiodurans

<400> SEQUENCE: 76

Val Lys Thr Gly Lys Lys Val Ala Val Val Gly Ser Gly Pro Ala Gly
 1               5                  10                  15

Leu Ala Ala Ala Gln Gln Leu Ala Arg Ala Gly His Asp Val Thr Val
             20                  25                  30

```
Phe Glu Lys Asn Asp Arg Val Gly Gly Arg Ile Glu Gln
            35                  40                  45

<210> SEQ ID NO 77
<211> LENGTH: 37
<212> TYPE: PRT
<213> ORGANISM: Arthrobacter nicotinovorans

<400> SEQUENCE: 77

Val Val Gly Gly Gly Phe Ser Gly Leu Lys Ala Ala Arg Asp Leu Thr
  1               5                  10                  15

Asn Ala Gly Lys Lys Val Leu Leu Glu Gly Gly Glu Arg Leu Gly
             20                  25                  30

Gly Arg Ala Tyr Ser
             35

<210> SEQ ID NO 78
<211> LENGTH: 52
<212> TYPE: PRT
<213> ORGANISM: Synechocystis sp.

<400> SEQUENCE: 78

Arg Ile Ala Ile Ile Gly Ala Gly Leu Ala Gly Met Ala Thr Ala Val
  1               5                  10                  15

Glu Leu Val Asp Ala Gly His Glu Val Glu Leu Tyr Glu Ala Arg Ser
             20                  25                  30

Phe Ile Gly Gly Lys Val Gly Ser Trp Val Asp Gly Asp Gly Asn His
         35                  40                  45

Ile Glu Met Gly
         50

<210> SEQ ID NO 79
<211> LENGTH: 57
<212> TYPE: PRT
<213> ORGANISM: Cercospora nicotianae

<400> SEQUENCE: 79

Ser Thr Ser Lys Arg Pro Thr Ala Ile Val Ile Gly Ser Gly Val Gly
  1               5                  10                  15

Gly Val Ser Thr Ala Ala Arg Leu Ala Arg Ala Gly Phe His Val Thr
             20                  25                  30

Val Leu Glu Lys Asn Asn Phe Thr Gly Gly Arg Cys Ser Leu Ile His
         35                  40                  45

His Glu Gly Tyr Arg Phe Asp Gln Gly
         50                  55

<210> SEQ ID NO 80
<211> LENGTH: 52
<212> TYPE: PRT
<213> ORGANISM: Zea mays

<400> SEQUENCE: 80

Arg Val Ile Val Val Gly Ala Gly Met Ser Gly Ile Ser Ala Ala Lys
  1               5                  10                  15
```

-continued

```
Arg Leu Ser Glu Ala Gly Ile Thr Asp Leu Leu Ile Leu Glu Ala Thr
            20                  25                  30

Asp His Ile Gly Gly Arg Met His Lys Thr Asn Phe Ala Gly Ile Asn
            35                  40                  45

Val Glu Leu Gly
    50
```